United States Patent [19]

Oswald et al.

[11] Patent Number: 5,030,774
[45] Date of Patent: Jul. 9, 1991

[54] PROCESS FOR THE HYDROFORMYLATION OF SULFUR-CONTAINING THERMALLY CRACKED PETROLEUM RESIDUE AND NOVEL PRODUCTS THEREOF

[75] Inventors: Alexis A. Oswald, Annandale, N.J.; Ram N. Bhatia, Baton Rouge, La.; Edmund J. Mozeleski, Califon, N.J.; Alexandr P. Glivicky, Sarnia, Canada; Barry G. Brueggeman, Baton Rouge, La.; John R. Hooton, Baton Rouge, La.; Charles M. Smith, Baton Rouge, La.; Chang S. Hsu, Bridgewater, N.J.

[73] Assignee: Exxon Research and Engineering Co., Florham Park, N.J.

[21] Appl. No.: 461,137

[22] Filed: Jan. 4, 1990

Related U.S. Application Data

[60] Division of Ser. No. 323,070, Mar. 10, 1989, which is a division of Ser. No. 105,171, Oct. 5, 1987, which is a continuation-in-part of Ser. No. 914,802, Oct. 3, 1986.

[51] Int. Cl.$^5$ ............................................. C07C 29/16
[52] U.S. Cl. ........................................ 568/882; 568/454; 568/880
[58] Field of Search ................ 568/451, 454, 492, 882

[56] References Cited

U.S. PATENT DOCUMENTS

| 2,760,994 | 12/1956 | Gwynn | 568/881 |
| 3,102,150 | 8/1963 | Hunter et al. | 568/881 |
| 3,321,534 | 5/1967 | Landgraf et al. | 568/881 |
| 4,401,834 | 8/1983 | King | 568/881 |
| 4,778,929 | 10/1988 | Zehner et al. | 568/454 |
| 4,871,879 | 10/1989 | Laird | 568/454 |

FOREIGN PATENT DOCUMENTS

| 1115232 | 1/1961 | Fed. Rep. of Germany | 568/881 |
| 0638585 | 12/1978 | U.S.S.R. | 568/881 |

Primary Examiner—Werren B. Lone
Attorney, Agent, or Firm—J. J. Mahon

[57] ABSTRACT

A catalytic process for the hydroformylation of olefinic, sulfur containing thermally cracked petroleum streams to produce aldehydes and/or alcohols is disclosed. The catalysts are homogeneous transition metal carbonyl complexes. Especially preferred catalysts for low and medium pressure hydroformylation are cobalt and rhodium carbonyl hydride complexes in which some of the carbonyl ligands have been replaced by trivalent phosphorus ligands. In a preferred high pressure hydroformylation, the sulfur-containing naphtha and gas oil distillate feeds are proudced from vacuum residue by high temperature thermal cracking. Such feeds contain more than 20% olefins with 1-n-olefins as the single major types. These olefin components are hydroformylated in the presence of a cobalt cabonyl complex to produce a novel type of semilinear aldehyde and/or alcohol product containing an average of less than one alkyl branch per molecule. The alcohols are converted to dialkyl phthalates and other esters having a unique balance of plasticizer properties. They are also useful for producing novel surfactants, particularly ethoxylated derivatives.

For the preparation of products containing minimal concentrations of sulfur compounds, narrow distillate fractions of thermally cracked residua are preferred. In the $C_6$ to $C_{11}$ carbon range, single carbon fractions of sharply reduced aromatic hydrocarbon and thiophenic sulfur content can be obtained. These fractions of increased linear olefin content can be advantageously used as hydroformylation feeds in the derivation of low sulfur containing alcohols and related products of increased linearity.

4 Claims, 18 Drawing Sheets

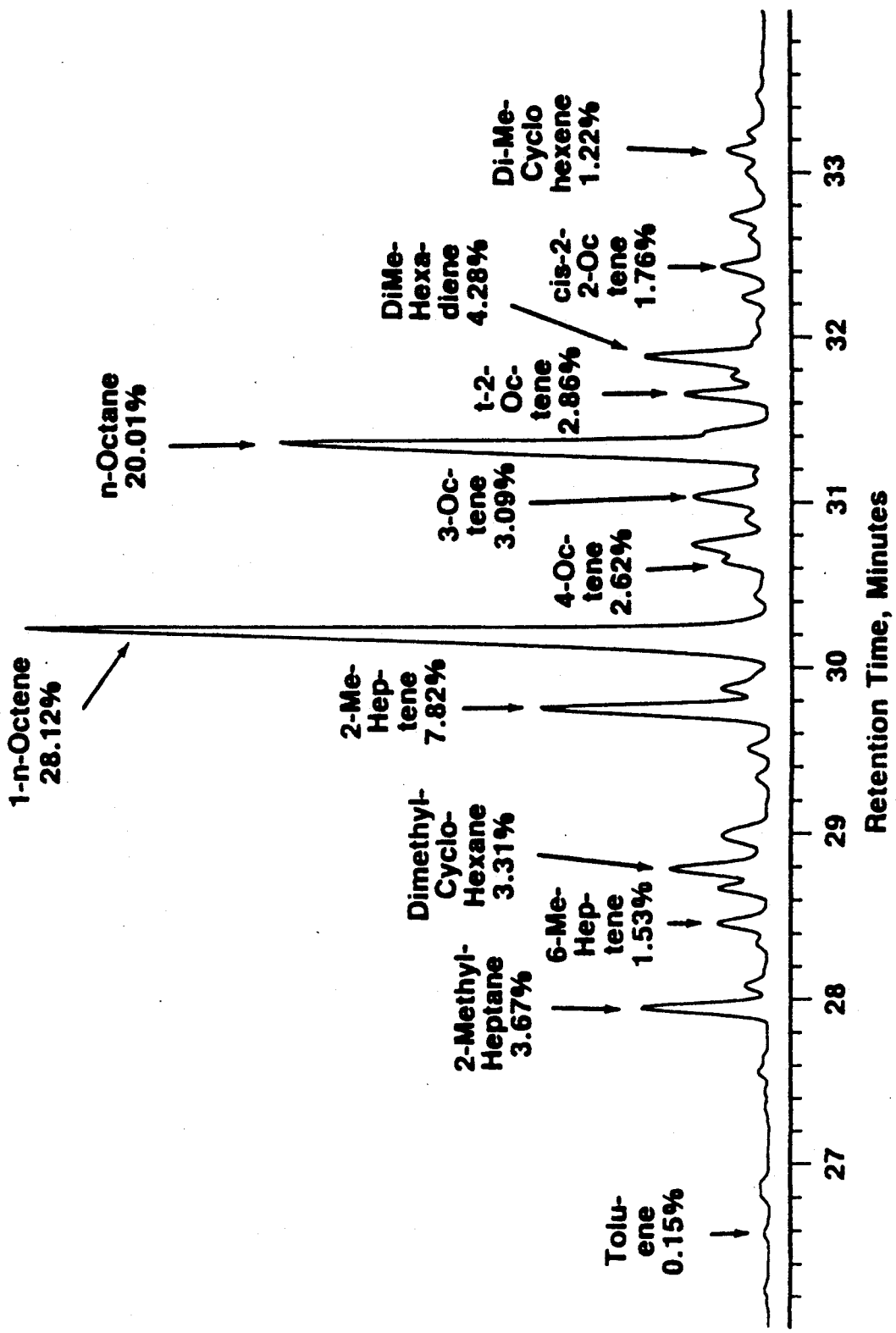

PROCESS FOR THE HYDROFORMYLATION OF SULFUR-CONTAINING THERMALLY CRACKED PETROLEUM RESIDUE AND NOVEL PRODUCTS THEREOF

This is a division of application Ser. No. 323,070 filed Mar. 10, 1989 which is a division of Ser. No. 105,171 filed Oct. 5, 1987 which is a continuation-in-part of Ser. No. 914,802 filed Oct 3, 1986.

FIELD OF THE INVENTION

This invention provides a catalytic process for the hydroformylation of certain olefinic, sulfur containing, thermally cracked petroleum distillates, readily available at low cost, to produce certain desirable semilinear aldehydes and alcohols, by reacting the olefin components with CO and $H_2$. The catalysts are preferably dissolved transition metal carbonyl complexes. Especially preferred catalysts are cobalt and rhodium carbonyl hydride complexes in which some of the carbonyl ligands have been replaced by trivalent phosphorus ligands. A preferred feed is produced by the high temperature thermal cracking of vacuum resids, particularly by Fluid-coking and Flexicoking.

One aspect of the disclosure is a description of the types and structures of the compounds produced by the thermal cracking of petroleum resids. The naphtha and gas oil distillate fractions derived by the cracking of vacuum resids in fluidized bed processes were investigated by a combination of high resolution capillary gas chromatography, mass spectrometry and nuclear magnetic resonance spectroscopy. The different types of olefin reactants and the potential sulfur compound inhibitors were particularly analyzed. The distribution of the sulfur compound components in the distillate feeds was analyzed by using a sulfur specific detector.

Another aspect of the disclosure is the correlation of the structures of the 1-n-olefin and the linear internal olefin reactant components of the feed and the various types of transition metal complex catalysts used, with the unique structures of the semilinear aldehyde and alcohol products. The high pressure cobalt carbonyl complex catalyzed hydroformylation of $C_5$ to $C_{15}$ naphtha and gas oil distillate fractions and the resulting aldehyde product mixtures, consisting mostly of the corresponding n-aldehydes, 2-methyl branched aldehydes and 2-substituted ethyl and higher n-alkyl aldehydes, are particularly described. The trace sulfur containing components of the aldehydes and their alcohol derivatives were also studied by sulfur specific gas chromatography.

A further aspect of the disclosure is the description of the reactions of the present aldehyde and alcohol products. The esterification of the alcohols leading to phthalate ester plasticizers having unique properties is particularly discussed. Ethoxylated surfactant derivatives of the alcohols are also described in some detail.

PRIOR ART VERSUS THE PRESENT INVENTION

Hydroformylation is a well-known reaction for the conversion of pure olefin streams with CO and $H_2$ to aldehydes but has not been generally suggested for use on dilute olefin streams, such as petroleum distillates, which contain high concentrations of sulfur compounds and some nitrogen compounds. Streams containing these sulfur and nitrogen containing impurities have been considered as unsuitable hydroformylation feedstocks.

Present olefin feeds for hydroformylation are mostly propylene and its oligomers plus ethylene oligomers. The $C_7$ to $C_{13}$ alcohols derived from propylene oligomers and propylene/butenes copolymers are generally highly branched. In contrast, the $C_9$ to $C_{15}$ alcohols derived from ethylene oligomers are usually highly linear. Both types of higher alcohols are widely used intermediates in the production of plasticizer esters and ethoxylated surfactants. For most applications linear or semilinear alcohol intermediates are preferred. However, the ethylene oligomer feeds of linear alcohol production are much more costly than the branched olefin feeds derived from $C_3/C_4$ olefins.

As a part of the present invention it was discovered that thermally cracked petroleum distillates, particularly those derived from residual fuel oil by Fluid-coking and Flexicoking, contain unexpectedly major quantities of linear olefins. These olefins are valued below distillate fuel cost, because such cracked distillates have high concentrations of sulfur compounds and have to be extensively hydrogenated before they can be used as distillate fuels. The olefin components are converted to paraffins during such hydrogenations.

Furthermore, it was found in the present invention, that the sulfur compounds in such thermally cracked petroleum distillates are mostly innocuous aromatic, thiophene type compounds rather than catalyst inhibiting mercaptans. This finding led to the discovery of the present hydroformylation process which comprises reacting the linear and lightly branched olefin components of thermally cracked petroleum distillates containing sulfur compounds with CO and $H_2$ to produce semilinear aldehydes and alcohols.

When such olefin components were reacted with $CO/H_2$ in the presence of cobalt carbonyl complex catalysts at high pressure, the major aldehyde products were n-aldehydes, 2-methyl and 3-methyl substituted aldehydes, 2-ethyl and higher alkyl substituted aldehydes in the order of decreasing concentrations.

As such, the present process produces novel, highly desired, semilinear chemical intermediates at a low cost. Due to the unique olefin composition of the present cracked distillate feeds, such a unique mixture of compounds cannot be produced by known processes.

When using thermally cracked petroleum residua of naphtha distillation range, it was found particularly advantageous to use narrow boiling distillates rich in a particular 1-n-olefin. Such distillates mostly contain compounds having the same number of carbon atoms per molecule. They were found enriched in 2-methyl-1-olefin and linear internal olefins. They have much lower aromatic hydrocarbon and thiophenic sulfur concentrations compared to the broad naphtha feed. They also provide hydroformylation products of more linear character than broad cut distillate feeds.

The process of the present invention is particularly advantageous when the cracked petroleum distillate is a high boiling gas oil fraction containing 10 to 20 carbon atoms per molecule. In contrast to higher molecular weight branched olefins are surprisingly reactive feeds for hydroformylation without prior treatment.

A group of preferred thermally cracked distillates, not previously considered as a hydroformylation feed, comprises naphtha and gas oil fractions produced in fluidized coking units. Integrated fluidized coking processes such as Fluid-coking and Flexicoking represent a superior refinery method for the conversion of residual fuel oil. The thermal cracking step of Fluid-coking and Flexicoking is identical. However, Fluid-coking does not utilize the residual coke produced with the coker distillate while Flexicoking employs the coke by-product for the production of low thermal value gas. A discussion of these processes is found in U.S. Pat. Nos. 2,813,916; 2,905,629; 2,905,733; 3,661,543; 3,816,084; 4,055,484 and 4,497,705 which are incorporated as references.

The preferred Fluid-coking and Flexicoking processes are low severity thermal cracking operations. Low severity is usually achieved by keeping the temperature relatively low in the range of 482 to 538° C. (900 to 1000° F.) while using a long residence, i.e., contact, time of about 20 to 60 seconds. Alternately, low severity can be achieved using high temperatures, in the order of 538 to 705° C. (1000 to 1300°) and contact times of less than 5 seconds. In a long residence time operation, additional amounts of the desired olefin components can be produced by reinjecting the heavy gas oil distillate products into the cracking line.

The residual fuel feeds for the above coking processes are usually vacuum residua which remain after most of the crude petroleum is removed by refinery distillation processes. As such, these residua typically possess boiling points above 565° C. (1050° F.) and have Conradson carbon contents above 15%. These residua contain most of the undesirable components of the crude, i.e. sulfur and nitrogen compounds and metal complexes. As a result of high temperature thermal cracking, major amounts of olefinic components are also formed and become major constituents of such distillates. In spite of their high monoolefin content such distillates generally were not considered as hydroformylation feeds because of their high sulfur and conjugated diolefin content.

Other residual fuel type feeds for coking are produced from heavy asphaltic oils and tar sands. The highly olefinic distillates produced by the thermal cracking of heavy tar oil are suitable feeds for the process for the present invention. A particularly attractive feed is produced by the coking of Cold Lake and Athabasca tar sands oil residues without prior removal of sulfur compounds.

While coker naphtha and gas oil distillates resulting from the high temperature thermal cracking of residual oil can be hydroformylated as such, their further fractionation is preferred. This results in feeds of improved hydroformylation process characteristics which lead to superior aldehyde and alcohol products.

The aldehyde and alcohol products of the present hydroformylation process contain 20% by weight or more linear, i.e. normal, isomer. The preferred products contain 20 to 50% normal isomers, 3 to 20% 2-methyl branched compounds and 3 to 15% 3-methyl branched compounds. 2-Ethyl and higher 2-alkyl branched compounds represent another significant type of constituents. The balance is composed of monobranched aldehydes or alcohols with minor amounts of dibranched aldehydes or alcohols. The average number of alkyl branches per product molecule is less than 1. As such the products have a uniquely branched semilinear character. They are considered to be novel products and constitute further embodiments of this invention.

The semilinear alcohol products of the present invention are attractive intermediates for plasticizer and surfactant products. The properties of these products critically depend on the branchiness of the alcohol intermediates. The dialkyl phthalate ester plasticizer showed a desirable combination of low temperature properties and heat stability. The ethoxylated alcohol surfactants had superior wetting properties. Surfactant and plasticizer derivatives of these semilinear alcohols are further embodiments of this invention.

Although sulfur compounds in general were regarded as catalyst inhibitors, the production of alcohols or aldehydes via the hydroformylation of the olefinic components of some refinery streams has been previously suggested. For instance, U.S. Pat. No. 4,454,353 to Oswald et al., issued June 12, 1984, teaches the use of trihydrocarbyl silyl substituted diaryl phosphine transition metal carbonyl hydride complex hydroformylation catalysts with "refinery streams of olefins, containing paraffin by-products such as $C_1$ to $C_{20}$ paraffins . . . ".

Haag and Whitehurst in U.S. Pat. Nos. 4,098,727 and 4,487,972 disclose the production of aldehydes and alcohols via the hydroformylation of olefinic streams in the presence of insoluble, polymer anchored complexed of Group VIII metals with nitrogen, sulfur, phosphine and arsine ligands. Example 32 shows the hydroformylation of a cracked gasoline feed containing 230 ppm sulfur in the presence of a rhodium amine complex attached to a styrene-divinylbenzen copolymer.

The process disclosed in U.S. Pat. No. 4,417,973 to Angevine et al., is one for "upgrading" various straight chain olefin-containing feedstocks, such as shale oil, FCC light cycle oil, and coker liquids, to branched paraffins. The process involves the sequential steps of hydroformylation and hydrotreating/hydrogen reduction, preferably, in the presence of heterogeneous supported Co/Mo catalyst. The reaction products of the hydroformylation step were neither separated nor identified. The final products are branched paraffins. The sulfur content of the various feedstocks are shown in the Examples to be 0.29 to 1.33 wt. %.

Other disclosures discussing the use of cobalt-based homogeneous catalysts are known.

For instance, a series of papers by Marko et al. teach the reacting of dicobalt octacarbonyl, a hydroformylation catalyst precursor, with elemental sulfur and organic sulfur compounds. Various sulfur-containing cobalt complexes were isolated. Reactions with sulfur led to $[Co_2S(CO)_5]_n$ and $Co_3S(CO)_9$. See, Chem. Ber., 94, 847-850 (1961); Chem. Ind., 1491-1492 (1961); Chem Ber., 96, 955-964 (1963). Hydrogen sulfide is said to react to give the same complexes. Mercaptans and disulfides lead mainly to sulfide derivatives of cobalt trimers and teramers. Marko et al. states that, under hydroformylation conditions, all these complexes are converted to catalytically inactive cobalt sulfide [Chem. Ber., 97, 926-933 (1964).] Cobalt thioether complexes are also said to be either inactive or less active in hydroformylation than unsubstituted dicobalt octacarbonyl [Acta Chim. Sci. Hung., 59, 389-396 (1969)].

Another series of papers by Marko and co-workers describes the hydroformylation/hydrogenation of $C_6/C_8$ olefins present in cracked gasoline. The papers describe a process for converting a sulfur-containing $C_7$ fraction of cracked gasoline using a 1 to 2 ratio of hydrogen to carbon monoxide at 200° C. under 300 atm (4,409 psi) pressure to produce 85% octyl alcohol, an intermediate for dioctyl phthalate plasticizer, with 10% higher boiling by-product formation {J. Berty, E. Oltay and L. Marko, Chem. Tech., (Berlin) 9, 283-286 (1957); M. Freund, L. Marko and J. Laky, Acta Chem. Acad. Sci. Hung., 31, 77-84 (1962)}. Under these reaction conditions, using cyclohexene as a model olefin, ethyl mercaptan and diethyl disulfide were found to be strong inhibitors of hydroformylation even in small amounts while diethyl sulfide and thiophene had no effect in molar concentrations up to tenfold of cobalt [L. Marko, Proc. Symp. Coordn. Chem. Tihany, Hungary, 271–279 (1964)]. Similar but more pronounced effects were observed on the hydrogenation of aldehyde intermediates to alcohols [J. Laky, P. Szabo and L. Marko, Acta Chim. Acad. Sci. Hung., 46, 247–254 (1965)]. Sulfur containing cobalt trimers, e.g., of the formula $Co_3(CO)_9S$ and $Co_3(CO)_6(S)(SR)$ were postulated as intermediates in the conversion of active $Co_2(CO)_8$ into soluble inactive CoS [L. Marko and M. Freund, Acta Chim. Acad. Sci. Hung., 57, 445–451 (1968)].

Russian researchers, particularly Rudkovskii and co-workers, also published a series of articles on the hydroformylation of olefin components in petroleum distillates with dicobalt octacarbonyl catalyst. These distillates were not characterized chemically. One paper describes the production of $C_{11}$ to $C_{17}$ alcohols from high boiling distillate fractions of contact coking. The process entails hydroformylation, preferably at 170° C. and 300 atm (4409 psi), followed by hydrogenation in a mixture with unreacted hydrocarbons over a $2NiS.WS_2$ catalyst [K.A. Alekseeva, D. M. Rudkovskii, M. I. Riskin and A. g. Trifel, Khim. i Tekhnol. Topliv i Masel 4 (5), 14–18 (1959)]. Another paper describes a similar hydroformylation of lower molecular weight cracked gasoline olefins [D. Rudkovskii, A. G. Trifel and K. A. Alekseeva, Khim. i Tekhnol. Topliv i Masel, 3(6), 17–24 (1958)]. Suitable $C_7$ to $C_8$ naphtha feeds from thermal cracking of a mixture of petroleum fractions, phenol extracts and petroleum were later described [P. K. Zmiewski, T. N. Klyukanova and G. M. Kusakina, Neft. i Gas Prom., Inform. Nauchn. Tekhn. Sb. (4) 48–49 (1964)].

Another journal article, appeared in Russian journal, Khim. i Tekhnol. Goryuch. Slantsev i Produktov ikh Pererabotki, on pages 325 to 332 of the 13th issue of 1964, and was authored by N. I. Zelenin and co-workers. This publication considered the hydroformylation of the olefin components of shale gasoline and diesel fractions to produce plasticizer and surfactant alcohols. It particularly discussed the removal of sulfur compounds which can be hydroformylation inhibitors.

A research report, Forschungsbericht T-84-064, was made to the German Federal Department of Research and Technology in April 1984. The authors, B. Fell, U. Buller, H. Classen, J. Schultz and J. Egenolf disclose the hydroformylation of a $C_5$ to $C_6$ cracked gasoline between 150–175° C. at 200 atm (2939 psi) in the presence of 0.4–0.2% cobalt to obtain oxo-products with 65% selectivity. The use of a triphenyl phosphine rhodium complex based catalyst system at this high pressure was reported to result in little conversion.

Two monographs on the organic chemistry of carbon monoxide by Falbe and co-workers of Ruhrchemie include major chapters on hydroformylation. The effect of hydroformylation of cobalt catalyst poisons, particularly sulfur compounds, is summarized on pages 18 to 22 of the first monograph [J. Falbe, Carbon Monoxide in Organic Synthesis, Chapter I, The Hydroformylation Reaction (Oxo Reaction/Roelen Reaction), pages 1 to 75, Springer Verlag, New York (1970)]. The second monograph also reviews the effect of poisons on modified rhodium catalysts and concludes that these catalysts, due to their low concentration, are more susceptible to poisoning [New Synthesis with Carbon Monoxide, Ed. J. Falbe, Chapter 1 by B. Cornils, pages 1 to 224, particularly page 73, Springer Verlag, New York, 1980].

Higher aldehydes derived via hydroformylation are known versatile chemical intermediates. They are utilized for the synthesis of primary alcohols, carboxylic acids and amines. The so called oxo-alcohols are the most important products. They are most widely used in the preparation of phthalate ester plasticizers and surfactants. However, known methods for the preparation of oxo-aldehydes and alcohols have carbon number and/or product linearity limitations.

Highly linear oxo-alcohols are the most desired for most applications. However, their preparation requires completely linear olefin feeds derived from ethylene which are prohibitively expensive for many applications. Highly branched oxo-alcohols derived via the hydroformylation of propylene oligomers are less costly to produce but their plasticizer derivatives have poorer low temperature properties and their surfactant derivatives are less biodegradable.

More recently, U.S. Pat. No. 4,598,162 by D. Forster, G. F. Schaefer and G. E. Barker disclosed the preparation of aldehydes and alcohols via the aldolization of oxo-aldehydes containing little branching in the 2-position. The alcohols derived via this route are more biodegradable than the prior art branched compounds. However, their preparation requires an additional step and leads to products having more than one branch per molecule.

Overall, the prior art taught away from the hydroformylation process of the present invention rather than suggesting it. In general, the use of cracked petroleum distillates containing high concentrations of sulfur was to be avoided. Soluble transition metal carbonyl complexes containing trivalent phosphorus ligands were never used successfully for the hydroformylation of such distillates. Known low pressure hydroformylation process have low sulfur limits for the feeds.

Although the high pressure hydroformylation of cracked gasoline of relatively low sulfur content was extensively studied by Marko et al. in the presence of added dicobalt octacarbonyl, the feeds and conditions of the present process were neither used or suggested. It was not proposed to utilize coker distillate feeds of high linear olefin and sulfur compound content for the production of aldehydes and alcohols by hydroformylation. The high pressure, cobalt catalyzed $C_7$ gasoline hydroformylation/hydrogenation process Marko et al. developed is run at 200° C. and produces $C_8$ alcohols in one step. In contrast, the temperature range of the present high pressure cobalt catalyzed process is 110 to 180° C., preferably 120 to 145° C. and the main products are aldehydes. Pure alcohol products in this process are produced in a separate step.

The present cobalt carbonyl complex catalyzed high pressure process employs $C_8$ to $C_{20}$ distillate feeds produced by high temperature fluid-coking of vacuum resids. These feeds contain more than 0.1% sulfur and more than 20% olefins of a unique isomer composition. More than 30% of the total olefins present are of Type I. More than 10% of the olefins are of Type II. The most prevalent Type III olefin components are 2-methyl-1-olefins.

Due to the specific linear olefinic character of the present feeds, such hydroformylations produce unique aldehyde and alcohol products of a semilinear character having less than one branch per molecule. The major components of the primary aldehyde products are n-aldehydes, 3-methyl-branched aldehydes, and 2-methyl-branched aldehydes. Much of the rest are 2-ethyl or higher 2-n-alkyl-branched aldehydes. However, the amount of higher 2-alkyl-branched compounds is much less than in prior art compositions prepared via aldolization. On hydrogenation they provide the corresponding alcohols. Such aldehyde and alcohol compositions cannot be directly prepared by any other method. Their preparation by blending the appropriate components would be economically prohibitive.

The novel semilinear alcohol products of the present invention can be converted to ester plasticizers and ethoxylated surfactants of unique properties. The $C_6$ to $C_{13}$ alcohols provide the corresponding dialkyl phthalates having a combination of superior low temperature properties and high temperature stability compared to branched alcohol derivatives. The $C_9$ to $C_{30}$ alcohols lead to ethoxylated surfactants of high biodegradability and superior wetting properties. In both, the case of plasticizers and surfactants, the unique properties are attributable to the unique semilinear structure of the alcohol precursors.

Dialkyl phthalate esters are a well known, large volume group of plasticizers for polyvinylchloride. As such they compete on the basis of their properties and cost. From the viewpoint of most of the desired properties, particularly the low temperature properties of plasticized PVC, phthalate esters derived from linear alcohols are superior to derivatives of highly branched primary alcohols. However, highly branched alcohols can be produced in a broad carbon range at a cost significantly below that of linear alcohols. Thus, there has been a continuing effort to produce low cost, less branched primary alcohols and their mixtures. However, to date, no low cost primary plasticizer alcohol with less than one branch per molecule is available.

Ethoxylated higher alcohols are a highly important class of nonionic surfactants. They are dominating the detergent industry where biodegradability is important. They are also widely used as sulfate derivatives. Most ethoxylated higher alcohols are derived from costly linear alcohols to enhance their biodegradability. The higher linear alcohols are solids and, as such, difficult to handle. In contrast, the present detergent range semilinear alcohols are low cost liquids of biodegradable character. As such, they combine the advantages of both branched and linear alcohol surfactant intermediates.

None of the references teach either alone or in combination the presently described and claimed process and/or products.

None of the references teach either alone or in combination the presently described and claimed process and products.

Figure 2:
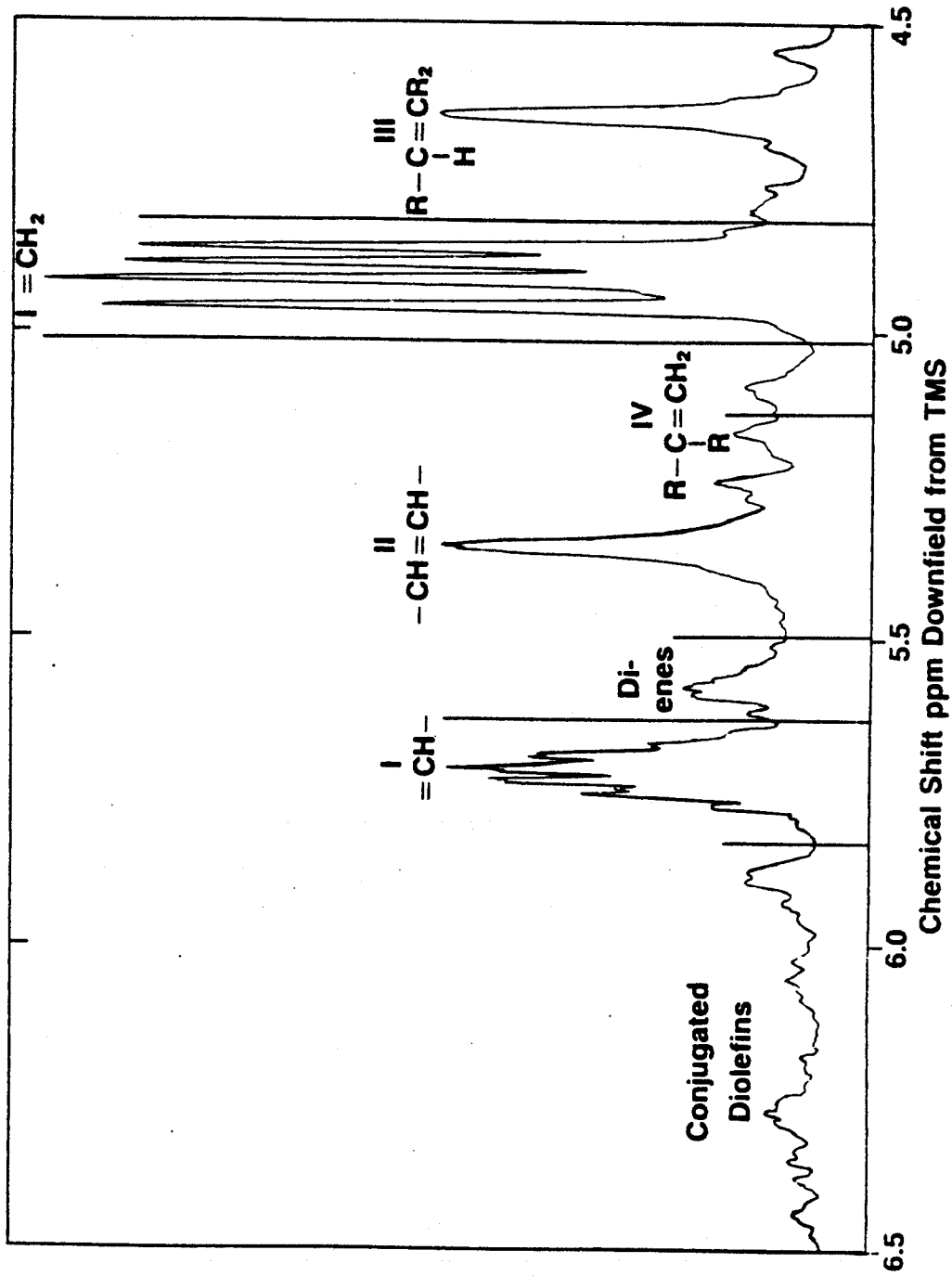

FIG. 2 shows the 400 MHz proton nuclear magnetic resonance spectrum of the olefinic protons of Fluid-coker naphtha feed, with an indication of the chemical shift regions of various types of olefins.

Figure 3B:
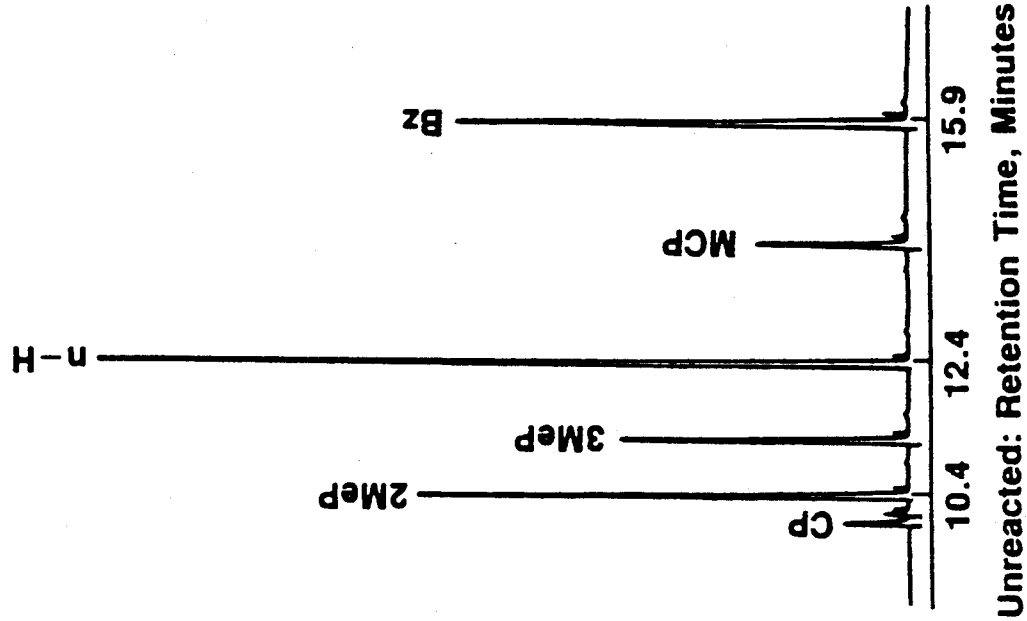
Figure 3A:
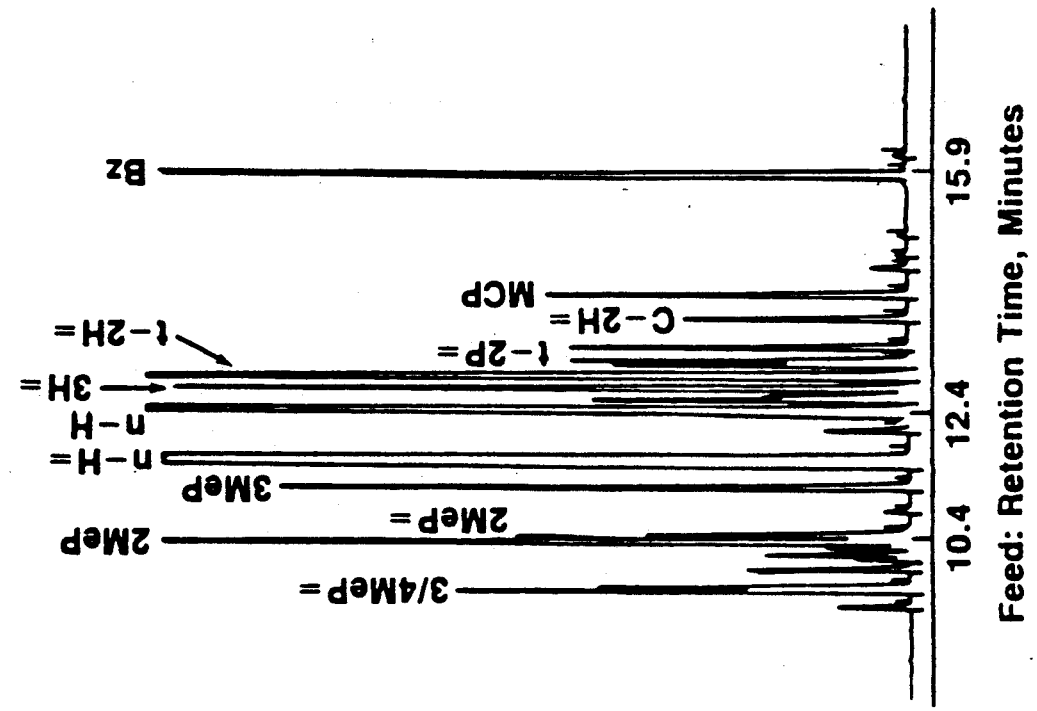

FIG. 3 shows the capillary gas chromatogram of the $C_6$ fraction of a Fluid-coker naphtha feed, with an indication of the major olefin and paraffin components.

FIG. 4 shows the capillary gas chromatogram of the $C_8$ fraction of Flexicoker naphtha feed with an indication of the major hydrocarbon components.

Figure 5A:
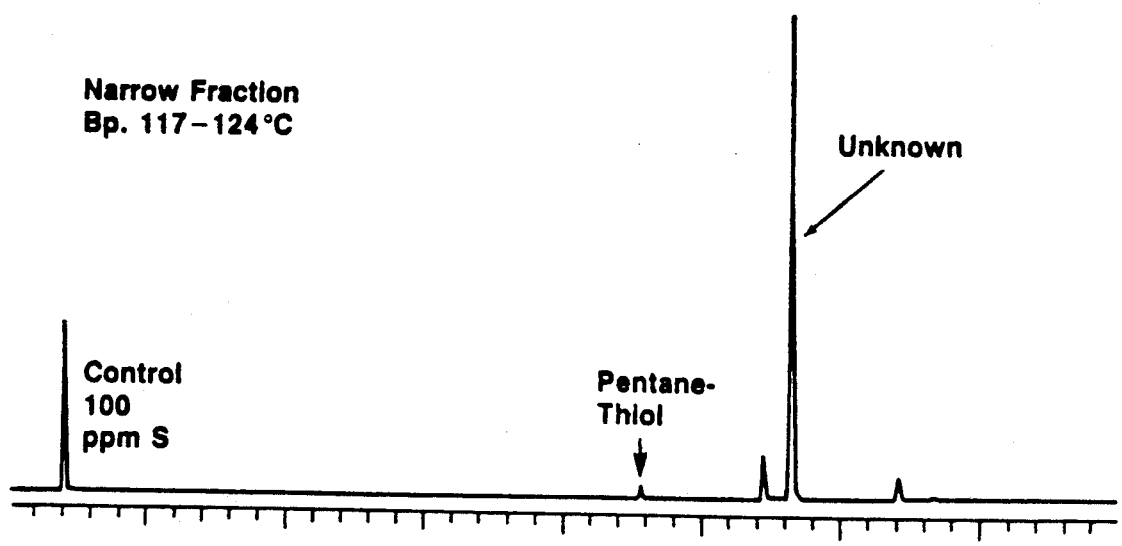
Figure 5B:
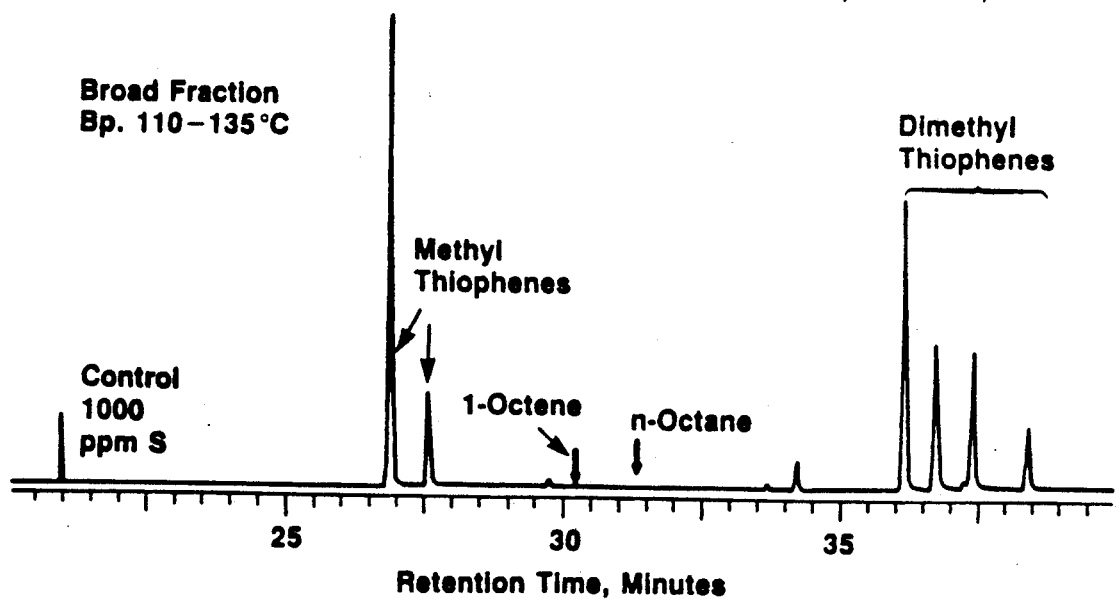

FIG. 5 shows the sulfur specific capillary gas chromatograms of the narrow and broad $C_8$ fractions of Flexicoker naphtha with an indication of the main methylthiophene and dimethylthiophene components.

Figure 6:
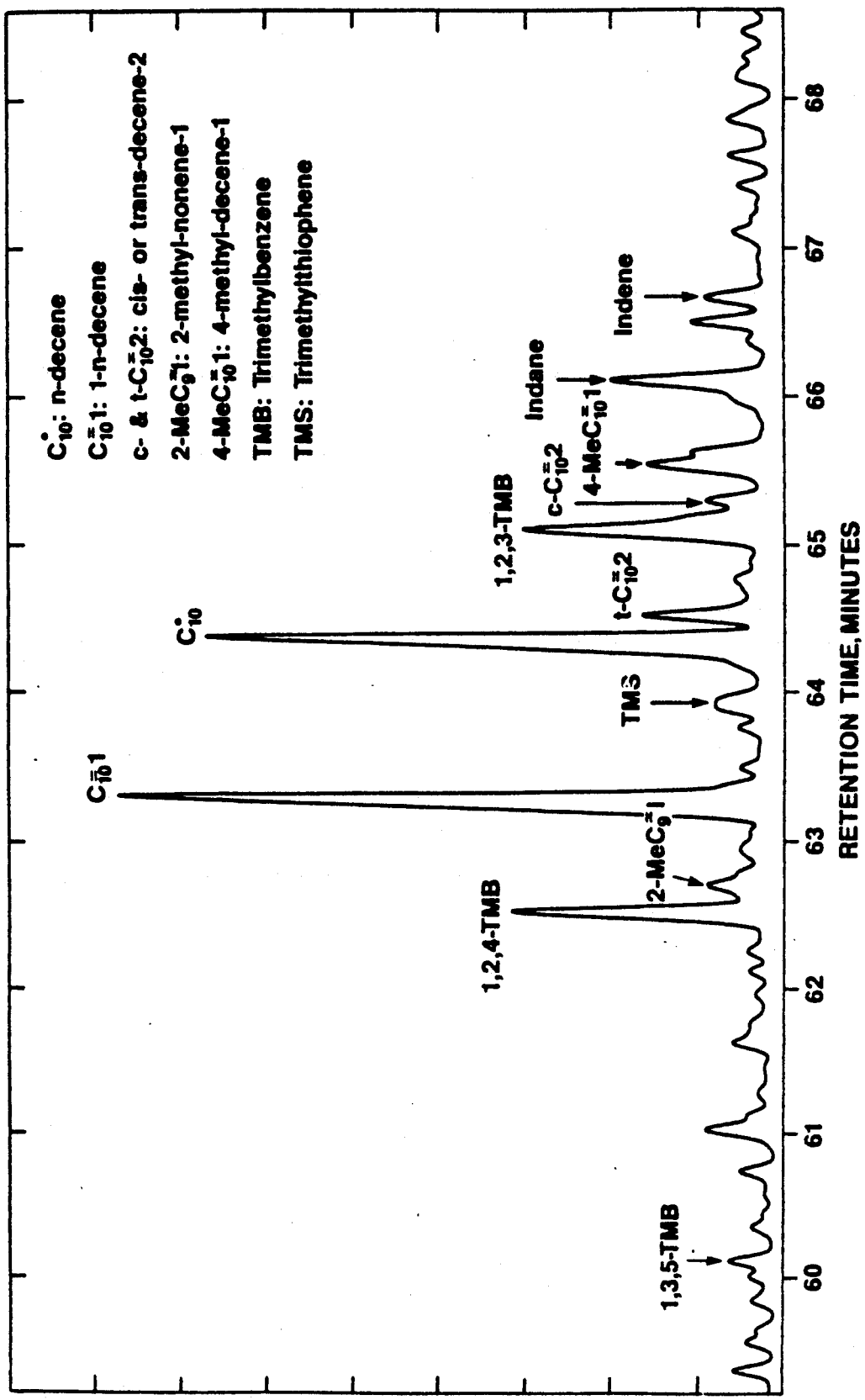

FIG. 6 shows the capillary gas chromatogram of the $C_{10}$ fraction of a Fluid-coker naphtha feed with an indication of the major olefin, paraffin and aromatic components.

Figure 7:
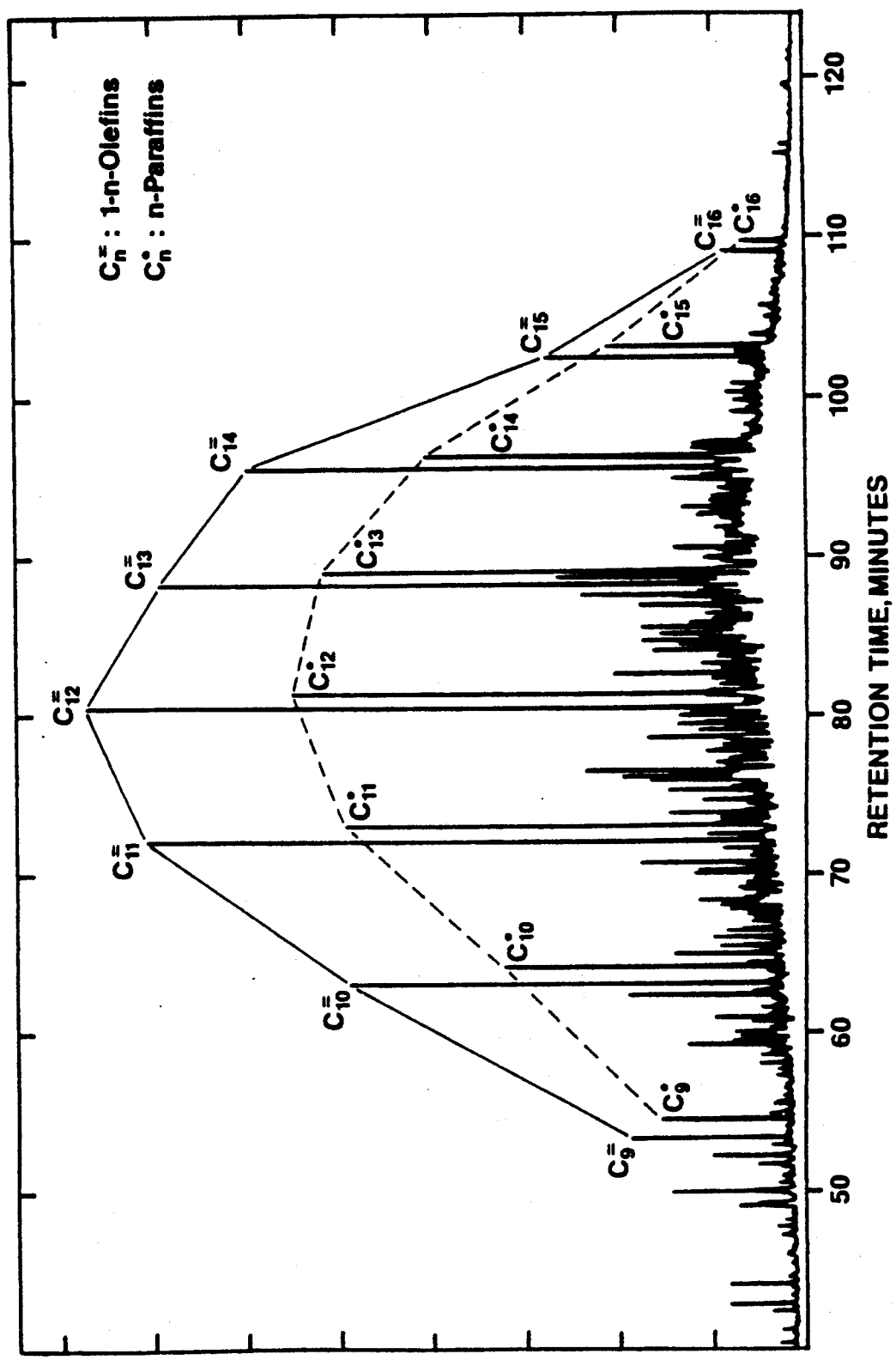

FIG. 7 shows the capillary gas chromatogram of the light Fluid-coker gas oil feed in the $C_9$ to $C_{16}$ range, with an indication of the major 1-n-olefin and paraffin components.

Figure 8:
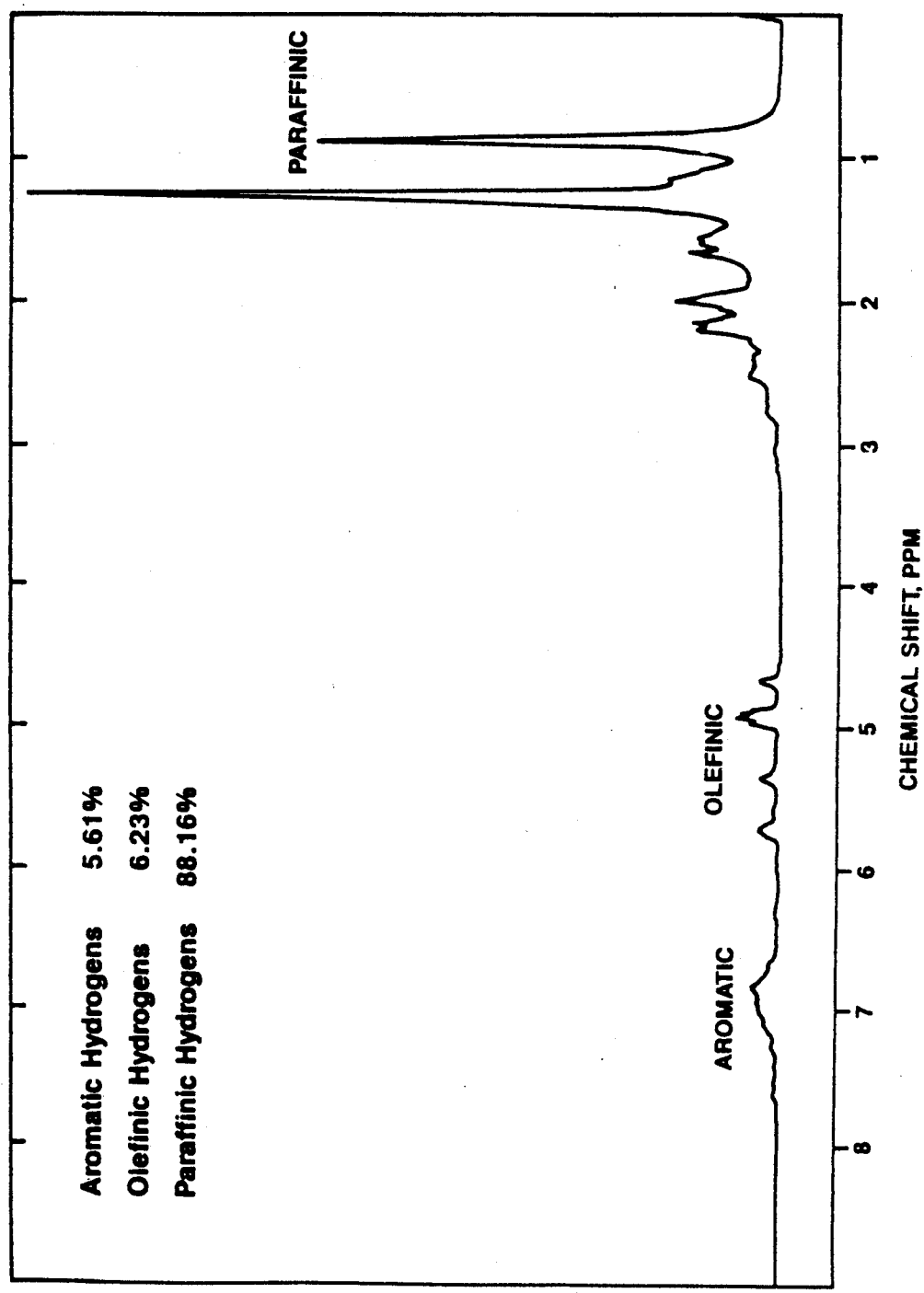

FIG. 8 shows the 500 MHz proton nuclear magnetic resonance spectrum of light Fluid-coker gas oil feed, with an indication of the olefinic, paraffinic and aromatic components.

Figure 9:
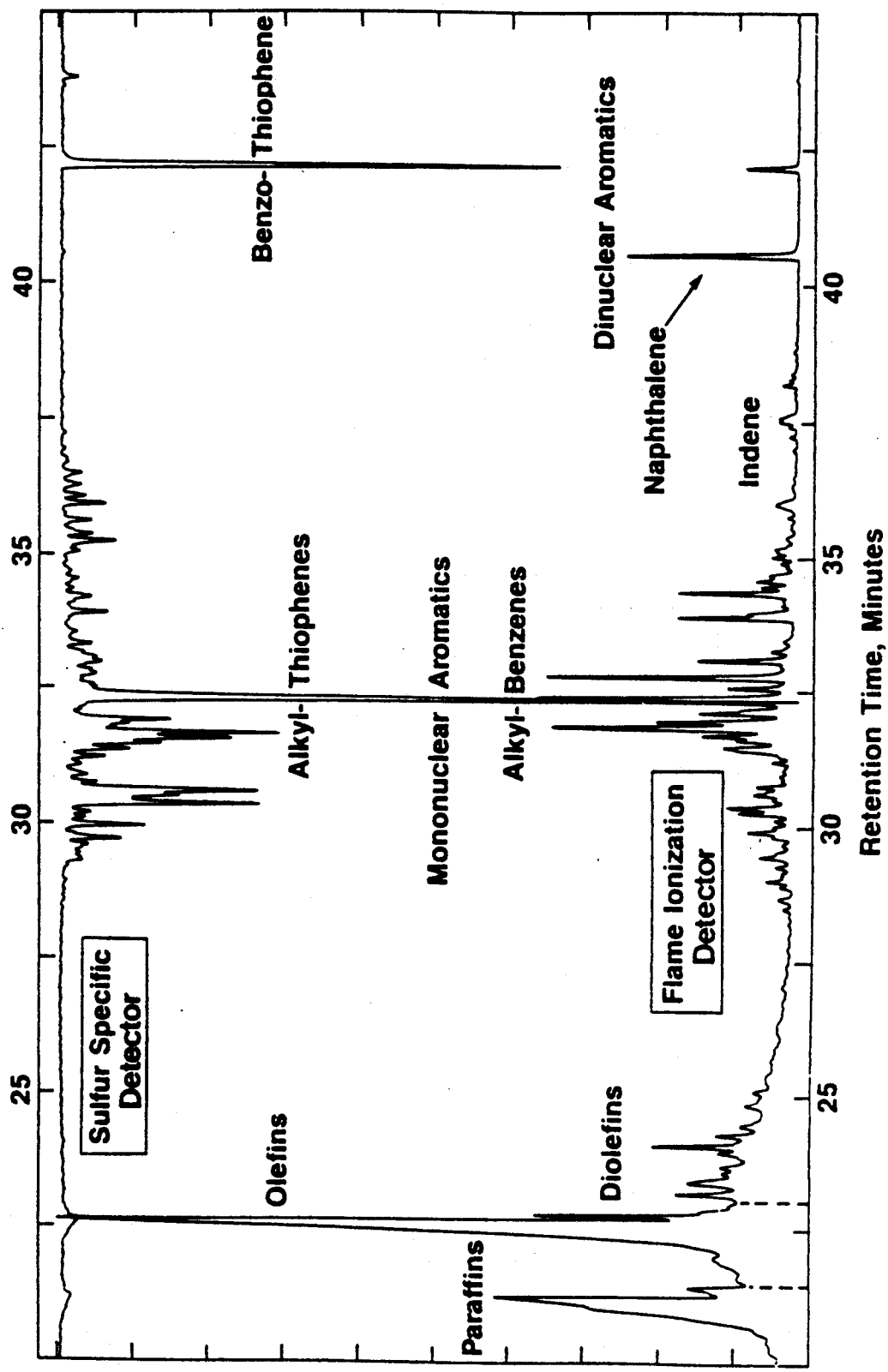

FIG. 9 shows the capillary gas chromatogram on a highly polar column of a $C_{12}$ fraction of light Fluid-coker gas oil, with separation of various types of aliphatic and aromatic components and sulfur compounds.

Figure 10:
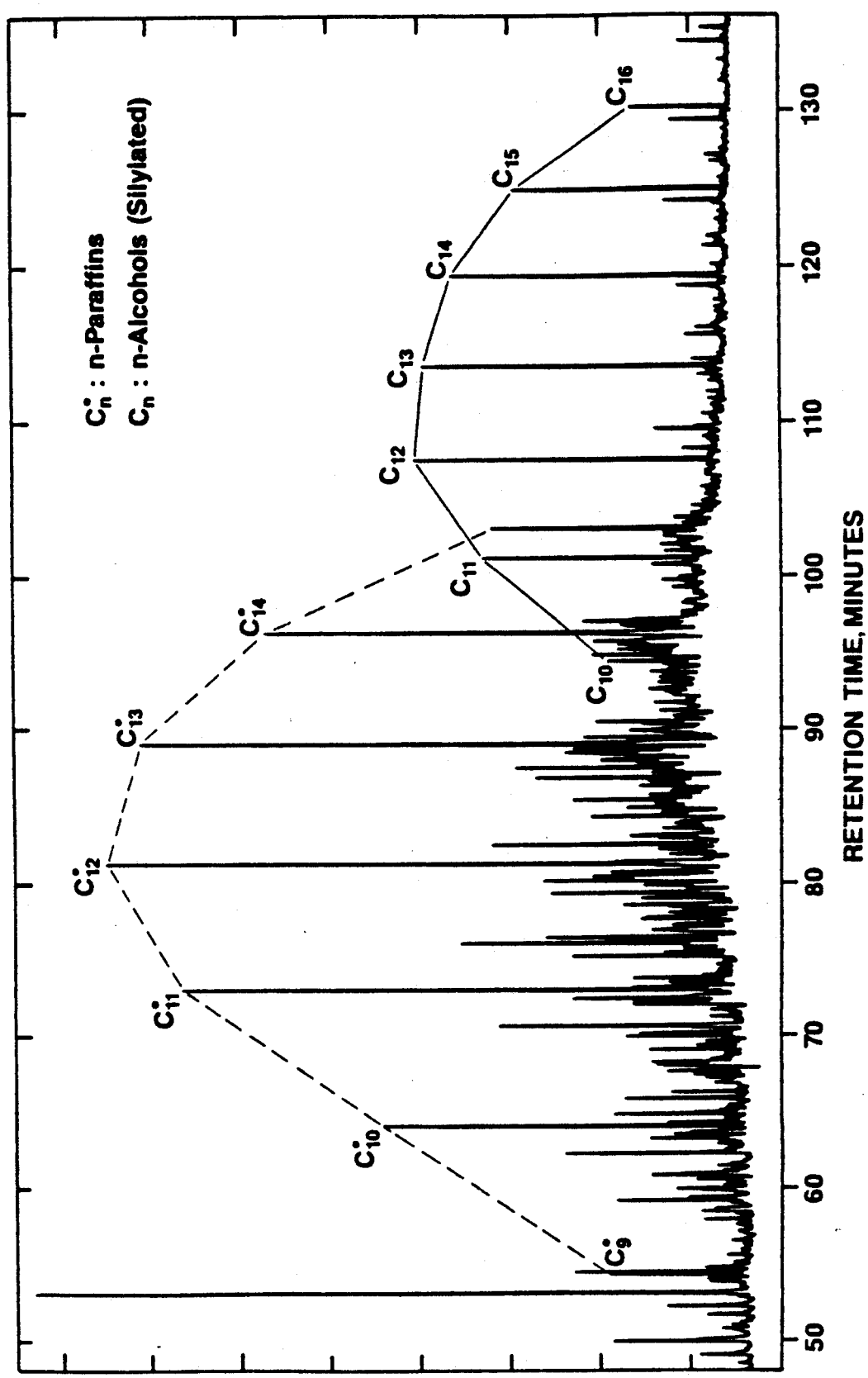

FIG. 10 shows the capillary gas chromatogram of a Fluid-coker light gas oil mixture after trioctyl phosphine cobalt complex catalyzed hydroformylation, with an indication of the major n-paraffin and capped n-alcohol components.

Figure 11:
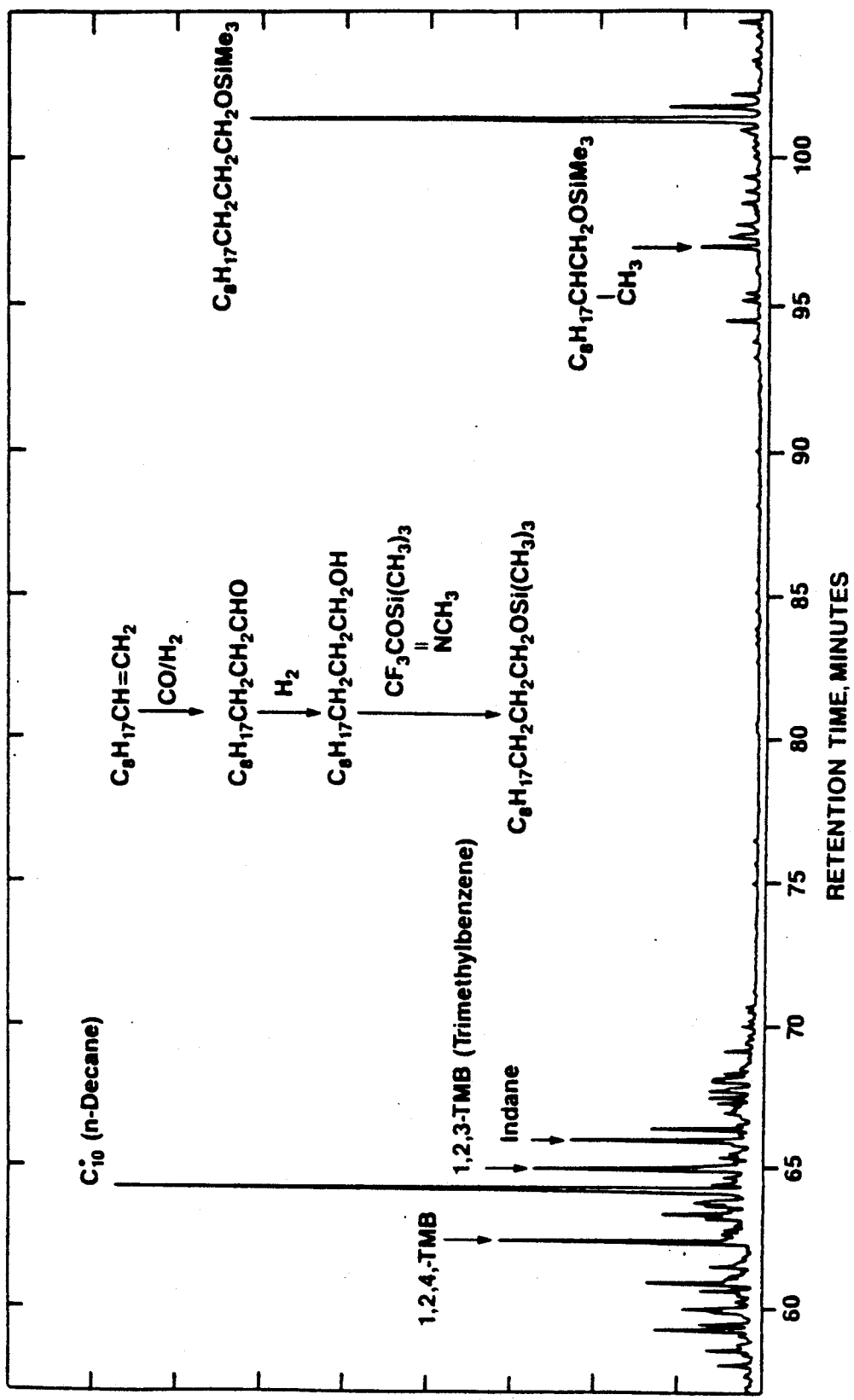

FIG. 11 shows the capillary gas chromatogram of a $C_{10}$ Fluid-coker gas oil after triethyl phosphine cobalt complex catalyzed hydroformylation, with an indication of the isomeric $C_{11}$ alcohol products formed.

Figure 12:
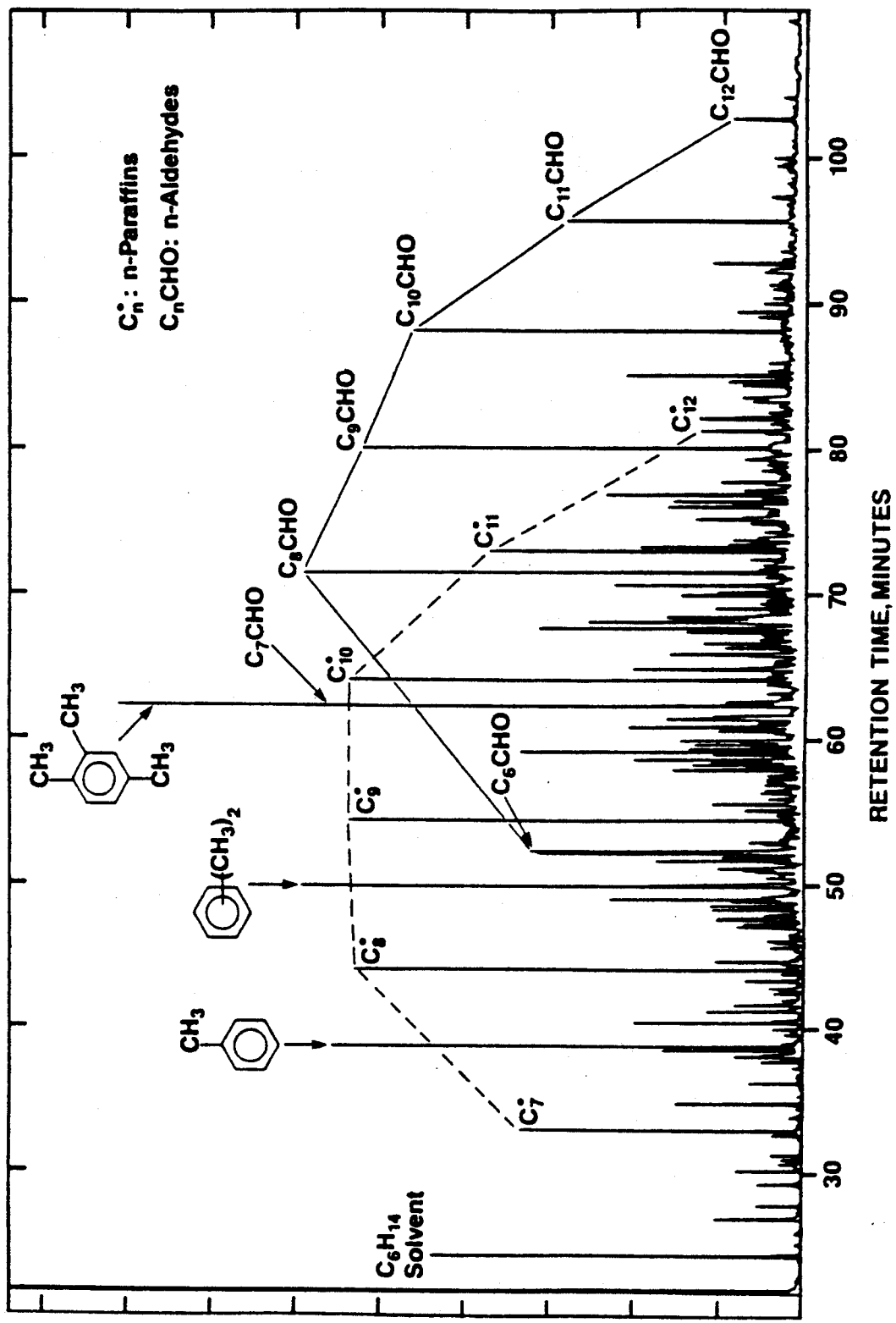

FIG. 12 shows the capillary gas chromatogram of a Fluid-coker naphtha mixture after cobalt catalyzed hydroformylation, with an indication of the major n-paraffin and n-aldehyde components.

Figure 13:
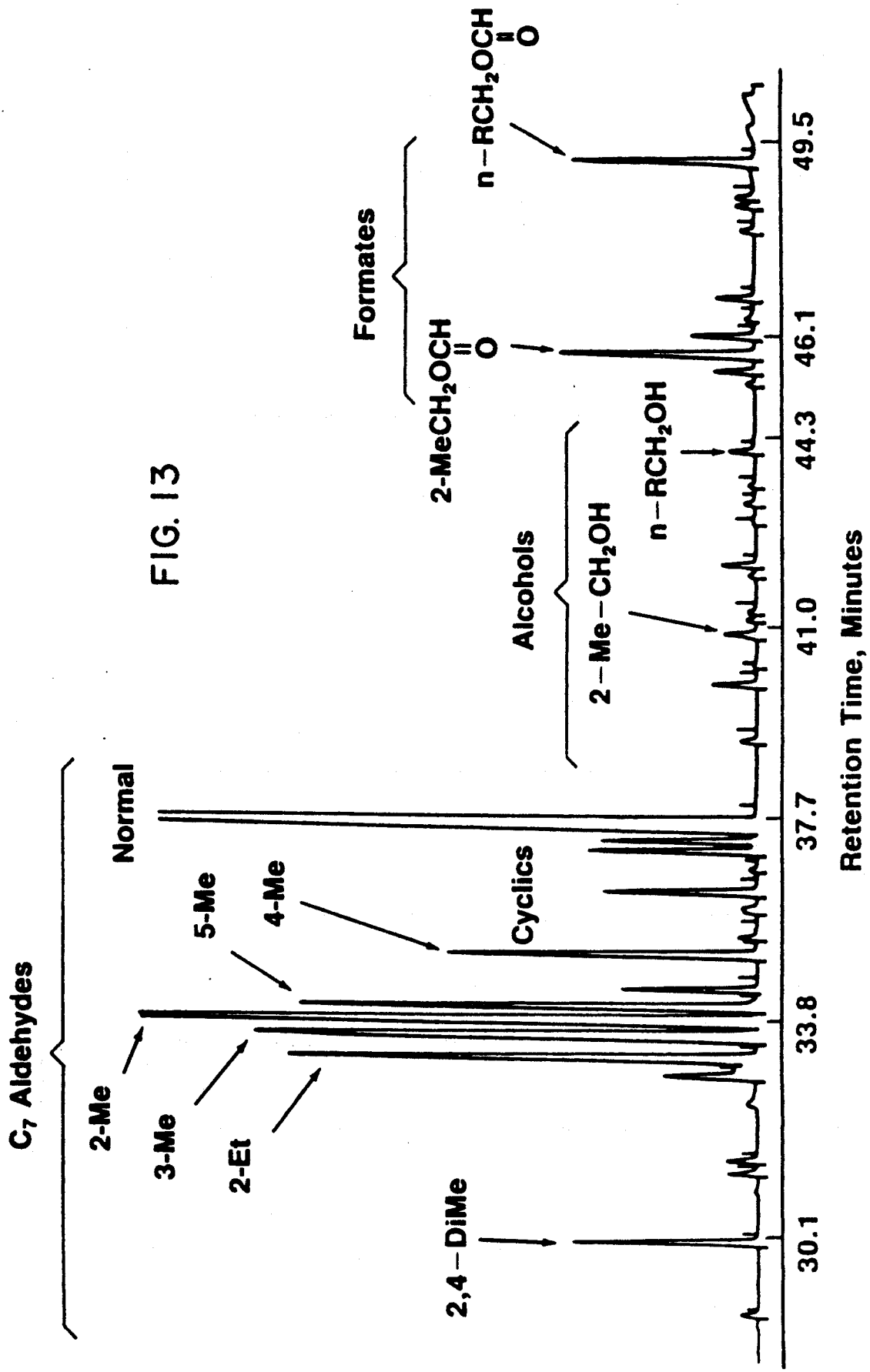

FIG. 13 shows the capillary gas chromatogram of the aldehyde region of the reaction mixture obtained in the cobalt catalyzed hydroformylation of a $C_6$ Fluid-coker naphtha fraction.

Figure 14:
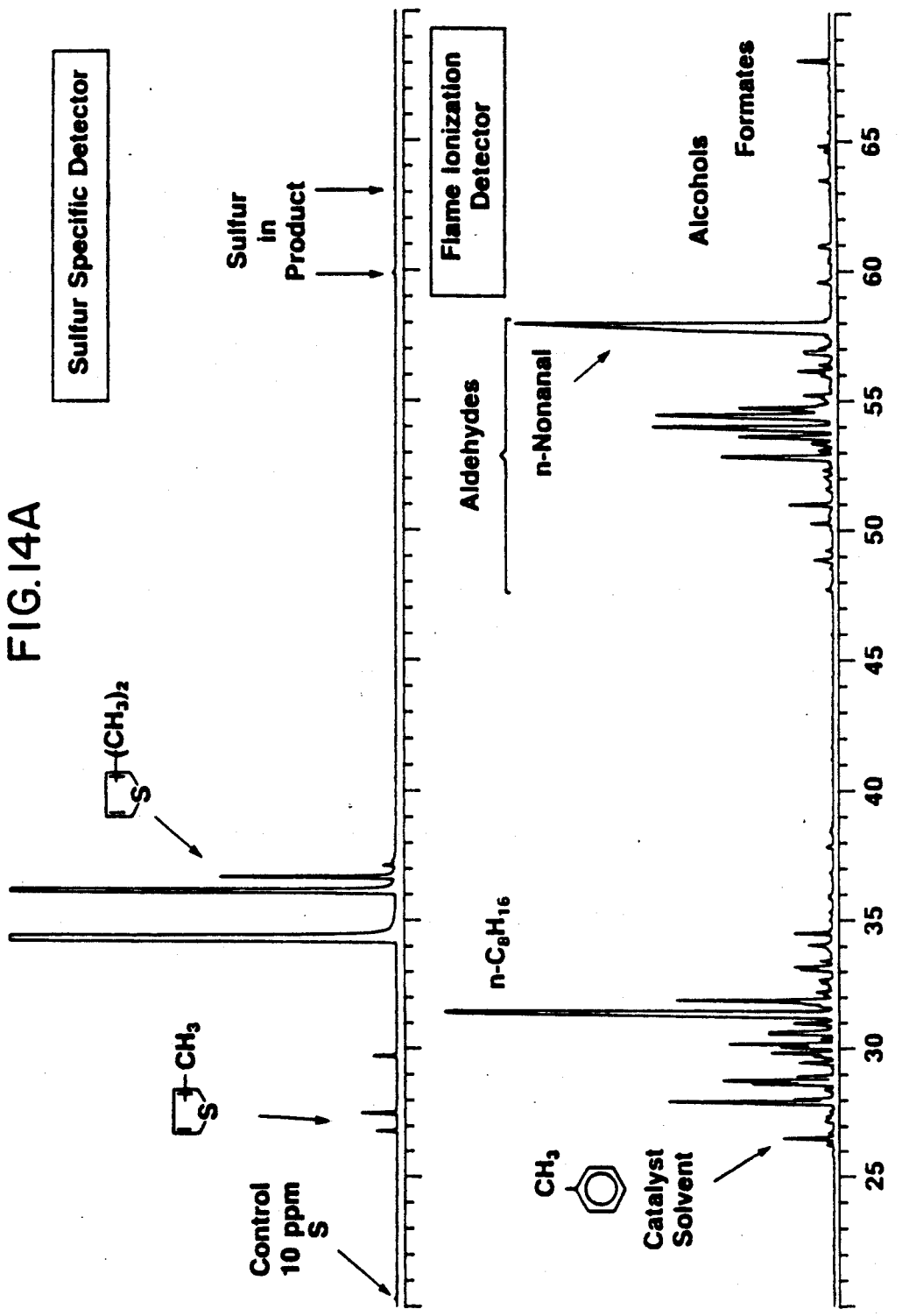

FIG. 14 shows the capillary gas chromatograms by flame ionization and sulfur specific detectors of the reaction mixture produced by the cobalt catalyzed hydroformylation of a $C_8$ Flexicoker naphtha fraction.

Figure 15:
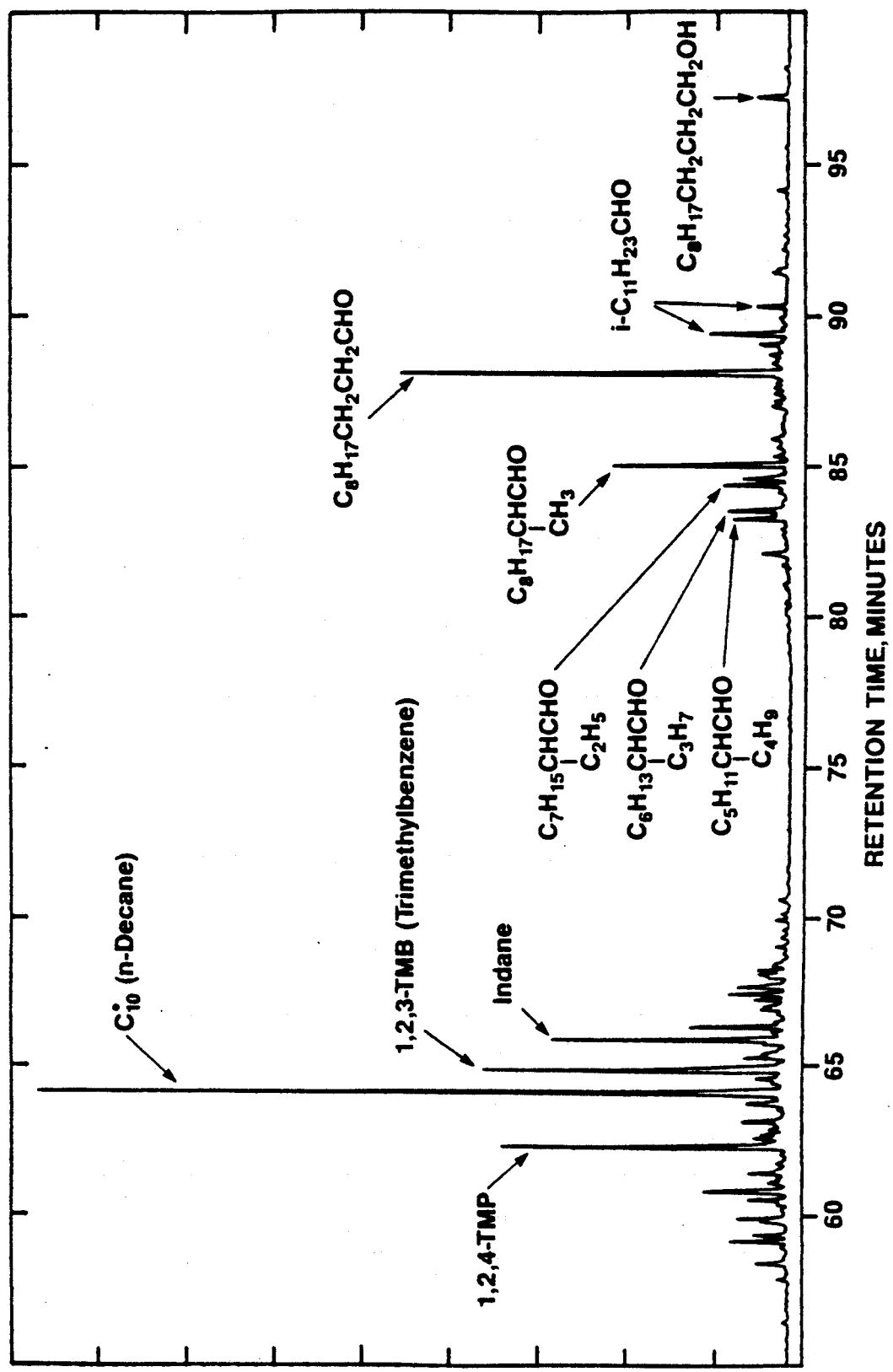

FIG. 15 shows the capillary gas chromatogram of a $C_{10}$ Fluid-coker naphtha after cobalt catalyzed hydroformylation, with an indication of the isomeric $C_{11}$ aldehyde products formed.

Figure 16:
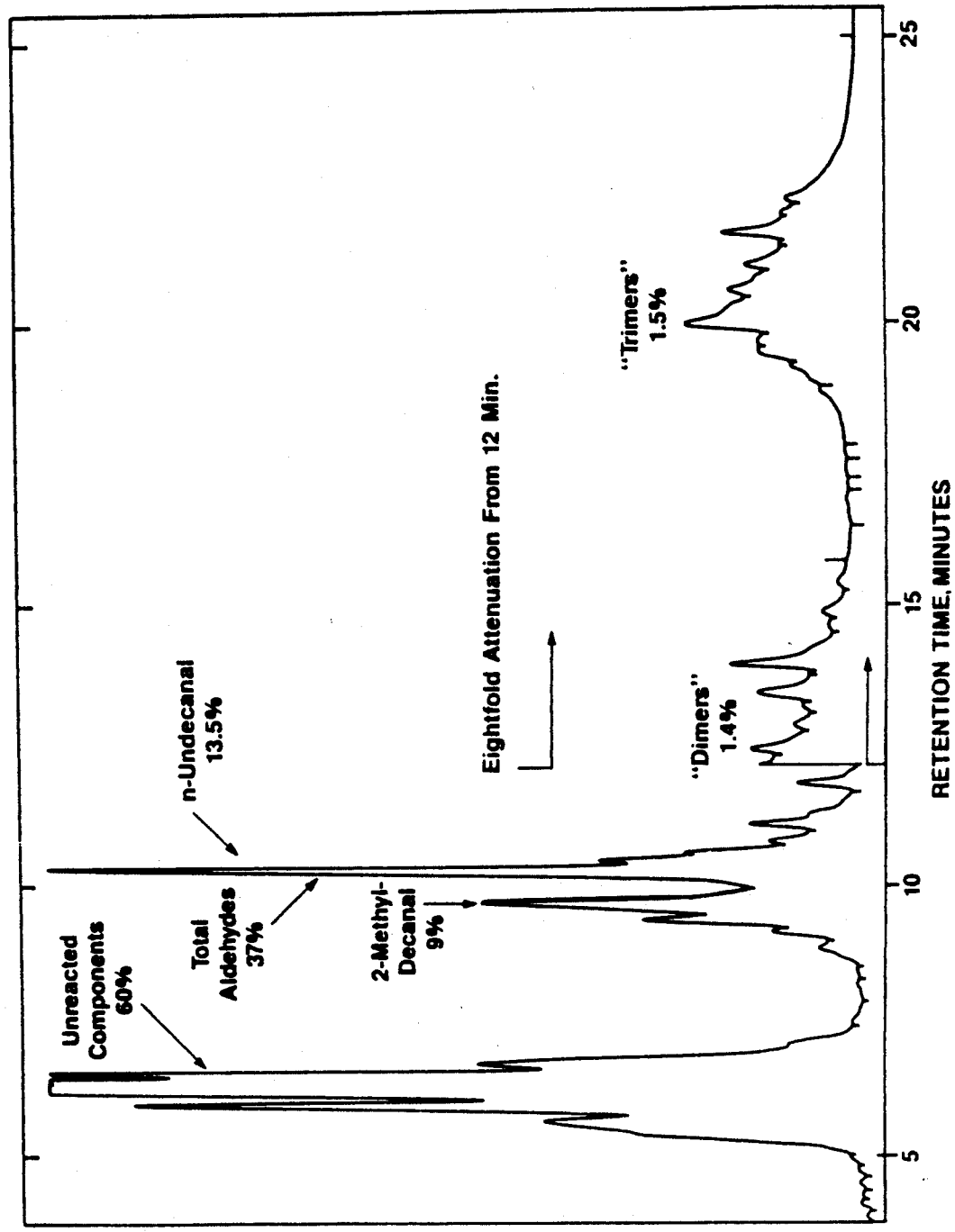

FIG. 16 shows the packed column gas chromatogram of a $C_{10}$ Fluid-coker naphtha after cobalt catalyzed hydroformylation, with an indication of the $C_{11}$ aldehyde products and dimer and trimer by-products.

Figure 17:
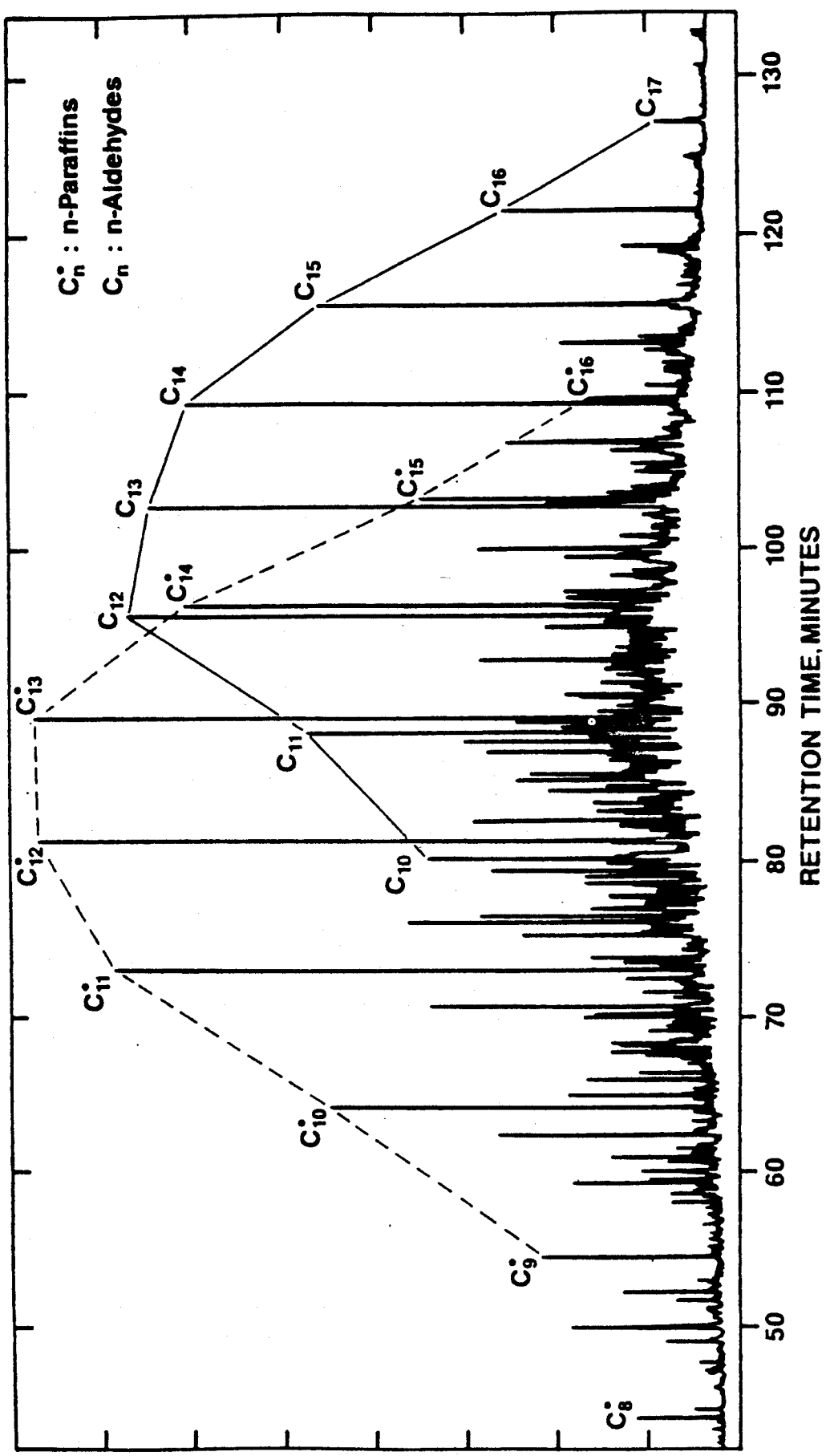

FIG. 17 shows the capillary gas chromatogram of a Fluid-coker light gas oil mixture after cobalt catalyzed hydroformylation, with an indication of the major n-paraffin and n-aldehyde components.

Figure 18:
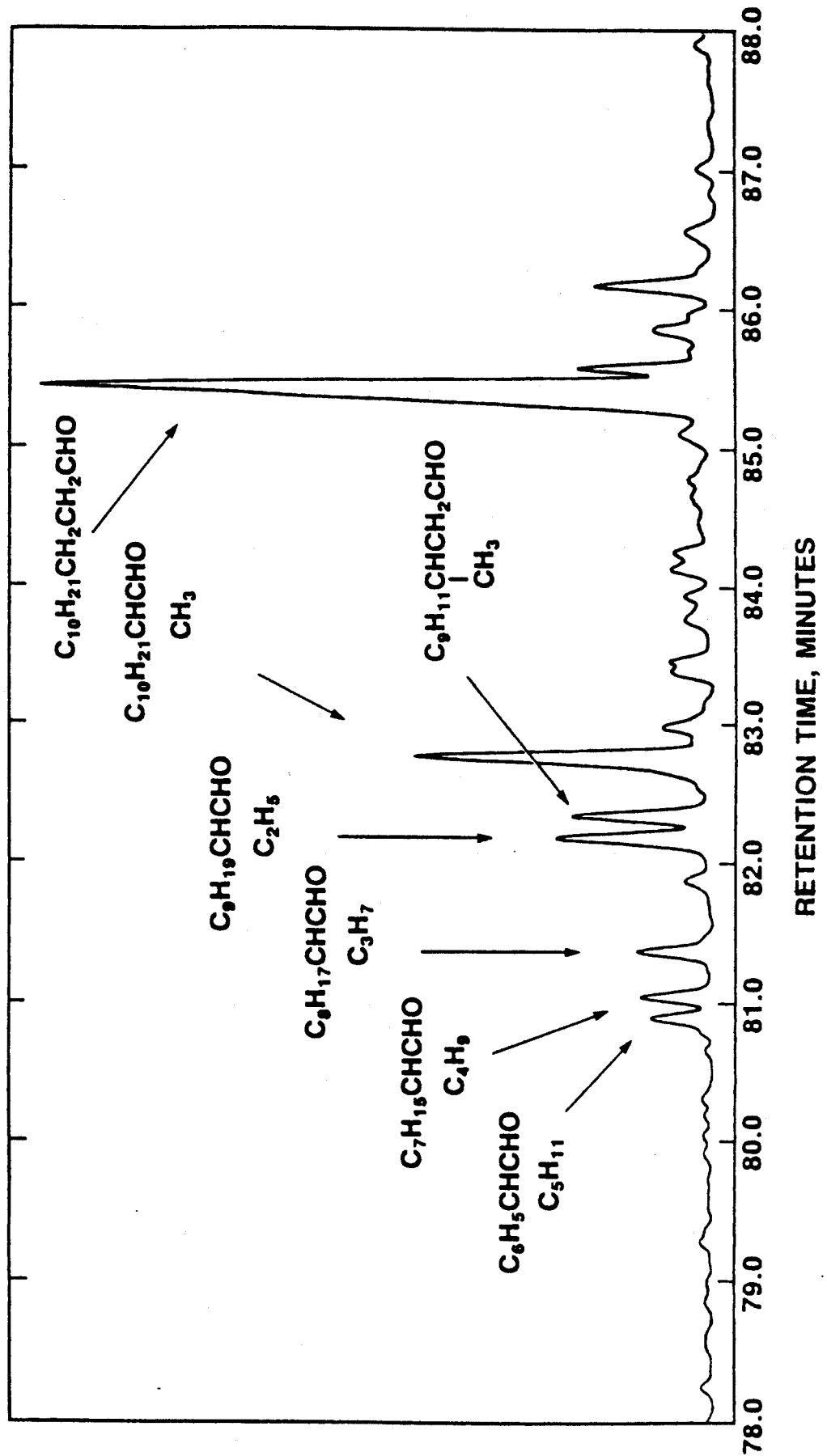

FIG. 18 shows the capillary gas chromatogram of the aldehyde region of the reaction mixture obtained in the cobalt catalyzed hydroformylation of $C_{12}$ Fluid-coker light gas oil fraction.

SUMMARY OF THE INVENTION

This invention describes a hydroformylation process in which the olefin components of a cracked petroleum distillate fraction containing substantial amounts of 1-n- olefins and sulfur bearing compounds are reacted with carbon monoxide and hydrogen in the presence of a homogeneous Group VIII transition metal carbonyl complex catalyst. The invention is also concerned with the novel products of the present process. These products are aldehydes and/or alcohols of largely linear character and as such preferably have less than one alkyl branch per molecule on the average. The products may be separated by distillation from the unreacted components of the distillate feed.

The preferred catalysts are soluble rhodium or cobalt carbonyl complex catalysts. The complex may be modified by a trivalent phosphorus, arsenic, nitrogen and/or sulfur ligand. Triorgano-phosphine ligands are most preferred. Cobalt carbonyl catalysts may also desirably be used without added phosphorus ligands.

The reaction conditions under which the feeds may be hydroformylated cover broad ranges. Temperatures ranging from 50 to 250° C. and pressures ranging from essentially atmospheric to 5000 psi (340 atm) may be used. The more preferred conditions depend on the type of the olefin to be reacted and the type of transition metal catalyst to be used.

When phosphorus ligand rhodium complex based catalysts are employed, low pressures between 50 and 2000 psi (3.4 and 136 atm), preferably 100 to 1500 psi (6.8 to 102 atm), are used. A broad range of temperatures preferably from 50 to 250° C., more preferably from 80 to 200° C., can be used.

Phosphine cobalt complex catalysts can be advantageously employed at pressures between 500 and 4500 psi (34 and 306 atm), preferably between about 500 and 2500 psi (34 and 170 atm), and at reaction temperatures between 150 and 200° C.

High pressure cobalt catalysts, in the absence of added ligands, require pressures between 2500 and 6000 psi (170 and 408 atm), preferably between 3000 and 4500 psi (204 and 306 atm). They are preferably employed between 100 and 180° C., more preferably between 100 and 170° C., most preferably between 120 and 145° C. Higher pressures of reactant gas, specifically CO, allow the use of higher reaction temperatures without catalyst decomposition and/or deactivation.

In summary, the dependence of reaction conditions on the type of catalyst systems employed is shown by the following tabulation:

| Group VIII Metal Employed | Trivalent P Ligand Employed | Reaction Conditions | | |
|---|---|---|---|---|
| | | Temperature °C. | Pressure psi | atm |
| Rh | Yes | 50–250 | 50–2000 | 3.4–136 |
| Co | Yes | 150–200 | 500–4500 | 34–306 |
| Co | No | 100–180 | 3000–4500 | 204–306 |

In the present process, the feed for the high pressure cobalt catalyst contains 1-n-olefins as the major type of olefins and is derived from the petroleum residua by Flexicoking or an equivalent high temperature thermal cracking process. Starting with this feed, the present process provides aldehydes and/or alcohols of a highly linear character having less than one alkyl branch per molecule on an average. This feed and product are also preferred for the other catalysts.

The preferred thermally cracked distillate feeds have a further increased 1-n-olefin content and a reduced aromatic hydrocarbon and sulfur content. In the $C_6$ to $C_{10}$ feed range this is advantageously achieved by a process additionally comprising the fractional distillation of cracked naphtha separating narrow feed fractions containing mainly linear aliphatic hydrocarbons from fractions containing major amounts of aromatic compounds including thiophenes.

The preferred high pressure cobalt catalyzed process of the present hydroformylation process is particularly suitable for the conversion of the olefins of the present feed to novel semilinear aldehydes having one carbon more than the parent olefins. The structure of the aldehydes containing less than one alkyl branch per molecule reflects the unique mixture of the starting olefins. The major components of the preferred aldehyde compositions are n-aldehydes, 2-methyl-aldehydes and 3-methyl-aldehydes derived from the major 1-n-olefin and 1-methyl-1-olefin components of the feed.

The invention is also concerned with the derivatives of the primary aldehyde products. These aldehydes can be hydrogenated during and/or after the hydroformylation process to provide the corresponding mixture of semilinear alcohols. Either the aldehydes or the alcohols can be converted to the corresponding amines and quaternary ammonium compounds.

The novel alcohol compositions can be converted to valuable ester plasticizers and ethoxylated surfactants. Polyvinylchloride plasticized with the phthalate esters shows a unique combination of low temperature flexibility, high temperature stability and reduced volatility attributable to present semilinear alcohol intermediates. Similarly, the ethoxylated and propoxylated surfactant derivatives of these alcohols show a desirable combination of biodegradability and wetting properties. Such surfactants will generally contain about 1 to 30 moles of ethylene oxide or propylene oxide per mole of semilinear alcohol.

DESCRIPTION OF THE PREFERRED EMBODIMENTS

This invention describes a hydroformylation process for the production of aldehydes and/or alcohols of a largely linear character, i.e., products stream having preferably less than one alkyl branch per mole on the average, from a cracked petroleum distillate feedstock containing substantial amounts of 1-n-olefins and sulfur compounds. The process comprises reacting the distillate with $CO/H_2$ in the presence of a Group VIII transition metal complex catalyst.

As such, the present hydroformylation process comprises reacting with hydrogen and carbon monoxide an olefinic cracked petroleum distillate feed, particularly in the $C_8$ to $C_{35}$ carbon range, preferably produced from petroleum residua by high temperature thermal cracking, and containing 1-n-olefins as the major type of olefin components, the percentage of Type I olefins being preferably more than 30%, said feeds also containing organic sulfur compounds in concentrations preferably exceeding 0.1%, more preferably exceeding 1%.

The hydroformylation reaction is carried out at temperatures between about 50 and 250° C. and pressures in the range of 50 and 6000 psi (3.4 and 408 atm) dependent on the particular catalyst employed.

The reaction takes place in the presence of effective amounts of a Group VIII transition metal carbonyl complex catalyst preferably selected from the group of Fe, Co, Rh, Ir and Os, more preferably Rh, Co, Ru and Ir, most preferably Co or Rh, a preferred group of complexes being modified by a trivalent phosphorus ligand, preferably triorgano-phosphine or phosphite ester.

Such hydroformylation produce aldehydes and/or alcohols, preferably aldehydes of a semilinear character, preferably having an average of less than one alkyl branch per molecule. These products more preferably contain n-aldehydes, 2-methyl and 3-methyl branched aldehydes as the major products, most of the rest being mainly various 2-ethyl or higher 2-n-alkyl branched aldehydes. The reduction of these aldehydes by hydrogen to the corresponding alcohols is preferably carried out in a separate step in the presence of a sulfur insensitive catalyst, preferably based on Co, No, Ni, W in a sulfided form.

Thus, according to another aspect of the invention, a hydroformylation-hydrogenation process comprises reacting the above described olefinic cracked petroleum distillate feed with carbon monoxide and hydrogen under the conditions already defined to produce said aldehyde products and then reacting said aldehydes and temperatures between 100 and 200° C. in the presence of a catalyst in effective amounts to produce the corresponding alcohols of a semilinear character having an average of less than one alkyl branch per molecule.

According to a further aspect of the invention, the novel aldehyde and alcohol compositions prepared via the present process are described. These isomeric aldehyde compositions comprise $C_7$ to $C_{21}$ mostly saturated aliphatic aldehyde mixtures of a semilinear character having an average of less than one branch per molecule. They contain more than 30% normal alkanal and major amounts of 2-methylalkanals and 3-methylalkanals and minor amounts of 2-ethyl and higher 2-n-alkylalkanals. Similarly, the isomeric alcohol compositions comprise $C_7$ to $C_{21}$ saturated aliphatic alcohol mixtures of a semilinear character having an average of less than one branch per molecule. These alcohols contain more than 20%, preferably more than 30%, normal alkanols, major amounts of 2-methylalkanols and 3-methylalkanols and minor amounts of 2-ethyl and higher 2-n-alkylalkanols.

Distillate Feeds

The cracked petroleum distillate feeds of the present hydroformylation process are preferably derived via thermal cracking. Thermal cracking processes produce hydrocarbons of more linear olefinic character than catalytic cracking. The presence of linear olefin components, particularly 1-n-olefins, in the cracked distillates is important for the production of normal, non-branched aldehydes and mono-branched aldehydes using hydroformylation. For example, the hydroformylation of 1-hexene can produce n-heptanal as the main n-aldehyde product and 2-methylhexanal as the minor iso-aldehyde product. These in turn can be hydrogenated to the corresponding alcohols:

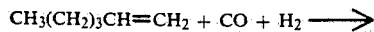

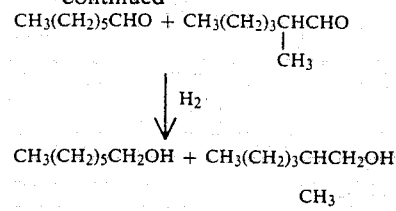

The linear normal aldehyde and alcohol products are generally more desired than the branched iso-compounds as intermediates for the production of high quality plasticizers and surfactants. Among the iso compounds, the 2-methyl branched products have the least adverse effect on product quality.

The percentage of 1-n-olefin components of thermally cracked petroleum distillates generally increases with the temperature of cracking. Therefore, the distillate products of high temperature thermal cracking processes such as Fluid-coking and Flexicoking are preferred feeds for the present process. Delayed coking, which is normally operated at a lower temperature, can also produce suitable feeds for the present process when operated at sufficiently high temperature. Other less preferred, milder cracking processes such as the thermal cracking of gas oils and the visbreaking of vacuum residues can also produce distillate feeds for the present process. Suitable distillate feeds can also be prepared in thermal processes employing a plurality of cracking zones at different temperatures. Such a process is described in U.S. Pat. Nos. 4,477,334 and 4,487,686. Each of these thermal cracking processes can be adjusted to increase the olefin contents of their distillate products. Higher distillate fractions of steam cracking can also be used as a feed in the present process.

The olefin content of the cracked distillate feeds of the present invention is above 20%, preferably above 30%, more preferably above 40%. The 1-n-olefins are preferably the major type of olefin components.

In the high pressure operation of the present process, using cobalt carbonyl complexes without any added phosphine ligand, the feeds should be thermally cracked distillates containing 1-n-olefins as the major olefin type. These feedstocks are preferably produced by the FLEXICOKING process or FLUID-COKING process and similar high temperature coking processes.

Distillate fractions of cracking processes can be hydroformylated without prior purification. However, the cracker distillate feeds may be treated to reduce the concentration of certain sulfur and nitrogen compounds prior to the hydroformylation process. These impurities, particularly the mercaptans, can act as inhibitors to the hydroformylation step. The disclosed process is operable in the presence of the impurities but adjustments to the catalyst level and/or to the reactant gas partial pressure (notably the CO pressure) are preferably made to compensate for the inhibition by the sulfur compounds.

One method for the removal of mercaptans, is selective extraction. Most of the extractive processes employ basic solvents. Examples of such processes include the use of aqueous and methanolic sodium hydroxide, sodium carboxylate (isobutyrate, naphthenate) sodium phenolate (cresolate) and tripotassium phosphate. Sulfuric acid of carefully controlled concentration and temperature can be also used although it is less selective than caustic. For example, a 30 minute treatment with 12% $H_2SO_4$ between 10 and 15° can be used.

The preferred cracked distillates of the present feed contain relatively high amounts of organic sulfur compounds. The sulfur concentration is preferably greater than 0.1% (1000 ppm), more preferably great than 1% (10000 ppm). The prevalent sulfur compounds in these feeds are aromatic, mainly thiophenic. Most preferably the aromatic sulfur compounds represent more than 90% of the total. This finding is important for the present process since thiophenes, benzothiophenes and similar aromatic sulfur compounds do not inhibit hydroformylation.

For the removal of sulfur, as well as nitrogen compounds, adsorption on columns packed polar solids, such as silica, fuller's earth, bauxite, can also be used. Treating columns containing such adsorptive solids can be regenerated, e.g., by steam. Alternatively, zeolites can be used to enrich the present feeds in 1-n-olefins and n-paraffins.

The aromatic hydrocarbon components of the feed can also be removed together with the aromatic sulfur compounds, preferably by methods based on the increased polarity of aromatics compared to the aliphatic components. Selective solvent extraction methods using a polar solvent such as acetonitrile may be employed for extracting the polar components. As a feed for extraction, preferably narrow distillate fractions of up to 3 carbon range are used.

Finally, sulfur compounds can also be converted to easily removable hydrogen sulfide by passing the cracked distillate through a high temperature fixed bed of either bauxite or fuller's earth or clay, preferably between 700 to 750° C. One disadvantage of this catalytic desulfurization method is the concurrent isomerization of olefin.

The cracked refinery distillate feed is preferably separated into various fractions prior to hydroformylation. Fractional distillation is the preferred method of separation. The different distillate fractions contain different ratios of the various types of olefins reactants and have different inhibitor concentrations. The preferred carbon range of the thermally cracked feeds is $C_5$ to $C_{35}$. The $C_8$ to $C_{25}$ range is more preferred. The most preferred range is $C_{11}$ to $C_{20}$. It is desirable to limit the carbon number range of any given distillates feed by efficient fractional distillation to 5 carbons, preferably three carbons, more preferably one carbon, to allow efficient separation of the products from the unreacted feedstock.

For example, a cracked distillate feedstock fraction might contain hydrocarbons in the $C_7$ to $C_9$ range. The main components of such a fraction would be $C_8$ hydrocarbons. Upon hydroformylating the olefinic components of such a fraction, $C_8$ to $C_{10}$ (mainly $C_9$) aldehydes and alcohols would be obtained. These oxygenated products all boil higher than the starting $C_7$ to $C_9$ hydrocarbons. The products could therefore be separated by distillation from the unreacted feed fraction.

For the preparation of plasticizer alcohols, olefin feeds containing from 5 to 12 carbon atoms are preferred. These can be converted to $C_6$ to $C_{13}$ aldehydes and in turn to $C_6$ to $C_{13}$ alcohols. The more preferred feeds contain $C_8$ to $C_{12}$ olefins and as such provide $C_9$ to $C_{13}$ alcohols. The most preferred feeds are $C_{10}$ to $C_{12}$ olefins. The alcohols may be reacted with phthalic anhydride to produce dialkyl phthalate plasticizers of appropriate volatility. The more linear the character of the alcohol employed, the better are the low temperature properties of the plasticized products e.g., plasticized PVC. The preferred feeds of the present invention are uniquely advantageous in providing low cost olefins for the derivation of high value plasticizers.

For the preparation of surfactants, higher molecular weight olefins are usually preferred. Their carbon numbers per molecule range from $C_8$ to $C_{35}$. These feeds can be used for the derivation of $C_9$ to $C_{36}$ aldehydes, $C_{12}$ to $C_{20}$ olefin feeds leading to $C_{13}$ to $C_{21}$ surfactant alcohols are more preferred. These aldehydes can be either reduced by hydrogen to the corresponding alcohols or oxidized by oxygen to the corresponding carboxylic acids. The alcohols can then be converted to nonionic surfactants, e.g., by ethoxylation; anionic surfactants, e.g., by sulfonation and cationic surfactants, e.g., by amination or cyanoethylation followed by hydrogenation.

Olefin Reactant Compounds

The main olefin reactant components of the present feed are nonbranched Types I and II or mono-branched Types III and IV as indicated by the following formulas (R=hydrocarbyl, preferably non-branched alkyl):

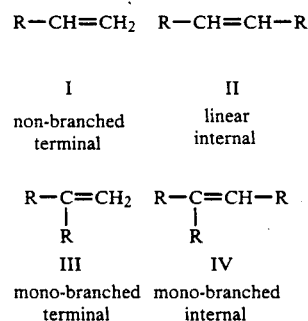

The concentration of Type I olefins is preferably greater than 30% of the total olefin concentration. The percentage of Type II olefins is greater than 15%. Type V olefins of the formula $R_2C=CR_2$ are essentially absent.

The n-alkyl substituted Type I olefins, i.e., 1-n-olefins, are generally present at the highest concentration in thermally cracked distillates among the various olefinic species. The main product of 1-n-olefin hydroformylation is the corresponding n-aldehyde having one carbon more than the reactant. The hydroformylation of Type II linear internal olefins and Type III mono-branched terminal olefins provides mono-branched aldehydes and in turn to alcohols:

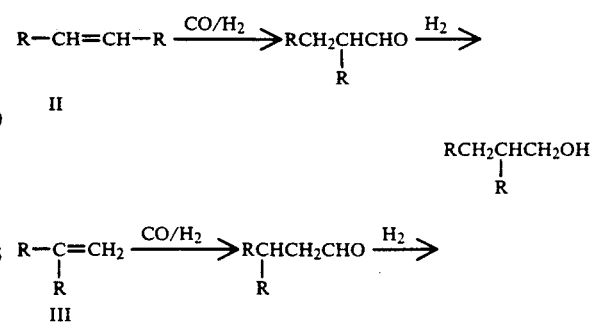

-continued $$RCHCH_2CH_2OH$$
$$|$$
$$R$$

The hydroformylation of Type IV mono-branched olefins leads to dibranched products.

$$R-C=CHR \xrightarrow{CO/H_2} RCH-CHCHO \xrightarrow{H_2}$$
$$|\quad\quad\quad\quad\quad\quad\quad|\quad|$$
$$R\quad\quad\quad\quad\quad\quad\quad R\quad R$$

$$RCH-CHCH_2OH$$
$$|\quad\quad|$$
$$R\quad\quad R$$

Characteristically, the alkyl branches of the Type III and IV olefins are mostly methyl groups. The absence of long alkyl branches is important in determining the properties of the oxo-derivatives of these feed components. Types I, II, III and IV olefins have a decreasing reactivity in this order. Thus it is possible, using the selective catalytic process of the present invention, to convert either to Type I, or the Types I and II, or the Types I to III olefins, selectively to products containing (on an average) less than one branch per molecule. Of course, the most linear products can be derived by hydroformylating only the Type I olefin.

Type II linear internal olefins can also be converted to non-branched aldehydes and alcohols via the present process. To achieve this conversion, combined isomerization-hydroformylation may be carried out. This process uses an internal-to-terminal olefin isomerization step followed by a selective hydroformylation of the more reactive terminal olefin isomer. For example, in the case of 3-hexene, the following reactions are involved:

$$CH_3CH_2CH=CHCH_2CH_3 \rightleftarrows CH_2CH_2CH_2CH=CHCH_3$$
$$\updownarrow$$
$$CH_3CH_2CH_2CH_2CH_2CH_2CHO \xleftarrow{CO/H_2} CH_3CH_2CH_2CH_2CH=CH_2$$

Due to its much greater reactivity, the terminal olefin is selectively hydroformylated even though its equilibrium concentration is smaller than those of the internal olefin isomers. The cobalt-phosphine-complex-based catalyst systems are particularly effective for coupling the isomerization and hydroformylation reactions.

CO/H₂ Synthesis Gas Feed

As a reactant gas for hydroformylating the olefin components of the present feed, mixtures of $H_2$ and CO, preferably in ratios ranging form 1- 2 to 10-1, can be used. Ratios between 1 and 2 are preferred. When reacting higher olefins, most of the total reactor pressure is that of $H_2$ and CO. High $H_2$/CO pressures, particularly high CO partial pressures, usually stabilize the catalyst system. The CO as a ligand competes with the sulfur compound ligands for coordination to the transition metal to form the metal carbonyl complex catalyst. The partial pressure of carbon monoxide affects the equilibria among catalyst complexes of different stability and selectivity. Thus, it also affects the ratio of linear to branched products (n/i) and the extent of side reactions such as hydrogenation.

High CO partial pressures are particularly important in forming and stabilizing the desired carbonyl complex catalysts of high pressure cobalt hydroformylation. They stabilize the catalyst complex against deactivation by he sulfur compound components of the feed. In a preferred operation, the active catalyst system is produced at a low $H_2$/CO ratio. Thereafter, the catalyst is operated at increasing $H_2$/CO ratios.

The effect of CO partial pressure on the n/i ratio of aldehydes and alcohol products is particularly important in the presence of rhodium complexes of trivalent phosphorus ligands, particularly phosphines. Phosphine ligands increase the strength of CO coordination to rhodium. Thus, the need for increased CO partial pressures to stabilize the catalyst complex is reduced. Increased CO partial pressures result in increased substitution of the phosphine ligands by CO; i.e., rhodium catalyst complexes leading to reduced n/i ratios. To produce products of high n/i ratios rhodium complexes containing only one CO per Rh are preferred. Thus in this case, the partial pressure of CO is preferably below 500 psi.

Catalyst Complexes and Selective Feed Conversions

Catalysts suitable for use in this hydroformylation process include transition metal carbonyl complexes preferably selected from the group of Fe, Co, Rh, Ir and Os. The more preferred transition metals are rhodium, cobalt, ruthenium and iridium. Rhodium and cobalt complexes are most preferred. A preferred group of catalysts consists of transition metal carbonyl hydrides. Some of the carbonyl ligands of these complexes may be replaced by ligands such as trivalent phosphorus, trivalent nitrogen, triorganoarsine and divalent sulfur compounds. Trivalent phosphorus ligands, and particularly triorganophosphines and phosphite esters are preferred.

The preferred triorganophosphine ligands include substituted and unsubstituted triaryl phosphines, diaryl alkyl phosphines, dialkyl aryl phosphines and trialkyl phosphines. These phosphines may be partially or fully open chain or cyclic, straight chain or branched. They may have various substituents, such as those disclosed in U.S. Pat. No. 4,668,809 by Oswald et al. which is incorporated herein by reference.

In general, the stable but not directly active catalyst complexes of the present invention are coordinatively saturated transition metal carbonyl hydrides. They include metal carbonyl cluster hydrides. In the case of Co, Rh and Ir they are preferably of the formula $$L_pM(CO)_qH$$

wherein L is a ligand, preferably P, N or As ligand, M is transition metal, p is 0 to 3 and q is 1 to 4, with the proviso that $p+q=4$. These complexes lead to catalytically active coordinatively unsaturated compounds via L and/or CO ligand dissociation

In the presence of the sulfur containing olefinic feeds of the present invention some of the CO and/or other ligands can be exchanged for appropriate sulfur ligands during hydroformylation.

A preferred subgenus of complex catalysts consists of penta-coordinate trialkyl phosphine rhodium carbonyl hydrides of the general formula

wherein R is a $C_1$ to $C_{30}$ unsubstituted or substituted alkyl; x is 2 or 3 and y is 1 or 2, with the proviso that $x+y$ is 4. The alkyl groups can be the same or different; straight chain or cyclic, substituted or unsubstituted. The trialkyl phosphine rhodium carbonyl complex subgenus of catalyst complexes shows outstanding thermal stability in the presence of excess trialkyl phosphine ligand even at low pressure. Thus, it can be advantageously employed at temperatures between 140–200° C. under pressures ranging from 100 to 1000 psi. Tri-n-alkyl phosphine complexes of this type can be employed for the selective hydroformylation of Type I olefins.

In general, phosphorus ligands of low steric demand, such as tri-n-alkyl phosphines and n-alkyl diaryl diphenyl phosphines, can lead to high n/i product ratios derived from Type I olefins in rhodium catalyzed hydroformylation. This requires a high P/Rh ratio in the catalyst system and a low partial pressure of CO.

Trialkyl phosphine complexes having branching on their α-or/and β- carbons have increased steric demand. They tend to form catalyst complexes of structures which have increased reactivity toward Type II and Type III olefins. For example, the α- branched tricyclohexyl phosphine and the β- branched tri-i-butyl phosphine

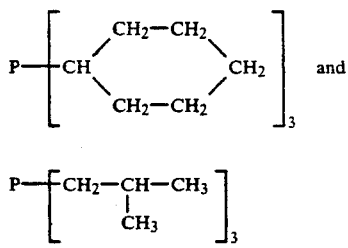

are attractive catalyst ligands of this type. These catalysts, while highly active, do not provide high n/i product ratios.

Another preferred type of phosphorus ligand for rhodium consists of alkyl diaryl phosphines of low steric demand. The tris-phosphine rhodium carbonyl hydride complexes of these ligands show a desired combination of operational hydroformylation catalyst stability and selectivity to produce high n/i product ratios.

In general, the hydrogenation activity of phosphine rhodium carbonyl complexes is relatively low. Thus, in the presence of these complexes, aldehyde products of hydroformylation can be produced in high selectivity without much alcohol and/or paraffin formation, particularly at low temperatures.

Another subgenus of suitable catalyst complexes is that of pentacoordinate trialkyl phosphine cobalt carbonyl hydrides of the formula:

wherein R is preferably a $C_1$ to $C_{30}$ alkyl as above, u is 1 or 2, v is 2 or 3 with the proviso that $U+v$ is 4. Tri-n-alkyl phosphine ligands are particularly advantageous in these cobalt phosphine catalysts since they provide high selectivity in the production of normal alcohol products when hydroformylating the 1-n-olefin and linear internal olefin components of the present cracked feeds. Tri-n-alkyl phosphine ligands include those wherein the n-alkyl substituents are part of a cyclic structure including the phosphorus, e.g.,

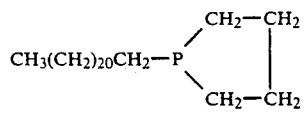

Using these catalysts, it is preferred to operate at high temperatures. Thus, the preferable temperatures are between 160 and 200° C. at pressures of 500 to 4500 psi. The more preferable pressure range is from 1000 to 3000 psi. Low medium pressures ranging from 1000 to 20000 psi are most preferred.

Another subgenus of catalysts is represented by cobalt carbonyl complexes free from phosphorus ligands. These catalysts include dicobalt octacarbonyl and tetracarbonyl cobalt hydride.

The latter compound is assumed to be an immediate precursor of catalytically active species. Cobalt carbonyl catalysts are stabilized by high $CO/H_2$ pressures ranging from 2000 to 6000 psi (136 to 408 atm) during hydroformylation. They are preferably used in the 100 to 180° C. temperature range. For a selective conversion of Type I olefins, lower temperatures up to 145° C. are used.

The above cobalt carbonyl complex can be generated by reacting cobalt or cobalt salts with CO and $H_2$. It is particularly advantageous to employ cobalt carboxylates as reactants for the generation of cobalt carbonyl catalyst precursors.

When the cobalt catalyzed hydroformylation is completed, the cobalt carbonyl complex is converted into $Co^0$, i.e. metallic cobalt or $Co^{2+}$, e.g. cobalt formate or acetate. The conversion to cobalt acetate can be advantageously carried out with hot aqueous acetic acid and molecular oxygen (air). This allows the recovery of cobalt in the aqueous phase. The cobalt acetate can then be converted to an oil soluble higher molecular weight carboxylate and recovered. For a more extensive description of the various methods of cobalt recovery and recycle see pages 162 to 165 of the Falbe reference.

In the high pressure cobalt catalyzed reaction of the present process using high sulfur feeds, dicobalt octacarbonyl is converted to partially sulfur ligand substituted components as it is indicated by the following schemes.

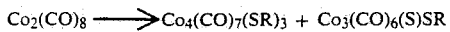

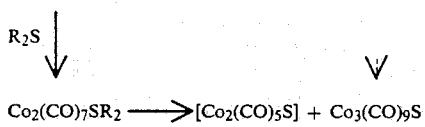

These and similar complexes and their hydride derivatives form equilibria with dicobalt octacarbonyl and tetracarbonyl cobalt hydride. The resulting catalyst system provides active catalyst species with or without sulfur. The sulfur containing species may also lead to insoluble and thus inactive CoS. The condition of the present process, particularly the CO partial pressure, are set to suppress CoS formation.

In general, the transition metal complex hydroformylation catalysts of the present invention are employed in effective amounts to achieve the desired olefin conversion to aldehydes and/or alcohols. The catalyst concentration is typically higher in the present process using feeds of high sulfur content than in other similar processes using pure olefin feeds. The transition metal concentration can range from 0.001 to 5%. The more preferred concentrations primarily depend on the metal employed. Cobalt concentrations range from 0.01 to 5%, preferably rom 0.01 to 5%, more preferably from 0.05 to 1%. Rhodium concentrations range from about 0.001 to 0.5%. Other factors determining the optimum catalyst concentration are the concentration and types of olefin in the feed and the desired olefin conversion. 1-n-Olefins are generally the most reactive. For a complete conversion of branched olefins, higher catalyst concentrations are needed.

The phosphorus, nitrogen and arsenic containing catalyst ligands are employed in excess. High excess ligand concentrations have a stabilizing effect on the catalyst complex. Particularly in the case of the phosphorus ligands, it is preferred to employ a minimum of 3 to 1 ligand to transition metal ratio. In the case of the phosphine rhodium complexes, the minimum P/Rh ratio is preferably greater than 10. P/Rh ratios can be as high as 1000. The sulfur-containing ligands may be provided in the feed.

The use of P-, N- and As-containing ligands, particularly phosphine ligands, leads to increased catalyst stability and selectivity for linear product formation. At the same time activity is usually decreased. Thus, the choice of metal to ligand ratio depends on the desired balance of catalyst stability, selectivity and activity. The S-containing ligands can improve the aldehyde selectivity of the present process.

High Pressure Low Temperature Cobalt Catalyzed Hydroformylation

The high pressure cobalt catalyzed hydroformylation in the absence of stabilizing added ligands such as phosphines is preferably carried out at low temperatures below 180° C. where the reduction of aldehyde products to alcohols and the aldol dimerization of aldehydes during hydroformylation is reduced.

The aldehyde primary products are generally of a semilinear character. The linear n-aldehydes are the largest single aldehyde type present in the products. The linearity of the alcohol products of hydrogenation is of course determined by that of the parent aldehdye mixture. The linearity of the aldehyde products in turn is mainly dependent on the unique feed of the present process and the catalyst and conditions of the conversion. In the following the aldehyde product mixtures are further characterized particularly for the cobalt catalyzed hydroformylation.

The major types of aldehydes are the n-aldehydes, the 2-methyl branched aldehydes and 3-methyl branched aldehydes. Much of the rest of the aldehydes are 2-ethyl or higher n-alkyl branched aldehydes. In general, the normal, the 2-methyl and 3-methyl branched products preferably represent more than 40% of the total.

At the lower temperatures, between 100 and 145° C., the Type I olefins, major components of the present feeds, are not effectively isomerized to the internal, Type II olefins of lesser reactivity. Thus a high concentration of the most reactive, terminal, Type I olefins is maintained. In addition, the low temperatures favor a higher n/i ratio of the hydroformylation products of Type I olefins:

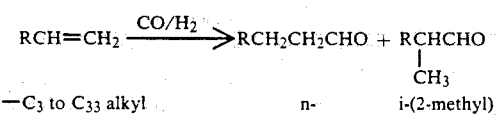

Thus, the use of low temperatures maximized the selectivity of the present process to the desired n-aldehyde and the 2-methyl substituted i-aldehyde products. For the Type II, linear internal olefins, 2-methyl, 2-ethyl, 2-propyl, etc. substituted aldehydes are formed in decreasing concentrations as indicated by the following scheme (R=$C_1$ to $C_{31}$ alkyl):

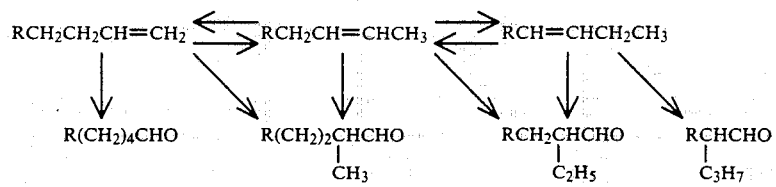

It was established by combined GC/MS studies that this product distribution of normal and 2-alkyl substituted i-aldehydes is a feature of the present process.

The 3-methyl substituted aldehydes are derived from 2-methyl-1-olefins which constitute most of the Type III olefin components of the feed. Some of the 2-methyl-2-olefins are isomerized to internal, methyl-branched Type IV olefins and lead to other isomeric methyl branched aldehydes, e.g.

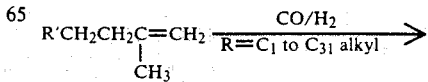

-continued

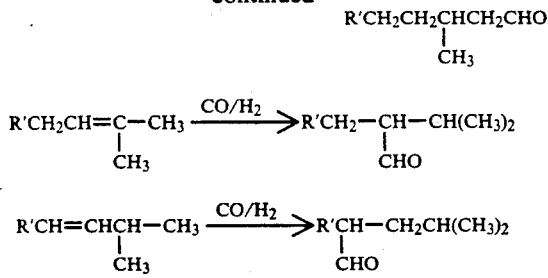

The low temperature cobalt catalyzed process results in high selectivity to aldehydes having one carbon more than their olefin precursors. Little aldol addition of the aldehyde products occurs during such hydroformylations. Thus, the so-called dimer by-products, consisting mainly of aldol condensation products are minimal. Similarly, the amounts of trimers, largely consisting of acetals and products of the Tischenko reaction of aldol adducts, is reduced.

A potential disadvantage of the low temperature operation is the relatively low reactivity of the Types II and III and particularly the Type III olefins. This can be overcome in a staged operation which involves the hydroformylation of Type I olefins in the low temperature regime and the hydroformylation of Type III olefins in the high temperature regime, between 145 and 180° C.

The low temperature operation can be effectively used for the selective conversion of Type I olefins to highly linear aldehydes. At low temperatures, the hydrogenation of the primary aldehyde products to the corresponding secondary alcohol products is insignificant. Thus, the aldehydes can be separated and utilized as versatile chemical intermediates in various reactions.

Under the conditions of the present process, the desired hydroformylation of the olefinic components of the feed occurs selectively without any significant conversion of the thiphenic aromatic sulfur compounds. The aliphatic sulfur compounds, particularly the thiol and disulfide components undergo a series of conversions, presumably via hydrogen sulfide. It was shown by sulfur specific gas chromatography (S GC) of the reaction mixture using a nonpolar capillary GC column that most of the trace sulfur compounds formed were beyond the aldehyde product boiling range. It was found by GC/MS that these sulfur compounds were thiol esters and alkyl sulfides. Their alkyl groups had one carbon more than the olefin reactants. This indicated that they were probably derived from the aldehyde products via the following reactions with thiol and H₂S respectively.

2 RCHO+RSH→RCOSR+RCH₂OH

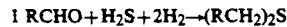

1 RCHO+H₂S+2H₂→(RCH₂)₂S

The hydroformylation reaction mixtures did undergo further reactions on prolonged standing. This resulted in the formation of significant amounts of higher boiling sulfur compounds, including some boiling in the aldehyde range. To obtain aldehydes and derivatives of low sulfur content, it is preferred to distill the reaction mixture without much delay after cobalt removal.

Hydroformylation-Acetalization in the Presence of Cobalt

Low temperature, high pressure, cobalt catalyzed hydroformylation can be advantageously carried out in the presence of added $C_1$ to $C_6$ monoalcohols, diols or triols such as methanol, ethanol, 1,6-hexanediol, glycerol. In the presence of these lower alcohols, preferably employed in excess, the aldehyde products of hydroformylation undergo diacetal formation catalyzed by cobalt carbonyl complexes. Using higher molecular weight alcohols, higher boiling acetals are formed. After the removal of the cobalt catalyst, these are readily separated from the reacted components of the cracked distillate feed by fractional distillation. Thereafter, the acetals are hydrogenated in the presence of added water to produce the corresponding alcohols as indicated by the general reaction scheme:

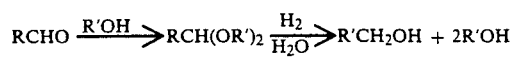

The added lower alcohols form water soluble cobalt complexes and thus also facilitate the removal of the cobalt catalyst after such combined hydroformylation acetalization reactions.

In an alternate sequence of operation, the hydroformylation can be carried out in the absence of added alcohol or in the presence of less than stoichiometric amounts to minimize reactor volume. Additional amounts of alcohol are then added to the reaction mixture after hydroformylation to complete the acetalization.

The use of added alcohols increases the stability of the catalyst system and the reaction rate. Due to rapid acetal formation, other secondary reactions of the aldehyde reaction products such as aldolization are suppressed. Another major advantage of producing the acetal derivatives is their ease of separation. In contrast to the aldehydes, which aldolize on heating during distillation, the acetals of the present invention can be separated without any significant yield loss by fractional distillation.

The hydroformylation-acetalization process of the present invention comprises reacting the previously described feed at first with CO and H₂ under hydroformylation conditions as described. The aldehyde products are then reacted with a $C_1$ to $C_6$ alcohol at temperatures between 15 and 250° C., pressures between 15 and 250° C. and pressures between 0 and 5000 psig during and/or after said hydroformylation. If the acetalization is carried out or completed after hydroformylation, the conditions are milder, preferably ranging from ambient temperature to 100° C. at atmospheric pressure.

Hydroformylation - Hydrogenation

The aldehyde and aldehyde plus alcohol products of hydroformylation are usually reduced to alcohols substantially free from aldehydes by hydrogenation. The hydrogenation catalysts are preferably sulfur resistant heterogeneous compositions based on Group VIII metals, particularly cobalt, molybdenum, nickel and tungsten. Cobalt sulfide and molybdenum sulfide are specifically preferred. They are preferably employed in the liquid phase at temperatures between about 50 and 250° C., preferably, 120 to 220° C., and pressures in the range of 50 and 6000 psi (3.4 and 408 atm), preferably 300 and 4000 psi (204 and 272 atm).

The hydrogenation of the aldehyde mixtures of the present invention can be advantageously carried out at variable temperatures, wherein the n-aldehydes are reduced to alcohols at first at lower temperatures than those needed for i-aldehydes. The n-aldehyde components are highly reactive and subject to conversion at high temperatures to low value n-paraffin by-products and aldol condensation-hydrogenation products. The 2-alkyl branched aldehydes require higher temperatures for their reduction to the desired aldehydes but have less tendency for paraffin and aldol by-product formation. Thus, a preferred selective hydrogenation process for the present aldehydes in the presence of a CoS/-MoS$_2$ based catalyst comprises hydrogenation of most of the n-aldehyde components in the temperature range of 130 to 190° C. followed by the hydrogenation of the rest of the aldehydes between 170 and 220° C. The temperatures employed of course will also depend on the catalysts used and the reaction time. Since most hydrogenations are carried out in a continuous manner, liquid hourly space velocities are another important factor in hydrogenation.

To increase the yield of the desired alcohol products, the hydrogenations are carried out in the presence of minor amounts of water, preferably 1 to 10% based on the aldehyde reactant. The upper level of the water is limited by the sensitivity of the catalyst. The water suppresses the formation of the dimer, trimer and formate by-products of hydroformylation to alcohols.

The hydrogenation of the present aldehydic feeds is preferably carried out under conditions not affecting the aromatic sulfur compounds, thiophens and benzothiophenes. In a preferred operation, the cobalt hydroformylation catalyst is removed and the cobalt free hydroformylation mixture is distilled to separate the unreacted hydrocarbons and aromatic sulfur compounds. The resulting aldehyde distillate or aldehyde distillation residue is then hydrogenated.

It was surprisingly found by sulfur specific GC analyses of the reaction mixtures that most of the sulfur compound components of the aldehyde boiling range are converted during hydrogenation to less volatile derivatives of the aldehyde dimer derivative range. Thus, essentially sulfur free alcohols could be obtained by a subsequent fractional distillation.

Dependent on the sulfur content of the aldehyde products, catalysts of varying sulfur sensitivity can be used. Such catalyst compositions include CuO and ZnO reduced by H$_2$ or CO. For the reduction of the low carbon number C$_5$ to C$_{10}$ aldehydes, a vapor phase rather than liquid phase hydrogenation process can be used.

Continuous Hydroformylation

The preferred mode of operating the present process is obviously continuous rather than batchwise. The reaction conditions of continuous and batchwise operation are nevertheless similar. Continuous hydroformylation can be carried out in a single reactor or in a series of reactors using various methods of separating the catalyst from the products and unreacted feed components. Stirred, packed and plug flow reactors can be employed. Reactants are continuously introduced.

When added stabilizing ligands (such as non-volatile phosphines are used, the products and unreacted feed may be separated from the catalyst system by flash distillation. In low pressure hydroformylation, direct product flash-off from the reaction vessel can be employed. At increased pressures, a recirculation flash-off mode of operation is preferred. This latter method would include a continuous removal of liquid reaction mixture from the reactor. This liquid is then depressurized and flash distilled at atmospheric pressure or in vacuo. The residual solution of the catalyst may then be continuously returned to the reactor. Stabilizing ligands of hydrophilic character may also be employed to make the transition metal complex water, rather than hydrocarbon, soluble. This allows biphase catalysis in a stirred water-hydrocarbon feed mixture and a subsequent separation and return of the aqueous catalyst solution to the reaction mixture.

In the absence of stabilizing ligands, the reaction mixture may be continuously withdrawn from the reactor and the transition metal carbonyl complex catalyst chemically converted to a water soluble, usually inactive form. After separation of the aqueous solution, the transition metal compound is reconverted to the precursor of the active catalyst which is then recycled to the reactor.

A variety of reactor schemes can be used for the optimum conversion of the olefin reactants in a continuous reactor. For instance, interconnected reactors may employ different catalyst systems. The first reactor may employ a phosphine-rhodium complex catalyst which selectively converts 1-n-olefins and employs direct product flash-off. This might be connected to a second reactor containing a phosphine cobalt complex catalyst which converts the linear internal olefins via isomerization-hydroformylation. Alternatively, cobalt alone may be used in the first reactor followed by a phosphine cobalt complex.

Hydroformylation-Aldolization

A further variation of the present process is the aldolization of the product aldehydes. A hydroformylation plus aldolization step in the presence of a base followed by a hydrogenation step converts a C$_{n+2}$ olefin to C$_{2n+6}$ aldehydes and alcohols. This is indicated in the following general scheme by the examples of Type I olefins.

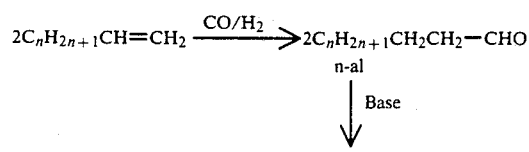

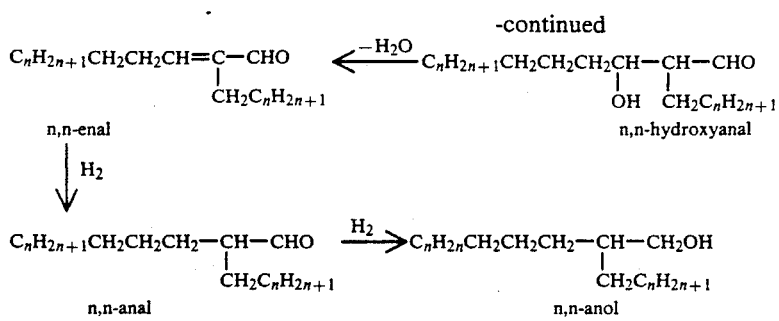

n,n-enal                          n,n-hydroxyanal n,n-anal                        n,n-anol wherein the simple n-aldehyde product of hydroformylation is "n-al", the thermally unstable primary product of aldolization is "n-hydroxyanal", the unsaturated aldehyde resulting from aldolization is "n,n-enal", the selectively hydrogenated saturated alcohol is "n,n-anal" and the final hydrogenated saturated alcohol is "n,n-anol". The n,n-prefixes indicate that both segments of the aldol compounds are derived from the terminal, i.e., normal, product of hydrogenation.

The hydrogenated saturated alcohol products of hydroformylation can be also derived by the Guerbet reaction of the alcohols produced from the primary aldehyde products of hydroformylation. e.g.

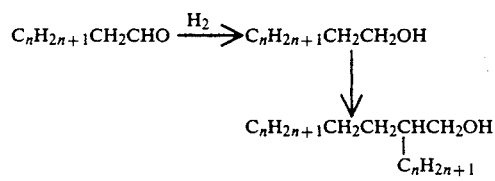

The Geurbet reaction is also a base and metal catalyzed conversion. It is carried out at elevated temperatures concurrent with the removal of the water condensation product.

Minor iso-aldehyde components of the aldehyde product mixture can also be converted in a so-called cross-aldolization reaction with the normal aldehyde:

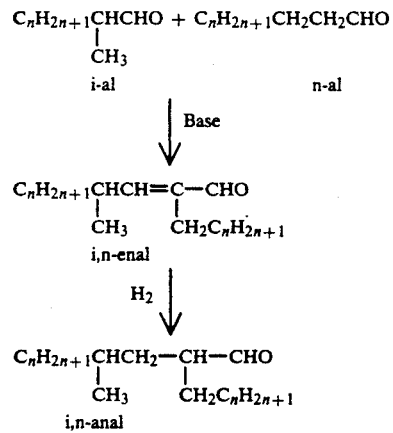

The rate of the above cross-aldolization process is slower than that of the simple aldolization. However, the relative rate of cross-aldolization increases with increasing temperature and decreasing n/i aldehyde ratios. The latter can be achieved by the addition of extra i-aldehyde to the reaction mixture.

The aldolization step can be carried out separately by condensing the aldehyde product intermediates in the presence of a base catalyst. Hydroformylation and aldolization plus hydrogenation can be combined by carrying out the hydroformylation in the presence of the above-described transition metal complex based catalysts plus a base aldolization catalyst.

A preferred mode of combined hydroformylation-aldolization is carried out in the presence of a trialkyl phosphine rhodium carbonyl hydride plus excess trialkyl phosphine hydroformylation catalyst system plus a base aldolization catalyst such as potassium hydroxide.

To carry out the present combined hydroformylation-aldolization process in the preferred homogeneous, liquid phase, solvent selection is important. The preferred solvent will dissolve all the widely different components of the reaction system. Solvency for the nonpolar olefin reactant and polar caustic catalyst and water by-product is therefore a compromise. Alcohols, particularly hydrocarbyloxyethyl alcohols are excellent choices. They may be of the formula, $$J(OCH_2CH_2)jOH$$

wherein $J=C_1$ to $C_4$ alkyl, preferably primary alkyl, most preferably methyl, $C_6$ to $C_{10}$ substituted or unsubstituted phenyl, preferably phenyl, j is 1 to 8, preferably 3 to 8. Desirable solvents include methoxytriglycol, $CH_3(OCH_2CH_2)_3OH$, and phenoxyethanol, $PhOCH_2$-$H_2OH$. In general, the weight proportion of the relatively nonpolar hydrocarbyl segment J to that of the highly polar oligo (-oxyethyl) alcohol segment determines the relative solvent power for the nonpolar versus polar components of the reaction mixture. As such, this type of a solvent can be readily optimized for any special application of the present process.

In a continuous combined hydroformylation-aldolization process, product flash-off is more difficult to realize because of the high boiling points of the aldol condensation products. Therefore, direct product flash-off is not generally feasible. Recirculation flash-off, aqueous catalyst separation and chemical catalyst recovery are preferred. Due to the high boiling point of the aldol condensation products, separation from the unreacted components of the distillate feed by fractional distillation is facilitated. Thus, broader carbon range distillate feeds can provide reaction mixtures suitable for aldol aldehyde or aldol alcohol separation by fractional distillation.

Since high aldolization rates can be readily achieved in the combined process, the reaction parameters can be readily adjusted to provide either the unsaturated or saturated aldehydes as the major products. Short reaction times, and low olefin conversions, preferably below 50%, plus high base concentration, favor the unsaturated aldehyde. However, mostly the saturated aldol condensation product is desired. This is, of course, the favored high conversion product.

Due to the improved thermal stability of the present trialkyl phosphine rhodium complex hydroformylation catalyst, the aldol condensation products can be flashed off or distilled without affecting the catalyst. However, strong bases have an adverse effect on the thermal stability of the system. These can be either removed before distillation or replaced with weaker base aldolization catalysts such as amines and Schiff bases. For example, basic ion exchange resins can be filtered off. For known, applicable aldolization catalysts, reference is made to Volume 16, Chapter 1 of the monograph "Organic Reactions", edited by A. C. Cope et al., published by J. Wiley & Sons, Inc., New York, N.Y., 1968.

The preferred concentration of the strong organic base, i.e., alkali hydroxide, aldolization catalyst is low, between about 0.01 and 1%, preferably between 0.05 and 0.5%. Of course, small caustic concentrations have less adverse effect on the stability of the reaction system.

Aldehyde Products and Derivatives

The present hydroformylation process, particularly the high pressure cobalt catalyzed reaction, leads to unique semilinear mixtures of aldehydes. Due to the specific mixture of olefins found in the hydroformylation feed, it is now possible to obtain a mixture of aldehydes which cannot be economically produced in any other way. The aldehyde products of the present invention are versatile chemical intermediates. They can be readily converted to alcohols, acetals, carboxylic acids and amines. The properties of these compounds and of their ester plasticizer and ethoxylated surfactant derivatives are distinct and desired. They reflect the semilinear character of their aldehyde precursors.

The semilinear aldehyde compositions have less than one branch per molecule. They have preferably $C_5$ to $C_{21}$, more preferably $C_7$ to $C_{21}$, most preferably $C_9$ to $C_{18}$ carbon atoms per molecule. They comprise 15 to 50% by weight of normal aldehyde which is preferably their major constituent. Other significant components are 3 to 20% of 3-methyl branched aldehyde and 3 to 20% of 2-methyl branched aldehydes. These components constitute preferably more than 40%, more preferably more than 50% of the total. The higher semilinear $C_7$ to $C_{21}$ aldehydes preferably also contain 3 to 20% of 2-ethyl and higher n-alkyl branched components.

The mixtures of semilinear $C_5$ to $C_{15}$ aldehydes possess alkyl moieties which make them suitable intermediates for the preparation of ester plasticizers having advantageous low temperature properties. Similarly mixtures of the semilinear $C_{10}$ to $C_{21}$ aldehydes have alkyl moieties which makes them suitable intermediates for surfactants having appropriate biodegradability.

The reactions leading to the formation of the present aldehyde mixtures were previously described. The structural formulas and percentages of the key aldehyde constituents are shown by the following tabulation:

$$CH_3(CH_2)_nCHO \quad CH_3(CH_2)_m\underset{\underset{CH_3}{|}}{C}HCHO \quad CH_3(CH_2)_p\underset{\underset{CH_3}{|}}{C}HCH_2CHO$$

15 to 50%     3 to 20%    3 to 20%
$n = 3–19$    $m = 1–17$    $p = 0–16$ $$CH_3(CH_2)_p\underset{\underset{C_2H_5}{|}}{C}HCHO \quad \text{and} \quad CH_3(CH_2)_q\underset{\underset{(CH_2)_rCH_3}{|}}{C}HCHO$$

$p = 0–16$    $q + r = 6–21$; $q \geq 2$; $r \geq 2$ 3 to 20%

An exemplary aldehyde mixture is a semilinear isomeric $C_{11}$ aldehyde having less than one branch per molecule and comprising 15 to 50% of normal undecanal, 3 to 20% of 3-methylundecanal and 3 to 20% of 2-methylundecanal, said $C_{11}$ aldehydes together constituting 40% or more of the total. Another exemplary composition is a semilinear isomeric $C_{13}$ aldehyde having less than one branch per molecule and comprising 15 to 50% of normal tridecanal, 3 to 20% of 3-methyldodecanal, and 3 to 20% of 2-methyldodecanal, said $C_{13}$ aldehydes together constituting 40% or more of the total. Percentages are by weight.

In spite of the high sulfur content of their olefinic feed precursors, the present aldehyde mixtures are preferably of low sulfur content. They have less than 1000 ppm, more preferably less than 200 ppm sulfur. Distilled aldehyde mixtures of narrow boiling range, containing mostly isomeric aldehydes of the same carbon number are preferred low sulfur compositions.

A preferred type of derivatives of the present aldehyde mixtures are the corresponding primary alcohol mixtures. They comprise semilinear $C_5$ to $C_{21}$ alcohol mixtures having less than one branch per molecule and comprising 15 to 50% of normal alcohol, 3 to 20% of 3-methyl branched alcohol and 3 to 20% of 2-methyl branched alcohol. The $C_7$ to $C_{21}$ alcohols preferably also contain 3 to 20% 2-ethyl and higher 2-alkyl branched alcohols. These alcohol constituents and their percentages by weight are defined by formulas of the following tabulation:

$$CH_3(CH_2)_nCH_2OH \quad CH_3(CH_2)_m\underset{\underset{CH_3}{|}}{C}HCH_2OH \quad CH_3(CH_2)_p\underset{\underset{CH_3}{|}}{C}HCH_2CH_2OH$$

15 to 50%    3 to 20%    3 to 20%
$n = 3–19$    $m = 1–17$    $p = 0–16$ $$CH_3(CH_2)_p\underset{\underset{C_2H_5}{|}}{C}HCH_2OH \quad \text{and} \quad CH_3(CH_2)_q\underset{\underset{(CH_2)_rCH_3}{|}}{C}HCH_2OH$$

$p = 0–16$    $q + r = 6–21$; $q \geq 2$; $r \geq 2$ 3 to 20%

The preferred subgroups of these alcohol mixtures are the same as those of their aldehyde precursors. The above 3 types of components preferably constitute more than 40%, preferably more than 50% of the total. The semilinear $C_5$ to $C_{15}$ primary alcohol mixtures provide ester plasticizers with advantageous low temperature properties. Similarly, the $C_{10}$ to $C_{21}$ alcohols are intermediates for biodegradable surfactants.

An exemplary alcohol mixture is an isomeric primary $C_9$ alcohol having less than one branch per molecule comprising 15 to 60% of normal nonanol, 3 to 20% of 3-methyloctanol, and 3 to 20% 2-methyloctanol said $C_9$ alcohols constituting 40% or more of the total alkyl groups. Similarly, a mixture of isomeric primary $C_7$ alcohols has less than one alkyl branch per molecule and comprises 15 to 60% of normal heptanol, 3 to 20% of 3-methylhexanol and 3 to 20% 2-methylhexanol. Said $C_7$ alcohols also constituting 40% or more of the total.

The plasticizer esters based on the present alcohols are neutral alkyl esters of mono-, di- and tribasic carboxylic acids and phosphorus acids such as phosphoric, phosphorus and phosphonic acids. On an average their alkyl groups have less than one alkyl branch and comprise 15 to 50% of normal alkyl, 3 to 20% 3-methyl branched alkyl and 3 to 20% 2-methyl branched alkyl groups and together they preferably represent more than 40% of the total.

Exemplary and preferred types of the present plasticizer compositions are alkyl benzoates, dialkyl phthalates, dialkyl adipates, trialkyl trimellitates, trialkyl phosphates, trialkyl phosphites, dialkyl benzenephosphonates.

The most preferred plasticizer ester derivatives of the present alcohols are the dialkyl phthalate esters. They are prepared by reacting the $C_5$ to $C_{15}$ alcohol mixtures with phthalic anhydride according to known methods. The two alkyl groups of these esters each have an average of less than one alkyl branch and comprise 15 to 30% normal alkyl, 3 to 20% 3-methyl branched alkyl, 3 to 20% 2-methyl branched alkyl moieties. Together they preferably represent 40% or more of the total.

A preferred exemplary phthalate ester of the present invention is ditridecyl phthalate having tridecyl groups with an average of less than one alkyl branch and comprising 15 to 50% normal tridecyl 3 to 20% 3-methyldodecyl and 3 to 20% 2-methyldodecyl groups, said tridecyl groups together representing 40% or more of the total.

The plasticizer esters of the semilinear alcohols of this invention may be employed to plasticize thermoplastic resins, especially the vinyl resins. Suitable resins include PVC resins derived from vinyl chloride monomer as well as copolymers of vinyl chloride and other mono- and di- olefinically unsaturated monomers copolymerizable therewith. The plasticizers may also be used in conjunction with other polymers or mixtures thereof including, for example, polyvinyl alcohol, polyvinyl acetate, polyvinyl butyral, polyvinylidene chloride, polyethyl acrylate, polymethyl acrylate and polymethyl methacrylate. Preferred are vinyl halides such as polyvinyl chloride and copolymers of vinyl halides such as those containing at least 70 wt. % vinyl halide, e.g., vinyl chloride. The plasticizers are employed in effective plasticizing amounts and generally from about 1 to 200 parts of plasticizer per hundred parts of resin by weight (phr) and preferably 10 to 100 phr. Plasticized resins containing the esters of this invention exhibit excellent low temperature flexibility, high temperature stability and reduced volatility.

Some of the esters of monocarboxylic acids, especially the acetic acid esters of the present semilinear $C_6$ to $C_{12}$ alcohols are also useful as solvents. The alkyl groups of these esters also possess less than one branch per molecule and comprise 15 to 50% normal alkyl, 3 to 20% 3-methyl branched alkyl and 3 to 20% 2-methyl branched alkyl groups.

The semilinear $C_8$ to $C_{21}$ primary alcohols of the present invention are attractive intermediates for ethoxylated and/or propoxylated nonionic surfactants. Sulfated or sulfonated surfactants derived from either the present alcohols or from their ethoxylated and/or propoxylated derivatives are of an anionic character. The preferred cationic surfactant derivatives of these alcohols, are primary, secondary and tertiary amines, ethoxylated and/or propoxylated tertiary amines and their quaternary ammonium derivatives, especially in their ammonium salt form. The semilinear alkyl moiety of the alcohol precursors advantageously affects the biodegradability of all three classes of surfactants. Besides the hydrophilic-lipophilic balance, the properties of nonionic, anionic and cationic surfactant mixtures of the present invention depend on the presence of semilinear $C_{10}$ to $C_{21}$ isomeric primary alkyl groups derived from the present alcohols.

The nonionic, anionic and cationic surfactant derivatives of the present semilinear alcohols are derived via known methods. Their derivation is exemplified by the following reaction schemes wherein the symbol of the $C_8$ to $C_{21}$ alcohol reactants is $RCH_2OH$.

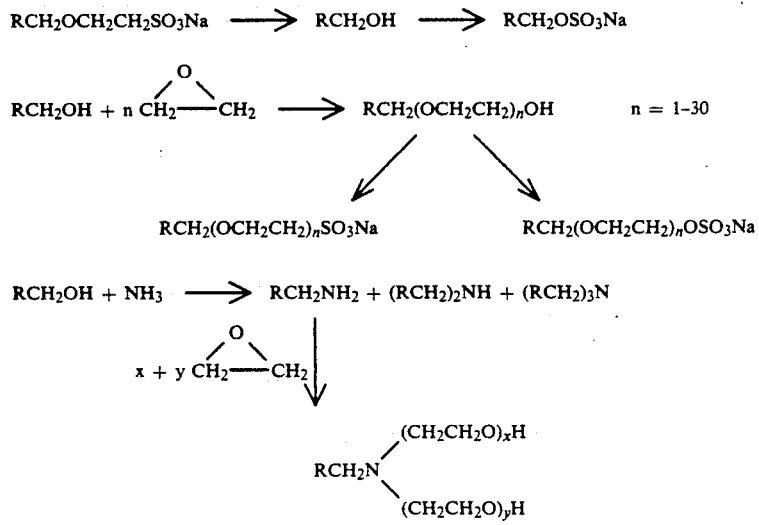

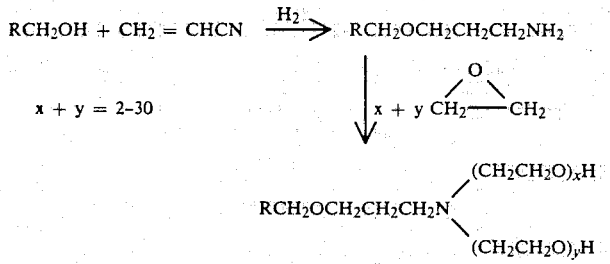

$x + y = 2-30$

As indicated by the product formulas of the above scheme, the preferred semilinear surfactants are selected from the group of nonionic surfactants consisting of ethoxylated and/or propoxylated alcohols; the group of anionic surfactants consisting of alkyl sulfates, ethoxylated and/or propoxylated alkyl sulfates or alkanesulfonates; the group of cationic surfactants consisting of alkylamines, ethoxylated and/or propoxylated alkylamines, ethoxylated and/or propoxylated alkyloxypropyl amines and quaternary salts of said alkylamines and alkyloxypropyl amines, wherein the isomeric $C_8$ to $C_{21}$, alkyl groups of said surfactants each have on an average less than one branch and comprise 15 to 50% normal alkyl, 3 to 20% 3-methylalkyl, 3 to 20% 2-methylalkyl and 3 to 20% 2-ethyl and higher n-alkyl groups together representing more than 50% of the total. These compounds preferably do not contain any completely substituted, i.e. quaternary carbon.

A preferred subclass of the present surfactants is that of the ethoxylated higher $C_8$ to $C_{21}$, preferably higher $C_{12}$ to $C_{16}$ alcohols wherein the alkyl groups are semilinear and defined as above and the ethoxylated moiety contains from 1 to 30 ethoxy units. These ethoxylated semilinear alcohols compare well with the corresponding ethoxylated branched and linear alcohols. They are better wetting agents than the linear derivatives. From the practical point of view, their biodegradability is of the same order as that of the more expensive linear compounds.

As specifically preferred, nonionic surfactant is a semilinear, isomeric ethoxylated tridecyl alcohol containing from 1 to 30 ethoxy units wherein the isomeric tridecyl groups are defined as above.

The semilinear $C_8$ to $C_{21}$ aldehydes of the present invention can be also advantageously used for the preparation of surfactants. Carboxylic acid surfactants of the anionic type can be produced by the oxidation of these aldehydes or their aldol aldehyde derivatives by molecular oxygen in the presence of a base. For example, with the normal aldehyde components, the following conversions are carried out:

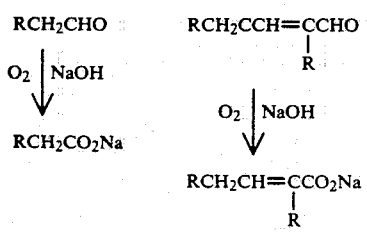

Cationic surfactants can be also derived from the semilinear aldehydes via reductive amination.

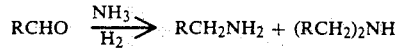

Amines can be also produced directly from the thermally cracked definic streams via hydroamination in the presence of rhodium complex catalysts, e.g.,

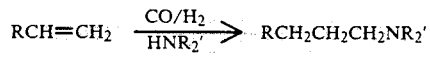

Wherein R' is $C_1$ to $C_8$ alkyl and substituted alkyl such as 2-hydroxyethyl.

EXAMPLES

In the following, examples are provided to illustrate the claimed hydroformylation process, but not to limit the invention. Prior to the examples the cracked distillate feedstocks are described. The description of the feedstocks details the structural types and amounts of reactive olefins present, this information being a key component of the invention. Thereafter, the low and high pressure hydroformylation procedures used and the product workup are outlined. Then the examples of the actual hydroformylation experiments are given in groups according to the feeds and catalysts employed. The summarized results of these experiments are also provided in tables.

The cobalt catalyzed high pressure hydroformylation of cracked distillate fractions is described in particular detail. The semilinear aldehyde products of varying carbon number are characterized. Their hydrogenation to the corresponding alcohols is also outlined. Finally, the conversion of the alcohols to phthalate ester plasticizers and ethoxylate surfactants is discussed. Some comparative data on plasticizer and surfactant properties are also provided.

Feedstocks

The feedstocks used in the following examples were fractions of liquid distillates produced by Fluid-coking and Flexi-coking in the temperature range of 482 to 538° C. (900 to 1000° F.). As high temperature thermal cracking processes, Fluid-coking and Flexi-coking produce distillate liquids and residual coke from vacuum residua. In Fluid-coking only the distillate products are utilized. The vacuum residue feeds and the thermal cracking step of Fluid-coking and Flexicoking are identical. However, the Flexicoking process is further integrated into the refinery by virtue of using the coke to manufacture low thermal value gas. Flexicoking is disclosed in U.S. Pat. Nos. 2,905,629; 2,905,733 and 2,813,916 which were previously discussed. Flexicoking is described in U.S. Pat. Nos. 3,661,543; 3,816,084;

4,055,484 and 4,497,705 which are incorporated as a reference.

The key factor in producing the present highly olefinic feed is the high temperature thermal cracking. However, another important factor is the origin and prior treatment of the petroleum residua to be cracked. The presence is desired, major 1-n-olefin components of the present feed depend on the presence of n-alkyl groups in the feed. These olefins are formed by the cracking and dehydrogenation of n-alkyl aromatics and n-paraffins. In the past the molecular structure of higher boiling coker distillates was not known. Thus the desired feeds of the present invention were not recognized.

The Fluid-coker distillate feeds were derived from a Northwest American crude. The Flexicoker distillates were produced from mixed crudes of Southwest American and Mideastern origin. Their compositions and those of other cracked distillates of different origins were remarkably similar.

An important step of the present invention was the structural analysis and recognition of the preferred distillate feeds. Since these feeds are extraordinarily complex, several analytical techniques were employed. The feeds were analyzed using packed column and capillary gas chromatographs (GC). The capillary GC was equipped with 50 m or 30 m fused silica columns coated with methyl silicones to determine the individual components. The sulfur compound components were also analyzed by capillary GC, using a dual detection system. The column effluent was equally divided and directed to a flame ionization detector (FID) and sulfur specific detector. Sulfur was detected either by a Hall TM Electroyltic Conductivity Dectector giving a linear response to sulfur or a Hewlett-Packard Flame Photometric Detector with a close to square dependance on sulfur concentration.

A high resolution, 400 MHz, proton resonance spectrometer (NMR) was used to estimate the various types of hydrocarbons, particularly olefins.

The structures of key feed components and products were determined by combined gas chromatography/mass spectrometry, GC/MS. A Finnigan TSQ-46B triple stage quadrupole GC/MS/MS was used in a single stage mode. Both electron impact ionization (EI) and chemical ionization (CI) were used for the identification of the components. EI provided information on the structure of the molecular fragments. It was particularly successful in determining the structure of the 2-alkyl branched aldehydes based on the fragments resulting from the McLafferty rearrangement. CI, using ammonia and deuterated ammonia as reagent gases, was used in determining the molecular weight and compound class of components.

The sulfur containing ions were recognized on the basis of the appearance of associated isotopic peaks. The natural abundance of the $^{34}S$ isotope is about 4% of the $^{32}S$ isotope. Therefore, besides the peak for the $^{32}S$ fragment, an appropriate weaker peak having a higher m/z value by 2 is exhibited for the isotopic $^{34}S$ moiety.

Elemental and group analysis techniques were used to determine total sulfur, mercaptan sulfur and total nitrogen contents.

Coker Naphtha

The composition of several coker naphtha distillates was analyzed by capillary GC, using temperature programmed 30 and 50 m columns. They key components of the mixture were identified by GC/MS with the help of standards as required.

Figure 1:
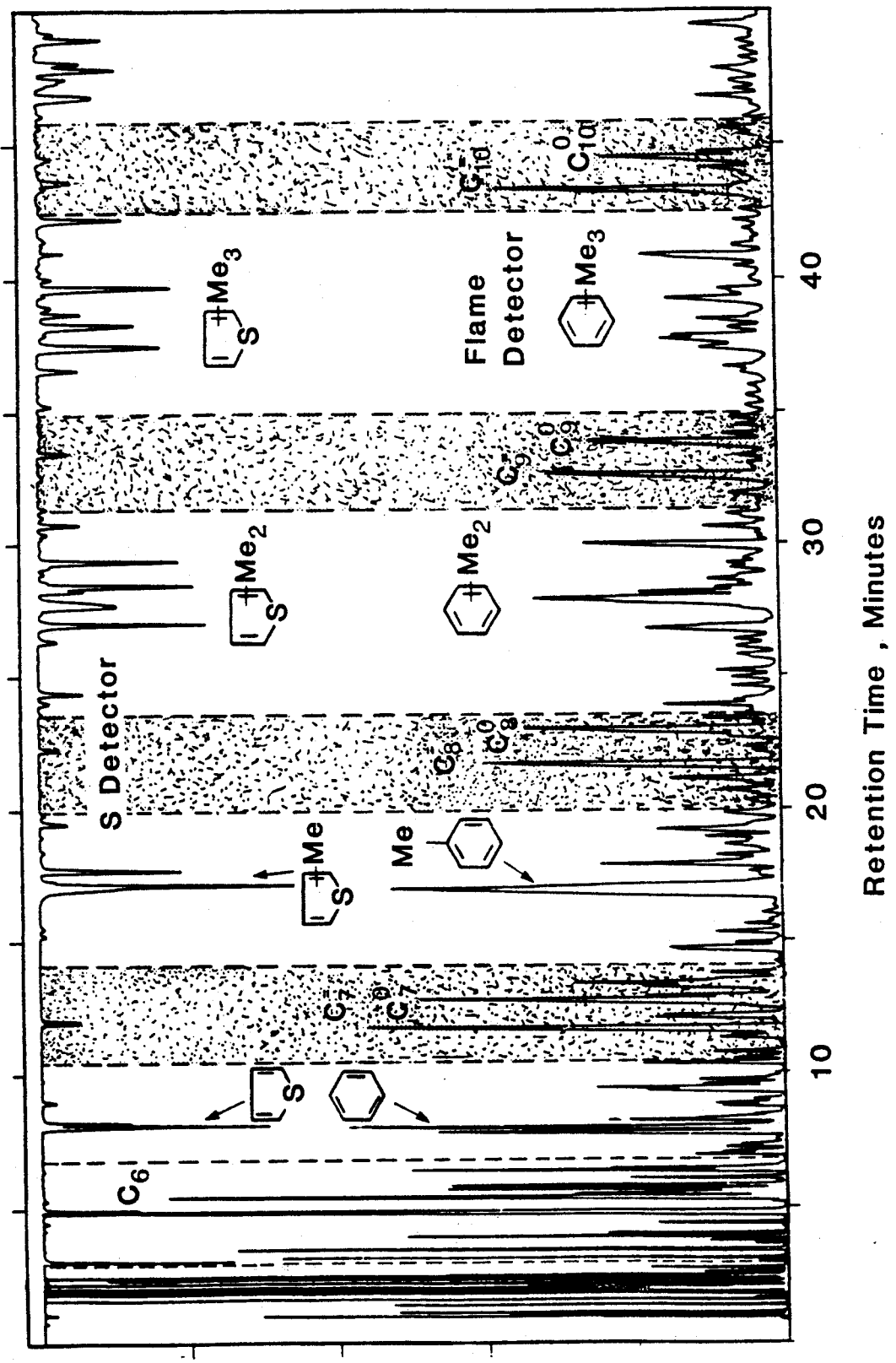
FIG. 1 shows the capillary gas chromatogram of a Fluid-coker naphtha feed in the $C_4$ to $C_{12}$ range, with an indication of the major 1-n-olefin and n-paraffin components by a flame ionization detector and the major thiophenic components by a sulfur specific detector.

The capillary gas chromatograms of FIG. 1 were obtained using a 30 m column with FID and S detectors to show the distribution of hydrocarbon and sulfur compounds in a Flexicoker naphtha.

The GC of they hydrocarbons (an organic compounds in general) in the bottom of the figure shows that the largest single types of components in the $C_6$ to $C_{10}$ range are the 1-n-olefins ($^=_n$) followed by the n-paraffins ($C^o_n$). This ratio is about 1.3. This ratio is very sensitive to the cracking conditions, particularly temperature. Among the aromatic compounds, toluene, xylene and trimethyl-benzenes are the main components in this carbon range.

The upper sulfur specific chromatogram shows that the major sulfur compounds present were aromatic: thiophene, mono- di- and trimethylthiophenes. The minor sulfur compounds were aliphatic thiols.

FIG. 1 indicates that the GC retention times and the boiling points of the thiophenic sulfur compounds and those of the aromatic hydrocarbon components largely coincide. Both differ from the boiling range of the major olefins present.

Thus, it is possible to separate highly olefinic $C_6$, $C_7$ and $C_8$ distillate fractions essentially free from aromatic sulfur compounds as it is shown by the shaded portions of the figure. The minor thiol components of these fractions can be removed by caustic wash or by converting them by oxidative methods to higher boiling compounds which can be then readily separated by distillation.

The hydrocarbon composition of the Fluid-coker naphtha was analyzed with a capillary GC equipped with a 50 m column which provided a higher resolution of the components. The 1-n-olefins and n-olefins were again in the main types of components in that order. The complete chromatogram is shown by FIG. 1 of the parent application.

The corresponding 1-n-olefin to n-paraffin ratios of the Fluid-coker naphtha are shown in Table I. In the $C_6$ to $C_{12}$ range these ratios range from about 1.1 to 2.1. In general, the 1-n-olefin to paraffin ratio increases with increasing carbon number.

TABLE I 1-n-Olefin Versus n-Paraffin Components of Fluid-Coker Naphtha

| Carbon No. | Component, GC % | | Ratio, Olefin Paraffin |
|---|---|---|---|
| | 1-n Olefin | n-Paraffin | |
| 3 | 0.120 | 0.169 | 0.7101 |
| 4 | 0.193 | 0.307 | 0.6287 |
| 5 | 0.418 | 0.523 | 0.7992 |
| 6 | 1.298 | 0.924 | 1.4048 |
| 7 | 1.807 | 1.496 | 1.2079 |
| 8 | 2.223 | 1.960 | 1.1342 |
| 9 | 2.164 | 1.651 | 1.3107 |
| 10 | 2.215 | 1.483 | 1.4936 |
| 11 | 1.534 | 0.989 | 1.5511 |
| 12 | 0.623 | 0.299 | 2.0836 |
| 3–12 | 12.295 | 9.801 | 1.2545 |

As summarized by Table I, in the $C_3$ to $C_{12}$ range, the naphtha contained 12.3% 1-n-olefins and 9.8% n-paraffins. Thus, the overall 1-n-olefin to n-paraffin ration was 1.25.

The ratio of 1-n-olefins to n-paraffins is a main factor indicating whether or not a given thermally cracked distillate is suitable feed in the present process, particularly in the case of the cobalt based catalysts. The ratio should be above 1, preferable above 1.2.

Lower cracking temperatures result in decreased olefin/paraffin ratios. For example, delayed coking which is carried out at a lower temperature than Fluid-coking gives distillates of lower ratios. An analysis of a naphtha fraction from a delayed coker gave an average of 0.3 1-n-olefin/n-paraffin ratio as it is shown in Table II.

TABLE II 1-n-Olefin versus n-Paraffin Components of Delayed Coker Naphtha

| Carbon No. | Component GC. % | | Ratio, Olefin Paraffin |
|---|---|---|---|
| | 1-n Olefin | n-Paraffin | |
| 6 | 1.956 | 5.008 | 0.3850 |
| 7 | 2.344 | 7.352 | 0.3188 |
| 8 | 1.879 | 6.707 | 0.2802 |
| 9 | 1.492 | 4.148 | 0.3596 |
| 10 | 0.374 | 0.994 | 0.3763 |
| 6–10 | 8.045 | 24.209 | 0.3323 |

A comparison of the olefin/paraffin ratios of Table I and Table II indicate that Fluid-coking provides an about 4 times greater olefin/paraffin ratio than delayed coking.

Many of the other components of the naphtha were also identified. Some of the illustrative details will be given in a discussion of certain distillate fractions.

The broad $C_{13}$ to $C_{12}$ coker naphtha fraction was fractionally distilled, using a column equivalent to 15 theoretical plates with reflux ration of 10, to produce distillates rich in olefins and paraffins of a particular carbon number. The boiling ranges and amounts of the distillate fractions obtained on distilling the naphtha are shown by Tables III and IV. The 1-n-olefin and n-paraffin components and a few key aromatic hydrocarbons present are also shown.

TABLE III 1-n-Olefin and n-Paraffin Components of $C_4$ to $C_8$ Distillate Fractions of Fluid Coker Naphtha Weight % Composition of Distillate Fractions and Starting Naphtha by Capillary GC

| | | | Pentenes | | | Hexenes | | | Heptenes | | | Octenes | | $C_3$–$C_{12}$ |
|---|---|---|---|---|---|---|---|---|---|---|---|---|---|---|
| Fraction No.: | Trap | 1 | 2 | 3 | 4 | 5 | 6 | 7 | 8 | 9 | 10 | 11 | 12 | Starting |
| Amount, g: | 705 | 590 | 526 | 698 | 951 | 1159 | 1854 | 3785 | 2508 | 1712 | 7920 | 2830 | 1985 | Naphtha |
| Bp. Up to °C.: | (23°) | −27° | 32° | −38° | −60° | 66° | −71° | −91° | −96° | −102° | −118° | −123° | −128° | |
| °F.: | (74°) | −80° | −90° | −100° | −140° | −150° | −160 | −195° | −205° | −215° | −245° | −254° | −262° | −410° |
| $C_3^=C_4^=$ | 21.5 | 1.1 | 0.3 | 0.1 | | | | | | | | | | 0.3 |
| 1-$C_4^=$ | 13.1 | 10.6 | 2.0 | 1.0 | 0.2 | | | | | | | | | 0.2 |
| $C_4°$ | 17.8 | 17.3 | 3.9 | 21.1 | 0.3 | | | | | | | | | 0.3 |
| 1-$C_5^=$ | 3.2 | 9.3 | 15.1 | 11.5 | 3.1 | 0.5 | 0.1 | | | | | | | 0.4 |
| $C_5°$ | 2.3 | 7.7 | 18.6 | 18.0 | 6.2 | 1.0 | 0.2 | | | | | | | 0.5 |
| 1-$C_6^=$ | | | | 0.1 | 16.1 | 29.6 | 16.3 | 3.4 | 0.2 | | | | | 1.3 |
| $C_6°$ | | | | | 3.0 | 15.6 | 16.3 | 3.9 | 0.3 | | | | | 0.9 |
| Cyclic $C_6$'s | | | | | 0.2 | 2.3 | 17.2 | 18.7 | 4.1 | 0.7 | | | | 1.7 |
| 1-$C_7^=$ | | | | | | | | 11.4 | 20.3 | 11.9 | 1.8 | | | 1.8 |
| $C_7°$ | | | | | | | | 3.8 | 16.9 | 16.8 | 2.9 | 0.1 | | 1.5 |
| Toluene | | | | | | | | 0.2 | 1.5 | 10.6 | 26.7 | 6.7 | 2.3 | 3.4 |
| 1-$C_8^=$ | | | | | | | | | | | 7.5 | 16.6 | 12.0 | 2.2 |
| $C_8°$ | | | | | | | | | | | 3.2 | 15.3 | 16.0 | 2.0 |
| Xylenes (m-, p-) | | | | | | | | | | | | 1.7 | 6.0 | 3.2 |
| 1-$C_9^=$ | | | | | | | | | | | | | | 2.2 |

1-$C_n^=$: 1-n-olefin of a certain carbon number; $C_n°$: Normal paraffin of a certain carbon number.

TABLE IV 1-n-Olefin and n-Paraffin Components[a] of $C_9$ to $C_{12}$ Distillate Fractions of Fluid Coker Naphtha Weight % Composition of Distillate Fractions

| | | Nonenes | | | Decenes | | Undecenes | | Dodecenes | | |
|---|---|---|---|---|---|---|---|---|---|---|---|
| Fraction No. | 13 | 14 | 15 | 16 | 17 | 18 | 19 | 20 | 21 | Residue |
| Amount, g | 10498 | 2280 | 1376 | 7979 | 4881 | 5793 | 5233 | 561 | 1520 | 3189 |
| Bp. Up to °C. | −145 | 149 | 153 | −168 | −177 | −190 | −199 | −210 | | |
| °F. | −290 | −300 | −307 | −335 | −350 | −374 | −390 | −410[b] | 425[c] | |
| 1-$C_8^=$ | 2.2 | | | | | | | | | |
| $C_8°$ | 3.7 | | | | | | | | | |
| Xylenes, m-, p- | 18.4 | 5.0 | 1.9 | 0.3 | | | | | | |
| 1-$C_9^=$ | 6.3 | 18.9 | 12.0 | 2.0 | | | 0.4 | | | |
| $C_9°$ | 2.4 | 16.3 | 16.3 | 3.5 | | | | | | |
| i-Propylbenzene | 0.3 | 2.2 | 2.5 | 0.7 | | | | | | |
| 1-$C_{10}^=$ | | | | 7.1 | 15.8 | 1.8 | 0.8 | 1.7 | | |
| $C_{10}°$ | | | | 2.6 | 13.7 | 2.7 | | | | |
| 1,2,3-Trimethylbenzene | | | | 1.1 | 7.3 | 2.4 | | | | |
| 1-$C_{11}^=$ | | | | | | 8.4 | 8.3 | 2.9 | 0.4 | |
| $C_{11}°$ | | | | | | 4.2 | 9.0 | 0.6 | | |
| Naphthalene | | | | | | | 0.8 | 5.9 | 5.1 | |
| 1-$C_{12}^=$ | | | | | | | 0.6 | 6.2 | 12.7 | |
| $C_{12}°$ | | | | | | | 0.1 | 2.9 | 8.8 | |
| 2-Methylnaphthalene | | | | | | | | | 0.4 | |

[a] 1-$C_n^=$ and $C_n°$ are symbols for n-olefins of a certain carbon number and n-paraffins of a certain carbon number, respectively.
[b] Atmospheric equivalent. The fraction was obtained between about 90 and 99° C. at 20 mm.
[c] Atmospheric equivalent; the fraction was obtained between 99 and 107° C. at 20 mm.

The results indicate that in the $C_5$ to $C_{10}$ range, distillates containing about 15.1 to 29.6% of individual 1-n-olefins could be produced. In the case of the higher boiling fractions, separation was more difficult and thus the maximum 1-n-olefin percentage in the case of 1- dodecene was 12.7%. The separation of $C_{10}$, $C_{11}$ and $C_{12}$ fractions was adversely affected by the presence of water in the distillation vessel. This effect could be eliminated by removing the water in vacuo.

The $C_4$ to $C_{12}$ naphtha and selected distillate fractions thereof were also studied proton NMR using a JEOL GX 400 MHz spectrometer. FIG. 2 shows the NMR spectrum of the olefinic region of the naphtha with an indication of the chemical shift regions assigned to the vinylic protons of various types of olefins. A quantitative determination of the olefinic protons of the various types of olefins was used to estimate olefin linearity. The relative mole percentages of olefins of varying carbon number were calculated on the basis of amounts of the different types of olefinic protons. The results of these calculations are shown in Table V.

The data of Table V show that the Type I olefins, i.e., monosubstituted ethylenes, are the major type of olefins in all the distillate fractions as well as in the starting $C_4$ to $C_{12}$ naphtha. THe percentage of Type I olefins in the distillation residue is, however, reduced to less than half of the original. It is assumed that this result is due to 1-n-olefin conversion during the high temperature distillation. Minor variations, between 32 and 50%, are also observed in Type I olefin content of distillate cuts. The reasons for this variation are unknown. The only Type I olefins indicated in the $C_8$ and higher carbon fractions are 1-n-olefins.

The second largest olefin type present in the naphtha and its distillate consists of 1,2-disubstituted ethylenes. The percentage of these Type II olefins varies between 18 and 26%. Most, if not all, of these olefins are linear internal olefins.

Type III olefins, i.e., 1,1-disubstituted ethylenes were found to be present in amounts ranging from 12 to 17%. The major olefins of this type were 2-methyl substituted terminal olefins. On the basis of MS studies of aldehydes derived from these olefins, it appears that their branching occurs mostly at the vinylic carbon.

Type IV olefins, i.e. trisubstituted ethylenes, were the smallest monoolefin components of these distillates.

Type V olefins, i.e., tetrasubstituted ethylenes, could not be determined by proton NMR. They are of little interest in the present invention since they are apparently unreactive in hydroformylation.

Finally, Table V also lists small but significant quantities (8 to 16%) of conjugated diolefins. The amounts listed for these olefins are approximate because conjugated olefins may have a different number of vinylic hydrogens per molecule dependent on the site of conjugation and the presence of branching at vinylic sites.

The NMR spectra of naphtha fractions were also analyzed in the area of aromatic and paraffinic protons to estimate the amounts of olefins. Table VI summarized the results. It shows the percentage distribution of various types of hydrogens. From this distribution and the elemental analyses of these fractions, the weight percentage of various types of compounds was estimated.

The Type I olefins, most 1-n-olefins were estimated to be present in these fractions in the range of 18.7 to 28.3%. These percentages depend on both the carbon number and the particular usually narrow boiling range of the olefinic fractions studied. In the $C_6$ to $C_{10}$ range these values for the Type I olefins approximately correspond to the values obtained for 1-n-olefin by GC.

The total olefin content of these fractions is in the 47 to 62% range as determined by NMR. It is noted that the conjugated diolefins are included in this percentage since they are converted to monoolefins under hydroformylation conditions or by a prior mild hydrogenation. The amounts of paraffins are generally decreasing with increasing carbon numbers while the amounts of the aromatics are generally increasing.

To illustrate the detailed composition of the present naphtha feeds, more detailed data are provided on the $C_8$ and $C_{10}$ fractions on the basis of GC and GC/MS analyses.

The composition of a heart cut $C_6$ Fluid-coker distillate fraction is shown by Table VII. This fraction was obtained by the redistillation using a 15 plate column and a 10 to 1 reflux ratio (15/10) of a broad $C_6$ cut. It

TABLE V

Relative Amounts of Various Types of Olefins in Fluid Coker Naphtha Determined by 400 MHz Proton Magnetic Resonance Spectroscopy

| Naphtha Carbon No. Boiling Point, °F. | $C_4$–$C_{12}$ | $C_5$ | $C_6$ | $C_7$ | $C_8$ | $C_8$ | $C_9$ | $C_{10}$ | $C_{11}$ | $C_{12}$ | Residue |
|---|---|---|---|---|---|---|---|---|---|---|---|
| Initial: | — | 80– | 140– | 195 | 245– | 254– | 293– | 335– | 374– | 410– | 425– |
| Final: | –410 | –100 | –150 | 205 | –257 | –262 | –30 | 359 | –390 | –425 | — |
| Olefin I: —CH=CH$_2$ | 37 | 31 | 50 | 42 | 36 | 32 | 44 | 43 | 39 | 36 | 16 |
| II: —CH=CH— | 20 | 25 | 18 | 25 | 26 | 26 | 22 | 22 | 23 | 28 | 28 |
| III: —C=CH$_2$ | 17 | 13 | 15 | 14 | 22 | 22 | 14 | 14 | 12 | 11 | 15 |
| IV: —C=CH— | 12 | 22 | 10 | 8 | 6 | 07 | 08 | 12 | 10 | 11 | 21 |
| Conjugated Diolefin$^a$ | 14 | 10 | 8 | 11 | 11 | 13 | 12 | 15 | 16 | 14 | 20 |

$^a$The conjugated diene values are only approximate.

Their relative molar concentrations is in the 6 to 12% range. Interestingly, the $C_8$ fractions contained the least of these olefins among the fractions examined.

distilled between 56 and 65° C. (133–149° F.) Table VII shows the composition of the broad cut feed and the heart cut product of distillation.

TABLE VI

Hydrogen Type Distribution Found and Olefins, Paraffins, Aromatics Estimate in Fluid Coker Naphtha by 400 MHz Proton Magnetic Resonance Spectroscopy

| Fraction Carbon Number | Boiling Range °C. | Hydrogen Distribution, Found % | | | | | | | Compound Types Estimated % | | | | | | | Total Olefins |
|---|---|---|---|---|---|---|---|---|---|---|---|---|---|---|---|---|
| | | Olefin Types | | | | Conj. Diene | Par- affins | Aro- matics | Olefin Types | | | | Conj. Diene | Par- affins | Aro- matics | |
| | | I | II | III | IV | | | | I | II | III | IV | | | | |
| 6 | 60–66 | 6.75 | 1.58 | 1.32 | 0.44 | 1.01 | 88.54 | 0.37 | 28.3 | 9.9 | 8.3 | 5.5 | 4.1 | 42.8 | 1.1 | 56.1 |
| 7 | 91–96 | 5.53 | 2.18 | 1.26 | 0.33 | 1.51 | 87.42 | 1.89 | 26.2 | 15.5 | 8.9 | 4.6 | 6.9 | 32.7 | 5.2 | 62.1 |
| 8 | 118–123 | 3.27 | 1.57 | 1.34 | 0.18 | 1.14 | 90.74 | 2.39 | 17.1 | 12.3 | 10.6 | 2.8 | 4.5 | 46.5 | 6.2 | 47.3 |
| 9 | 145–149 | 4.58 | 1.55 | 1.00 | 0.28 | 1.23 | 88.03 | 3.34 | 26.2 | 13.4 | 8.6 | 4.8 | 7.1 | 26.3 | 13.6 | 60.1 |

TABLE VI-continued

Hydrogen Type Distribution Found and Olefins, Paraffins, Aromatics Estimate in Fluid Coker Naphtha by 400 MHz Proton Magnetic Resonance Spectroscopy

| Fraction Carbon Number | Boiling Range °C. | Hydrogen Distribution, Found % | | | | | | | Compound Types Estimated % | | | | | | | Total Olefins |
|---|---|---|---|---|---|---|---|---|---|---|---|---|---|---|---|---|
| | | Olefin Types | | | | Conj. Diene | Par- affins | Aro- matics | Olefin Types | | | | Conj. Diene | Par- affins | Aro- matics | |
| | | I | II | III | IV | | | | I | II | III | IV | | | | |
| 10 | 168–177 | 3.28 | 1.11 | 0.74 | 0.23 | 0.97 | 89.97 | 3.70 | 20.8 | 10.6 | 7.0 | 44 | 6.0 | 33.9 | 17.3 | 48.8 |
| 11 | 190–199 | 1.11 | 0.57 | 0.25 | 1.13 | 1.13 | 89.75 | 4.37 | 19.1 | 11.2 | 5.8 | 5.1 | 7.5 | 28.7 | 22.6 | 48.7 |
| 12 | 210–218 | 2.39 | 1.25 | 0.47 | 0.24 | 0.90 | 89.03 | 6.02 | 18.7 | 14.0 | 7.1 | 4.5 | 7.0 | 23.5 | 25.2 | 51.3 |
| 4–12 | Feed | 4.26 | 1.57 | 1.29 | 0.45 | 1.66 | 85.52 | 5.27 | | | | | | | | |
| 12+ Residue | 425+ | 0.91 | 1.03 | 0.55 | 0.40 | 1.12 | 91.19 | 4.80 | | | | | | | | |

TABLE VII

COMPONENTS OF THE $C_6$ DISTILLATE CUT OF A FLUID-COKER NAPHTHA BEFORE AND AFTER REDISTILLATION

| Seq. No. | Component Name | Abbreviation | Boiling Point (Literature) –°F. approx. | °C. | Component GC, % Feed | Heart Cut | GC Retention Time Min |
|---|---|---|---|---|---|---|---|
| 1 | 1-Pentene | | 112 | 44.242 | 2.30 | — | 6.79 |
| 2 | n-Pentane | | 97 | 36.065 | 3.06 | — | 7.17 |
| 3 | 2-Methylbutene-2 | | 101 | 38.568 | 3.30 | 0.10 | 7.94 |
| 4 | Cyclopentene | CP= | 112 | 44.242 | 2.33 | 0.37 | 9.40 |
| 5 | 4-Methylpentene-1 | 4MeP= | 129 | 53.865 | 2.45 | 2.44 | 9.65 |
| 6 | 3-Methylpentene-1 | 3MeP= | 130 | 54.178 | 1.84 | 1.60 | 9.71 |
| 7 | Cyclopentane | CP | 121 | 49.262 | 1.91 | 0.81 | 9.97 |
| 8 | 2,3-Dimethylbutane | 2,3-DiMeB | 136 | 57.988 | 0.17 | 0.27 | 10.15 |
| 9 | 2,3-Dimethylbutene-1 | 2,3-DiMeB= | 132 | 55.616 | 0.68 | 0.78 | 10.20 |
| 10 | cis-4-Methylpentene-2 | c-4MeP=2 | 133 | 56.387 | 0.34 | 0.44 | 10.33 |
| 11 | 2-Methylpentane | 2MeP | 141 | 60.271 | 3.28 | 5.53 | 10.40 |
| 12 | trans-4-Methylpentene-2 | t-4MeP=2 | 139 | 58.612 | 1.71 | 2.37 | 10.48 |
| 13 | 3-Methylpentane | 3MeP | 146 | 63.282 | 1.76 | 3.58 | 11.22 |
| 14[a] | 2-Methylpentene-1 | 2MeP= | 144 | 62.113 | | | |
| 15 | 1-n-Hexene | n-H= | 146.5 | 63.485 | 21.13 | 42.00 | 11.65 |
| 16 | 3-Methylcyclopentene | 3MeCP= | 149 | 64.91 | 0.24 | 0.50 | 12.06 |
| 17 | n-Hexane | n-H | 156 | 68.736 | 10.61 | 13.71 | 12.38 |
| 18 | cis-3-Hexene | c-3H= | 152 | 66.450 | 1.50 | 2.45 | 12.52 |
| 19 | trans-3-Hexene | t-3H= | 153 | 67.088 | 3.15 | 4.25 | 12.69 |
| 20 | trans-2-Hexene | t-2H= | 154 | 67.884 | 5.18 | 8.38 | 12.86 |
| 21 | trans-3-Methylpentene-2 | t-3MeP=2 | 159 | 70.438 | 1.12 | 1.46 | 13.04 |
| 22 | 4-Methylcyclopentene | 4MeCP= | 150 | 65.67 | 1.05 | 1.93 | 13.11 |
| 23 | cis-2-Hexene | c-2H= | 156 | 68.891 | 1.64 | 1.64 | 13.31 |
| 24 | 2,3-Dimethylbutadiene | 2,3-DiMeB== | 154 | 67.78 | 0.16 | 0.20 | 13.46 |
| 25 | cis-3-Methylpentene-2 | c-2MeP=2 | 154 | 67.707 | 2.16 | 1.12 | 13.76 |
| 26 | Methylcyclopentane | MCP | 161 | 71.812 | 4.26 | 2.04 | 14.14 |
| 27[b] | 1,1,1-Trichloroethane | Cl$_3$CCH$_3$ | 165 | 74.10 | — | 0.05 | 15.02 |
| 28 | Methylcyclopentadiene | MeCP== | | | 0.59 | 0.12 | 15.02 |
| 29 | 1-Methylcyclopentene | 1-MeCP= | 168 | 75.49 | 0.54 | — | 15.79 |
| 30 | Benzene | Bz | 176 | 80.100 | 8.38 | 1.26 | 15.92 |
| 31 | Thiophene | S | 184 | 84.16 | 0.10 | 0.06 | 16.22 |
| | Total Identified | | | | 86.94[c] | 99.46 | |

[a]2-Methylpentene-1 was not separated from 1-n-hexene on the column used. It amounted to about 2%.
[b]Trichloroethane was present as an impurity as a result of using it as a solvent for cleaning the distillation apparatus.
[c]The feed contained significant amounts of higher boiling components.

Table VII shows that the largest components of both the feed and the heart cut were 1-n-hexene (n-H=) and n-hexane (n-H). There were also significant amounts of linear internal hexenes (16.7%) and methylpentenes (9.4% plus 2-methylpentene-1) in the heart cut. In addition, 1.9% of 4-methylcyclopentene and 0.5% of 3-methylcyclopentene were identified. Thus the amount of linear internal and monobranched olefins is about 28.5%. Only 0.8% of a dibranched olefin, 2, 3-dimethylbutene was found.

The composition of the heart cut is illustrated by the gas chromatogram of FIG. 3. The components are identified by the symbols explained in Table VII. FIG. 3 also shows the chromatogram of unconverted hydrocarbons remaining after the hydroformylation of the heart cut. The major unconverted components were n-hexane, methylpentanes and benzene as expected. The comparison of the chromatograms of the hydrocarbon components of the hydroformylation feed and the final reaction mixture greatly helped in the identification of the feed components.

Table VIII shows the composition of two $C_8$ fractions of a Fluid-coker naphtha. It is apparent that beside the major 1-octene component, there are significant quantities of all the linear internal octene isomers. The trans-isomers of octene-2,3, and 4 were identified. 2-Methylheptene-1 was also identified as the largest single branched octene. Toluene, ethylbenzene and xylenes were also present.

One fraction is richer in 1-n-octene, the other in n-octane. The sum of identified olefins in these fractions is 33.1% and 20.1%, respectively. Some of the octene isomers were not identified. The first fraction richer in olefins was used as the feed in the $C_8$ naphtha hydroformylation experiments.

The composition of $C_8$ Flexicoker naphtha fractions was also studied in some detail. At first a broad $C_8$ cut was obtained by a 15/10 fractional distillation between 110 and 135° C. (230-275° C.). Part of this broad cut was then redistilled with a 36 plates column using a reflux ratio 20 (26/20). Fractions of the 36/20 distillation boiling between 117 and 124° C. (243-255° F.) were combined to provide a narrow cut in about 42% yield.

Table IX shows the composition of the above broad and narrow $C_8$ Flexicoker naphtha fractions. A comparison of the capillary GC data of Tables VIII and IX indicates that the composition of these Fluid-coker and Flexicoker naphthas is similar in spite of their different crude sources. The narrow cut Flexicoker naphtha feed contains higher amounts of linear octenes than the broad fraction (36.45 versus 16.09).

TABLE VIII

Major Olefin, Paraffin and Aromatic Hydrocarbon Components of Distillate Fractions of Fluid Coker Naphtha in the C8 Range

| Designation of Fraction | Weight % Composition by GC | | | |
|---|---|---|---|---|
| | 1-Octene Rich | | n-Octane Rich | |
| Fraction No. | 11 | | 12 | |
| Quantity, g | 2072 | | 1034 | |
| Boiling Point Range, °F. | 245-254 | | 254-262 | |
| °C. | 118-123 | | 123-128 | |
| | Others % | Olefins % | Olefins % | Others % |
| Toluene | 4.3 | | | 1.3 |
| 2-Methylheptene-1 | | 6.3 | 3.2 | |
| Octene-1 | | 18.5 | 10.3 | |
| trans-Octene-4 | | 1.0 | 0.6 | |
| trans-Octene-3 | | 2.1 | 1.3 | |
| n-Octane | 19.9 | | | 16.3 |
| trans-Octene-2 | | 3.6 | 2.8 | |
| cis-Octene-2 | | 1.6 | 1.8 | |
| Ethylbenzene | 0.6 | | | 6.1 |
| m-Xylene | 0.1 | | | 5.1 |
| p-Xylene | | | | 1.8 |
| o-Xylene | | | | 0.8 |
| Nonene-1 | | | | |
| Sum of Identified Compounds | 24.9 | 33.1 | 20.1 | 31.4 |

TABLE IX

Key Components of the $C_8$ Baytown Flexicoker Naphtha Feeds

| Component Identification[a] | | | Concentration of Components, % | |
|---|---|---|---|---|
| | Boiling Point | | Broad Bp. 110-135° C. 230-275° F. | Narrow Bp. 117-124° C. 243-255° F. |
| Name | °C. | °F. | | |
| 1-n-Heptene | 94 | 201 | 0.14 | — |
| n-Heptane | 98 | 208 | 0.32 | — |
| Methylcyclohexane | 101 | 214 | 0.57 | — |
| 3-Methylcyclohexene[b,c] | 104 | 219 | 0.38 | 0.15 |
| Toluene[d] | 111 | 232 | 6.39 | 0.15 |
| 4-Methyl-1-Heptene | 113 | 235 | 2.47 | 0.49 |
| 2-Methylheptane | 117 | 243 | 2.94 | 3.67 |
| 6-Methyl-1-Heptene[b] | | | 1.38 | 1.53 |
| 1,3-cis-Dimethylcyclohexane[b] | 120 | 248 | 2.02 | 3.31 |
| 2-Methyl-1-Heptene[e] | 118 | 244 | 4.08 | 7.82 |
| 1-n-Octene | 121 | 250 | 11.07 | 28.12 |
| 4-Octene | | | 0.97 | 2.62 |
| 3-Octene | 123 | 253 | 0.98 | 3.09 |
| n-Octane | 126 | 259 | 9.98 | 20.01 |
| trans-2-Octene | 125 | 257 | 1.82 | 2.86 |
| Dimethylhexadiene[b] | | | 1.78 | 4.28 |
| cis-2-Octene | 126 | 259 | 1.25 | 1.76 |
| Dimethylcyclohexene[b] | | | 1.72 | 1.22 |
| Ethylbenzene | 136 | 277 | 3.22 | 0.09 |
| 2.6-Dimethyl-1-Heptene[b] | | | 2.18 | — |
| m,p-Xylenes | 138 | 280 | 6.03 | — |
| o-Xylene | 144 | 291 | 1.02 | — |
| 1-n-Nonene | | | 0.57 | — |
| n-Nonane | 151 | 304 | 0.23 | — |

[a]Identification based on GC, GC/MS and boiling point correlations.
[b]The identification is tentative.
[c]1-Methyl-cyclohexene is also indicated.
[d]2.4-Dimethyl-1-hexene is also indicated.
[e]3-Methyl-1-heptene is also indicated.

Most significantly, the percentage of 1-n-octene in the narrow cut is 28.12% while it is only 11.07% in the broad cut.

The broad cut naphtha is richer in branched olefins including $C_7$ and $C_9$ compounds of an open chain and branched character. In contrast to the narrow fraction, the broad cut had significant amounts of aromatic compounds; 6.39% toluene, 3.22% ethylbenzene, 7.05% xylenes.

In the broad cut naphtha the presence in small amounts of a high number of monobranched olefins was indicated. The largest of these 2-methyl-1-heptene is present in both the broad and narrow cuts in concentrations of 4.08 and 7.82%, respectively. There are also other methyl branched, mainly terminal, methylheptenes present. However, the exact structures of these compounds are not known with certainty. In addition, there are branched, cyclic olefins present, particularly methylcyclohexene and dimethycyclohexene.

FIG. 4 illustrates the composition of the narrow cut $C_8$ Flexicoker naphtha. It is noted that most of the olefin components are linear or monobranched compounds. The cyclic olefins are largely excluded from this fraction.

The sulfur content of the broad $C_8$ fraction is 1% while that of the narrow $C_8$ fraction is 0.2%. The concentration of the main sulfur containing compounds, i.e.

methylthiophenes and dimethylthiophenes is drastically cut in the narrow fraction. The distribution of the sulfur compounds in the two fractions is indicated by the sulfur specific gas chromatograms of FIG. 5. Although the sulfur response of the detector is close to quadratic rather than being linear, the figure shows that the thiophenic sulfur was largely removed by fractionation from the narrow fraction.

Extraction of the narrow cut with 30% KOH solution in methanol containing 2% water resulted in a further reduction of the sulfur content. It was specifically shown by sulfur GC that the pentanethiol component was completely removed.

FIG. 6 illustrates the composition of the $C_{10}$ naphtha fraction. As it is indicated, besides the main 1-n-decene component several of the linear decenes and 2-methyl nonene-1 were identified. It was also shown that indene, a reactive, aromatic cycloolefin, is also present in this fraction. The main aromatic hydrocarbon components are trimethylbenzenes and indane.

The naphtha and its distillate fractions were also analyzed for sulfur and nitrogen compounds. Table X shows the carbon, hydrogen mercaptan and total sulfur plus total nitrogen contents.

The mercaptan content of the $C_8$ and higher fractions is surprisingly low compared to the high total sulfur content when determined by mercaptan titration by silver nitrate. It is believed that this is in part due to the facile cooxidation of mercaptans and activated olefins. The total sulfur content generally increased with the carbon number of the distillates from the $C_6$ fraction upward. Assuming the sulfur compounds of the various fractions had two fewer carbons per molecule than the corresponding hydrocarbon compounds, it was calculated that in the $C_5$ to $C_{12}$ range the approximate percentage of sulfur compounds has increased from 0.4 to 7%. In contrast to sulfur, the total nitrogen content of the $C_4$ to $C_{12}$ fractions was generally less than 160 ppm.

The mercaptan content of the two combined $C_8$ fractions (shown in Table X) was also determined be difference. At first, the total sulfur was determined by sulfur specific GC. Then the mercaptans were removed by precipitating them as silver mercaptides. Based on such an analysis, the following ppm concentrations were obtained for the various sulfur compounds in the order of their retention times: 2-methyl- and 3-methyl thiophenes, 962 and 612; n-pentane and n-hexanethiols, 106 and 78; $C_6$ branched thioether, 200; 1-hexanethiol, 384; 2,5-, 2,4-, 2,3-, 3,4-dimethylthiophenes, 1245, 945, 728, 289; unknown sulfur compounds, 11. Thus, this analysis provided a total sulfur content of 5560 ppm and a mercaptan content of 568. The main group of sulfur compounds were thiophenes in a concentration of 3781 ppm.

Coker Gas Oil

Similar characterizations were performed on a light coker gas oil produced by the same Fluid-coking unit from which the coker naphtha was taken.

FIG. 7 shows the capillary GC of the light gas oil in the $C_9$ to $C_{16}$ range. About 90% of the components are in the $C_{10}$ to $C_{15}$ carbon range. The $C_{11}$ to $C_{13}$ components are particularly large. Obviously, there is some overlap between this composition and that of the broad cut naphtha.

As it is indicated by the symbols of the figure, the main components are the 1-n-olefins and the n-paraffins. In general, the concentrations of the 1-n-olefins are greater than those of the corresponding paraffins. The 1-n-olefins to n-paraffin ratio is apparently maintained with increasing carbon numbers.

The light gas oil fraction was fractionally distilled to produce narrow cur distillates of a particular carbon number. The fractions obtained were then analyzed by GC. The data are summarized in Tables XI and XII. The tables show the amounts of the individual cuts, the percentage concentration of the main paraffin and olefin components and separately list the heart cuts of particularly high content of a 1-n-olefin of a certain carbon number. These heart cuts were utilized in subsequent hydroformylation experiments.

The data of the tables show that 54% (44,439 g) of the distillate were in the $C_{12}$ to $C_{15}$ olefin range. It is noted that the percentage values for the 1-n-olefin and n-paraffin components are relative. Absolute values could not be determined. With the increasing molecular weight of these fractions, the number of isomers is sharply increasing. Thus, the GC resolution is decreased and absolute accuracy decreased. Nevertheless, it appears at least in a qualitative sense that the 1-n-olefin concentrations are maintained.

The $C_9$ to $C_{16}$ gas oil and selected distillate fractions were also studied by proton NMR. The results are illustrated by the spectrum of FIG. 8 which shows the aromatic, olefinic and paraffinic hydrogens. A quantitative analysis of the spectrum showed that this gas oil is highly olefinic with a strong aliphatic character in that 88.2% of the hydrogens in the mixture are on saturated carbons, 6.2% on olefinically unsaturated carbons and only 5.6% on aromatic rings. Overall, the gas oil has a significantly higher percentage of linear olefins than does the coker naphtha as is shown by the following tabulation:

TABLE X

Elemental Analyses of Distillate Fractions of Fluid Coker Naphtha

Carbon Hydrogen Sulfur and Nitrogen Content of Naphtha and its Fractions

| Naphtha Carbon Number Boiling Point, °F.: Initial Final | $C_4$-$C_{12}$ — −410 | $C_5$ 80— −100 | $C_6$ 140— −150 | $C_7$ 195— −205 | $C_8$ 245— −257 | $C_9$ 290— −300 | $C_{10}$ 335— −350 | $C_{11}$ 374— −390 | $C_{12}$ 410— −425 | Residue 425— — |
|---|---|---|---|---|---|---|---|---|---|---|
| Carbon, % | | | 85.64 | 85.81 | 85.83 | 86.10 | 86.41 | 86.11 | 85.98 | 85.23 |
| Hydrogen, % | | | 14.39 | 14.01 | 13.49 | 13.18 | 12.95 | 12.39 | 12.33 | 10.75 |
| Mercaptan Sulfur (SH), ppm | 600 | 1770 | 850 | 450 | 80 | 20 | 60 | 30 | 100 | 490 |
| Total Sulfur, ppm | 8900 | 1700 | 1300 | 2200 | 5100 | 5900 | 8800 | 12,000 | 13200 | — |
| Total Nitrogen, ppm | 159 | 141 | 46 | 25 | 45 | 158 | 134 | 135 | 136 | 1022 |
| % SH (100 SH/Total) | 6.74 | ~100 | 65.38 | 20.45 | 1.57 | 0.34 | 0.68 | 0.25 | 0.76 | |
| Total Sulfur Compounds, % | | 0.40 | 0.36 | 0.71 | 1.86 | 2.42 | 3.99 | 5.96 | 7.14 | |

*The percentages of sulfur compounds in the various distillate fractions were calculated, assuming that they contain 2 carbon less per molecule than the hydrocarbon compounds of the fraction of a certain carbon number.

TABLE XI

$C_7$-$C_{11}$ Distillate Fractions of Light Coker Gas Oil

| Fraction No. E-7315 | Boiling Range, °F. Atmospheric (Calculated) | Boiling Range, °F. Vacuum Found/mm | Weight % of Total | Weight Amount g | Main Components, Carbon No. & % 1-n-Olefin | Main Components, Carbon No. & % n-Paraffin | Main Components, Carbon No. & % 1-n-Olefin | Main Components, Carbon No. & % n-Paraffin | Combined Heart Cuts Wt. % of Total | Combined Heart Cuts Amount g | Combined Heart Cuts Carbon Number | Combined Heart Cuts 1-n-Olefin % | Combined Heart Cuts n-Paraffin % |
|---|---|---|---|---|---|---|---|---|---|---|---|---|---|
| III | −250/750 | — | 1.95 | 1608 | $C_7^=4.8$ | $C_7^°4.7$ | $C_8^=4.0$ | $C_8^°3.0$ | | | | | |
| IV | 250-262/750 | — | 0.45 | 373 | $C_8^=10.8$ | $C_8^°11.1$ | | | 0.45 | 373 | 8 | 10.8 | 11.8 |
| V | 262-293/750 | — | 1.69 | 1393 | $C_8^=3.1$ | $C_8^°3.9$ | $C_9^=6.5$ | $C_9^°3.4$ | | | | | |
| VI | 293-307/750 | — | 1.38 | 1132 | $C_9^=12.5$ | $C_9^°11.9$ | | | 1.38 | 1132 | 9 | 12.5 | 11.9 |
| VII | 307-3331/750 | — | 3.58 | 2944 | $C_9^=4.9$ | $C_9^°5.4$ | $C_{10}^=9.9$ | $C_{10}^°3.8$ | | | | | |
| VIII | 331-335/750 | — | 0.81 | 667 | $C_9^=1.3$ | $C_9^°1.6$ | $C_{10}^=15.3$ | $C_{10}^°9.17$ | | | | | |
| IX | 335-345/750 | — | 2.39 | 1965 | $C_9^=0.7$ | $C_9^°0.7$ | $C_{10}^=18.3$ | $C_{10}^°13.7$ | 2.39 | 1965 | 10 | 18.3 | 13.7 |
| X | 345-355/750 | — | 1.90 | 1560 | $C_{10}^=10.6$ | $C_{10}^°8.5$ | $C_{11}^=1.7$ | $C_{11}^°3.4$ | | | | | |
| XI | 355-365/750 | — | 2.30 | 1892 | $C_{10}^=5.3$ | $C_{10}^°4.9$ | $C_{11}^=19.5$ | $C_{11}^°10.5$ | | | | | |
| XII | 365-371/750 | — | 2.66 | 2189 | $C_{10}^=2.9$ | $C_{10}^°2.9$ | $C_{11}^=19.5$ | $C_{11}^°10.5$ | | | | | |
| XIII | (371-375/At) | −220/50 | 1.77 | 1458 | $C_{10}^=2.5$ | $C_{10}^°2.5$ | $C_{11}^=12.7$ | $C_{11}^°4.5$ | 7.65 | 6290 | 11 | 19.5 | 10.2 |
| XIV | (375-385/At) | 220-229/50 | 3.58 | 2947 | $C_{11}^=22.8$ | $C_{10}^°11.8$ | | | | | | | |
| XV | (385-395/At) | 229-238/50 | 3.66 | 3011 | $C_{11}^=6.6$ | $C_{11}^°13.3$ | | | | | | | |
| XVI | (395-405/At) | 238-246/50 | 3.58 | 2946 | $C_{11}^=1.3$ | $C_{11}^°3.1$ | $C_{12}^=2.1$ | $C_{12}^°0.3$ | | | | | |

TABLE XII
$C_{12}$-$C_{16}$ Distillate Fractions of Light Fluid Coker Oil

| Fraction No. E-7315 | Boiling Range, °F. Atmospheric (Calculated) | Boiling Range, °F. Vacuum Found/mm | Weight % of Total | Weight Amount g | Main Components, Carbon No. & % 1-n-Olefin | Main Components, Carbon No. & % n-Paraffin | Main Components, Carbon No. & % 1-n-Olefin | Main Components, Carbon No. & % n-Paraffin |
|---|---|---|---|---|---|---|---|---|
| XVII | 405–412 | −213/20 | 3.73 | 3070 | $C_{12}$=13.3 | $C_{12}°4.4$ | | |
| XVIII | 412–415 | 213–216/20 | 1.70 | 1401 | $C_{12}$=25.7 | $C_{12}°12.6$ | | |
| XIX | 415–423 | 216–222/20 | 3.72 | 3060 | $C_{12}$=22.5 | $C_{12}°23.5$ | | |
| XX | 425–425 | 222–2224/20 | 0.93 | 769 | $C_{12}$=13.3 | $C_{12}°27.7$ | | |
| XXI | 425–432 | 224–230/20 | 3.61 | 2967 | $C_{12}$=5.4 | $C_{12}°10.5$ | | |
| XXII | 432–435 | 230–232/20 | 1.28 | 1050 | $C_{12}$=0.8 | $C_{12}°4.1$ | | |
| XXIII | 435–442 | 232–238/20 | 3.82 | 3146 | $C_{13}$=4.0 | $C_{13}°0.9$ | | |
| XXIV | 442–445 | 238–242/20 | 2.07 | 1700 | $C_{13}$=15.9 | $C_{13}°6.2$ | | |
| XXV | 445–448 | −216/10 | 3.81 | 3134 | $C_{13}$=23.0 | $C_{13}°12.2$ | | |
| XXVI | 448–455 | 216–221/10 | 3.62 | 2977 | $C_{13}$=23.1 | $C_{13}°26.6$ | | |
| XXVII | 455–455 | 221–222/10 | 0.70 | 576 | $C_{13}$=12.2 | $C_{13}°27.8$ | | |
| XXVIII | 455–465 | 222–230/10 | 3.81 | 3134 | $C_{13}$=5.2 | $C_{13}°12.5$ | | |
| XXIX | 465–472 | 230–236/10 | 3.05 | 2506 | $C_{13}$=0.7 | $C_{13}°2.2$ | $C_{14}$=4.8 | $C_{14}°1.2$ |
| XXX | 472–475 | 236–238/10 | 1.15 | 947 | $C_{14}$=13.0 | $C_{14}°4.7$ | | |
| XXXI | 475–481 | 238–243/10 | 3.75 | 3086 | $C_{14}$=19.8 | $C_{14}°10.2$ | | |
| XXXII | 481–485 | 243–246/10 | 3.30 | 2717 | $C_{14}$=21.9 | $C_{14}°24.3$ | | |
| XXXIII | 485–495 | −229/5 | 3.27 | 2692 | $C_{14}$=4.5 | $C_{14}°13.6$ | | |
| XXXIV | 495–505 | 229–237/5 | 2.66 | 2187 | $C_{14}$=0.3 | $C_{14}°0.3$ | | |
| XXXV | 505–515 | 237–245/5 | 0.86 | 709 | $C_{15}$=35.0 | $C_{15}°31.2$ | | |
| XXXVI | 517–522 | 245–273/5–8 | 3.78 | 3111 | $C_{15}$=23.2 | $C_{15}°27.6$ | $C_{16}$=3.4 | $C_{16}°2.3$ |
| XXXVIII | 525–535 | −242/3 | 1.96 | 1614 | $C_{16}$=16.0 | $C_{16}°21.7$ | $C_{17}$=3.6 | $C_{17}°3.1$ |
| Total Distillates Tables I & II | | | 88.31 | 72638 | | | | |
| XXXVIII Distillation Residue | | | 11.69 | 9620 | | | | |

| Fraction No. E-7315 | Combined Heart Cuts Wt. % of Total | Combined Heart Cuts Amount g | Combined Heart Cuts Carbon Number | Combined Heart Cuts 1-n-Olefin % | Combined Heart Cuts n-Paraffin % |
|---|---|---|---|---|---|
| XVII XVIII XIX XX XXI XXII XXIII XXIV XXV | 10.09 | 8300 | 12 | 18.8 | 16.4 |
| XXVI XXVII XXVIII XXIX XXX XXXI | 10.20 | 8387 | 13 | 19.7 | 18.2 |
| XXXII XXXIII XXXIV XXXV | 7.05 | 5803 | 14 | 20.8 | 16.8 |
| XXXVI XXXVIII | 4.63 | 3810 | 15 | 24.7 | 28.2 |
| Total Distillates Tables I & II | 49.50 | 35.960 | | | |

| Type | Vinylic Segment | Mole % Unsaturation Gas Oil $C_{10}$-$C_{15}$ | Mole % Unsaturation Naphtha* $C_4$-$C_{12}$ |
|---|---|---|---|
| I | —CH=CH$_2$ | 42 | 37 |
| II | —CH=CH— | 22 | 20 |
| III | —C=CH$_2$ | 16 | 17 |
| IV | —C=CH— | 7 | 12 |
| Conj. Diolefin | —C=C—C=C— | 14 | 14 |

*From Table IV.

Type I olefins represent about 42% of the total olefin content in the gas oil and about 37% in the naphtha. Most of the Type I olefins are 1-n-olefins which do not have branching anywhere on their hydrocarbon chain. The mass spectrometry data indicated that branching is mostly by methyl groups on the vinylic double bonds.

Selected distillate cuts of the light gas oil were also analyzed by NMR in a similar manner. The distribution of their vinylic hydrogens was particularly studied to determine the relative amounts of the various types of olefins present. The results are summarized in Table XIII.

The data of Table XIII show that the relative olefin percentages of the distillate cuts vary. However, the percentages of the Type I olefins, including the desired 1-n-olefins, is generally more than a third of the total. The Type I and II olefins combined, which includes all the linear olefins represent more than 55% of the total. The vinylically branched olefins are present in less than 35% amounts. The percentages of the conjugated diolefins are included in the table since they are converted to monoolefins during hydroformylation. However, the diene structures are uncertain and as such of approximate values.

Table XIII also shows the distribution of olefin types in the case of four narrow cut $C_{12}$ distillate fractions. As expected, varying amounts of the different types of olefins of different boiling points were found to be present. Thus the proportion of the Type I olefins changed from 45.5 to 33.8%.

pounds according to polarity in the lower part of the Figure. The upper chromatogram produced by the

TABLE XIII

Relative Amounts of Various Types of Olefins in Light Fluid Coker Gas Oil Determined by 400 mHz Proton Magnetic Resonance Spectroscopy

| Gas Oil Carbon Number | $C_9$-$C_{16}$ | $C_9$ | $C_{11}$ | $C_{12}$ | $C_{13}$ | $C_{14}$ | $C_{15}$ | $C_{16}$ | Narrow $C_{12}$ Cuts | | | |
|---|---|---|---|---|---|---|---|---|---|---|---|---|
| Boiling Point, °F. Initial | 293 | 335 | 365 | 405 | 442 | 475 | 505 | 525 | 405 | 412 | 415 | 423 |
| Calcd. for 1 Atm. Final | 307 | 345 | 385 | 425 | 454 | 485 | 522 | 535 | 412 | 415 | 423 | 425 |
| Olefin I: —CH=CH$_2$ | 42 | 37.1 | 43.6 | 40.0 | 38.5 | 43.5 | 44.0 | 37.9 | 43.4 | 45.5 | 42.5 | 33.8 |
| II: —CH=CH— | 22 | 16.4 | 16.8 | 22.0 | 17.3 | 21.2 | 21.6 | 16.2 | 19.6 | 17.5 | 20.3 | 23.4 |
| III: —C=CH$_2$ $\mid$ | 16 | 16.4 | 12.3 | 13.4 | 18.7 | 16.1 | 12.2 | 18.6 | 15.6 | 12.3 | 12.0 | 14.5 |
| IV: —C=CH— $\mid$ | 7 | 18.3 | 15.9 | 12.7 | 15.5 | 9.1 | 13.1 | 15.9 | 9.5 | 14.7 | 14.0 | 15.1 |
| Conjugated Diolefins | 14 | 11.8 | 11.3 | 11.9 | 10.1 | 10.1 | 9.1 | 11.3 | 11.9 | 9.9 | 11.2 | 13.2 |

The percentages of various types of olefinic hydrogens, are shown by Table XIV. From the hydrogen distributions, the weight percentages of the various types of olefins were estimated. As it is shown by Table XII, the estimate of total olefins including dienes is between 50.4 and 61.7%. It is noted that the 61.7% value is for the $C_{16}$ fraction which was distilled with decomposition. As a result of cracking this fraction contained not only $C_{16}$ range, four narrow cut fractions were analyzed to determine changes in the proportion of different types of compounds. Only moderate changes were found in total olefin concentration (45.5 to 54.4%).

To illustrate the detailed composition of the present gas oil feeds, more detailed data are provided on a narrow $C_{12}$ fraction on the basis of GC/MS analyses. Such a cut cannot be separated on a nonpolar (boiling point) methylsilicone GC column. However, it was found that a highly polar type CP Sil 88 column (with a cyanopropylated silicone stationary phase) separated the various types of components according to their polarity. [This column is particularly suitable for the analysis of high boiling fractions since it has a high use temperature limit (about 275° C.)]. These components could then be largely identified via GC/MS studies. Two capillary GC traces with the groups of components identified are shown by FIG. 9.

The effluent of the above polar capillary column was split and led to a flame ionization and a sulfur specific detector. The chromatogram of the flame ionization detector shows the distribution of the organic compounds according to polarity in the lower part of the Figure. The upper chromatogram produced by the sulfur specific detector shows the elution of the sulfur compounds in the order of their polarity.

The lower GC of FIG. 9 shows good separation of the aliphatic, monoaromatic and diaromatic hydrocarbon components of the $C_{12}$ fraction. With the help of GC/MS the aliphatic components could be broken down to paraffins, olefins plus diolefins. Their percentages were 18.6 and 50.5%, respectively. The monoaromatics included alkylbenzenes, naphthenobenzenes and trace amounts of alkylthiophenes. The total amount of monoaromatics was 28.2%. The main diaromatic compounds were indene, nephthalene and benzothiophene. Surprisingly, trace amounts of trimethyl phenols were also found.

The upper, sulfur specific GC of FIG. 6 shows that essentially all the sulfur compounds of the $C_{12}$ fraction were aromatic.

The majority were alkyl thiophenes. Benzothiophene was also present in significant amounts.

A similar analysis of the $C_{14}$ fraction showed an even better separation of the components according to their polarity. In this case the distribution of the aliphatic components was similar but the major aromatic components were dinuclear: methylnaphthalenes and methylbenzothiophenes.

The distillate fractions of light gas oil were also analyzed for elemental composition, particularly for sulfur and nitrogen compounds and mercaptans. The data obtained are summarized in Table XV.

TABLE XIV

Hydrogen Distribution and Percentage of Various Types of Olefins Estimated in Light Fluid Coker Gas Oil by 400 MHz Proton Nuclear Magnetic Resonance Spectroscopy

| Distillate Fraction | | Hydrogen Distribution Found % | | | | | | | Olefin Types Estimated, % | | | | | |
|---|---|---|---|---|---|---|---|---|---|---|---|---|---|---|
| Carbon Number | Boiling Range °C./mm | Olefin Types | | | | Conj. Diene | Paraffins | Aromatics | Olefin Types | | | | Conj. Dienes | Total Olefins |
| | | I | II | III | IV | | | | I | II | III | IV | | |
| 9 | 145–153/Atm | 3.76 | 1.10 | 1.10 | 0.62 | 1.21 | 86.45 | 5.77 | 19.9 | 8.8 | 8.8 | 9.8 | 6.3 | 53.5 |
| 11 | 185–196/Atm | 3.71 | 0.96 | 0.70 | 0.45 | 0.97 | 88.44 | 4.78 | 24.4 | 9.5 | 6.9 | 8.9 | 6.3 | 56.0 |
| 12 | 100–106/20 | 3.15 | 1.16 | 0.70 | 0.25 | 0.96 | 88.80 | 4.99 | 21.8 | 12.0 | 7.3 | 6.9 | 6.5 | 54.4 |
| 13 | 114/20–105/10 | 2.68 | 0.80 | 0.90 | 0.36 | 0.71 | 88.14 | 6.41 | 19.4 | 8.7 | 9.4 | 7.8 | 5.1 | 50.4 |
| 14 | 114–119/10 | 2.76 | 0.90 | 0.68 | 0.19 | 0.64 | 88.48 | 6.35 | 21.1 | 10.3 | 7.8 | 4.4 | 4.9 | 47.5 |
| 15 | 114–118/5 | 2.42 | 0.79 | 0.45 | 0.24 | 0.50 | 90.50 | 5.10 | 19.8 | 9.7 | 5.5 | 5.9 | 4.0 | 45.5 |
| 16 | −117/3 | 2.56 | 0.73 | 0.84 | 0.36 | 0.78 | 89.97 | 4.75 | 23.4 | 10.0 | 11.5 | 9.8 | 7.0 | 61.7 |
| 12 | 100/20 | 2.99 | 0.90 | 0.72 | 0.44 | 0.83 | 83.37 | 6.75 | 19.7 | 8.9 | 7.1 | 4.3 | 5.4 | 45.5 |
| 12 | 100–102/20 | 3.54 | 0.91 | 0.64 | 0.38 | 0.72 | 89.22 | 4.57 | 24.7 | 9.5 | 6.7 | 8.0 | 5.4 | 54.4 |
| 12 | 102–105/20 | 3.09 | 0.98 | 0.58 | 0.34 | 0.72 | 90.60 | 3.69 | 21.6 | 10.3 | 6.1 | 7.1 | 5.7 | 50.8 |
| 12 | 105–110/20 | 2.33 | 1.06 | 0.66 | 0.34 | 0.83 | 91.12 | 3.66 | 16.6 | 11.5 | 7.1 | 7.4 | 6.5 | 52.1 |

The percentage of carbon and hydrogen were rather well maintained with increasing molecular weights. They indicate that the aliphatic character of the gas oil was fairly maintained. The total sulfur content remained at about 1% in the $C_9$ to $C_{12}$ range. Thereafter, there was a rapid increase of sulfur up to 2.82% in the $C_{16}$ fraction. It is noted that there was increasing decomposition during the distillation of these fractions. When the $C_{16}$ fraction was redistilled a broad molecular weight range of 1-n-olefins was found in the distillates. This suggests the breakdown of nonvolatile aliphatic sulfur compounds to generate olefins and mercaptans.

The total nitrogen contents of the distillates were more than an order less than that of the total sulfur. The mercaptan content is generally even lower. However, both the nitrogen and mercaptan contents rose sharply in the $C_{15}$ and $C_{16}$ fractions.

Experimental Procedures

Except as otherwise specified in the examples, the processes found in those examples were carried out using the following experimental procedures.

Low and Medium Pressure Hydroformylation

The low and medium pressure hydroformylation experiments employed 300 ml and 150 ml steel autoclaves, respectively. Both autoclaves were equipped with impeller type stirrers operating at 1500 rpm. The total liquid feed was 100 g and 50 g, respectively.

In a standard hydroformylation experiment, 80% of the feed was placed into the autoclave and deoxygenated with repeated pressurization with nitrogen. The solution, now at atmospheric nitrogen pressure, was then sealed and pressured with 1:1 $H_2/CO$ to 50% of the reaction pressure.

The catalyst precursors, i.e., rhodium carbonyl acetylacetonate, dicobalt tetracarbonyl or dicobalt octacarbonyl plus the appropriate phosphorus ligand, were dissolved in 20% of the feed and placed into a pressure vessel connected to the initial $H_2/CO$ feed line and the autoclave.

The autoclave was then heated to the reaction temperature. Thereafter the catalyst solution, about 40 or 80 ml dependent on the volume of the autoclave, was pressured into the autoclave by the initial feed gas and the desired reaction pressure was established without stirring.

Thereafter, a switch was made to the feed gas pressure vessel of known volume which contained an appropriate mixture of $H_2/CO$ at higher initial pressure. Then the stirring of the reaction mixture started. This resulted in efficient contact of the gaseous $H_2/CO$ with the liquid reaction mixture. As the reaction proceeded, the reactor pressure dropped due to the $H_2/CO$ reactant gas consumption. In response, feed gas was automatically provided as needed to maintain the pressure in the reactor. The feed gas had an appropriately high $H_2/CO$ ratio above one so as to provide $H_2$ not only for the main hydroformylation reaction but the hydrogenation side reactions as well.

The progress of the hydroformylation was followed on the basis of the CO and $H_2$ consumed. The latter was calculated on the basis of the pressure drop in the 1 liter $H_2/CO$ cylinder. Reactant conversion was estimated by plotting the CO consumption against the reaction time. In some cases, reaction rates were also estimated in spite of the complexity of the feeds and were expressed as the fraction of the theoretical $H_2/CO$ consumer per minute. Reaction rate constants were normalized for 1 M transition metal concentration, assuming a first order rate dependence on the metal concentration.

When the reaction was discontinued, the $H_2/CO$ valve was shut and the autoclave immediately cooled by water. The synthesis gas in the head space of the autoclave was analyzed to determine the $H_2$ to CO ratio. After the release of excess $H_2/CO$, the residual liquid reaction mixture was also analyzed to determine conversion selectivity. For these analyses a capillary gas chromatograph with a 50 m fused silica column was used.

Reactant conversions and product selectivities were also estimated on the basis of the gas chromatograms of the reaction mixture. The conversion of 1-n-olefins could be usually determined on the basis of the reduction of their peak intensities compared to those of the inert paraffins. These conversions could be correlated with the formation of the corresponding n-aldehyde and 2-methyl branched aldehyde products. When comparing hydrocarbon signal intensities with those of alde-

TABLE XV

| | Elemental Composition of Light Fluid Coker Gas Oil | | | | | | | | | | | |
|---|---|---|---|---|---|---|---|---|---|---|---|---|
| Gas Oil Carbon Number | $C_9$ | $C_{10}$ | $C_{11}$ | $C_{12}$ | | | | | $C_{13}$ | $C_{14}$ | $C_{15}$ | $C_{16}$ |
| Boiling Point, °F.  Initial | 293 | 335 | 365 | 405 | 405 | 412 | 415 | 423 | 442 | 475 | 505 | 525 |
| (Calcd. for 1 Atm) Final | 307 | 345 | 385 | 425 | 412 | 415 | 423 | 425 | 454 | 485 | 522 | 535 |
| Carbon, % | 86.10 | 85.62 | 85.77 | 86.17 | 85.71 | 85.11 | 85.48 | 86.14 | 85.74 | 85.65 | 84.51 | 84.77 |
| Hydrogen, % | 12.58 | 12.40 | 12.81 | 12.29 | 11.79 | 12.47 | 12.47 | 12.89 | 11.92 | 11.69 | 11.69 | 12.22 |
| Total Sulfur, % | 1.06 | 1.06 | 1.01 | 1.15 | 1.39 | 1.14 | 0.96 | 1.56 | 2.34 | 2.62 | 2.82 | |
| Total Nitrogen, % | .0163 | .0244 | .0243 | 0.0131 | .0294 | .0364 | .0352 | .0289 | .0395 | .0306 | .0652 | .0713 |
| Mercaptan Sulfur, % | .0084 | | .0105 | .0118 | .0132 | .0115 | .0116 | .0127 | .0061 | .0084 | .0825 | 0.1395 |
| Sulfur Compounds, %[a] | 4.17 | 4.63 | 4.86 | 5.53 | 6.69 | 5.49 | 4.62 | 4.68 | 7.50 | 12.28 | 14.90 | 17.27 |

[a]The weight percentages of sulfur compounds were calculated on the basis of total sulfur found assuming that the sulfur compounds were $C_3$ to $C_5$ alkylthiophenes in the $C_9$ to $C_{11}$ olefin range, benzothiophene in the $C_{12}$-$C_{13}$ range, $C_1$ to $C_{13}$ benzothiophenes in the $C_{14}$ to $C_{16}$ range hydes and alcohols, a correction factor of 0.7 was assumed for the oxygenated compounds.

When the major products of the present hydroformylation process were alcohols, e.g. in cobalt-phosphine catalyzed reactions, samples of the reaction mixtures were silyated prior to GC analyses. An excess of N-methyl-O-trimethylsilyl-trifluoroacetamide was used to convert the alcohols to trimethylsilyl derivatives:

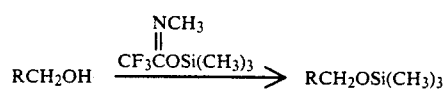

These derivatives of increased retention time are easier to chromatographically resolve and determine than their alcohol precursors.

High Pressure Hydroformylation

In the high pressure hydroformylation experiments, a 1 liter and a 1 gallon stirred autoclave were used. In these experiments, the amounts of synthesis gas consumed were not monitored quantitatively. However, the liquid reaction mixture was sampled, usually after 10, 30, 120 and 180 minutes, and analyzed to determined olefin conversions and product selectivities. Also, the relative reaction rates were estimated by periodically shutting off the synthesis gas reactant supply and determining the rate of pressure drop per minute in the reactor.

In the one liter autoclave, the thermally cracked distillate was usually diluted with an equal amount of n-hexane, to provide a hydroformylation feed for standard experiments. However, about 20% of the diluent was employed to dissolve the catalyst, usually dicobalt octacarbonyl. In the one gallon autoclave, the cracked distillate was placed as such without solvent. The catalyst was usually dissolved in toluene solvent amounting to about 5% of the distillate reactant.

The high pressure experiments were carried out in a manner basically similar to those employed in the low pressure experiments. The distillate reactant was typically preheated to the reaction temperature with stirring under an initial $H_2/CO$ pressure equally about ¾ of the final reaction pressure. The catalyst solution was then pressured into stirred mixture using the initial $H_2/CO$ at reaction pressure and the pressure was maintained with additional, $H_2/CO$ feed gas as the reaction proceeded. During the periodical sampling of the liquid mixture, significant losses of $H_2/CO$ occurred, thus the $H_2/CO$ ratio thereafter was that of the feed gas rather than the initial gas. At the completion of the experiment the reaction mixture was rapidly cooled under $H_2/CO$ pressure and discharged when cold.

For a more detailed study of some of some of the products of high pressure cobalt hydroformylation, particularly those prepared in the one gallon reactor, the reaction mixtures were fractionally distilled. To avoid decomposition, the cobalt was removed as cobalt acetate by hot aqueous acetic acid plus air treatment. In a typical procedure, a 200% excess of acetic acid is used as an about 6% aqueous solution. As a reaction vessel a three necked glass vessel equipped with a mechanical stirrer, sintered glass bubbler, reflux condenser and a bottom valve for liquid takeoff, was used.

The stirred mixture of the cobalt hydroformylation reaction mixture and the theoretical amount of aqueous acetic acid was heated to reflux temperature while introducing air. Thereafter, stirring and aeration were continued for 20 minutes while refluxing. As indicated by the lightening of the color of the reaction mixture, cobalt conversion was usually substantially complete by the time refluxing started. The mixture was then allowed to cool and settle. Thereafter, the bottom pink aqueous phase was separated. The organic phase then was treated the same way again. After the second acid wash, the mixture was filtered if there were any solids present. Thereafter, two washed with distilled water followed. Lack of color of the aqueous washings indicated a complete prior removal of cobalt.

The cobalt free organic phase was fractionally distilled in vacuo using a 1 to 2 ft. long, glass beads packed column or an Oldershaw column with 22 theoretical plates. The composition of distillate fractions was monitored by capillary GC to help appropriate fractionation. Many of the fractions were also analyzed by a sulfur specific GC detector. Selected fractions were also anaylzed by a combined gas chromatograph/mass spectrometry (GC/MS).

Aldehyde Hydrogenation to Product Alcohols

Typically, the aldehyde hydrogenations were carried out a 3000 psi (206 atm) pressure in a 1 gallon (about 3.8 liter) rocking autoclave using about 1800 g reactant. The aldehyde reactant was used as such or in a hydrocarbon solution. Five percent by weight of water was added to the aldehyde to inhibit the formation of dimeric and trimeric by-products during hydrogenation.

As a preferred hydrogenation catalyst, cobalt sulfide - molybdenum sulfide on alumina was used. Alternatively, molybdenum sulfide on carbon support was employed. Ten percent by weight of catalyst was used. In the presence of the CoS/MoS based catalyst, the hydrogenations could be carried at lower temperatures in the range of 130 to 170° C. The low temperatures are important for avoiding the undesired conversion of aldehydes to paraffins and sulfur transfer from the metal sulfides to form sulfur containing by-products. In the presence of molybdenum sulfide the hydrogenations were carried out at 232° C. (450° F.). At this temperature, paraffin formation was significant (10 to 30%).

The hydrogenations were substantially completed in five hours. However, they were generally continued for a total period of 20 to 24 hours to assure a complete conversion of the aldehydes. The alcohol products were usually colorless or very light in color. They were characterized by GC and GC/MS and fractionally distilled in vacuo to provide colorless liquids. Some of the alcohols were washed with 10% aqueous sodium hydroxide to remove hydrogen sulfide and other potential acidic impurities.

Low Pressure Hydroformylation of $C_4$-$C_{12}$ Naphtha Fractions in the Presence of Phosphine-Rhodium Complexes

EXAMPLES 1-12

The previously described $C_4$ to $C_{12}$ Fluid-coker naphtha and its distillate fractions were hydroformylated without prior treating in the presence of rhodium complexes of various phosphines under varying low pressure conditions.

The rhodium catalyst systems employed and the reaction conditions used are summarized together with some results for orientation in Table XVI. In general, in the presence of sufficient amounts of phosphine-rhodium catalyst complexes, rapid and selective hydroformylation occurs at low pressure. Very little hydrogenation occurs. GC analysis provides a quantitative measure of the two major aldehyde products and a more qualitative estimate of the total aldehyde products.

TABLE XVI

Hydroformylation of Fluid Coker Naphtha with Phosphine-Rhodium Complex Catalysts

| Feed Carbon No. | Rh Conc. mM | Phosphine Ligand Conc. M | Phosphine Ligand Structure | Reaction Conditions Temp. °C. | Press. psi | Time Min | H$_2$/CO Final | GC Analyses Two Major Products n/i | Yield, %[a] | Total Products Yield, %[a] | 1-n-Olefin Based H$_2$/CO Consumed % | Rate K$_N$ 1 min. |
|---|---|---|---|---|---|---|---|---|---|---|---|---|
| 4–12 | 10 | 0.14 | (C$_4$H$_9$)$_3$P | 180 | 1000 | 40 | 1.95 | ~2 | | | | |
| 10 | 2 | 0.14 | (C$_8$H$_{17}$)$_3$P | 180 | 1000 | 60 | 1.08 | 1.88 | 118 | 177 | 238 | 1042 |
| 10 | 2 | 0.14 | (C$_8$H$_{17}$)$_3$P | 180 | 350 | 60 | 1.05 | 2.0 | 119 | 187 | 224 | 554 |
| 10 | 1 | 0.14 | (i-C$_8$H$_9$)$_3$P | 180 | 100 | 60 | 1.05 | 1.64 | 94 | 128 | 210 | 630 |
| 7 | 2 | 0.14 | (C$_4$H$_9$)$_3$P | 180 | 1000 | 12 | ~1 | 2.3 | 115[b] | 133[b] | 71 | 360[b] |
| 7 | 10 | 0.14 | (C$_4$H$_9$)$_3$P | 180 | 1000 | 1 | 1.47 | 2.15 | 118 | 165 | 161 | 720 |
| 7 | 1 | 0.14 | (C$_4$H$_9$)$_3$P | 180 | 1000 | 20 | ~1 | 2.3[b] | — | — | 27[c] | — |
| 10 | 4 | 1.0 | (C$_4$H$_9$)$_3$P | 180 | 1000 | 60 | 0.95 | 2.02 | 102 | 130 | 238 | 210 |
| 10 | 2 | 0 | — | 180 | 1000 | 120 | 1.0 | 1.93 | 77 | | 95 | 7 |
| 10 | 2 | 1.0 | (C$_4$H$_9$)$_3$P | 180 | 350 | 60 | 5.1 | 3.20 | 101 | 147 | 210 | 88 |
| 10 | 2 | 1.0 | Ph$_2$PC$_{18}$)H$_{37}$ | 145 | 350 | 60 | 5.75 | 6.76 | 106 | 164 | 214 | 308 |
| 10 | 2 | 0.14 | (i-C$_4$H$_9$)$_3$P | 180 | 1000 | 60 | 1.05 | 1.25 | 90 | 11161[d] | 309 | 3610 |

[a]Expressed in percent compared to the amount theoretically required for the conversion of the 1-n-olefin component.
[b]According to G.C. only 42% of the 1-n-heptene reacted before inhibition occured.
[c]According to G.C. only 155 of the 1-n-heptene reacted. H$_2$/CO uptake ceased in 1 minute.
[d]The total yield of aldehydes plus alcohols was 165%, according to G.C.

At low pressure, the total aldehyde products could be more reliably estimated, on the basis of the H$_2$/CO consumed, by comparing the found values with the amounts calculated for converting the 1-n-olefin component. Based on the initial rates of H$_2$/CO consumption (0–1 minute) the hydroformylation rates of the most reactive 1-n-olefin components were also compared in the presence of different catalyst complexes.

Comparative 1-n-decene hydroformylation experiments with the C$_{10}$ naphtha fraction as a feed showed that the activity and selectivity of rhodium complex catalysts could be controlled by the chemical structure and excess concentration of the phosphine ligand added, as it will be discussed in the individual examples.

Example 1

Hydroformylation of a C$_4$–C$_{12}$ Naphtha with a Tributyl Phosphine Rhodium Complex A broad naphtha cut previously described was hydroformylated in the presence of a catalyst system containing 10 nM rhodium, employed as dicarbonyl acetylacetonate, and 0.14 M tri-n-butyl phosphine. The reaction was run at 180° under 1000 psi (6900 kPa) pressure for 40 minutes. The initial H$_2$/CO ratio was 1, the H$_2$/CO feed ratio employed during the run 1.22 and the final head space ratio 1.95. The increase of the H$_2$/CO ratio during the run indicated that very little hydrogenation side reaction occurred.

The final reaction mixture was analyzed by GC. The chromatogram showed no 1-n-olefin components, indicating their complete conversion. The main products were the n-aldehydes. Among the minor aldehyde products, those of the 2-methyl substituted aldehydes were readily recognizable. Table XVII shows the signal intensities of these two types of aldehyde products and those of the n-paraffin components. The paraffin components represent multiple internal standards which were present in the starting reactants in amounts comparable to the 1-n-olefin reactants of corresponding carbon numbers. The data of the table qualitatively show that the conversion of the 1-n-olefins resulted in the formation of the expected normal aldehyde and 2-methyl branched aldehyde products:

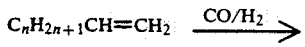

-continued $$C_nH_{2n+1}CH_2CH_2CHO + C_nH_{2n+1}\underset{\underset{CH_3}{|}}{C}HCHO$$

TABLE XVII

Major Aldehyde Products and n-Paraffin Components of Fluid Coker Naphtha

| Alkyl Carbon No. | GC Signal Intensity, % Normal Aldehyde | 2-Methyl Aldehyde | Normal Paraffin |
|---|---|---|---|
| 5 | 1.104 | 0.926 | 0.798 |
| 6 | 1.837 | | 1.468 |
| 7 | 1.796 | | 2.927 |
| 8 | 2.259 | 1.586 | 3.064 |
| 9 | 2.047 | 1.350 | 2.208 |
| 10 | 2.182 | 1.115 | 2.043 |
| 11 | 1.423 | 0.715 | 1.409 |
| 12 | 0.514 | 0.239 | 0.393 |
| 5–12 | 13.162 | | 14.310 |

The n/i ratio of these linear versus branched aldehydes is about 2. Using the present catalyst system and conditions, this ratio is in the range of n/i values obtained on the hydroformylation of pure 1-n-olefins and Type I olefins, in general. As the 1-n-olefins were converted, the reaction rate decreased and the reaction was discontinued. Thus, the results of this example indicate that the 1-n-olefin components of the distillate feed can be selectively hydroformylated in the presence of phosphine rhodium complex based catalysts.

Example 2

Hydroformylation of C$_{10}$ Naphtha With a Tri-n-octyl Phosphine Rhodium Complex at 1000 psi The previously described C$_{10}$ fraction of the Fluid coker-naphtha was hydroformylated at 180° C. under 1000 psi, using the low pressure procedure. The catalyst system was derived from 2 mM rhodium dicarbonyl acetylacetonate and 0.14 M tri-n-octyl phosphine. The reaction period was 60 minutes. The ratio of the initial H$_2$/CO was 1; the H$_2$/CO feed was of 51 to 49 ratio. The final H$_2$/CO ratio of the head space was 52 to 48, indicating a virtual absence of hydrogenation.

The reaction was very fast during the initial period of about 5 minutes, then the reaction became slower and slower. Apparently, the 1-n-decene component of the feed was rapidly hydroformylated while the isomeric Type II and Type III decenes were more sluggish to react.

A GC analysis of the final reaction mixture showed that 1-n-decene was absent. Apparently, it reacted to form n-undecanal and 2-methyl decanal. The latter compounds constituted about 69% of the total aldehydes formed. The ratio of the normal to the iso aldehyde produced was 1.88.

On the basis of the original concentration of 1-n-decene in the feed, the theoretical amount of $C_{11}$ aldehydes was calculated. The total aldehydes were 171% of the amount which could have been derived from 1-n-decene. Apparently major amounts of the Type II decene components of the feed were also hydroformylated. On the other hand, the GC showed that 2-methylnonene was still substantially unconverted in the reaction mixture. This indicated that the Type III olefins of the feed are of low reactivity in the presence of this catalyst system.

Example 3

Hydroformylation of $C_{10}$ Naphtha With a Tri-n-octyl Phosphine Rhodium Complex at 350 psi The experiment of Example 2 was repeated at 350 psi instead of 1000 psi pressure. Qualitatively, the reaction was very similar. The reaction rate was only slightly lower. The final $H_2/CO$ ratio in the head space was 51/49.

The ratio of the two major products, n-undecanal versus 2-methyldecanal was about 2. These two aldehydes represent 119% of the calculated yield based on the starting 1-n-decene. The total aldehyde yield is 187% of the 1-decene based value. Thus, the amount of the above two aldehydes is about 62% of the total.

Example 4

Hydroformylation of $C_{10}$ Naphtha With a Tri-i-octyl Phosphine Rhodium Complex Example 2 was repeated using the rhodium complex of tri-i-octyl phosphine [tris-(2,4,4-trimethyl-pentyl)-phosphine] as the catalyst instead of that of tri-n-octyl phosphine. The reaction was very similar to that of Example 2 except for the lower n/i ratio of the two main products. The ratio of n-undecanal to 2-methyl decanal was 1.64 in the present experiments while a ratio of 1.88 was found in Example 2. The reduced n/i ratio was apparently a result of the steric crowding effect of the bulky tri-i-octyl phosphine ligand.

The two main aldehyde products represent 94% of the theoretical yield based on the 1-n-decene content of the feed. On the same basis, the yield of the total aldehydes was found to be 128%. Thus, the two main aldehydes amounted to about 74% of the total aldehydes produced.

Example 5-7

Hydroformylation of $C_7$ Naphtha With Tri-n-butyl Phosphine Rhodium Complex

The previously described $C_7$ fraction of the Fluid coker naphtha was hydroformylated at 180° C. under 1000 psi pressure with the standard low pressure procedure using 1/1 $H_2/CO$ as reactant. Three hydroformylation experiments were carried out using different concentrations of rhodium in the presence of excess tri-n-butyl phosphine at 0.14 M concentration. The rhodium was provided as a dicarbonyl acetylacetonate derivative in 1,2 and 10 mM concentration. Reasonably fast reaction occurred with 2 mM rhodium. The result of this experiment (Example 5) will be discussed at first.

Gas consumption data indicate that initially the reaction rate was very high, but started to drop in 2 minutes. When the reaction was discontinued after 12 minutes, gas absorption was minimal. The $H_2/CO$ ratio remained close to 1 during the reaction.

Gas chromatography showed that 42% of the 1-n-heptene component of the feed was reacted. The 1-n-heptene derived component of the product was mostly n-octanal and 2-methylheptanal. The n/i ratio of these products was 2.3. The amount of the two compounds was 115% of the calculated value based on the converted n-1-heptene. The total aldehyde products correspond to 133% of that value. Apparently, minor amounts of other heptene isomers besides 1-n-heptene were also reacted.

In another experiment (Example 6) the same reaction was run in the presence of 10 mM rhodium. This resulted in an extremely fast reaction. About 0.645 moles of $H_2/CO$ mixture was consumed within the one minute reaction time. The run gas used had a 52/48 ratio. The final ratio of $H_2/CO$ was 1.47, a substantial increase over the initial $H_2/CO$ ratio of 1. Apparently, no significant hydrogenation occurred.

The gas chromatogram of the reaction mixture showed that all the 1-n-heptene was converted. The two main products were again n-octanal and 1-methyl heptanal, in a ratio of 2.15. The sum of these two corresponds to 19% more than the amount which could have been theoretically derived from 1-heptene. The total amount of aldehyde product is 165% of the amount derivable from 1-heptene. Thus, the n-octanal formed equals to 48% of the total aldehydes formed.

In a third experiment (Example 7) only 1 mM rhodium was employed. At this low catalyst concentration, little reaction occurred. In 20 minutes only 15% of the 1-n-heptene was consumed. The n/i ratio of the two main products was 2.3.

Example 8

Hydroformylation of $C_{10}$ Naphtha with Rhodium Complex in the Presence of 1 M Tributyl Phosphine The $C_{10}$ fraction of the coker naphtha was hydroformylated under the conditions of Example 2. However, 1 M tri-n-butyl phosphine was used instead of 0.14 M tri-n-octyl phosphine to ascertain the effect of an increased excess of phosphine ligand. Also, 4 mM instead of 2 mM rhodium was used to counteract the inhibitory effect of the added ligand.

The initial reaction was very fast. All the 1-n-decene was converted in about 140 second. Thereafter, the internal decenes were being converted at a much slower rate. At 60 minutes, the $CO/H_2$ consumption rate was quite low. The reaction was discontinued after 60 minutes.

A GC analysis of the reaction mixture showed that the two main reaction products, n-undecanal and 2-methylnonanal were formed at an increased ratio. Due to the increased excess trialkyl phosphine ligand concentration, the n/i value was significantly higher, 2.02. (In the presence of the smaller liquid concentration Example 3, the n/i ratio was 1.88). The amount of the two major products was 102% of the value calculated for the amounts derivable for 1-n-decene. The total amount of aldehyde products formed was 130% of the theoretical value calculated for 1-n-decene.

Example 9

Hydroformylation of $C_{10}$ Naphtha With Rhodium Dicarbonyl Acetylacetonate

The same $C_{10}$ naphtha was also hydroformylated under the conditions of the previous example, but without any phosphine catalyst modifier. In this example, the usual rhodium catalyst precursor, rhodium dicarbonyl acetylacetonate was used alone in amounts corresponding to 2 mM rhodium concentration.

Apparently due to the absence of phosphine modifying ligand, the reaction was slow. Although the reaction time was increased to 120 minutes, even the conversion of the most reactive olefin component of the feed, 1-n-decene, remained incomplete. Also, the amount of the $CO/H_2$ reactant gas consumed was only about half of that of the previous example (The 1/1 ratio of $H_2/CO$ was well maintained during reaction).

The main products of the reaction were again undecanal and 2-methyldecanal derived from 1-n-decene. They represented about 77% of the aldehyde products. No alcohol product was observed. The n/i ratio of the two main products was 1.93.

Example 10

Hydroformylation of $C_{10}$ Naphtha with Tri-n-butyl Phosphine Rhodium Complex at 350 psi 5/1 $H_2/CO$ Pressure The $C_{10}$ naphtha was hydroformylated under the conditions of Example 8, but at reduced pressure, at 350 psi of 5/1 $H_2/CO$. The amount of rhodium was cut to 2 mM. The tri-n-butyl phosphine concentration was the same, 1 M. The 5/1 $H_2/CO$ ratio was maintained by a feed gas ratio of 53/47.

The sharply reduced CO partial pressure of this reaction significantly increased in n/i ratio of the two major aldehdye products without a major drop in the reaction rate.

Compared to Example 8, the n/i ratio of the two main products increased from 2.02 to 3.2. These two products represented 68.5% of the total aldehyde yield. No alcohols were formed during the 60 minutes reaction time. The yield based on 1-decene was 101% for the two main aldehydes. The total aldehydes amounted to 147% of the 1-decene based calculated yield, indicating a significant conversion of some of the other olefin components of the feed. The amount of $H_2/CO$ needed to hydroformylate all the 1-decene was consumed during the first 7 minutes of the experiment.

Example 11

Hydroformylation of $C_{10}$ Naphtha With a Rhodium Complex of n-Octadecyl Diphenyl Phosphine at 145° C.

The $C_{10}$ naphtha fraction was hydroformylated with the rhodium complex of an alkyl diaryl phosphine to produce a higher ratio of normal versus iso aldehyde products. To derive the catalyst system, 2 mM rhodium and 1 M n-octadecyl diphenyl phosphine were used. The reaction was run at 145° C. under 350 psi 5/1 $H_2/CO$ pressure. During the reaction a 53/47 mixture of $H_2/CO$ was fed. This feed gas more than maintained the initial $H_2/CO$ ratio during the 60 minutes run. The final $H_2/CO$ ratio was 5.75, indicating the absence of major hydrogenation side reaction. Compared to the previous example the difference is in the type of phosphine ligand used and the reaction temperature.

The use of the alkyl diaryl phosphine ligand resulted in a much increased selectivity of 1-n-decene hydroformylation to n-undecanal. The n/i ratio of the two main aldehyde products was 6.76. Also, in the presence of this ligand a faster hydroformylation rate was observed. An amount of $H_2/CO$ sufficient to convert all the 1-n-decene was consumed within 3 minutes.

After the 60 minutes reaction time, GC analyses indicated that the amount of the two main aldehyde products was 106% of the calculated yield for 1-n-decene. The total aldehyde product were 164% of this yield and no alcohols were formed.

Example 12

Hydroformylation of $C_{10}$ Naphtha with a Rhodium Complex of Tri-i-butyl Phosphine The $C_7$ naphtha fraction was hydroformylated under conditions similar to those in Examples 2, i.e., at 180° C. under 1000 psi 1/1 $H_2/CO$ pressure. However, instead of a tri-n-alkyl phosphine, a sterically crowded tri-i-alkyl phosphine, tri-2-methylpropyl phosphine (tri-i-butyl phosphine) was used. The phosphorus ligand concentration was 0.14 M, the rhodium concentration 2 mM. Feeding a 51/49 mixture of $H_2/CO$ as usual maintained the equimolar synthesis gas reactant mixture during the 60 minutes reactions time.

The use of the tri-i-butyl phosphine ligand resulted in a fast reaction of low n/i selectivity. Enough $H_2/CO$ reactant was consumed during the first minute of the reaction to convert all the 1-n-decene in the reaction mixture. The n/i ratio of the two main aldehyde products was 1.25. After the complete run, GC showed that the combined yield of the two main products formed was 90% of the value calculated for 1-n-decene. The total aldehyde yield corresponded to 161% of this value. In this reaction minor amounts of alcohols were also formed. Thus, the combined yield of aldehydes and alcohols was 165% of the theoretical yield of the hydroformylation of the 1-n-decene component.

Example 13

Hydroformylation of $C_{16}$–$C_{18}$ Gas Oil with Tri-i-butyl Phosphine Rhodium Complex at 180° C. and 1000 psi A broad cut light gas oil from a Fluid coker was distilled in vacuo to provide a $C_{16}$–$C_{18}$ fraction, having a boiling range of 74–82° C. at 0.1 mm. A capillary GC analysis of this fraction showed that it contained approximately the following percentages of 1-n-olefins ($C_n=$) and n-paraffins ($C_n°$) : $C_{15}=$, 0.30; $C_{15}°$, 0.28; $C_{16}=$, 10.06; $C_{16}°$, 6.25; $C_{17}=$, 9.55; $C_{17}°$, 7.90; $C_{18}=$, 3.34; $C_{18}°$, 3.10; $C_{19}=$, 0.78; $C_{19}°$, 0.62.

About 100 g of the above distillate feed was hydroformylated using the low pressure hydroformylation procedure under 1000 psi 1/1 $H_2/CO$ pressure at 180° C. in the presence of 2 mM rhodium and 140 mM triisobutyl phosphine.

The gas consumption data indicated a very fast initial reaction, apparently a very effective conversion of the 1-n-olefin components. After this initial stage, the rate was steadily declining as the less reactive olefins were being converted. At a gas consumption calculated for a 50% conversion of a $C_{17}$ feed of 50% olefin content, the reaction was discontinued.

Capillary GC analysis of the reaction mixture showed a complete conversion of the 1-n-olefins and the formation of the corresponding 1-n-aldehydes and 2-methyl substituted aldehydes having one carbon more than the parent olefin. The ratio of these n- and i-aldehyde products was 1.35. Together, they represented 69% of the total aldehydes formed. A comparison of the intensities of the peaks of the two major types of aldehyde products and the n-paraffins showed that the yield of these aldehydes is about 61% of the calculated value for the 1-n-olefins. Thus a significant 1-n-olefin to internal olefin isomerization occurred during hydroformylation. The linear olefins formed were converted to 2-ethyl and higher alkyl substituted aldehydes which constitute most of the minor $C_{17}$–$C_{19}$ aldehyde products.

The reaction mixture was distilled in vacuo to separate the feed from the products. About 15 g of clear yellow-greenish product was obtained as a distillate, boiling in the range of 102 to 124° C. at 0.05 mm.

Medium Pressure Hydroformylation in the Presence of Phoshine-Cobalt Complexes

Examples 14–18

The previously described, untreated $C_4$ to $C_{12}$ Fluid coker naphtha and its distillate fractions were also hydroformylated in the presence of cobalt complexes of trialkyl phosphine complexes. The reaction conditions used and results obtained are summarized in Table XVIII.

In general, the substitution of cobalt for rhodium in these phosphine complex catalyst systems changes the activity and the selectivity of the system. The inherent activity of the cobalt systems is about 2 orders of magnitude smaller. In contrast to rhodium, the cobalt complexes are multifunctional catalysts. Olefin isomerization is extensive; this results in an increase of the n/i ratio of the products. Aldehyde to alcohol hydrogenation is also extensive. Since the major products are alcohols and the reactions are performed at medium rather than low pressure, syn gas consumption based olefin converstions are relative rather than absolute values.

Example 14

Hydroformylation of a $C_4$ to $C_{12}$ Naphtha With a Tributyl Phosphine Cobalt Complex About 93.8 g of the broad cut naphtha feed previously described was hydroformylated in the presence of a catalyst system containing 80 mM of cobalt, added as dicobalt octacarbonyl, and 0.24 M tri-n-butyl phosphine (P/Co=3). The reaction was run under the conditions of the first example (180° C., 1000 psi) but, for a longer period (60 minutes). While the initial $H_2$/CO ratio was again 1/1, the synthesis gas added during the run had a significantly higher $H_2$/CO ratio of 3/2. This higher run gas ratio was employed because cobalt phosphine complexes catalyze both olefin hydroformylation to aldehydes and aldehyde reduction to alcohols.

During the reaction about 1 mole of $H_2$/CO mixture was consumed. In contrast to the first example, no significant reduction in the reaction rate was observed. The final head space ratio of $H_2$/CO dropped to 0.68, indicating that hydrogenation took place to a major degree.

The final reaction mixture was again analyzed by GC. The chromatogram obtained showed an essentially complete conversion of the 1-n-olefin components and the formation of major amounts of the corresponding n-aldehyde and alcohols.

TABLE XVIII

Hydroformylation of Fluid Coker Naphtha with Phosphine Cobalt Complex Catalysts
The reactions were carried out at 180° C. using an initial $H_2$/CO feed ratio of 1 and a run gas ratio of 3/2, in the presence of sufficient tri-n-butyl phosphine to provide an P/Co ratio of 3

| Exp- ample No. | Feed Carbon No. | Co Conc. nM | Reaction Conditions | | 1-n-Olefin Based Rate Data | | | Total Product Yield %$^c$ | 4 Major Products Yield % C | Normal Products in Total % | Alcohol Products in Total % | n/i Ratio 4 Major Products$^d$ |
|---|---|---|---|---|---|---|---|---|---|---|---|---|
| | | | Press. psi | Time min. | $H_2$/CO Consumed % (Total)$^a$ | Normalized Rate $K_N$ (Period) | Period$^b$ Measured Min. | | | | | |
| 13 | 4–12 | 80 | 1000 | 60 | | | | | | | | |
| 14 | 10 | 40$^e$ | 1500 | 120 | 155 | 4 | 10–20 | 139 | 73.5 | 52.1 | 92.1 | 7.62 |
| 15 | 7 | 40 | 1000 | 60 | 70 | 0.8 | 10–20 | 38.8 | 28.6 | 56.0 | 58.3 | 10.06 |
| 16 | 10 | 40 | 1500 | 120 | 160 | 1 | 15–20 | 63.2 | 35.7 | 49.5 | 91.2 | 7.00 |
| 17 | 10 | 120 | 1500 | 60 | 191 | 1.6 | 5–6 | 129 | 64.8 | 44.8 | 92.8 | 8.45 |

$^a$Expressed in percent theoretically required for the conversion of the 1-n-olefin component to the corresponding alcohol.
$^b$The hydroformylation rate increases with time.
$^c$Expressed as percent of the theoretical amount of the product of the hydroformylation of the 1-n-olefin component of the feed.
$^d$The four major products are two aldehydes and the two alcohols which can be derived from the 1-n-olefin component feed.
$^e$Instead of tri-n-butyl phosphine, tri-n-octyl phosphine was used as a ligand.

Example 15

Hydroformylation of $C_{10}$ Naphtha With a Tri-n-octyl Phosphine Cobalt Complex at 1500 psi The $C_{10}$ fraction of the Fluid-coker naphtha used in the previous examples was also hydroformylated using a catalyst system based on dicobalt octacarbonyl and tri-n-octyl phosphine. The concentrations were 40 mM cobalt and 120 mM phosphine ligand (P/Co=6). The reaction was carried out at 180° C. under 1500 psi for 2 hours. The initial $H_2$/CO ratio was 1. During the run an $H_2$/CO ratio of 60/40 was used. The final $H_2$/CO ratio of the head space was 48/50. There was no apparent decrease of hydroformylation rate during the reaction. The maximum rate was reached after about 10 minutes. In 120 minutes, the $H_2$/CO feed consumed was about 155% of the amount theoretically required to convert the 1-n-decene component to undecyl alcohol.

The gas chromatogram of the final reaction mixture shows no significant amounts of 1-n-decene present. However, other decene isomers appear to be present in increased amounts as a consequence of concurrent isomerization-hydroformylation.

The hydroformylation produced the expected two significant aldehyde products derived from 1-n-decene. However, these were largely hydrogenated to the corresponding alcohols, as shown by the reaction scheme:

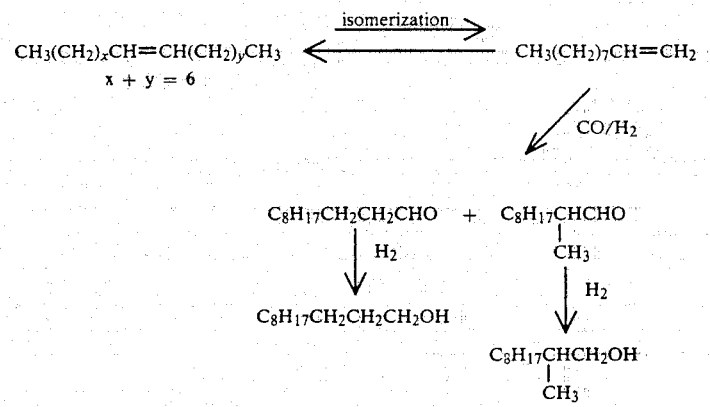

The amount of the above 4 products is about 75.5% of the calculated yield for 1-decene.

The total yield of aldehydes plus alcohols was also estimated on the basis of the capillary GC analysis of the final reaction mixture. It was 139% of the products calculated for a complete conversion of the 1-n-decene component. The n-aldehyde plus n-alcohol amounted to 52.1% of the total products. Most of the products, 92.1% were alcohols. Only about 7.9% were aldehydes. The n/i ratio of the 4 major products, mostly derived from 1-n-decene was high, 7.62.

Example 16

Hydroformylation of $C_7$ Naphtha With a Tributyl Phosphine Cobalt Complex

The $C_7$ fraction of the Fluid-coker naphtha employed in Examples 5, 6, and 7 was also hydroformylated with a catalyst system derived from dicobalt octacarbonyl and trioctyl phosphine. Forty mM cobalt and 0.12 mM ligand were used (P/CO=3). The reaction conditions were similar to those in Example 6; 180° C., 1500 psi and 1 hour using a 60/40 ratio of run gas. The initial and final ratio of $H_2$/CO in the reactor were both very close to 1. The $H_2$/CO feed consumed was about 70% of the amount calculated for the conversion of the 1-n-heptene components to octanols.

According to GC there was no unconverted 1-n-heptene left in the reaction mixture. Besides hydroformylation, isomerization occurred. The major hydroformylation products present were n-octanal, 2-methylheptanal and the corresponding alcohol hydrogenation products. The overall n/i ratio of these products is about 10.06. These four products represent about 56% of the total aldehyde and alcohol products. About 58.3% of the total products were alcohols. The significant percentage, 41.7%, of the aldehydes present indicated that the hydrogenation reaction was incomplete.

Examples 17 and 18

Hydroformylation of $C_{10}$ Naphtha With a Tri-n-butyl Phosphine Cobalt Complex The $C_{10}$ fraction of the coker naphtha was hydroformylated in the presence of dicobalt octacarbonyl plus tri-n-butyl phosphine catalyst systems having a P/Co ratio of 3. The reactions were run at 180° C. under 1500 psi 1/1 $H_2$/CO pressure. The high $H_2$/CO ratio was maintained by the addition of a 60/40 feed gas mixture during the reaction.

The rate of absorption of the $H_2$/CO reactant gas showed that the reaction has an initial inhibition period, dependent on the concentration of catalyst. At 40 mM cobalt, this inhibition period is about 5 minutes; at 120 mM Co, it is less than 1 min. At 40 mM cobalt (Example 16), it takes about 35 minutes to consume enough $H_2$/CO for a complete converstion of the 1-n-decene component of the naphtha cut. At 120 mM cobalt (Example 17), only about 10 minutes are required to achieve this conversion. The rate of absorption indicates a first order reaction rate dependence on cobalt concentration.

The first reaction with 40 mM cobalt (Example 16) was run for a total of 1290 minutes. In that time 0.254 moles of $H_2$/CO was consumed. This is about two and a half fold of the amount necessary to convert the 1-decene component to the corresponding aldehydes. However, most of the primary aldehyde products were reduced to the corresponding alcohols. The two main aldehyde products and the corresponding alcohols are derived from 1-decene via combined isomerization hydroformylation as described in Example 14. Capillary GC indicated that the yield of the total oxygenated products 63.2% of the value calculated for a complete conversion of the 1-decene component. About half of the products were of straight chain. Most of the products, 91.2% were alcohols rather than aldehydes. The n/i ratio of the four major products was 7.

The second reaction with 120 mM cobalt (Example 17) was run for a total of 60 minutes and consumed 0.292 moles of $H_2$/CO. This is almost 3 fold of the amount needed to convert 1-decene to aldehydes. Again most of the aldehydes formed were reduced to alcohols. Capillary GC indicated that the increased catalyst concentration resulted in approximately doubling the total product yield to 129% of the calculated value for the 1-n-decene feed component. The yield of the four major products which could be derived from 1-n-decene was 64.8%. The n/i ratio of these products was 8.45. About 44.8% of the total products was completely linear.

Examples 19 and 20

Hydroformylation of 2-Butene with a Tri-n-Butyl Phosphine Cobalt Complex and Added Thiol Comparative hydroformylation experiments were carried out with 2-butene as a model olefin reactant under the conditions of Example 13 to demonstrate that thiol inhibition can be overcome by the use of cobalt phosphine complex catalysts in the present process.

Two reactions were carried out, each starting with 100 g reaction mixture containing 20 g (0.1 mole) 2- butene, 2.43 g (12 milimole) tri-n-butylphosphine and 0.68 g (2 milimole) dicobalt octacarbonyl in 2-ethylhexyl acetate as a solvent. One of the reaction mixtures also contained 38.8 mg (0.626 milimole) ethyl mercaptan to provide 200 ppm mercaptan sulfur. Both reactant solutions were reacted with 1/1 $H_2/CO$ under 1000 psi pressure at 180° C. An equimolar ratio of $H_2/CO$ was maintained during the run by supplying additional $H_2/CO$ in a 3/2 ratio during the reaction.

Both reaction mixtures were hydroformylated with similar selectivity. The only significant difference was in the reaction rates. The 2-butene was more reactive in the absence of ethanethiol. In the absence of the thiol, 50% olefin conversion was achieved within 18 minutes. In the presence of the thiol, a similar conversion took 36 minutes.

After the reaction, both mixtures were analyzed. The most significant difference between the mixtures was the selectivity to 1-butene; 10.5% in the absence of thiol versus 5.8% in its presence. This indicated inhibition by the thiol of the isomerization of 2-butene to produce the more reactive 1-butene which is then hydroformylated to produce n-valeraldehyde with high selectivity. The latter is largely converted by hydrogenation to n-amyl alcohol.

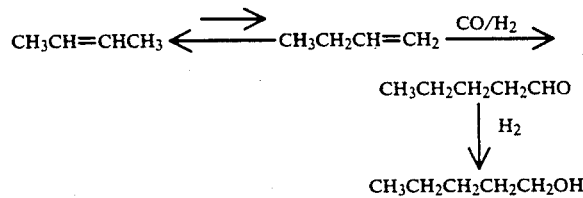

The selectivities toward the various oxygenated products were similar in the absence and presence of thiol; overall n/i 8.15 vs. 8.92; alcohol/aldehyde 0.52 vs. 0.57; aldehyde n/i 6.81 vs. 7.34; alcohol n/i 12.6 vs. 13.8.

Example 21

Hydroformylation of $C_9$–$C_{16}$ Light Gas Oil With Trioctyl Phosphine Cobalt Complex The previously described $C_9$–$C_{16}$ light gas oil was hydroformylated using a tri-n-octyl phosphine cobalt complex based catalyst system at 180° C. under 1000 psi pressure and a 3/2 $H_2/CO$ reactant ratio. Cobalt carbonyl was employed as a catalyst precursor; its concentration was 40 mM, i.e., 0.0472% cobalt metal. The phosphine ligand was employed in 240 mM concentration to provide a 3/1 P/Co ratio. It was added to stabilize the cobalt and to obtain a more linear product.

The reaction was carried out without solvent. No induction period was observed. The reaction was discontinued after 60 minutes, although $H_2/CO$ uptake continued throughout the reaction period. The amount of $H_2$ and CO consumed indicated that hydroformylation and hydrogenation both occurred to a great extent. GC indicated that the products were mainly alcohols. To enhance the analysis of the alcohol products in the GC, the reaction mixtures were treated with an excess of a silylating reagent which acts to convert the —CH$_2$OH groups of the alcohols to —CH$_2$OSi(CH$_3$)$_3$ groups. The retention time of the resulting capped alcohols in the GC column is significantly increased. The shifts of retention times by silylation confirmed that the main products were alcohols.

The GC of the final silylated reaction mixture is shown by FIG. 10. The GC above that none of the 1-n-olefin components of the feed remain in the product stream. The capped alcohol products are mostly n-alcohol derivatives. Although many branched alcohol derivatives are present, they are mostly in minor amounts. Due to their increased retention time, the peaks of most of the capped alcohols is beyond those of the hydrocarbon feed.

A comparison of the peak heights of the capped n-alcohol products derived from gas oil indicated a distribution similar to that of the starting 1-n-olefins (and n-paraffins). Thus, the reactivity of the feed 1-n-olefins is essentially independent of the olefins' carbon number in the presence of the phosphine cobalt complex catalyst.

Example 22

Hydroformylation of $C_{10}$ Gas Oil with Triethyl Phosphine Cobalt Complex The hydroformylation of the previously described $C_{10}$ coker gas oil fraction was also attempted in the presence of a tri-n-alkyl phosphine cobalt complex catalyst at high pressure, i.e., 3000 psi. Example 14–18 have shown us that phosphine cobalt complexes catalyze coker naphtha hydroformylation under low pressure, i.e., 1000 psi at 180° C. and medium pressure i.e., 1500 psi at 180° C. The purpose of the present experiments was to determine the effect of pressure on the stability and selectivity of the catalyst system.

Triethyl phosphine was selected as the ligand because it is potentially applicable in the present high temperature process. Triethyl phosphine is fairly volatile (bp. 130° C.), thus excess ligand can be removed as a forerun by distillation if desired. Triethyl phosphine can be also readily removed form the reaction mixture by an aqueous acid wash and then recovered by the addition of a base.

As a precursor for the phosphine complex, dicobalt octacarbonyl was employed. An amount equivalent to 0.472% Co was used [0.04 M $Co_2(CO)_8$]. The triethyl phosphine added was 2.9% (0.24 M). Thus the P/Co ratio was 3. The triethyl phosphine catalyst was dissolved in the naphtha feed which was then heated under $H_2/CO$ pressure. Under the reaction conditions, a concentrated solution of the dicobalt octacarbonyl was added to the reaction mixture to preform the catalyst and start the reaction.

The reaction was followed by capillary GC analyses of samples taken after 10, 30, 60, 120 and 180 minutes. Extensive isomerization of 1-n-decene to internal decenes occurred in 30 minutes. Hydroformylation and hydrogenation of the aldehyde were rather slow. As expected, the phosphine complex of the cobalt is a more stable, but less active, hydroformylation catalyst.

To increase the GC and GC/MS sensitivity for alcohols and to increase their retention time, the reaction mixture was treated with a silylating agent. The capillary GC of the resulting mixture is shown by FIG. 11.

The GC/MS established that most of the reaction products were primary alcohols. The only detectable aldehyde components present were minor amounts of n-undecanal and 2-methyldecanal. They are present in amounts less than 5% of the total oxygenated products.

As it is apparent from the figure, the main product of the reaction was the n-$C_{11}$ alcohol, undecanol. It represents 50% of the total reaction mixture. Thus, only about 50% of the products have branching. Significant amounts of 2-methyldecanol were also formed. The n/i ratio of these two products was about 10. This means that the hydroformylation of 1-decene was highly selective, since both of these compounds were derived from it. The minor alcohol components could not be identified because of similarities in their mass spectra. Based on the relatively short GC retention time the isomeric $C_{12}$ alcohols were probably dibranched compounds.

The reaction mixture was also analyzed using packed column GC to estimate the amount of heavies formed. The heavies were only about 0.3% in the residual product. The presence of the phosphine ligand apparently inhibited the formation of the heavy by-products.

The reaction was stopped after 180 minutes. Thereafter, the remaining 1704 g of the product catalyst mixture was worked up. The excess phosphine and then the unreacted components were first removed in high vacuo at room temperature. However, in the absence of excess phosphine, the remaining product plus catalyst mixture was unstable when heated to 90° C. in vacuo. Thermal decomposition was indicated by a loss of vacuum. Therefore, the attempted distillation was discontinued and the catalyst was removed from the residue by aqueous acetic acid plus air treatment as usual. The water-organic mixture was diluted with hexane to facilitate the separation of the organic phase. After the removal of the solvent in vacuo, the residual product weighed 420 g. This is about 25 weight percent of the crude reactant mixture. Disregarding the weight increase of the olefinic reaction mixture during the reaction, the above amount of total oxygenated products corresponds to the conversion of 25% of the gas oil fraction employed as a feed.

The cobalt free residual product was distilled under 0.12 mm pressure. The isomeric undecyl alcohol products were obtained as a clear, colorless liquid distillate between 80 and 90° C. The dark residual heavy by-products amounted to about 5% of the total oxygenates.

Examples 23-25

Hydroformylation of $C_{16}$-$C_{18}$ Gas Oil with Triethyl Phosphine Cobalt Complex at 180° C. and 1500 psi The broad cut light gas oil of the previous example was hydroformylated using the medium pressure procedure in the presence of 0.23 M cobalt and 0.72 M triethyl phosphine. The reaction was carried out at 180° C. using an initial 1/1 $H_2$/CO reactant at a pressure of 1500 psi. The pressure was maintained with a feed gas of 3/2 $H_2$/CO ratio.

In the first example (23), a rapid initial reaction took place. GC analyses indicated that, assuming 50% olefin content for the feed, about half of the olefins were hydroformylated in 12 minutes. The major reaction products were the $C_{17}$-$C_{19}$ n-aldehydes and 2-methyl aldehydes in a n/i ratio of about 5.

In the second example (24), the same feed was used under the same conditions, but after about a month's storage at room temperature, without an antioxidant. No reaction occurred. The cobalt was precipitated. Testing of the aged feed for peroxide was positive.

In the third example (25), the aged feed was distilled in vacuo prior to being used in another hydroformylation experiment under the same conditions. The results with the redistilled feed were about the same as those with the fresh feed of Example 23.

High Pressure Hydroformylation of $C_4$ to $C_{12}$ Naphtha Fractions in the Presence of Cobalt Complexes Examples 26-47

The previously described $C_4$ to $C_{12}$ Fluid coker naphtha containing 1-n-olefins as the major type of olefin reactant was also hydroformylated successfully in the presence of cobalt complexes without phosphine modifiers at high pressure. $C_{10}$ and $C_8$ feeds were studied in detail. The reaction conditions used and some of the results obtained are summarized in Table XIX.

In general, the omission of the trialkyl phosphine modifying ligand from these cobalt carbonyl complex catalysts resulted in greater hydroformylation activity. However, the ratio of n-aldehydes to the 2-methyl branched aldehydes was drastically reduced to values between about 1.9 and 3.2. The cobalt catalysts could be used not only at high, but at low temperatures as well. In the low temperature region of 100 to 145° C., the process was selective for the production of these major aldehyde isomers. The rate of olefin isomerization was drastically reduced. The n/i ratio of the products and the amount of aldehyde dimer and trimer products were inversely proportional with the reaction temperature.

Example 26

Hydroformylation of a $C_4$ to $C_{12}$ Naphtha by $H_2$/CO with Dicobalt Octacarbonyl at 150° C. and 4500 psi The previously described broad naphtha cut was hydroformylated as a 1/1 mixture with hexane in the presence of 0.2% CO at 150° C. by an approximately 55 to 45 mixture of $H_2$ and CO at 4500 psi, using the high pressure procedure.

TABLE XIX

| | Hydroformylation of Billings Fluid Coker Naphtha With Cobalt Complexes Derived from $Co_2CO_8$ | | | | | | | | | | |
|---|---|---|---|---|---|---|---|---|---|---|---|
| | Feed | Diluent | Co | Reaction Conditions | | | Reaction Time | | Two Major Products | | Total Products |
| Example No. | Carbon No. | 50% cyclo- hexane | Conc. % | Temp. °C. | Press. psi | $H_2$/CO Ratio | Total Period | To react 1-n-olefin | n/i | Yield | Yield, % |
| 26 | 4-12 | Yes | 0.2 | 150 | 450 | 55/45 | 180 | 120 | | | |
| 37 | 10 | Yes | 0.2 | 130 | 3000 | 60/40 | 120 | 60 | 3.15 | 105 | 203 |
| 38 | 10 | Yes | 1.0 | 130 | 3000 | 60/40 | 120 | 10 | | | |
| 39 | 8 | Yes | 0.2 | 130 | 3000 | 60/40 | 120 | 120 | 2.78 | 92 | 144 |
| 40 | 8 | Yes | 0.2 | 130 | 300 | 1/1 | 180 | 100 | 2.84 | 98 | 187 |
| 41 | 8 | Yes | 0.2 | 150 | 3000 | 60/40 | 120 | >120 | | | |
| 42 | 8 | Yes | 0.2 | 150 | 3000 | 1/1-3/2 | 120 | 30 | 1.92 | 84 | 201 |
| | 8 | Yes | 0.2 | 150 | 3000 | 1/1 | 120 | 120 | 2.48 | 86 | 170 |
| 43 | 8 | Yes | 0.2 | 150 | 4500 | 3/2 | 120 | 30 | 2.90 | 105 | 291 |
| 44 | 10 | No | 0.2-0.3 | 130 | 3000 | 1/1 | 300 | 120 | 2.70 | 104 | 253 |
| 45 | 10 | No | 0.2-0.4 | 130 | 3000 | 3/2 | 180 | 10 | 2.50 | 89 | 257 |

The reaction mixture was sampled after 10, 30, 60, 120 and 180 minutes to follow the progress of the reaction by capillary GC analyses.

The GC data indicated a long induction period. Up to 30 minutes, no n-1-olefin conversion was observed. For example, the ratio of n-1-decene to n-decane component remained the same. However, thereafter a fast reaction occurred. The GC of the 120 minute sample showed that all the 1-n-olefin components were completely converted. The major product peaks of the GC are those of the corresponding n-aldehydes. The minor, but distinct aldehyde products are 2-methyl substituted aldehydes. The n/i ratio of these major products is about 2.8.

The GC of the final reaction mixture is shown in FIG. 12. It expressly shows the major $C_5$ to $C_{13}$ aldehyde products formed and the $C_5$ to $C_{12}$ n-paraffins. A comparison of the hydrocarbon region of the figure with FIG. 1 of the naphtha feed clearly indicates that on hydroformylation the 1-n-olefin components were essentially completely converted to provide mainly the n-aldehyde products. FIG. 7 also shows that the peaks of the hydrocarbon and sulfur compound components of the feed in the $C_9$ to $C_{12}$ n-paraffins region overlap with those of the $C_7$ to $C_{10}$ aldehyde products. Since the GC retention times of components are approximately proportional to their boiling points, this indicates that the overlapping components cannot be separated by fractional distillation.

Examples 26 and 27

Hydroformylation of $C_5$ Naphtha by 1/1 $H_2$/CO with 0.2% Cobalt at 130° C. and 3000 psi and the Hydrogenation of the $C_6$ Aldehyde Product About 2500 g of a broad $C_5$ Flexicoker naphtha fraction with a boiling range (bp.) of 24 to 34° C. was washed three times with 1250 ml cold 25% agneous NaOH solution and once with distilled water to remove the thiol components. Thereafter it was fractionally distilled using a 22 plate Oldershaw column to obtain hydroformylation feeds free from higher boiling disulfides. The feed compositions and the results of two hydroformylation experiments are shown in Tables XX and XXI.

A $C_5$ feed of bp. 25–28° C., containing about 33% 1-pentene and 13% n-pentane, was hydroformylated in the presence of 0.2% Co added as $Co_2(CO)_8$ at 130° C. by a 1/1 mixture of $H_2$/CO at 3000 psi for 6 hours. The reaction mixture was periodically sampled for packed column and capillary GC analyses.

TABLE XX

Hydroformylation of $C_5$ Olefinic Fractions of Flexicoker Naphtha at 130° C. in the Presence of 0.2% Cobalt Catalyst Derived from $Co_2(CO)_8$ with 1/1 $H_2$/CO at 3000 psi

| Example No. | Reaction Time Min. | Pressure Drop psi/min. | Components of Total Mixture by Packed Column GC, % | | | |
|---|---|---|---|---|---|---|
| | | | Unreacted | Aldehydes | Alcohols & Formates | Dimers Trimers |
| 26 | 60 | 21 | 92.4 | 6.2 | 0.3 | 1.1 |
|  | 120 | 160 | 78.2 | 19.5 | 0.3 | 2.0 |
|  | 180 | 32 | 28.9 | 65.9 | 1.2 | 4.0 |
|  | 240 | 12 | 22.5 | 68.5 | 3.8 | 5.2 |
| 27 | 60 | 94 | 93.5 | 4.8 | 0.4 | 1.3 |
|  | 120 | 188 | 66.3 | 29.0 | 0.5 | 4.2 |
|  | 180 | 20 | 29.8 | 61.8 | 2.9 | 5.5 |
|  | 240 | 8 | 25.9 | 63.5 | 4.2 | 6.4 |

TABLE XXI $C_6$ Aldehyde Isomers Derived via the Hydroxyformylation of $C_5$ Olefinic Fractions of Flexi-coker Naphtha at 130° C. in the Presence of 0.2% Cobalt Catalyst Derived From $Co_2(CO)_8$ with 1/1 $H_2$/CO at 3000 psi

| Example No. | Reaction Time, Min. | $C_5$ Hydrocarbon Components, % | | | | | $C_6$ Aldehyde[a] Components % | | | | | Normal/iso Ratios[b,c] | |
|---|---|---|---|---|---|---|---|---|---|---|---|---|---|
| | | 1-Pentene | 2-Me 1-Butene | n-Pentene | t-2-Pentene | 2-Me 2-Butene | 2-Et $C_4$ | 2,3-DiMe $C_4$ | 3-Me $C_5$ | 4-Me $C_5$ | Normal $C_6$ | n / 2-Me | n / i |
| 21 | 0 | 33.1 | 15.4 | 12.9 | 5.4 | 1.5 | | | | | | | |
|  | 60 | 33.0 | 16.0 | 14.6 | 6.2 | 2.3 | | | 15.3 | 18.8 | 13.0 | 37.0 | 1.97 | 0.59 |
|  | 120 | 28.2 | 15.2 | 16.8 | 6.5 | 3.8 | | 0.9 | 18.0 | 18.3 | 12.3 | 46.6 | 2.55 | 0.77 |
|  | 180 | 0.9 | 6.5 | 37.7 | 4.4 | 8.3 | 0.2 | 1.1 | 17.2 | 19.5 | 11.6 | 49.3 | 2.52 | 0.84 |
|  | 240 |  | 2.4 | 44.0 | 1.7 | 6.6 | 0.3 | 1.2 | 17.1 | 21.1 | 11.8 | 47.0 | 2.18 | 0.77 |
| 22 | 0 | 31.2 | 16.2 | 20.0 | 9.2 | 3.2 | | | | | | | |
|  | 60 | 30.3 | 16.2 | 22.0 | 9.8 | 4.4 | | | 18.5 | 22.1 | 13.1 | 46.3 | 2.09 | 0.86 |
|  | 120 | 21.8 | 14.8 | 28.0 | 10.6 | 6.3 | | 0.8 | 19.7 | 19.7 | 7.3 | 52.0 | 2.64 | 1.08 |
|  | 180 | 0.4 | 2.8 | 57.9 | 3.0 | 10.1 | 0.3 | 1.1 | 21.1 | 20.4 | 9.0 | 47.5 | 2.32 | 0.90 |
|  | 240 |  | 0.9 | 64.1 | 0.8 | 6.1 | 0.4 | 1.2 | 20.6 | 22.7 | 8.6 | 45.9 | 2.02 | 0.85 |

[a]The branched $C_6$ aldehydes in the order of their listing are: 2-ethylbutanal, 2,3-dimenthylbutanal, 2-methylpentanal, 3-methylpentanal, 4-methylpentanal.
[b]The ratio n/i means normal to total iso aldehyde
[c]The ratio n/2-Me means normal hexanal to 4-methylpentanal A higher boiling $C_5$ feed of bp. 28–32° C., containing about 31% 1-n-pentene and 20% n-pentane was similarly converted.

The packed GC data of Table XX show a selective conversion of the olefinic components to aldehydes. The observed rates of pressure drop indicate that maximum reaction rates were reached between 1 and 3 hours. By the end of the 4 hour reaction period, the hydroformylation was practically complete and according to GC, the final reaction mixture contained more than 60% $C_6$ aldehydes.

The capillary GC data of Table XXI show the selectivity of the olefin conversion and the isomer composition of the aldehyde products formed.

The change in the distribution of the major hydrocarbon components of the $C_5$ feed indicate that 1-pentene, 2-pentenes and the methyl substituted 1-butenes are converted to n-hexanal and the corresponding 2-, 3-and 4-methyl branched pentanals. The 2-methyl-1-butene component is much less reactive and as such is only partially converted under the reaction conditions used.

The main aldehyde product is n-hexanal. According to capillary GC, it is more than 45% of the $C_6$ aldehyde products. The three methyl branched $C_6$ aldehydes, 2-, 3- and 4-methylpentanal, are present in comparable quantities and not completely separated by GC. n-Pentanal and these monobranched aldehydes amount to more than 95% of the reaction mixture. Slightly more than 1% 2-ethylbutanal is present. Similar amounts of 2,3-dimethylbutanal are found.

Sulfur specific GC of the reaction mixture did not indicate any sulfur containing impurities in the aldehyde range. However, there were low boiling sulfur compounds including H₂S in the feed range.

The reaction mixture was distilled to isolate the products. The C₆ aldehydes were obtained between 47 and 51° C. at about 50/mm pressure. During the distillation, most of the cobalt complex catalyst decomposed and precipitated. Significant aldehyde dimerization and trimerization occurred during distillation as a side reaction. The recovered C₅ hydrocarbon feed was free of sulfur indicating that desulfurization by cobalt also occurred during the distillation.

The distilled aldehyde product contained 37.8% n-hexanal, 55.8% isohexanals, 1.8% alcohols and 4.6% formates according to packed GC. The reduced percentage of n-hexanal in the distillate compared to the reaction mixture was due to its preferential aldolization over the isohexanals.

The distilled aldehyde washed with 10% aqueous sodium hydroxide solution to remove the small amounts of HCo(CO)₄ which codistilled during the separation. The washed aldehyde (1730 g) plus 5% distilled water (86.5 g) was then hydrogenated in the presence of a 160 g (270 ml) CoS/MoS based catalyst. The reaction mixture was presured to 1500 psi (103 atm) with hydrogen and heated to 130° C. The pressure was set to 3000 psi and the temperature was increased by 10° C. every hour. Once the temperature reached 160° C., it was kept there for the total reaction time of 20 hours. Subsequent capillary GC and 400 MHz ¹H NMR analyses indicated that essentially all aldehydes were hydrogenated to the corresponding alcohols. Capillary GC indicated that 38.4% of the C₆ alcohols formed was n-hexanol. According to packed GC, dimeric and trimeric by-products were formed in comparable amounts. They mounted to about 15% of the reaction mixture. No paraffin by-products were observed. Sulfur specific GC detected no sulfur.

A 2 to 1 mixture of the crude, C₆ alcohol product was washed with a 10% agneous solution of NaOH and then with water. After drying over MgSO₄, the alcohol was distilled to recover the hexanols as a clear, colorless liquid mixture between 109 and 115° C. at 200 mm. The n-hexanol content of the distillate product was 35.8%. The dimer by-product was distilled at 12 mm. It was obtained as a colorless liquid between 103 and 113° C. Capillary GC indicated that it contained isomeric C₁₂ aldol alcohols. The distillation residue was mostly the trimer presumably formed from the aldol adduct of the aldehyde via the Tischenko reaction:

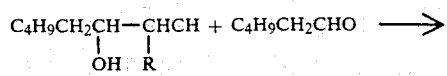

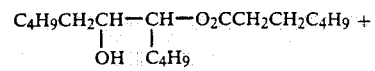

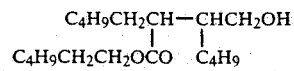

Similar trimerization side reactions occur with the other aldehyde products of the present process.

Examples 28 and 29

Hydroformylation of C₆ Naphtha by 1/1 H₂/CO with Cobalt at 130 and 150° C. under 3000 psi and the Hydrogenation of the C₇ Aldehyde Product A heart cut C₆ Fluid-coker naphtha of bp. 56–65° C. fraction was used as a feed for hydroformylation. It contained about 42% 1-hexene. Its detailed composition was previously discussed and given in FIG. 3. The reactions were carried out with an equimolar mixture of H₂ and CO at 3000 psi, (206 atm). About 2000 g of the feed was used per run. As a catalyst CO₂(CO)₈ was added in benzene solution. In the first run, the cobalt equivalent of the catalyst was 0.4% and the reaction temperature 130° C. In the second experiment, 0.2% Co was used at 150° C. Rapid olefin conversion was observed in both experiments.

Analyses of periodic samples of the reaction mixtures by packed column GC are shown by Table XXII. The pressure drop data of the Table indicate that the hydroformylations were essentially complete in both experiments in 180 minutes. By that time, the percentage of unconverted hydrocarbons in the reaction mixture was reduced close to the minimum in the 30% range. The combined percentages of aldehyde plus some alcohol and formate ester products reached a maximum in about 180 minutes. More aldehydes (62.3%) were obtained at 130° C. than at 150° C. (53.6%). The significantly reduced aldehyde concentration after 360 minutes (52.1 and 37.6%, respectively) is clearly due to dimer and trimer formation (19.4 and 33.4%) respectively.

Capillary GC provided an effective separation of the volatile isomeric components of the reaction mixture. Most of the isomeric C₇ aldehyde, C₇ alcohol and C₇ alkyl formate ester products could be identified by a combination of capillary and mass spectrometry (MS). In the capillary GC of the isomeric aldehydes product, shown in FIG. 13, all the aldehydes which can be derived from linear hexenes and four of the aldehydes derived from monobranched heptenes were separated and identified. The reaction schemes of the presumed hydroformylations leading to the various heptanol isomers are shown in the following:

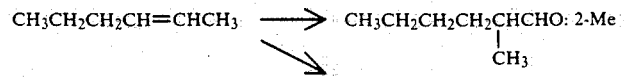

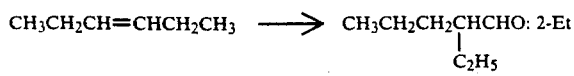

TABLE XXII
COMPOSITION BY PACKED COLUMN GC OF PERIODIC SAMPLES OF REACTION MIXTURES OF THE HYDROFORMYLATION OF A $C_6$ OLEFINIC DISTILLATE FRACTION OF FLUID-COKER NAPHTHA BY $H_2/CO$ AT 3000 PSI (20680 kPa)

| No. Temp. Cat. | Time Min. | Pressure Drop[a] psi Min. | GC Composition, % | | | | Aldehydes, n/i Ratio |
|---|---|---|---|---|---|---|---|
| | | | Hydrocarbons[b] | Aldehydes n[c] | i | Dimers Trimers | |
| 28 | 10 | 94 | 97.0 | 1.4 | 0.8 | 0.8 | 0.56 |
| 130° C. | 30 | 77 | 45.1 | 27.0 | 24.1 | 3.8 | 1.12 |
| 0.4% Co | 60 | 32 | 39.7 | 29.6 | 27.8 | 2.9 | 1.06 |
| | 180 | 11 | 30.3 | 31.5 | 30.8 | 7.4 | 1.02 |
| | 240 | 8 | 29.6 | 29.6 | 29.9 | 10.9 | 0.99 |
| | 360 | — | 28.5 | 25.0 | 27.1 | 19.4 | 0.92 |
| 29 | 10 | 118 | 89.0 | 3.7 | 3.5 | 3.8 | 1.06 |
| 150° C. | 30 | 273 | 74.6 | 12.1 | 9.2 | 4.1 | 1.31 |
| 0.2% Co | 60 | 201 | 42.5 | 26.4 | 24.4 | 6.7 | 1.08 |
| | 180 | 11 | 28.7 | 26.4 | 27.2 | 17.7 | 0.97 |
| | 240 | 10 | 26.3 | 23.8 | 25.1 | 24.8 | 0.95 |
| | 360 | — | 29.0 | 20.0 | 17.6 | 33.4 | 1.14 |

[a]Pressure drop while supply of additional $H_2/CO$ is shut.
[b]Unconverted feed components.
[c]The percentage of n-aldehydes also includes alcohols and formate esters.

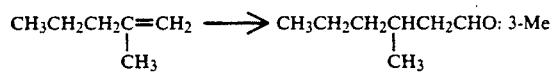

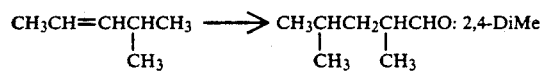

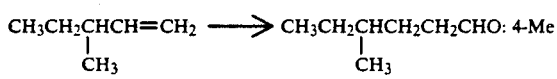

Capillary GC also indicated the presence of minor amounts heptyl alcohol and heptyl formate secondary products. The main isomers were the normal heptyl and 2-methylhexyl derivatives derived from normal heptanal and 2-methylhexanal as indicated by the following reaction scheme:

GC peak patterns were the same as those of the corresponding aldehydes.

Analyses by capillary GC of samples periodically taken from the reaction mixtures of 130 and 150° C. Hydroformylations provided detailed information on the progress of the reactions and side reactions. The data obtained are summarized in Table XXIII.

In general, the capillary GC results also indicate that the primary reaction, i.e. hydroformylation, was essentially complete in 180 minutes. In this period, the hydrocarbon content of the mixtures decreased to about 35%. Determination of the concentrations of 1-hexene and 3-hexene reactants relative to that of the unreactive 3-methylpentane component indicated rapid olefin conversion. 1-Hexene conversion was essentially complete within one hour. 3-Hexenes conversion took about three hours. In that period 2-methyl-1-pentene was also reacted. The residual olefin content of the hydrocarbon feed after 3 hours was about 5%. Thus the total olefin conversion is about 92%.

Determinations of the 3-hexene concentrations in the 150° C. reaction mixtures indicated a slight increase rather than decrease during the first hour. This increase is apparently due to the isomerization of 1-hexene to internal hexenes concurrent with the hydroformylation. Olefin isomerization is much reduced at 130° C.

Hydroformylations were continued at both 130 and 150° C. for a total reaction time of 6 hours (360 min.). During the last 3 hours largely secondary reactions took place. The concentration of formate esters more than doubled. Formates were 7.1% of the oxygenated products at 130° C. and 8.2% at 150° C. The alcohol concentration decreased from 3.2 to 1.7% during the last 3 hours at 150° C. This was apparently due to the formation of heavy by-products not observable by capillary GC.

Table XXIII also shows the percentage distribution of the main aldehyde products in the reaction mixture. After 3 hours reaction time, the main aldehyde products amounted to 93.1% of the total oxygenates at 130° C. and 95.7% at 150° C. The n-aldehyde component was 36.2 and 31.2%, respectively. As expected the n-alde-

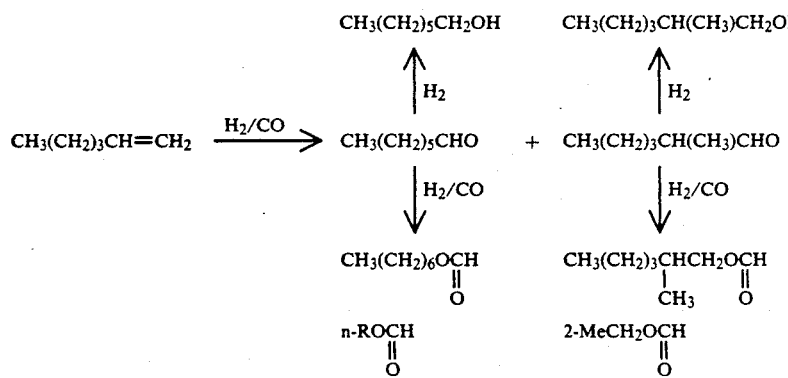

In case of the alcohol by-products only normal heptanol and 2-methylhexanol, the two main isomers, were identified. However, all the significant isomeric heptyl formate by-products could be recognized since their hyde concentration decreased with increasing reaction time. More and more of the internal and branched olefin components reacted to form other branched aldehydes.

Table XXIII separately lists the percentage in the oxygenates of the three isomeric heptanals, i.e. n-heptanal, 2-methylhexanal and 2-ethylpentanal. These aldehydes are derived from linear hexenes as it was previously shown by the reaction schemes.

fraction at 130 and 150° C. were separately decobalted with aqueous acetic acid plus air treatment as usual. Neither precipitation nor separation problems were encountered. In case of the 150° C. reaction mixture, the percentage of dimers plus trimers was reduced from

TABLE XXIII

COMPOSITION BY CAPILLARY GC OF PERIODIC SAMPLES OF REACTION MIXTURES OF THE HYDROFORMYLATION OF A $C_6$ OLEFINIC DISTILLATE FRACTION OF BILLINGS FLUID-COKER NAPHTHA BY $H_2/CO$ AT 3000 PSI (20,680 kPa)

| | | | | Composition of Oxygenates | | | | | | | | | |
|---|---|---|---|---|---|---|---|---|---|---|---|---|---|
| Ex. No. Temp. | Time Min. | Press. Drop psi Min. | Hydro-carbon % in Total | n-Hexanes Conversion, % | | $C_7$ Aldehydes, % | | | | Aldehyde Ratios | | Formate Ester, % | |
| | | | | 1- | 3- | n | 2-Me | 2-Et | Others | n 2-Me | n i | n | 2-Me |
| 28 | 10 | 94 | 95 | 10 | 6 | 52.2 | 15.8 | 3.9 | 28.1 | 3.30 | — | — | — |
| | 30 | 77 | 51 | 98 | 36 | 43.3 | 19.0 | 6.6 | 28.9 | 2.28 | 0.76 | 0.5 | 0.3 |
| 130° C. | 60 | 32 | 43 | — | 65 | 41.8 | 17.9 | 6.2 | 31.2 | 2.33 | 0.72 | 0.7 | 0.4 |
| 0.4% Co | 180 | 11 | 35 | — | 99 | 36.2 | 15.4 | 5.7 | 35.8 | 2.35 | 0.57 | 1.2 | 1.8 |
| | 240 | 8 | 33 | — | — | 35.1 | 15.1 | 5.6 | 35.4 | 2.32 | 0.54 | 2.5 | 1.7 |
| | 360 | — | 35 | — | — | 33.1 | 15.2 | 6.0 | 35.6 | 2.20 | 0.50 | 3.6 | 2.5 |
| 29 | 10 | 118 | 91 | 23 | —[a] | 43.8 | 22.5 | 7.0 | 26.1 | 1.95 | | 0.6 | — |
| | 30 | 273 | 76 | 67 | —[a] | 43.1 | 22.7 | 7.0 | 22.9 | 1.90 | 0.76 | 0.4 | |
| 150° C. | 60 | 201 | 49 | 99 | 39 | 41.4 | 19.8 | 6.6 | 31.3 | 2.09 | 0.71 | 0.5 | 0.3 |
| 0.2% Co | 180 | 11 | 35 | 99 | 98 | 31.6 | 15.3 | 5.7 | 43.1 | 2.06 | 0.46 | 2.0 | 1.4 |
| | 240 | 10 | 36 | — | — | 28.3 | 14.1 | 5.5 | 47.2 | 2.01 | 0.39 | 2.8 | 2.1 |
| | 360 | — | 42 | — | — | 25.6 | 14.7 | 6.5 | 45.1 | 1.74 | 0.34 | 4.6 | 3.6 |

[a]Due to a concurrent isomerization of 1-hexene to internal hexenes, there was no decrease in the concentration of 3-hexenes.

Their combined percentage after 3 hours is 57.3% at 130° C. and 52.6% at 150° C. It is noted that these percentages are way below the percentage of linear olefins in the total identified olefins of the feed (86%). This and particularly the lower than expected percentage of the n-aldehyde component are due to the presence of significant amounts of unidentified methylcyclopentenes in the feed and the preferential conversion of the primary normal aldehyde isomer products to higher boiling secondary by-products.

The percentage distribution of identified lower boiling oxygenated compounds is shown in Table XXIV. It is noted that in this table the sum of the aldehydes derived from linear hexenes (Normal, 2-Me and 2-Et) in 180 minutes is 65.6% at 130° C. and 61.1% at 150° C. These increased percentages are due to the exclusion of cyclic $C_7$-aldehyde products from the calculations.

The primary $C_7$ aldehyde products of the hydroformylation of $C_6$ olefinic coker distillate feed and the secondary products derived via the condensation of these aldehydes were separated by distillation for further studies. At first, the two reaction mixtures resulting from the hydroformylation of the $C_6$ olefinic naphtha 33.4% to 18.5% during decobalting, probably due to acetal and ester hydrolysis.

The decobalted yellow liquid reaction mixtures (1834 g and 2288 g) were fractionally distilled under atmospheric pressure using a two foot packed column.

Most of the unconverted hydrocarbons were removed from the reaction mixtures as colorless liquid distillates boiling between 55 and 65° C., using a heating bath of 120 to 130° C. Thereafter, the aldehyde products were distilled at reduced pressure. The aldehydes from the 130° C. reaction were distilled at 29 to 31° C. under 0.2 mm. Those of the 140° C. hydroformylation were received between 30 and 50° C. at 10 mm pressure. The heating, particularly during the atmospheric distillation, resulted in the formation of additional amounts of dimers and trimers. In the case of the 130° C. reaction mixture, the heavy by-products increased by 60% (from 18.9 to 31.9%) during distillation. In the case of the 150° C. reaction mixture, the increase was 82% (from 18.5 to 33.6%).

TABLE XXIV

SELECTIVITY OF THE HYDROFORMYLATION OF $C_6$ OLEFINIC DISTILLATE FRACITON OF BILLINGS FLUID-COKER NAPHTHA TO VARIOUS ISOMERIC $C_7$ ALDEHYDES

| | | Capillary GC Composition of Main Products and By-Products, % | | | | | | | | | | |
|---|---|---|---|---|---|---|---|---|---|---|---|---|
| | | Aldehydes | | | | | | | Alcohols | | Formates | |
| Temp. Cat. | Time Min. | 2,4-DiMe | 2-Et | 3-Me | 2-Me | 4-Me | 5-Me | Normal | 2-Me | Normal | 2-Me | Normal |
| 130° C. | 10 | 0.9 | 4.3 | 9.0 | 17.3 | 6.4 | 4.8 | 57.3 | — | — | — | — |
| 0.4% Co | 30 | 2.3 | 7.2 | 9.1 | 20.9 | 7.5 | 4.0 | 47.4 | 0.3 | 0.4 | 0.3 | 0.6 |
| | 60 | 2.2 | 6.9 | 9.9 | 19.8 | 8.2 | 4.6 | 46.1 | 0.4 | 0.6 | 0.5 | 0.8 |
| | 180 | 2.5 | 6.5 | 11.9 | 17.6 | 9.0 | 5.9 | 41.5 | 0.6 | 1.0 | 1.4 | 2.1 |
| | 240 | 2.4 | 6.4 | 12.2 | 17.3 | 8.9 | 5.9 | 40.2 | 0.7 | 1.2 | 1.9 | 2.8 |
| | 360 | 2.5 | 6.8 | 12.5 | 17.2 | 8.5 | 5.8 | 37.7 | 0.6 | 1.5 | 2.8 | 4.1 |
| 150° C. | 10 | 2.0 | 7.5 | 7.5 | 24.2 | 6.0 | 4.0 | 47.2 | — | 1.0 | — | 0.6 |
| 0.2% Co | 30 | 2.2 | 7.6 | 6.9 | 24.8 | 6.6 | 3.5 | 47.1 | 0.2 | 0.7 | — | 0.4 |
| | 60 | 2.4 | 7.3 | 8.5 | 21.7 | 7.9 | 4.3 | 45.4 | 0.6 | 0.9 | 0.4 | 0.6 |
| | 180 | 2.7 | 6.6 | 11.0 | 17.8 | 9.0 | 5.8 | 36.7 | 2.7 | 3.7 | 1.7 | 2.3 |
| | 240 | 2.7 | 6.5 | 10.7 | 16.7 | 8.4 | 5.5 | 33.6 | 4.3 | 5.9 | 2.4 | 3.3 |
| | 360 | 2.9 | 8.0 | 11.5 | 18.1 | 7.7 | 5.0 | 30.7 | 2.5 | 3.6 | 4.3 | 5.7 |

The distilled $C_7$ aldehyde products of the two hydroformylation runs were combined to provide 1353 g (11.87 moles) aldehyde intermediate. The composition of this combined aldehyde product with the distribution of the various heptanal isomers is provided in Table XXV.

The heptyl formate rich distillate fractions were also sition of the formate esters occurred to an increasing degree as the temperature of the heating bath increased to 150° C. Thus the last small distillate fraction (11 g) consisted of 70% heptanols, 12% dimers and 18% trimers.

TABLE XXV
COMPOSITION OF THE C₇ ALDEHYDE PRODUCTS AND FORMATE BY-PRODUCTS DERIVED FROM A C₆ OLEFINIC DISTILLATE FRACTION OF FLUID-COKER NAPHTHA

| | | | Composition by Capillary GC | | |
|---|---|---|---|---|---|
| | | | Aldehydes | | Formates |
| Seq. No. | Name of Component | Designation of Component | % of Total Cmpds. | % of Listed Cmpds. | % of Listed Cmpds.$^a$ |
| 1 | 2,4-Dimethylpentanal | 2,4-Di-Me—CHO | 2.22 | 13.50 | 18.10 |
| 2 | 2-Ethylpentanal | 2-Et—CHO | 8.07 | 9.77 | 0.68 |
| 3 | 3-Methylpentanal | 3-Me—CHO | 11.15 | 13.50 | 1.99 |
| 4 | 2-Methylpentanal | 2-Me—CHO | 15.50 | 18.76 | 2.53 |
| 5 | 5-Methylpentanal | 5-Me—CHO | 6.74 | 8.71 | 1.23 |
| 6 | 4-Methylpentanal | 4-Me—CHO | 4.55 | 5.52 | 0.90 |
| 7 | n-Heptanal | n-C₆—CHO | 26.20 | 31.72 | 8.98 |
| 8 | 2-Methylhexanol | 2-Me—CH₂OH | 0.45 | 5.39 | 10.82 |
| 9 | n-Heptanol | n-C₆—CH₂OH | 0.31 | 0.38 | 12.53 |
| 10 | 2-Ethylpentyl formate | 2-Et formate | 0.10 | 0.12 | 0.67 |
| 11 | 3-Methylhexyl formate | 3-Me formate | 0.51 | 0.62 | 2.88 |
| 12 | 2-Methylhexyl formate | 2-Me formate | 2.93 | 3.55 | 18.10 |
| 13 | 5-Methylhexyl formate | 5-Me formate | 0.80 | 0.97 | 5.72 |
| 14 | 4-Methylhexyl formate | 4-Me formate | 0.46 | 0.56 | 3.78 |
| 15 | n-Heptyl formate | n-C₇ formate | 2.59 | 3.14 | 28.90 |
| 16 | Total aldehydes | R—CHO's | 74.43 | 90.13 | 16.60 |
| 17 | Total alcohols | R—CH₂OH's | 0.76 | 0.92 | 23.35 |
| 18 | Total formates | R—CH₂O₂CH's | 7.39 | 8.95 | 60.05 |
| 19 | Sum Total | | 82.58 | 100.00 | |

$^a$The high boiling "dimer and trimer" components were not eluted from the capillary GC column. According to packed column GC there were about 2% dimers and about 30% trimers present.

combined to provide 396 g of another intermediate for hydrogenation. This colorless liquid fraction contains about 50% formate ester. Its boiling range is from 43 to 65° C. at 10 mm. The rest are aldehydes and alcohols and their condensation products. Thus the product is equivalent to about 3 moles. As such, it is the calculated amount for the hydroformylation of 252 g (3 moles) of hexene. The isomer composition of this formate rich product is comparable to that of the aldehyde in Table XXV.

The aldehyde product consists of about 90% aldehydes, 9% formates and 1% alcohol. About 82.6% of all the components of the aldehyde fraction were specifically identified. Of the total identified aldehydes, 35.2% is n-heptanal. The n/i ratio of aldehydes is 0.54. Most of the iso-aldehydes are monobranched C₇-aldehydes. Only one dibranched aldehyde, 2,4-dimethylpentanal, was found. On an average the aldehyde product mixture contained 0.63 branches per molecule.

The higher boiling formate rich fraction (E-7170-II) could be only partially analyzed by capillary GC. The high boiling dimer and trimer components were not eluted from the capillary column. According to packed column GC, the formate fraction contained small amounts of dimers (about 2%), but large amounts of trimers (about 30%). The relative percentage of formates among these components is 60%. It is interesting to observe that the alkyl carbon backbones of these isomeric heptyl formates correspond to those of the primary aldehyde products.

After distilling off most of the aldehydes, the residual reaction mixtures were combined and their fractional distillation continued at 10 mm using an 18 in. packed column. Further distillate fractions containing increasing amounts of C₇ alcohol and heptyl formate secondary reaction products were obtained between 50 and 66° C. at 10 mm. During the distillation, thermal decomposition of the formate esters occurred to an increasing degree as the temperature of the heating bath increased to 150° C. Thus the last small distillate fraction (11 g) consisted of 70% heptanols, 12% dimers and 18% trimers.

After the decomposition of the formate ester by-products, the rest of the residue was distilled using a one foot column at 0.1 mm. About 640 g of a distillate consisting of about 70% dimer and 21% alcohol was obtained as a clear, pale yellow liquid boiling between 55 and 74° C. Thereafter, a trimer rich fraction (80%) and a tetramer rich fraction (58%) were also obtained as yellow liquid distillates. The "trimer" fraction distilled at 130 to 132° C. at 0.1 mm with decomposition.

The final distillation residue was only 116 g, i.e. 2.8% of the starting reaction mixtures. However, the recovery of pure distillate products was poor, due to the concurrent decomposition of the formates and heavier by-products. The present results suggest the hydrogenation of the complete reaction mixture immediately subsequent to cobalt removal. This should result in much improved recovery of the desired hepanols.

The sulfur compound components of C₆ olefinic coker naphtha feed and the hydroformylation feed were also studied primarily to determine sulfur distribution according to boiling point. The total sulfur contents of feed plus selected product and by-product fractions is shown by the following tabulation:

| Boiling Point °C./mm | Main Component (%) | Sulfur ppm |
|---|---|---|
| 56–65/760 | Hydrocarbon Feed (100) | 640 |
| 55–59/760 | Recovered Hydrocarbon (99) | 575 |
| 31/02 | Aldehyde (85) and Higher | 92 |
| 58–65/10 | Formate (46) and Lower | 123 |
| 55–57/0.1 | Dimer (82) and Lower | 1740 |
| 130–132/0.1 | Trimer (80) and Lower | 3380 |
| — | Distillation Residue | 596 |

The data indicate that some of the sulfur compounds of the feed are converted to high boiling compounds. The aldehyde product has a relatively low sulfur content.

An investigation of the sulfur distribution by GC/MS showed that the thiol components of the feed were largely converted to $H_2S$ and to high boiling sulfur compounds while the thiophene component remained mostly unconverted. The main sulfur compound impurity in the aldehyde fraction was thiophene, due to poor separation.

The sulfur containing compounds in the dimer fractions were thiolheptanoic acid propyl and butyl esters. It is assumed that the propyl ester was derived by the reaction of the propanethiol component of the feed with the $C_7$ aldehyde product $$2\ C_6H_{13}CHO + C_3H_7SH \rightarrow C_6H_{13}COSR + C_6H_{13}CHO$$

The corresponding butyl ester could have been derived via butadiene derived from thiophene according to the following hypothetical set of reaction equations:

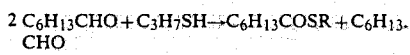
$$+ 2H_2 \longrightarrow CH_2=CH-CH=CH_2 + H_2S$$

$$2\ C_6H_{13}CHO \longrightarrow C_6H_{13}CO_2H + C_6H_{13}CH_2OH$$

$$C_6H_{13}CO_2H + H_2S \longrightarrow C_6H_{13}COSH + H_2O$$

$$C_6H_{13}COSH + CH=CH-CH=CH_2 \longrightarrow C_6H_{13}COSCH_2CH=CHCH_3$$

$$\downarrow H_2$$

$$C_6H_{13}COSCH_2CH_2CH_2CH_3$$

The above hypothesis is supported by a model experiment. A 9 to 1 mixture of 1-hexene and thiophene was hydroformylated under the previously used conditions in the presence of 0.02% cobalt in a highly exothermic reaction between 140 and 185° C. GC/MS studies indicated that 5% of the thiophene was converted to butyl thiolheptanoate and propyl thiolheptanoate.

The main sulfur containing components of the trimer fraction were found to be diheptyl sulfides. These were presumable derived from the heptanal products as indicated by the following hypothetical sequence of reactions:

$$C_6H_{13}CHO \xrightarrow{H_2S} [C_6H_{13}CHS] \xrightarrow{H_2} C_6H_{13}CH_2SH$$

$$C_6H_{13}CH_2SH \xrightarrow{C_6H_{13}CHO} C_6H_{13}CH(OH)SCH_2C_6H_{13}$$

$$\downarrow H_2$$

$$C_6H_{13}CH_2SCH_2C_6H_{13}$$

Whether the above hypotheses of the course of sulfur compound conversions are right or wrong, the present example demonstrates that, in the present process, the sulfur containing impurities of the feed are partially converted to high boiling thiol esters and sulfides rather than sulfur compounds of the aldehyde boiling range. Thus aldehydes of low sulfur content can be isolated by fractional distillation.

The aldehyde product was hydrogenated as a 2 to 1 mixture with toluene in the presence of 5% water and 10% CoS/MoS based catalyst at about 160° C. under 3000 psi for 20% hours. Probably as the result of the high temperature employed, significant dimerization occurred. According to packed column GC, the distribution of the oxygenated components of the final reaction mixture was the following: 56% alcohols 39% dimeric aldol alcohols and 5% trimers. Sulfur specific GC indicated no sulfur in the alcohol range, but $H_2S$ and high boiling sulfur compounds in the dimer range.

The crude alcohol product was further diluted with toluene to produce a 1 to 1 mixture. This was washed with 10% aqueous sodium hydroxide and then with water to remove the $H_2S$ and other acidic impurities. The resulting organic phase was then fractionally distilled using a 24 plate Oldershaw column. The heptanol product was obtained as a colorless, pleasant smelling liquid between 98 and 103° C. at 55 mm. The dimeric aldol alcohol distilled in the 74 to 99° C. range at 3 mm. The trimer by-product remained as the distillation residue. No sulfur could be detected by GC in the alcohol product, but minor sulfur impurities were noted in the dimer.

The heart cut heptanol product containing 2% n-normal isomer was converted to semilinear diheptyl phthalate which was evaluated as a plasticizer.

Example 30

Hydroformylation of $C_7$ Naphtha by 1/1 $H_2$/CO with 0.2% Cobalt at 130° C. under 3000 psi and the Hydrogenation of the $C_8$ Aldehyde Product.

A broad cut $C_7$ Fluid-coker naphtha was redistilled to provide an olefin enriched oxo-feed. The narrow fraction of a 15/10 distillation, boiling between 88 and 94° C., was utilized. It contained about 6.5% 2-methylheptene, 30% 1-n-heptene, 12% n-heptane, 4.3% trans-2-heptene, 2.8% cis-2-heptene. Only small amounts of aromatic hydrocarbon were present: 0.1% benzene and 0.5% toluene. A sulfur specific GC of this distillate prior to use as a feed indicated that some of the sulfur containing components were converted to high boiling compounds.

The hydroformylation of the above feed was carried out using a 1 to 1 mixture of $H_2$/CO under 3000 psi at 130° C. with 0.2% Co catalyst, added as a solution of $Co_2(CO)_8$ in the feed, in the manner described in the previous example. A maximum rate of pressure drop was observed about an hour after the start of the reaction. The conversion of 1-heptene was essentially complete in two hours. The reaction was completed in four hours. The reaction was highly selective to aldehydes. The distribution of the various types of components of the final reaction mixture by packed column GC was the following: 33.7% unconverted $C_7$ hydrocarbons, 59.1% $C_8$ aldehydes, 4.2% $C_7$ alcohols and $C_7$ alkylformates, plus 3% dimers and trimers. Capillary GC provided the following isomer distribution of $C_7$ aldehydes: 43.8% n-octanal, 11.7% 2-methylheptanal, 8% 3-methylheptanal, 5.8% 2-ethylhexanal and 1.7% 2-propylpentanal. A sulfur specific GC of the reaction mixture indicated the presence of $H_2S$, some volatile sulfur compounds in the C₇ feed range and minor nonvolatile sulfur compounds in the dimer range. There were no measurable sulfur compounds in the aldehyde range.

The hydroformylation reaction mixture was decobalted by aeration with hot aqueous acetic acid. Thereafter, the cobalt free mixture was hydrogenated without prior removal of the unreacted C₇ hydrocarbons and volatile sulfur compounds. Two hydrogenation experiments were performed in the presence of 10% CoS/MoS based catalyst and 5% water under 300 psi (206 atm) pressure. The first experiment was carried out at 150° C. After 20 hours only about half of the aldehydes were reduced. Thus the reaction was completed in 40 hours. The second experiment was carried out at temperatures increasing from 130 to 160° C. in four hours in the manner described in Example 26 and 27. After an additional 16 hours at 160° C., the hydrogenation was complete.

Hydrogenation at 150° C. resulted in the formation of major amounts of dimers. The ratio of $C_8$ alcohols to the $C_{16}$ aldol alcohols in the reaction mixture was 64 to 37. There was also significant $C_8$ paraffin formation as indicated by the 78/22 ratio of $C_7$ and $C_8$ hydrocarbons. In contrast, the better controlled, variable temperature hydroformylation was highly selective: The ratio of $C_7$ alcohols to dimer alcohols was 91 to 9 and the $C_7$ to $C_8$ hydrocarbon ratio 92 to 8. The n-aldehyde reactants were preferably dimerized. Hydrogenation at 150° C. produced $C_8$ alcohols containing 36.4% n-octanol, while the more controlled variable temperature reaction gave a $C_8$ alcohol containing 40.3% normal isomer.

The crude $C_8$ alcohols were washed with 10% aqueous NaOH and then with water. Thereafter, the mixture was fractionally distilled using a 22 plate Oldershaw column. The $C_8$ alcohol product was obtained as a clear, colorless liquid between 81 and 87° C. at 13 mm. It contained 33% n-octanol. No sulfur could be detected by GC. The compound was converted to a semi-linear dioctyl phthalate plasticizer.

Examples 31 to 34

Hydroformylation of Broad and Narrow Cut $C_8$ Naphtha Fractions With and Without Prior Caustic Treatment in the Presence of Cobalt with 1/1 $H_2$/CO at 300° C. and 3000 psi The broad and narrow cut $C_8$ Flexicoker naphtha distillate fractions, described earlier by Table IX and FIGS. 4 and 4, were utilized as oxo-feeds. Half of each of these feeds were extracted with a 30% KOH solution in methanol containing 2% water to remove the thiol components. The caustic treated fractions were then washed with water and hydroformylated under the same conditions as the untreated fractions. The synthesis gas reactant was a 1 to 1 CO/$H_2$ mixture. The reactions were carried out at 130° C. (266° F.) at 3000 psi (207 atm).

As a catalyst precursor, $Co_2(CO)_8$ was added as a 6% toluene solution under reaction conditions. The catalyst addition was mostly in increments providing 0.1% cobalt to the reaction mixture. The occurrence of hydroformylation was tested by shutting off the synthesis gas supply and observing the rate of pressure drop. In general, some pressure drop was always observed on catalyst addition, but it was not sustained if the amount of cobalt was insufficient. In such cases, an additional 0.1% cobalt was added every 60 minutes until a sustained reaction resulted. With sufficient amounts of cobalt, the pressure drop increased during catalyst preforming and then gradually decreased as the olefin reactants were depleted.

The reaction mixtures were periodically sampled and analyzed by packed column and capillary gas chromatography (GC). The pressure drop and packed column GC data were used to estimate reaction rates, feed conversion and overall selectivity to aldehydes, alcohols plus formates and aldehyde dimers plus trimers. The results obtained by capillary GC are summarized in Table XXVI.

Table XXVI shows that the four feeds exhibited increasing reactivities in this order: untreated broad, caustic washed broad, untreated narrow and caustic washed narrow. For these four feeds the minimum effective concentration of cobalt catalyst was 0.4, 0.4, 0.3 and 0.2%, respectively. Although the effective catalyst concentration was 0.4% cobalt for both the untreated and the caustic washed feeds, the caustic washed feed was much more reactive.

The packed GC data of Table XXVI show that the GC percentage of the total oxo-products by the end of the reaction ranged from about 39.3% to about 58.6%. Since the GC response factor for aldehydes is about 1.3, these GC percentages correspond to 45.7 wt. % and 64.8 wt. % oxo-products, respectively.

The percentages of oxo-products derived from the narrow olefinic feeds are higher than those from the broad feeds. This is expected based on the different olefin reactant content of the two types of feeds. It is unexpected that the selectivity to total aldehydes is also higher in case of the narrow feeds. It is believed that the decreased amount of by-products in the reaction mixtures derived from the narrow feeds are due to the lower percentage of cobalt catalyst used. The selectivity was clearly the highest in the case of the narrow, caustic treated feed where the least catalyst was employed.

The composition of the hydroformylation reaction mixtures was further studied using a combination of capillary gas chromatography and mass spectrometry. The main aldehyde products were identified primarily on the basis of the characteristic MS fragmentation patterns involving the McLafferty rearrangement. The formation of the isomeric $C_9$ aldehyde isomers found from the $C_8$ olefin isomers of the feed by hydroformylation is outlined by the following reaction schemes:

TABLE XXVI

The Conversion of the Olefinic Components of $C_8$ Fractions of Fluid-Coker Naphtha by Hydroformylation with 1/1 $H_2$/CO at 130° C. and 3000 psi in the Presence of Cobalt Catalyst Derived from $Co_2(CO)_8$

| Run No. and Feed Used | Total Time Min. | Effective Time Min. | Co Conc. % | P Drop,[b] psi Min. | Concentration in the Reaction Mixture by Packed GC, %[a] | | | |
|---|---|---|---|---|---|---|---|---|
| | | | | | Unreacted Feed[c] | Aldehydes | Alcohols[d] | Dimers |
| Untreated Broad | 120 | 150 | 0.2 | 1.4 | 93.2 | 1.9 | 3.6 | 1.3 |
| | 180 | 100 | 0.3 | 2.5 | 93.2 | 3.1 | 3.1 | 0.6 |

TABLE XXVI-continued

The Conversion of the Olefinic Components of $C_8$ Fractions of
Fluid-Coker Naphtha by Hydroformylation with 1/1 $H_2$/CO at 130° C. and 3000 psi
in the Presence of Cobalt Catalyst Derived from $Co_2(CO)_8$

| Run No. and Feed Used | Total Time Min. | Effective Time Min. | Co Conc. % | P Drop,[b] psi Min. | Concentration in the Reaction Mixture by Packed GC, %[a] | | | |
|---|---|---|---|---|---|---|---|---|
| | | | | | Unreacted Feed[c] | Aldehydes | Alcohols[d] | Dimers |
| | 240 | 0 | 0.3 | 1.2 | 92.3 | 3.7 | 3.3 | 0.7 |
| | 300 | 60 | 0.4 | | 89.4 | 6.2 | 3.6 | 0.8 |
| | 450 | 210 | 0.4 | 14.3 | 61.2 | 28.9 | 5.2 | 4.7 |
| | 530 | 290 | 0.4 | | 57.3 | 33.7 | 5.4 | 3.6 |
| Broad | 60 | | 0.2 | 2.5 | 93.2 | 2.5 | 3.1 | 1.2 |
| Caustic | 120 | 0 | 0.3 | 3.6 | 92.4 | 3.6 | 3.3 | 0.7 |
| Washed | 180 | 60 | 0.4 | 9.1 | 88.9 | 6.5 | 3.9 | 0.7 |
| | 240 | 120 | 0.4 | 53.2 | 72.2 | 19.4 | 5.7 | 2.7 |
| | 300 | 180 | 0.4 | 6.0 | 59.6 | 28.2 | 5.8 | 6.4 |
| | 450 | 230 | 0.4 | — | 50.4 | 37.0 | 7.1 | 5.5 |
| | 530 | 310 | 0.4 | — | 49.8 | 36.9 | 8.1 | 5.2 |
| Narrow | 60 | 0 | 0.2 | 5.0 | 95.5 | 3.0 | 0.4 | 1.1 |
| | 120 | 60 | 0.3 | 43.8 | 55.8 | 39.8 | 1.6 | 2.8 |
| | 180 | 120 | 0.3 | 16.6 | 48.8 | 47.0 | 2.4 | 1.8 |
| | 270 | 210 | 0.3 | 5.0 | 42.7 | 50.4 | 3.4 | 3.5 |
| | 350 | 290 | 0.3 | — | 41.4 | 51.5 | 4.2 | 2.9 |
| Narrow | 60 | 0 | 0.1 | 7.0 | 96.9 | 2.9 | 0.1 | 0.1 |
| Caustic | 120 | 60 | 0.2 | 43.2 | 86.3 | 13.4 | 0.2 | 0.1 |
| | 180 | 120 | 0.2 | 40.6 | 61.6 | 36.1 | 1.6 | 0.7 |
| | 270 | 210 | 0.2 | 11.1 | 50.1 | 46.3 | 2.0 | 1.6 |
| | 350 | 290 | 0.2 | 7.0 | 46.7 | 50.8 | 1.8 | 0.7 |

[a]GC concentrations are recorded as such; no conversion factors were used.
[b]The rate of pressure drop was observed while $H_2$/CO supply was shut off from the reactor.
[c]Benzene solvent for the catalyst was excluded from the calculations.
[d]Also includes formate esters.

| | Abreviation |
|---|---|
| $C_3H_7CH_2CH_2CH_2CH=CH_2 \longrightarrow C_3H_7CH_2CH_2CH_2CH_2CH_2CHO$ | n- |
| $C_3H_7CH_2CH_2CH=CHCH_3 \longrightarrow C_3H_7CH_2CH_2CH_2CHCHO$ with $CH_3$ branch | 2-Me |
| $C_3H_7CH_2CH=CHCH_2CH_3 \longrightarrow C_3H_7CH_2CH_2CHCHO$ with $C_2H_5$ branch | 2-Et |
| $C_3H_7CH=CHCH_2CH_2CH_3 \longrightarrow C_3H_7CH_2CHCHO$ with $C_3H_7$ branch | 2-Pr |
| $(CH_3)_2CHCH_2CH_2CH=CHCH_3 \longrightarrow (CH_3)_2CHCH_2CH_2CH_2CHCHO$ with $CH_3$ branch | 2,6-Di-Me |
| $(CH_3)_2CHCH_2CH_2CH=CHCH_3 \longrightarrow (CH_3)_2CHCH_2CH_2CHCHO$ with $C_2H_5$ branch | 2,5-Et,Me |
| $(CH_3)_2CHCH_2CH=CHCH_2CH_3 \longrightarrow (CH_3)_2CHCH_2CHCHO$ with $C_3H_7$ branch | 2,4-Pr,Me |

The linearities of the $C_8$ aldehyde products derived from the two pairs of $C_8$ feeds are described by the capillary GC data of Table XXVII. As expected, $C_9$ aldehydes containing a higher percentage of normal nonanal were derived from the narrow feeds than from the broad feeds. The final n-nonanal percentages for the narrow feed derived products are 37.2 and 40%. From the broad feeds final products containing 28% and 23.7% n-nonanal were derived. The difference between the products derived from untreated and caustic washed feeds of the same hydrocarbon composition is due to their different degrees of conversion.

With increasing conversion, the linearity of the products is decreasing. At first higher amounts of n-nonanal and 2-methylhaptanal (2-Me) are formed from the most reactive 1-n-octene feed component. As more and more of the less reactive internal and branched octenes are hydroformylated, the ratio of normal to iso-aldehydes is decreasing. In case of the broad feeds, the final n/i ratio is 0.39 and 0.31. Due to the higher percentage of 1-n-octene in the narrow feed, the final n/i ratio of aldehydes there is 0.59 and 0.67.

on cyclic $C_7$ olefins which are not present in significant quantities in the narrow feed.

The total percentage of some by-products having longer retention times than n-nonanal is also shown in Table II. These components are cyclic $C_9$ aldehydes, $C_9$ alcohols and $C_9$ alkyl formates. Their total in the final reaction mixtures derived from the broad cut $C_8$ feeds is 18.9 and 17.2%. The same by-products derived from the narrow $C_8$ feeds amount to only 6.42 and 4.41%, respectively. The greater amounts of broad feed derived by-products are due to the formation of higher amounts of cyclic aldehydes.

To assess the further processability of the hydrofor-

TABLE XXVII

The Linearity of $C_9$ Aldehydes Derived Via with 1/1 $H_2$/CO Hydroformylation of $C_8$ Olefinic Fractions of Billings Fluid-Coker Naphtha In the Presence of Cobalt Catalyst Derived from $Co_2(CO)_8$ at 130° C. and 3000 psi

| Ex. No. | $C_8$ Feed Fraction | Total Co Conc. | Total Time Min. | Effective Time Min. | Concentration of Isomeric $C_9$ Aldehydes[a] in Total $C_9$ Aldehydes by Capillary GC, % | | | | | | | | Aldehyde Linearity | | By-Prod.[k] $C_{10}$ Cyclic Aldehydes, Alcohols, Formates % |
|---|---|---|---|---|---|---|---|---|---|---|---|---|---|---|---|
| | | | | | Normal[b] | Cyclic 1[c] | 2-Me[d] | Cyclic 2[c] | 2-Et[e] | 2-Pr[f] | 2,6-Di-Me[g] | 2,5-Et,Me[h] | n[i]/i | n[j]/2-Me | |
| 31 | Broad | 0.1 | 120 | | | | | | | | | | | | |
| | | 0.3 | 240 | 0 | | | | | | | | | | | |
| | | 0.4 | 300 | 60 | 36.5 | 5.55 | 10.6 | 8.79 | 4.02 | 4.58 | 2.74 | 0.58 | 0.58 | 3.45 | |
| | | | 450 | 210 | 32.0 | 5.47 | 9.69 | 9.65 | 4.04 | 6.28 | 3.26 | 0.84 | 0.47 | 3.30 | 12.8 |
| | | | 530 | 290 | 28.0 | 6.51 | 9.01 | 9.89 | 3.82 | 7.06 | 3.35 | 0.90 | 0.39 | 3.11 | 18.9 |
| 32 | Broad Caustic Washed | 0.2 | 60 | | | | | | | | | | | | |
| | | 0.3 | 120 | 0 | | | | | | | | | | | |
| | | 0.4 | 180 | 60 | | | | | | | | | | | |
| | | | 240 | 120 | 37.2 | 5.83 | 1.0 | 7.89 | 3.81 | 4.68 | 2.61 | 0.68 | 0.59 | 3.39 | |
| | | | 300 | 180 | 33.1 | 6.33 | 10.0 | 9.22 | 4.00 | 5.79 | 2.97 | 0.76 | 0.49 | 3.30 | |
| | | | 450 | 230 | 25.5 | 6.20 | 8.15 | 10.1 | 3.68 | 8.30 | 3.42 | 0.88 | 0.34 | 3.12 | 20.8 |
| | | | 530 | 310 | 23.7 | 6.13 | 8.25 | 10.4 | 3.75 | 9.07 | 3.43 | 0.90 | 0.31 | 2.89 | 17.2 |
| 33 | Narrow | 0.2 | 60 | 0 | | | | | | | | | | | |
| | | 0.3 | 120 | 60 | 46.2 | 4.49 | 14.9 | 11.1 | 5.07 | 5.42 | 1.52 | 0.64 | 0.86 | 3.10 | 2.97 |
| | | | 180 | 120 | 41.4 | 4.92 | 13.8 | 12.2 | 5.08 | 6.35 | 1.82 | 0.90 | 0.71 | 3.00 | 4.28 |
| | | | 270 | 210 | 38.0 | 5.15 | 13.1 | 13.2 | 5.24 | 7.25 | 1.96 | 0.98 | 0.61 | 2.90 | 5.10 |
| | | | 350 | 290 | 37.2 | 5.03 | 12.6 | 13.2 | 4.98 | 7.65 | 2.02 | 1.08 | 0.59 | 2.96 | 6.42 |
| 34 | Narrow Caustic Washed | 0.1 | 60 | 0 | | | | | | | | | | | |
| | | 0.2 | 120 | 60 | 51.1 | 3.91 | 15.7 | 11.1 | 5.03 | 4.90 | 1.35 | 0.51 | 1.04 | 3.25 | |
| | | | 180 | 120 | 46.8 | 4.39 | 15.5 | 11.0 | 5.02 | 5.26 | 1.48 | 0.60 | 0.88 | 3.02 | |
| | | | 270 | 210 | 43.2 | 4.83 | 14.2 | 12.2 | 5.18 | 6.13 | 1.81 | 0.88 | 0.76 | 3.04 | 3.49 |
| | | | 350 | 290 | 40.0 | 5.26 | 13.8 | 12.8 | 5.09 | 6.77 | 1.92 | 0.97 | 0.67 | 2.90 | 4.41 |

[a]Listed in the table in the order of their decreasing retention times.
[c]Cyclic aldehyde of unidentified structure.
[d]2-Methyloctanal.
[e]2-Ethylheptanal.
[f]2-Propylhexanal.
[g]2,6-Dimethylheptanal.
[h]2-Ethyl-5-methylhexanal.
[i]The ratio of n-nonanal to the aldehyde products having shorter retention times.
[j]The ratio of n-nonanal to 2-methyloctanal.
[k]By-products as a percentage of total $C_8$, $C_9$ and $C_{10}$ oxo-products.

Among the minor branched aldehyde components of the reaction mixture, significant quantities of 2-ethylheptanal (2-Et: 3.75 to 5.09%) and 2-propylhexanal (2-Pr) are formed. (The percentage of 2-propylhexanal includes the GC response for an overlapping peak.) These two aldehydes and 2-methylheptanal plus-n-nonanal are all derived from linear octenes.

The two major cyclic $C_9$ aldehydes (cyclic 1 and 2) were also formed in significant amounts ranging from 16.40 to 18.23% of the $C_8$ oxo-products. Compared to these, only lesser amounts of identified dibranched aldehydes, 2,6-dimethylheptanal (2,6-Di-Me) and 2-methyl-5-ethylpentanal (2,5-Me,Et) were found. Their combined total ranged from 2.89 to 4.25%.

Among the products derived from the broad $C_8$ feeds, there were also significant quantities of 2-propyl-4-methyl-pentanal (2,4-Me,Pr) and cyclic $C_8$ aldehydes. However, these lower boiling aldehydes not listed in the table since most of their derivation clearly depends mylation reaction mixtures, they were further analyzed by capillary GC using both a flame ionization detector (FID) for organic compounds and a sulfur specific detector (SSD) with quadratic response. As expected two different types of chromatograms were obtained for the reaction mixtures derived from the broad and narrow feeds. Whether the feed was caustic treated or not did not make a perceptible difference as far as the composition of the reaction mixture was concerned. The pentanethiol components of the untreated feeds were essentially all converted during hydroformylation. The thiophenic sulfur compounds remained essentially unchanged in all cases.

Only trace amounts of sulfur compounds (5-50 ppm range) boiling in the $C_9$ aldehyde range were formed during hydroformylation. Sulfur specific GC showed that their formation was concurrent with the early fast period of hydroformylation. No high boiling sulfur compounds could be detected in the reaction mixture. It is recalled that the amount of dimers and trimers is minimal under the mild hydroformylation conditions used.

In the following, the composition of the reaction mixtures is illustrated by FIG. 14, showing comparable chromatograms based on FID and SSD detection. FIG. 14 shows chromatograms of a final, untreated mixture derived from the methanolic potassium hydroxide washed narrow feed.

The lower FID trace of FIG. 14 shows, that in the case of the narrow cut feed there is a wide separation between the higher boiling $C_8$ aromatic hydrocarbon feed components and the lower boiling dibranched $C_9$ aldehyde products. It is also noted that the total aldehyde product selectivity is high. There are only small amounts of high boiling dimer and trimer by-products in the reaction mixture.

The upper SSD trace of FIG. 14 shows that most of the sulfur is in the region of the unconverted hydrocarbons. The thiophenic sulfur components of the feed remained unchanged. However, some other sulfur components were converted mostly to sulfur compounds of unknown structure. Minor amounts of $H_2S$ are present in the reaction mixture. There are also two very minor higher boiling sulfur compounds present. They have GC retention times slightly greater than the aldehyde products. The sulfur concentration of these two sulfur compounds is about 20 ppm while the sulfur concentration in the hydrocarbon region is about 2,000 ppm.

All four reaction mixtures were aerated in the presence of refluxing aqueous acetic acid to convert the cobalt compounds to water soluble cobalt acetate. In case of the reaction mixture derived from the untreated broad cut feed some dark precipitate was formed on standing. This was not dissolved completely during the cobalt removal procedure. Thus, the mixture was filtered to remove it. All the other reaction mixtures were decobalted without complication. The products derived from the narrow feed were easier to process. The methanolic KOH treated feed gave a mixture which was particularly easy to phase separate after caustic washing.

Capillary GC analysis of the cobalt free reaction mixtures indicated no significant change during decobalting. However, the decobalted mixtures do not appear to be storage stable. During two months standing at room temperature, the formation of high boiling sulfur compounds was observed by sulfur specific GC analysis of the decobalted reaction mixture derived from the untreated broad cut feed. Also, more dimer formation occurred during distillation if the decobalted aldehyde was aged. (It is also noted that the distilled aldehyde also tends to dimerize, i.e. aldolize, slowly during long term storage. In addition, the aged aldehyde forms more heavies during hydrogenation.)

The distillation of the decobalted aldehyde was carried out at a very low pressure to avoid any thermally induced dimerization. At first the unconverted $C_8$ hydrocarbons were distilled at about 20-25° C. under 1.2 mm pressure. Most of the hydrocarbon fractions from the broad cut feeds and all the hydrocarbon distillates from the narrow cut feed were colorless. Thereafter, the vacuum was decreased to 0.1 mm and the aldehydes were distilled. The aldehydes derived from the broad cut were fractionated between about 20 and 35° C., while those of the narrow cut feed were obtained between 23 and 31° C. Several aldehyde fractions were taken. Most of them were colorless but some of them were slightly yellow. The alcohols and formate esters were distilled between about 31 and 42° C. at 0.1 mm. They were also clear, colorless liquids. However, distillation of the formates at higher temperature (i.e. under increased pressure) resulted in decomposition and a slightly yellow distillate. There was no attempt made to obtain pure alcohol and formate fractions.

The results of the distillations of the various hydroformylation mixtures were summarized and compared. The aldehyde plus alcohol and formate distillates were combined in each case and designated as oxo-products. Based on the results the yields of oxo-products and residual heavy (dimeric and trimeric) by-products per 1000 g reaction mixture were calculated. The comparative data obtained are tabulated below:

| Yields of Oxo-Distillate Products and Residual By-Products From Various Hydroformylation Mixtures, g/1000 g Derived From Different $C_8$ Flexicoker Naphtha Fractions | | | | |
|---|---|---|---|---|
| | Broad Untreated | Broad Caustic-treated | Narrow Untreated | Narrow Caustic-treated |
| Aldehydes | 397 | 494 | 525 | 534 |
| Dimers | 85 | 79 | 72 | 53 |

The tabulation shows that the yield of distilled aldehydes per 1000 g reaction mixture varied widely, from 394 to 534 g. As expected, greater yields of distilled oxo-products were obtained from the narrow $C_8$ cut feeds of higher olefin content than from the broad $C_8$ fractions. From the two broad cuts, the caustic treated led to a much higher yield than the untreated because of the higher feed conversion (See Table I).

The $C_9$ aldehyde distillates (90% or more) obtained from the different $C_8$ Flexicoker naphtha fractions were mostly combined to provide feeds for hydrogenation to produce the corresponding $C_9$ alcohol products.

It is noted that in the case of the products derived from the narrow cut untreated distillates, the normal n-nonanal content was generally lower and the higher boiling components were more prevalent than in the narrow cut feed derived products. All the hydrogenations were carried to in the previously described manner in the presence of 5% water and 10% CoS/MoS based catalyst at 160° C. under 3000 psi pressure for 20 hours. The same catalyst was used repeatedly in the present tests.

Analysis of the hydrogenated reaction mixtures by packed and capillary GC indicated that the $C_9$ aldehydes were reduced to the corresponding $C_9$ alcohols n a selective manner. Alcohol selectivities ranged from 85 to 97%.

According to packed GC, the hydrogenation of the aldehyde derived from the broad $C_8$ fraction occurred with less than 2% dimer formation. In the case of the narrow cut derived aldehydes, dimer formation was about 15%.

Capillary GC indicated that paraffin formation was minimal, less than 5%, in all cases. n-Nonane was by far the largest paraffin by-product. Its concentration was less than 4% of the alcohol products. In general, the selectivity toward the isomeric nonyl alcohol products, was very high.

Sulfur specific GC shows that most of the low boiling sulfur impurities are dimethylthiophenes, i.e. components of the broad cut $C_8$ feed. There was no sulfur in the alcohol retention time range. However, all of the mixtures showed the presence of some sulfur in the dimer range. Apparently, the minute amounts of aldehyde range sulfur compounds, which were present in the feed, were converted during hydrogenation into sulfur derivatives of low volatility.

The composition of the low boiling components of the aldehyde feeds and alcohol product mixtures was studied by capillary GC and compared in Table XXVIII. The data of Table XXVIII show that both of the feeds and the products derived from the broad $C_8$ cut contain less normal, i.e. less $C_9$ straight chain, oxygenates and more higher boiling components than those of the narrow feeds.

TABLE XXVIII

Hydrogenation of the $C_9$ Aldehydes Derived Via the Hydroformylation of Various $C_8$ Flexicoker Naphtha Fractions

| Type of Mixture Analyzed | Components in Relation to Their Retention times to Normal Isomer[a] | Composition by Capillary GC % (of Reactants and Products Derived from Various $C_8$ Fractions[b]) | | | |
|---|---|---|---|---|---|
| | | Broad Un-treated | Broad Caustic Treated | Narrow Un-treated | Narrow Caustic Treated |
| Aldehyde Reactant | Shorter[c] | 57 | 52 | 64 | 56 |
| | Normal[a] | 27 | 21 | 33 | 37 |
| | Longer[d] | 16 | 27 | 3 | 7 |
| Alcohol Product | Paraffins[e] | 1 | 4 | 2 | 0 |
| | Shorter[f] | 61 | 52 | 60 | 59 |
| | Normal[a] | 22 | 17 | 29 | 35 |
| | Longer[g] | 16 | 27 | 9 | 6 |

[a]Normal n-nonanal reactant or n-nonyl alcohol product.
[b]Based on analyses of hydrogenation feeds and reaction mixtures.
[c]Branched aldehydes of shorter retention time.
[d]Aldehdyes of longer retention time.
[e]$C_8$ Paraffin by-products.
[f]Alcohols of shorter retention times.
[g]Alcohols of longer retention time, excluding dimers.

The concentration of n-nonyl alcohol products is generally lower than that of their n-nonanal presursors. This is due to the preferred aldolization of n-nonanal to provide the corresponding dimer. The exact concentrations of dimers could not be determined by capillary due to their limited volatility. The concentration of volatile $C_8$ paraffin by-products was generally very low, 0 to 4%, as indicated by the Table XXIII.

The hydrogenation reaction mixtures were washed with 10% aqueous sodium hydroxide solution and then water to remove hydrogen sulfide and carboxylic acid by-products. The separation of the aqueous and organic phases occurred readily. After a final wash, the mixtures were fractionally distilled to recover the alcohol products.

A 24 plate Oldershaw, column was employed to separate the hydrocarbon solvent and by products from alcohol product fractions. The dimer and trimer by-products were usually obtained as a distillation residue. The fractional distillations were carried out under reduced pressure using a heating bath of less than 200° C. to avoid the decomposition of sulfur containing dimeric by-products.

All the $C_9$ alcohol distillates were colorless clear liquids. The alcohol fractions of the reaction mixture derived from the broad $C_8$ feed fractions, were distilled between 91 and 111° C. at 18 mm. As expected, the alcohol distillates derived from the narrow $C_8$ feed had a narrower boiling range. They were obtained between 95 and 107° C. at 18 mm. The dimer by-product derived from the narrow $C_8$ feed was also distilled. It was obtained as a clear colorless liquid between 88 and 98° C. at 0.05 mm.

The alcohol distillate products derived from each of the four $C_8$ Flexicoker feeds were analyzed by capillary GC and combined to provide four alcohol products. The distillation residues consisting of undistilled alcohols, dimers and trimers were analyzed using a packed column GC. The yields of products and by-products, obtained from the crude products and by-products, obtained from the crude product mixture after distilling of the hydrocarbons, are shown together with the yields of combined alcohol distillates in the following tabulation:

| | Yields of Alcohol Distillate Products and Residual Products, wt % (Derived from Different $C_8$ Flexicoker Fractions) | | | |
|---|---|---|---|---|
| | Broad Un-Treated | Broad Caustic Treated | Narrow Un-Treated | Narrow Caustic Treated |
| Alcohol Distillate | 90 | 58 | 77 | 60 |
| Residue | 10 | 42 | 23 | 40 |
| Alcohol | 9 | 10 | 3 | 10 |
| Dimer | 1 | 31 | 18 | 30 |
| Trimer | — | 1 | 2 | 1 |

As it is shown by the above data, the yields of alcohol distillates range from 58 to 90%. The large differences in $C_9$ alcohol yields are apparently due to the different degrees dimer by-product formation. The dimers are derived from the aldehyde reactants via aldolization hydrogenation. It is noted that there is less dimer formation from the aldehydes derived from the untreated $C_8$ feeds, possibly due to the presence of aldolization inhibitors.

For a comparative characterization of the composition of the free alcohols based on their capillary GC, the concentrations of the components, having shorter retention times than n-nonyl alcohol, were added up. Similarly, the total percentage of the components having longer retention times was determined. These percentages were then compared with that of the n-nonyl alcohol component. They are shown for all four alcohol products by the following tabulation:

| Grouping of Components According to GC Retention Times | Composition of $C_9$ Alcohol Distillate Products (Derived from Different $C_8$ Flexicoker Fractions)% | | | |
|---|---|---|---|---|
| | Broad UnTreated | Broad Caustic Treated | Narrow UnTreated | Narrow Caustic Treated |
| Shorter | 64.2 | 73.7 | 63.5 | 67.0 |
| n-Nonanol | 26.3 | 19.1 | 34.5 | 31.6 |
| Longer | 9.5 | 7.2 | 2.0 | 1.4 |

The data of the tabulation show that the broad $C_8$ feed derived alcohols have a lower percentage of n-nonyl alcohol component than those based on narrow $C_8$ feeds. The difference between the n-nonanol content of distilled alcohol products derived form untreated and caustic treated $C_8$ feeds appear to be due to differences in alcohol recovery. The distillation of higher boiling alcohol components was less complete from the product mixtures derived from the caustic treated feeds.

The above discussed four $C_9$ alcohol distillates did not contain any sulfur detectable by the capillary GC method employed (This method would have detected any single sulfur compound present in 5 ppm concentration or more). Samples of these distillates were submitted for total sulfur analyses. The broad untreated and treated distillates were found to contain 22 and 43 ppm sulfur while the corresponding distillates derived from the narrow cut feed contained 13 and 31 ppm, respectively. Overall, the above analytical results and other observations suggest that most of the sulfur compounds, distilling in the dimer by-product range, were formed during the aldehyde to alcohol hydrogenation.

A series of comparative odor tests were carried out with the alcohol products. The results showed that these alcohols have odors typical of $C_9$ oxo alcohols in general.

The alcohols were converted to semilinear diheptyl phthalate which was evaluated as a plasticizer.

Examples 35 and 36

Hydroformylation of a $C_9$ Olefinic Fraction of Naphtha by $H_2$/CO with Cobalt at 3000 psi in the 130–150° C. Temperature Range The $C_9$ olefinic feed for the present hydroformylation experiments was derived from a $C_4$ to $C_{12}$ Fluid-coker naphtha by a double 15/10 type distillation. The second distillation started with a broad $C_{10}$ cut of bp. 145 to 155° C. and produced a narrow cut of bp. 143 to 148 in about 40% yield. The concentration of the major components of the broad and narrow boiling fractions is shown by the following tabulation:

| Identification | Boiling Point C.° | °F. Approx. | $C_9$ Olefinic Feeds components, % Narrow Cut Bp. (143–148° C.) | Broad Cut Bp. (145–155° C.) |
|---|---|---|---|---|
| Ethylbenzene | 136.2 | 277 | 0.35 | 2.10 |
| 2,5-DiMe-Thiophene | 136.7 | 278 | | |
| p-Xylene | 138.3 | 281 | 1.82 | 7.04 |
| m-Xylene | 139.1 | 282 | 0.64 | 2.05 |
| o-Xylene | 144.4 | 292 | 4.93 | 7.90 |
| 1-Nonene | 146 | 295 | 24.09 | 21.06 |
| n-Nonane | 150.8 | 303 | 17.43 | 15.45 |
| 2,3,5-TriMe-Thiophene | 160.1 | 320 | | |
| 1-Me, 3-Et-Benzene | 161.3 | 322 | 0.75 | 2.17 |

It is apparent that the second 15/10 distillation was not sufficiently effective to produce the desired narrow 1-n-nonene rich fraction in a high yield. However, it was possible to exclude most of the aromatic components from the narrow nonenes fraction by accepting a low distillate yield. Sulfur GC indicated that most of dimethylthiophenes and trimethylthiophenes were removed during the second fractionation with the xylenes and 1-methyl-3-ethylbenzene respectively. The sulfur content was reduced from about 1.5 to 0.2%.

The narrow, olefinic fraction of the $C_9$ Fluid-coker naphtha (E-7285) was hydroformylated using a 1/1 mixture of $H_2$ and CO in the presence of 0.2% Co. The cobalt catalyst was introduced as a 13% solution of its precursor, $Co_2(CO)_8$, in toluene. The reaction was carried out at 3000 psi at variable temperatures. The temperature was increased during the course of the reaction to convert the various types of olefins at their minimum reaction temperature.

The solution of the $Co_2(CO)_8$ catalyst precursor was added at 120° C. This reaction temperature was maintained for 1 hour. Thereafter, the reaction temperature was raised to 130° C. Similarly, the temperature was increased to 140° and then 150° C. after 1 and 2 hours, respectively. After a total reaction time of 4 hours, the reaction was discontinued.

The results of the hydroformylation are shown by Table XXIX. For comparison, Table XXIX also lists some of the data obtained in an experiment carried out with 0.1% catalyst in an identical manner.

The composition of the reaction mixtures by packed GC showed that the reaction was highly selective to aldehydes. After 4 hours in the presence of 0.2% Co, the hydroformylation reaction was essentially complete. According to GC, the concentration of aldehydes in the reaction mixture reached 45%. Experiments to determine GC response factors with n-decane, n-decanal, n-decanol mixtures indicated that the 45% GC response corresponds to about 50% by weight of aldehyde. To reach this aldehyde concentration, a minimum of 44.7% olefins in the feed had to be hydroformylated. At this point, the reaction mixture still contained only about 5% alcohols plus formate esters and about 3% dimers and trimers.

The isomeric $C_{10}$ aldehyde distribution by capillary GC showed that the n-decanal was far the most reactive 1-n-nonene olefin component of the feed. Thus, its percentage of the total oxo-products was particularly high (58.2%) during the early phase of the reaction. At the completion of the reaction, the percentage of the n-decanal was 44.8%. The percentage of the second largest $C_{10}$ aldehyde isomer, 2-methylnonanal was 16.2%. Thus, these two aldehyde isomers which can be derived from 1-n-nonene made up 61% of the oxo products. As expected the other 2-alkyl substituted $C_{10}$ aldehydes derived from linear internal octenes (2-ethyloctanal, 3-propylheptanal and 4-butyloctanal) were other significant product isomers, in a total concentration of 71.3%. Thus, the total concentration of oxo products derived form linear olefins is about 84.8%.

Capillary GC also indicated the formation of comparable amounts of isomeric alcohols and their formate esters having alkyl structures corresponding to the isomeric decanal products.

TABLE XXIX

HYDROFORMYLATION OF $C_{10}$ OLEFINIC FRACTIONS OF FLUID COKER NAPHTHA IN THE PRESENCE OF 0.2% CO CATALYST DERIVED FROM $CO_2(CO)_8$ AT TEMPERATURES INCREASING FROM 120 TO 150° WITH 1/1 $H_2$/CO AT 3000 PSI

| Reaction Conditions | | Cat. Conc. | Components of Total Mixture by Packed GC, % | | | | Composition of Products by Capillary GC | | | | | | |
|---|---|---|---|---|---|---|---|---|---|---|---|---|---|
| | | | | | | | Isomeric $C_9$ Aldehydes in Oxo-Products[c], % | | | | Linearity of Aldehydes | | Ratio of n-Alcohol |
| Time Hrs. | Temp. °F. | Co % | Unreacted | Aldehydes | Alcohols[a] | Dimers[b] | Normal | Methyl[d] | Ethyl[e] | Propyl[f] | n/i | n/Me | to n-Formate |
| 1 | 120 | 0.2 | 95.2 | 4.6 | 0.2 | | | | | | | | |
| 2 | 130 | | 64.9 | 32.6 | 1.8 | 0.7 | 58.2 | 18.0 | 4.9 | 3.7 | 1.39 | 3.23 | 0.47 |

TABLE XXIX-continued

HYDROFORMYLATION OF $C_{10}$ OLEFINIC FRACTIONS OF FLUID COKER NAPHTHA IN THE PRESENCE OF 0.2% CO CATALYST DERIVED FROM $CO_2(CO)_8$ AT TEMPERATURES INCREASING FROM 120 TO 150° WITH 1/1 $H_2$/CO AT 3000 PSI

| Reaction Conditions | | Cat. Conc. | Components of Total Mixture by Packed GC, % | | | | Composition of Products by Capillary GC | | | | Linearity of Aldehydes | | Ratio of n-Alcohol to n-Formate |
|---|---|---|---|---|---|---|---|---|---|---|---|---|---|
| | | | | | | | Isomeric $C_9$ Aldehydes in Oxo-Products[c], % | | | | | | |
| Time Hrs. | Temp. °F. | Co % | Unreacted | Aldehydes | Alcohols[a] | Dimers[b] | Normal | Methyl[d] | Ethyl[e] | Propyl[f] | $\frac{n}{i}$ | $\frac{n}{Me}$ | |
| 3 | 140 | | 51.0 | 44.9 | 1.9 | 2.2 | 48.3 | 16.5 | 5.0 | 3.9 | 0.93 | 2.93 | 0.59 |
| 4 | 150 | | 46.5 | 45.9 | 4.6 | 3.0 | 44.8 | 16.2 | 5.4 | 4.1 | 0.81 | 2.77 | 0.62 |
| 3 | 140 | 0.1 | 90.5 | 9.3 | | 0.2 | | | | | | | |
| 4 | 150 | | 72.8 | 25.4 | 1.3 | 0.5 | 56.4 | 20.1 | 5.5 | 4.1 | 1.29 | 2.81 | — |

[a]Includes formate esters of the alcohols.
[b]Includes aldehyde dimers and trimers.
[c]The oxo-products are mostly aldehydes but include isomeric decyl alcohols and decyl formate esters.
[d]2-Methylnonanal.
[e]2-Ethyloctanal.
[f]2-Propylheptanal.

These secondary by-products were rich in the normal isomers, particularly the alkyl formates.

The decobalted combined hydroformylation reaction mixtures were fractionally distilled in vacuo using a two foot packed column. At first 1160.5 g (34.7%) of unreacted hydrocarbon components were removed at close to room temperature under 1 mm pressure. Thereafter, the remaining 2184.5 g (65.3%) mixture of oxygenated products was fractionated. Most of the isomeric $C_{10}$ aldehyde products were received between 43 and 49° C. at 0.5 mm. The total amount of the aldehyde distillates was 1197.5 g (35.8% of the reaction mixture). No attempt was made to separate the $C_{10}$ alcohol and $C_{10}$ alkyl formate products. They were distilled between 40 and 55° C. at 0.05 mm and received as 466.5 g (14%) of a colorless to light yellow liquid. Thus, the combined weight percentage of alcohols and alcohol precursors in the reaction mixture was 49.8. The $C_{20}$ dimer products of aldehyde condensation were largely distilled between 118 and 122° C. at 0.05 mm. About 296 g (11.8%) of these dimers were obtained as a pale yellow liquid. Finally, 102.5 g (3.2%) $C_{30}$ trimers were also obtained largely at about 215° C. at 0.5 mm. as a clear yellow distillate. The last of the trimers were distilled with some decomposition. The distillation residue was 22 g (0.5%) of the reaction mixture.

To prepare the desired semilinear $C_{10}$ alcohol, a combined $C_{10}$ aldehyde feed of the following composition was used.

| | | | |
|---|---|---|---|
| 2-Butylhexanal | 1.0 | n-Decanal | 23.4 |
| 2-Propylhexanal | 3.3 | n-Decanol | 2.1 |
| 2-Ethyloctanal | 3.9 | n-Decyl Formate | 4.2 |
| 2-Methylnonanal | 10.1 | | 29.7 |
| | 18.3 | | |

The percentage of the n-decanal in this feed (23.4%) is low due to its preferential condensation and further side reactions of n-decanal during distillation. Sulfur GC of this aldehyde showed no sulfur compounds in the aldehyde range. Trimethylthiophenes were present in about 40 ppm concentration indicating an imperfect separation of feed hydrocarbons from product aldehydes by distillation.

The above $C_{10}$ aldehyde feed was hydrogenated in the presence of 5% water 10.7 wt. % CoS/MoS catalyst at 150° C. (302° F.) under 3000 psi (307 atm) for 40 hours. The desired aldehyde to alcohol conversion was complete. Combined GC/MS analyses indicated the absence of aldehydes.

The percentage of n-decyl alcohol in the crude product 29.6%. This percentage corresponds to the combined concentration of n-decanal, n-decyl formate plus n-decyl alcohol in the aldehyde feed.

Sulfur GC of the crude alcohol indicated that the trimethylthiophenes were the main components (61%). However, minor amounts of sulfur (39%, about 14 ppm) was also present in the alcohol range. These latter sulfur compounds were apparently formed from the low molecular weight sulfur compounds during hydrogenation.

Most of the crude $C_{10}$ alcohol hydrogenation product (1356 g) was fractionally distilled using a 24 plate Oldershaw column. An early product fraction (47 g) containing aromatic hydrocarbons and trimethylthiophenes was obtained between 21 and 110° C. at 19 mm.

After the above fraction, six colorless, clear isomeric decyl alcohol distillate fractions were obtained. Their amounts, boiling ranges, linearity and total sulfur content are listed in the following:

| Fraction No. | Amount g | Bp. °C./mm | Alcohols, % | | | Approx. S, ppm |
|---|---|---|---|---|---|---|
| | | | Decyl- | | Higher[a] | |
| | | | n- | i- | | |
| IV | 82 | 111/19 | | | | |
| V | 222 | 111–116/19 | .6.7 | 93.3 | | 50 |
| VI | 222 | 116–117/19 | 14.1 | 84.7 | 2.2 | 20 |
| VII | 423 | 117–121/19 | 41.9 | 49.0 | 9.1 | 40 |
| VIII | 196 | 121/19 | 58.3 | 41.7 | 17.3 | 30 |
| XI | 38 | 58/0.1 | 2.0 | 83.0 | 83.0 | |

The higher alcohols having retention times longer than n-decyl alcohol are probably dibranched undecanols.

The above tabulation shows that fractions enriched in the linear alcohol can be obtained. Fractions VI, VII and VIII were selected as heart cuts for conversion to semilinear didecyl phthalate esters, which are evaluated as plasticizers.

Altogether 1230 g (86%) of, clear, colorless, alcohol products were recovered by distillation between 111 and 121° C. at 19 mm. About 45 g (3.4 wt. % of the feed) of a clear yellow distillate was recovered in the broad dimer range. Apparently, some aldehyde condensation occurred during hydrogenation. Most of the dimer distilled between 165 to 172° C. at 0.1 mm. Packed GC of the distillation residue (18 g) indicated that its volatile components were in the trimer range. The aldehyde fraction had no sulfur detectable by GC. However, the dimeric aldol alcohol contained about 1.2% sulfur.

Examples 37 and 38

Hydroformylation of $C_{10}$ Naphtha By 3/2 $H_2/CO$ with 0.2 and 1% Cobalt at 130° C. and 3000 psi The previously described $C_{10}$ fraction of the Fluid coker naphtha was hydroformylated as a 1/1 mixture with hexane at 130° C. by an about 60/40 mixture of $H_2/CO$ at 3000 psi, using the high pressure procedure. The catalyst precursor was dicobalt octacarbonyl.

In the first experiment, the cobalt complex catalyst used was equivalent to 0.2% cobalt, i.e., 34 mM. The reaction mixture was periodically sampled and analyzed by capillary GC. The progress of the reaction was followed by determining both the 1-decene reactant consumed and the aldehyde product. The main aldehyde products were the n-aldehyde and 2-methyl substituted aldehyde derived from 1-decene. The data obtained are tabulated in the following:

|  | Reaction Time, Min | | | |
| --- | --- | --- | --- | --- |
|  | 10 | 30 | 60 | 120 |
| 1-Octene Converted, % | 12 | 54 | 100 | 100 |
| Major Aldehydes Formed, % | 7 | 51 | 93 | 105 |
| Total Aldehydes Formed, % |  |  | 143 | 203 |
| n/i Ratio of Major Aldehydes |  | 3.35 | 3.39 | 3.15 |

It is apparent from the data that the 1-n-decene was converted at first. However, by the end of the 2 hour reaction period a significant reaction of the isomeric decenes also occurred. The final ratio of the two major aldehydes formed was 3.15. No significant secondary reaction took place. Alcohol formation was negligible. High boiling by-products were virtually absent.

In the second experiment, the same reaction was carried out in the presence of 1% cobalt. This resulted in a very fast reaction. In 10 minutes, the 1-decene component was completely converted. The amount of the two major aldehydes formed was 105% of the theoretical quantity derivable from 1-decene. The total aldehydes formed were 212% of this calculated value. The n/i ratio of the two major aldehyde products was 2.71.

The second experiment was also run for 2 hours. During the second hour much hydrogenation occurred. By the end of the second hour, essentially all the primary aldehyde products were converted to the corresponding alcohols.

Examples 39 and 40

Hydroformylation of $C_8$ Naphtha by 3/2 and 1/1 $H_2/CO$ with Cobalt at 130° C. and 3000 psi The $C_8$ fraction of the previously described naphtha was hydroformylated in hexane in the presence of 0.2% cobalt at 130° C. and 3000 psi in two experiments. The $H_2/CO$ reactant ratio was about 60/40 in the first experiment while an equimolar mixture of synthesis gas was used in the second.

Qualitatively, the reaction of octenes in this example was similar to that of decenes as described in the previous examples. However, the reaction rates were generally lower. A summary of data obtained in the first experiment with 60/40 $H_2/CO$ is provided by the following tabulation:

|  | Reaction Time, Minutes | | | |
| --- | --- | --- | --- | --- |
|  | 10 | 30 | 60 | 120 |
| 1-Octene Converted, % | 6 | 14 | 29 | 100 |
| Major Aldehyde Formed, % | 3 | 10 | 21 | 92 |

The reaction had an induction period during the first hour. However, the conversion of 1-n-octene and some of the isomeric octenes was rapid during the second hour. The total amount of aldehydes formed was 144% of the theoretical amount produced from 1-n-octene. Nevertheless, due to the low reaction temperature, no aldehyde hydrogenation to alcohol occurred. The n/i ratio of the two major products was 2.78, definitely lower than in the analogous experiment of the previous example.

The second experiment of this example was carried out under the same process conditions, but using a 1/1 rather than 3/2 mixture of $H_2$ and CO reactant. The results of the two experiments were very similar; the $H_2/CO$ reactant ratio had no apparent major effect at this temperature. The second experiment using 1/1 $H_2/CO$ appeared to have a slightly longer induction period. However, during the second hour of the reaction, a rapid conversion took place. By the end of the second hour, all the 1-n-octene was converted. The reaction was continued for a third hour. Additional conversion of the other isomers occurred. After three hours reaction time, the total amount of aldehyde formed was 187% of the theoretical yield calculated for the 1-n-octene component of the feed. On the same basis, the yield of the total aldehydes formed in 2 hours was 125%.

Examples 41-42

Hydroformylation of $C_8$ Naphtha by $H_2/CO$ Mixtures of Varying Ratios with Dicobalt Octacarbonyl at 150° C. and 3000 psi $C_8$ naphtha fraction was hydroformylated in hexane solution as usual in the presence of 0.2% cobalt provided as dicobalt octacarbonyl. Compared to the previous example, the only significant difference was the use of a higher temperature, 150° C. Three experiments were run with different initial and/or final $H_2/CO$ ratios.

In the first experiment, where a 3/2 ratio of $H_2/CO$ was used all through the reaction, a severe inhibition of hydroformylation was observed. After 1 and 2 hours reaction time, the amounts of reacted 1-n-octene were only 20 and 27%, respectively. As expected, the significant products were n-nonanal and 2-methyl octanal. Their ratio was 3.48.

In the second experiment with an initially equimolar $H_2/CO$ reactant, a much faster reaction was observed. About 20% of the 1-n-octene component reacted in 10 minutes according to GC; all the 1-octene reacted in 30 minutes. In 60 minutes, much of the linear octenes and 2-methyl heptene-1 were also converted. The product data obtained on GC analyses of product samples were the following.

|  | Reaction Time, Min | | |
| --- | --- | --- | --- |
|  | 30 | 60 | 120 |
| Two Major Aldehydes Formed, % | 59 | 92 | 84 |
| Total Aldehydes Formed, % | 82 | 182 | 201 |

-continued

|  | Reaction Time, Min | | |
|---|---|---|---|
|  | 30 | 60 | 120 |
| n/i Ratio of Major Aldehydes | 2.59 | 2.41 | 1.92 |

The data indicate that significant amounts of olefin isomerization occurred during hydroformylation. During the first part of the reaction, the major 1-n-octene component was partly isomerized to the thermodynamically favored linear octenes. Thus, no 1-octene was shown in the reaction mixture after 30 minutes, even though only 59% of the products derivable from 1-n-octene were formed. Most of the hydroformylation took place during the subsequent 30 minutes. An apparent side reaction during the second hour was the hydrogenation of aldehyde products to the corresponding alcohols. By the end of the reaction, 11% of the total n-octanal formed was converted to n-octanol. However, the hydroformylation of internal octenes during the same period more than made up for the loss of total aldehydes via hydrogenation. During the second half of the hydrogenation period, the yield of the total aldehydes formed increased from 182% to 201% of the calculated yield for 1-n-octene. At the end of the reaction, less than half of the aldehydes were derived from 1-n-octene. As the amount of aldehydes formed from isomeric octenes rather than 1-n-octene increased with time, the n/i ratio of the two main aldehyde products dropped from 2.59 to 1.92. The apparent increase of 2-methyloctanal formed in part was due to the overlap of GC peaks. However, additional amounts were formed from 2-octene.

It is noted that although the initial $H_2/CO$ mixture used to pressure the reaction vessel was equimolar, the feed gas during the reaction had a $H_2/CO$ ratio of about 60/40. Since the liquid reaction mixture was sampled four times with considerable gas lass, by the end of the reaction the $H_2/CO$ ratio increased to 60/40. It is felt that the initially low value of $H_2/CO$ was critical in overcoming reaction inhibition.

In the third experiment, the $H_2/CO$ reactant ratio of both the initial and run synthesis gas was equimolar. However, the maintenance of the low $H_2/CO$ ratio resulted in decreased reaction rates when compared to the previous experiment.

The amounts of 1-octene converted after 10, 30, 60 and 120 minutes, were 30, 38, 79 and 100%, respectively. The yields of the two major products, n-octanal plus 2-methyl heptanal, after 60 and 120 minutes were 44 and 86%, respectively, based on 1-n-octene. During the same last two periods, the yield of the total aldehydes formed was 61 and 170%. The n/i ratio of the two major products was 2.70 and 2.48, respectively. By the end of the reaction, 3.5% of the n-octanal was hydrogenated to n-octanol. Overall, the GC data obtained showed that although 1-octene conversion started immediately, the final extent of hydroformylation was lower than in the previous example. High CO partial pressure was important in overcoming the initial inhibition, but the $H_2$ partial pressure was insufficient to assure a high hydroformylation rate.

Example 43

Hydroformylation of $C_8$ Naphtha by 3/2 $H_2/CO$ with Dicobalt Octacarbonyl at 150° C. and 4500 psi A hexane solution of $C_8$ naphtha was hydroformylated as usual in the presence of 0.2% cobalt by 3/2 $H_2/CO$ at 150° C. and 4500 psi. The conditions were identical to those of the first experiment of the previous example, except the pressure was increased in the present experiment from 3000 to 4500 psi. This resulted in a drastically reduced initiation period and a much more complete conversion of the olefin components during the two hour reaction period.

In ten minutes, 19% of the 1-n-octene was converted and n-octanal was formed in amounts corresponding to 11% of the starting 1-n-octene reactant. Thereafter, a rapid reaction took place. In 30 minutes, essentially all the 1-n-octene and the 2-methyl heptene-1 were converted. GC analyses provided the following data on the products formed.

|  | Reaction time, Min. | | |
|---|---|---|---|
|  | 30 | 60 | 120 |
| Two Major Aldehydes Formed, % | 95 | 120 | 105 |
| Total Aldehydes Formed, % | 149 | 247 | 291 |
| n/i Ratio of Major Aldehydes | 2.9 | 2.7 | 2.5 |
| n-Octanal Converted to n-Octanol, % | 10 | 16 |  |

It is particularly noted, that after the initial conversion of the 1-n-octene in 30 minutes, the total yield of aldehydes increased from 149 to 291% of the calculated yield for 1-n-octene. This increase is due to the conversion of internal olefins. It should also be noted that the final n/i ratio of the two major aldehyde products was fairly high (2.5), considering the high conversion of internal olefins.

During the second hour of the reaction period, there was a slight decrease of the two major aldehydes in the mixture. This is apparently due to hydrogenation of aldehydes to alcohols. A comparison of the GC signal intensities indicated that about 16% of the n-octanal formed was converted to n-octanol.

Thus the results show that at the increased pressure of the 3/2 $H_2/CO$ mixture, the concentration of CO is sufficient to overcome the sulfur inhibition. The high partial pressure of hydrogen results in a high reaction rate of both 1-n-olefins and internal olefins.

Example 44

Hydroformylation of $C_{10}$ Naphtha By $H_2/CO$ Mixtures of Varying Ratios and With Varying Concentrations of Cobalt and Separation of $C_{11}$ Aldehyde Products THe $C_{10}$ fraction used was a high boiling naphtha fraction. THe 1-decene content of this fraction by GC was about 16%. Based on an NMR analysis, the type distribution of the decene components was the following:

| $RCH=CH_2$ | $RCH=CHR$ | $R_2C=CH_2$ | $R_2C=CHR$ | Decadiene |
|---|---|---|---|---|
| I | II | III | IV | Conjugated |
| 43% | 22% | 14% | 9% | 12% |

Assuming that 1-decene is the only type I olefin present, the total percentage of olefinic unsaturates was 37%.

About 1900 g portions of a $C_{10}$ Fluid-coker naphtha fraction similar to the one previously described were hydroformylated without any significant amount of added solvent in a 1 gallon reactor. The cobalt catalyst was added as an approximately 10% solution of dicobalt octacarbonyl in toluene. The resulting essentially non-diluted feeds contained increased concentrations of both olefin reactants and sulfur inhibitors. As such, they required greater amounts of cobalt for effective catalysis.

There were two experiments carried out using dicobalt octacarbonyl as a catalyst precursor at 130° C. under 3000 psi pressure, with 1/1 $H_2$/CO and 3/2 $H_2$/CO reactant gas, respectively. The initial amount of the catalyst employed was equivalent to 0.2% cobalt in both cases. This amount of catalyst did not lead to any significant hydroformylation in 5 hours in either case. Thereafter, an additional 0.1% and 0.2%, respectively, of cobalt were added after cooling the mixture and starting the reactions again.

When the first experiment was resumed in the presence of a total of 0.3% cobalt, hydroformylation occurred at a moderate rate. All the 1-n-decene was consumed in 120 minutes. The total reaction time was 5 hours. GC analysis of the final reaction mixture indicated a total aldehyde product yield of about 253%, based on the amount of 1-n-decene in the feed. The n/i ratio of the two major aldehydes was about 2.7. The percentage of these aldehydes in the total aldehyde mixture was 41%. In the case of the second experiment (Example 30), with a total of 0.4% cobalt, the hydroformylation was fast. All the 1-decene was converted within 10 minutes. This reaction was continued with the increased amounts of cobalt for 3 hours.

Overall, the two experiments gave similar results, and indicated that the initial small amounts of cobalt catalyst were deactivated, but the inhibitors were thus consumed. Thus, the added amounts of cobalt showed high activity which was little dependent on the $H_2$/CO ratios employed.

The composition of the combined final reaction mixtures is shown by capillary GC and packed column GC's in FIGS. 8 and 9, respectively.

FIG. 15 shows a typical reaction mixture containing major amounts of n-paraffin and n-aldehyde. Clearly, recognizable isomeric aldehyde products are also shown. These 2-alkyl substituted aldehydes are apparently derived from the various linear olefin isomers of the feed. Their structure was established in GC/MS studies on the basis of the characteristic ions formed on electron impact ionization. As it is indicated by the spectrum, decreasing amounts methyl, ethyl, propyl and butyl branched aldehydes are present.

FIG. 16 shows the packed column GC of the same reaction mixture. This GC shows less separation of the individual components, but extends the analysis to the high boiling aldehyde dimer and trimer by-products. It indicated that they amount only to about 2.9% of the total reaction mixture.

For a more detailed study of the products, it was decided to distill the reaction mixtures. The two products were combined. The cobalt was removed as cobalt acetate by hot aqueous acetic acid plus air treatment. The organic phase (976 g) was then fractionally distilled in high vacuo using a one foot packed column. The unreacted $C_{10}$ hydrocarbons were distilled at room temperature at 0.1 mm and were collected in a cold trap, (491 g, 50 wt%). Thereafter, the $C_{10}$ aldehydes were distilled. During the distillation, some thermal decomposition of the residual liquid (probably of the formate by-products) took place. As a consequence, the vacuum dropped to 0.5 mm. However, while the bath temperature was slowly increased to 100° C., the decomposition has subsided, the vacuum improved and the $C_{11}$ aldehyde products were distilled between about 50 and 60° C. at 0.1 mm and received as colorless liquids (371 g, 38 wt%). The residual liquid dimers and trimers were 112 g. 12 wt%. Packed GC indicated that about 2/3 of this residue was consisted of very high boiling compounds, probably trimers. A large percentage of these heavy by-products was formed upon heating the mixture during fractional distillation.

The distillation results indicate that the total oxygenated product corresponds to the yield calculated for a feed at 45% olefin content assuming complete conversion. The isolated aldehyde content is less, it corresponds to an effective utilization of about 36% of the total feed.

Capillary GC of the distillate product showed that the two major aldehyde products are derived via the hydroformylation of 1-n-decene:

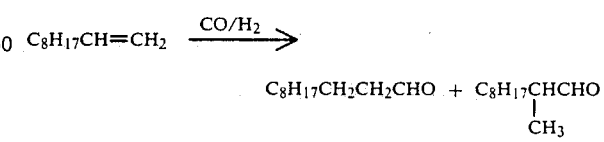

These two major products, n-undecanal and 2-methyldecanal, constitute 49% of the aldehyde. Their ratio is 2.23. Other minor aldehydes were also identified by GC/MS.

Based on the above detailed analyses, it was calculated that the total oxygenated products contain 0.65 branch per molecule.

The $C_{11}$ aldehyde products were reduced to the corresponding $C_{11}$ alcohols which were converted to semilinear diundecyl phthalates. The latter were evaluated as plasticizers.

Examples 45–47

Hydroformylation of Atmospherically and Vacuum Distilled $C_{10}$ Naphtha Fractions with Cobalt A series of three hydroformylation experiments was carried out with three different $C_{10}$ naphtha fractions in a manner described in the previous two examples to determine the effect of the conditions of the fractional distillation of the naphtha feed on the reactivity. Information about the feeds and hydroformylation results is summarized in Table XXX.

TABLE XXX

Hydroformylation of $C_{10}$ Olefinic Fractions of Fluid Coker Naphtha in the Presence of 0.2 Cobalt Catalyst Derived From $Co_2(CO)_8$ at 130° C. (266° F.) with 1/1 $H_2$/CO at 3000 psi

| Example No. | Feed Reactant Carbon Number | Feed Components % by Capillary GC | | | Catalyst Conc. Co, % | Reaction Time Min. | Total Mixture % by Packed Column GC | | | Two Main Products[a] by Capillary GC | | |
|---|---|---|---|---|---|---|---|---|---|---|---|---|
| | | 1-n-Decene | n-Decane | Higher | | | Unreacted | Aldehydes[b] | Dimers[c] | n/i Ratio | n-% | n + i % |
| 45 | $C_{10}$ Naphtha Atmospherically Distilled | 10.9 | 13.7 | 55.5 | 0.1 +0.1 | 360 +60 120 180 | 97.7 91.8 79.1 70.3 | 2.3 8.2 20.9 29.6 | 0.1 | 3.4 3.4 3.3 3.1 | 33.4 30.0 28.4 | 43.8 38.7 37.2 |

TABLE XXX-continued

Hydroformylation of $C_{10}$ Olefinic Fractions of Fluid Coker Naphtha in the Presence of 0.2 Cobalt Catalyst Derived From $Co_2(CO)_8$ at 130° C. (266° F.) with 1/1 $H_2/CO$ at 3000 psi

| Example No. | Feed Reactant Carbon Number | Feed Components % by Capillary GC | | | Catalyst Conc. Co, % | Reaction Time Min. | Total Mixture % by Packed Column GC | | | Two Main Products[a] by Capillary GC | | |
|---|---|---|---|---|---|---|---|---|---|---|---|---|
| | | 1-n-Decene | n-Decane | Higher | | | Unreacted | Aldehydes[b] | Dimers[c] | n/i Ratio | n-% | n+i % |
| 46 | $C_{10}$ Naphtha Distilled in Vacuo (240 mm) | 17.0 | 15.0 | 42.7 | 0.1 +0.1 | 360 360 +60 120 180 | 64.0 96.0 70.9 65.8 62.6 | 35.2 4.0 29.0 33.6 36.6 | 0.8 0.1 0.6 0.8 | 3.0 3.4 3.2 3.0 3.1 | 26.3 37.1 33.0 34.0 | 34.7 48.3 44.7 44.8 |
| 47 | $C_{10}$ Naphtha Distilled Atmospherically & in Vacuo (50 mm) | 19.5 | 16.5 | 23.1 | 0.1 +0.1 120 | 360 +60 180 | 97.7 88.1 69.9 63.8 | 2.3 11.8 27.0 35.9 | 0.1 0.1 0.3 | 3.3 3.2 43.2 3.0 | 49.7 56.6 38.3 | 65.5 51.1 |

[a] n-Undecanal and 2-methyldecanal expressed as a percentage of total $C_{11}$ aldehyes.
[b] Mostly $C_{11}$ aldehydes; minor amounts of higher aldehydes and traces of $C_{11}$ alcohols are included
[c] The amounts of trimers were not determined in this series. Workup of the mixtures showed less trimers and dimers.

The first fraction employed as a feed was an atmospherically distilled $C_{10}$ cut between 342 and 350° F. (172-177° C.). According to capillary GC, it contained 10.9% 1-n-decene and 13.9% n-decane. About 55.5% of the components of this cut had longer retention times than n-decane. These compounds included indene.

The second fraction was obtained at reduced pressure under 240 mm. It contained 17.0% 1-n-decene and 15.0% n-decane plus 42.7% of higher boiling components.

The third fraction was derived from an atmospherically distilled $C_{10}$ fraction by redistilling it in vacuo at 50 mm. This vacuum distilled fraction mainly consisted of compounds boiling in the range of 1-n-decene, n-decane or lower. The n-decene and n-decane contents were 19.5 and 16.5% respectively. Only 23.1% of this fraction had GC retention times greater than that of n-decane.

The above described, somewhat different, three $C_{10}$ fractions were used ad hydroformylation feeds in the presence of 0.1% and then an additional 0.1% Co Catalyst, both added as $Co_2(CO)_8$. Each run was carried out using 1/1 $H_2/CO$ as reactant gas under 3000 psi at 130° C. (266° F.). The reaction mixtures were sampled at intervals and analyzed by packed and capillary GC columns. The results are summarized in Table XXX.

The GC composition data of the three $C_{10}$ reaction mixtures hydroformylated in the presence of 0.1% cobalt in athe a series of experiments in Table XXX) show that no significant hydroformylation occurred in 360 minutes. There was some initial reaction as indicated by a small pressure drop and minor aldehyde formation during the first ten minutes. However, the reaction soon virtually stopped. It is apparent that the cobalt carbonyl was deactivated by the inhibitors present in the $C_{10}$ coker distillate feed.

After the unsuccessful attempts of reacting the three $C_{10}$ fractions in the presence of 0.1% cobalt, an additional 0.1% cobalt was added to the reaction mixtures. This resulted in effective hydroformylation in all three cases (in the b series of experiments). However, the hydroformylation rates were somewhat dependent on the particular $C_{10}$ feed as described in the following.

The atmospherically distilled $C_{10}$ naphtha was the least reactive. Even after the addition of the incremental cobalt the reaction was slow to start and sluggish as it indicated by the minor amounts of products formed in an hour. The vacuum distilled naphtha fraction was significantly more reactive. When the additional amount of cobalt was added, major amounts of aldehyde products (29%) were formed within an hour. The reaction was essentially complete in 3 hours. The atmospheric $C_{10}$ naphtha cut which was redistilled in vacuo was somewhat more reactive. However, the vacuum distilled naphtha was more active than the atmospheric naphtha redistilled in vacuo. This seems to indicate that the inhibitors formed during atmospheric distillation are not removed on redistillation in vacuo.

The data of the table also show that there was very little dimer by-product formation in all cases. The amount of dimers formed during these reactions was less than 3% of the main aldehyde products. Although the amounts of trimers formed were not determined in this series of experiments, it is noted that as a rule considerably less trimer is formed than dimer.

Analyses by capillary GC show that, as expected, the two main products of these hydroformylations were n-undecanal and 2-methyldecanal, derived from 1-n-decene. As it is shown by Table XXX, the n/i ratio of these two main products in the final reaction mixture was in the 2.9 to 3.7 range. There were, of course, other minor branched aldehydes present. These were derived from internal and branched olefins. The amount of the completely linear aldehyde, n-decanal, in the final reaction mixtures ranges from 31.1 to 38.3%. This variation clearly reflects the different percentages of 1-n-decene present in these feeds. Similarly, as a consequence of the varying feed composition, the combined amounts of n-undecanal and 2-methyldecanal (n+i) changes from 41.7% to 51.1%. The rest of the product largely consisted of other monobranched 2-alkyl substituted $C_{11}$ aldehydes such as 2-ethylnonanal, 2-propyloctanal and 2butylheptanal. These monobranched aldehydes were apparently derived from isomeric linear internal decenes.

In general, comparisons of samples, taken from the reaction mixtures at different intervals, indicate that the 1-n-decene component reacted at first, as expected. Consequently, the products of partially reacted feeds were mainly consisting of n-undecanal and 2-methyldecanal. As the reaction proceeded, and the internal and branched olefinic components were also converted, various branched aldehydes were formed and the relative amounts of the two major products derived from 1-n-decene decreased.

Only minimal amounts of the aldehyde hydroformylation products were reduced by hydrogen to the corresponding alcohols. The only identifiable alcohol by-product was n-indecanol. Its amount was below 1% of the $C_{11}$ aldehyde products.

The three final reaction mixtures obtained were brown, as usual. Some of the brown color of the mixture derived from the atmospherically distilled feed persisted after the removal of the cobalt by the usual aqueous acetic acid, air treatment. However, the brown color of the mixtures derived from the vacuum distilled feeds changed to dark yellow upon cobalt removal.

The cobalt free reaction mixtures were fractionally distilled, using a 2 ft. packed column in vacuo, at pressures in the range of 0.1-50 0.2 mm. The unconverted feed components were distilled as colorless liquids with a yellow tint at ambient temperatures (20 to 30° C.) using a dry ice cooled receiver. The aldehyde products were obtained as light yellow liquids between 47 and 57° C. at 0.1 mm pressure.

Due to the relatively low distillation and heating bath temperatures (100-135° C. bath), relatively little aldehyde dimerization and trimerization occurred during distillation. For example, in the experiment using vacuum redistilled feed, 1700 g of the crude reaction mixture was distilled to obtain 570 g product and 51 g distillation residue. GC analysis indicated that this residue contained 31% product, 43% dimer and 26% trimer. Thus, the combined dimer and trimer product was 35.2 g i.e., about 6% of the main product.

The aldehyde distillate products of the three runs were combined. The combined product contained 37.1% n-undecanal, 10.4% 2-methyldecanal, about 8.6% of other 2-alkyl substituted monobranched aldehydes, about 28.7% of aldehydes having retention times longer than that of n-decanal. These latter compounds include doubly branched and possibly $C_{12}$ aldehydes. The amount of n-undecanol is minimal, about 0.2%.

Hydroformylation of $C_9$-$C_{15}$ Fluid Coker Light Gas Oil Fractions with Cobalt Examples 48-64

The previously described $C_9$ to $C_{15}$ light coker gas oil and its distillate fractions were hydroformylated without prior treating in the presence of cobalt at high pressure.

The hydroformylation of the non-fractionated $C_9$ to $C_{16}$ light gas oil was studied with cobalt in the presence and in the absence of added phosphine ligand. Thereafter, the hydroformylation of narrow single carbon distillate fractions from $C_{11}$ to $C_{15}$ was investigated in the presence of cobalt at 3000 psi. In general, it was found that the gas oil fractions were more reactive than the naphtha fractions, particularly when distilled in vacuo. The reaction rates were directly related to the temperature, in the 110 to 170° C. range. The n/i ratio of the aldehyde products was inversely related to the reaction temperature. The isomeric aldehyde products were isolated from the reaction mixtures by fractional distillation in vacuo. The two major types of products were n-aldehydes and the corresponding 2-methyl aldehydes. The aldehydes products were reduced to the corresponding alcohols, in the presence of a sulfur resistant Co/Mo catalyst.

Example 48

Hydroformylation of $C_9$-$C_{15}$ Whole Coker Light Gas Oil With Cobalt at 150° C. and 4500 psi The previously described $C_9$-$C_{15}$ light gas oil was hydroformylated without solvent by a 1:1 mixture of $H_2$/CO. A toluene solution of $Co_2(CO)_8$ was introduced at 120° C. temperature and 3000 psi pressure into the reaction mixture to provide a cobalt concentration of 0.4%. When no reaction occurred, the conditions were changed to 150° C. and 4500 psi. After a 30 minute induction period, a rapid hydroformylation reaction occurred. This agrees with the hypothesis that there are equilibria among the various sulfur substituted cobalt carbonyl complexes. Dependent upon the types and amounts of sulfur compounds present in the feed, sufficiently high concentrations of CO are required to avoid the formation of inactive carbonyl-free complexes.

After a total reaction period of 3 hours, the reaction was discontinued. The capillary GC of the resulting mixture is shown by FIG. 17. It is apparent from the figure that the prominent 1-n-olefin peaks of the gas oil feed are absent after hydroformylation. The 1-n-olefins were converted mainly to n-aldehydes which show up as prominent peaks in the high retention region of the GC. The relative intensities of the $C_{11}$ to $C_{16}$ aldehyde peaks are about the same as those of the parent $C_{10}$ to $C_{15}$ olefins. The 1-n-olefins of the feed appear to be of similar reactivity without regard to their carbon number. This is in contrast to the behavior of branched higher olefins whose reactivity is rapidly decreasing with increasing carbon number.

Examples 49-51

Hydroformylation of Atmospherically and Vacuum Distilled $C_{11}$ Naphtha and Gas Oil Fractions with Cobalt A series of three hydroformylation experiments was carried out with a $C_{11}$ fraction of naphtha and the combined $C_{11}$ light gas oil fractions of a Fluid-coker distillate in the manner described in Examples 41 to 45. The experiments were designed to determine the effect of the conditions of the distillation of the gas oil feed on reactivity. Information about the feeds used and the hydroformylation results obtained is summarized in Table XXXI. Some of the details are described in the following.

A narrow cut $C_{11}$ naphtha fraction boiling between 63 to 71° C. (146 to 150° F.) under 238 mm pressure was used in Example 49. In Example 50, the previously described combined $C_{11}$ fractions of light Fluid-coker gas oil, were employed. These fractions were obtained between 185 to 196° C. (365 to 385° F.) at atmospheric pressure. Part of the same $C_{11}$ fraction of light coker gas oil was redistilled without fractionation at 50 mm pressure. This redistillation of the orange $C_{11}$ fractions gave a yellow distillate, used as a hydroformylation feed in Example 51.

Each of the above $C_{11}$ feeds was hydroformylated in the presence of 0.1% Co, added as $Co_2(CO)_8$. Each run was carried out using 1/1 $H_2$/CO under 3000 psi at 130° C. (266° F.). The reaction mixtures were sampled at intervals and analyzed by packed column and capillary GC.

The GC composition data of the reaction mixtures of Table XIX show that all the $C_{11}$ fractions could be hydroformylated under the above conditions but at different rates. The vacuum distilled naphtha fraction was more reactive than the atmospherically distilled gas oil fraction (Examples 49 to 50, Seq. Nos. 1 and 2). The gas oil redistilled in vacuo was the most reactive $C_{11}$ fraction of all (Example 51).

It is clear from the comparative reactivities observed that distillation in vacuo rather than at atmospheric pressure resulted in increased reactivity. While the present invention is independent of the explanation of these findings. We hypothesize that atmospheric distillation at high temperature results in the thermal decomposition of some of the thiol components to $H_2S$ plus olefin. Some of the $H_2S$ formed may dissolve in the atmospheric distillate and inhibit the hydroformylation process.

lighter colored mixtures persisted. All the mixtures were clear, free of any precipitate.

The cobalt free reaction mixtures were fractionally distilled using a 2 ft. packed column, at about 0.1 mm pressure. The unconverted feed components were distilled at close to ambient temperatures (20 to 30° C.). The aldehyde product was obtained between 57 to 67°C. Both distillates were light yellow, clear liquids. Due to the relatively low distillation temperature of the aldehyde products, relatively little aldehyde dimeriza-

TABLE XXXI

Hydroformylation of $C_{11}$ Olefinic Fractions of Naphtha and Light Gas Oil from a Fluid Coker in the Presence of 0.1% Cobalt Catalyst Derived from $Co_2(CO)_8$ at 130° C. (266° F.) with 1/1 $H_2$/CO at 3000 psi

| Example No. | Reactant Carbon Number | Reaction Time Min. | Total Mixture, %[a] | | | Two Main Products[b] | | | 2-Alcohols[d] n + i |
|---|---|---|---|---|---|---|---|---|---|
| | | | Unre-acted | Alde-hydes[e] | Dimers (Trimers) | n/i Ratio | n-[c] % | n+i[c] % | |
| 49 | $C_{11}$ Naphtha | 60 | 88.5 | 11.3 | 0.2 | 3.3 | 54.3 | 71.1 | <0.1 |
| | Distilled | 120 | 73.1 | 26.3 | 0.6 | 3.2 | 39.9 | 52.2 | 0.2 |
| | in Vacuo | 180 | 68.5 | 30.7 | 0.8 | 3.1 | 39.3 | 51.9 | 0.3 |
| 50 | $C_{11}$ Gas Oil | 60 | 91.9 | 8.0 | 0.1 | 3.3 | 60.0 | 66.7 | <0.1 |
| | Atmospherically | 120 | 80.7 | 18.4 | 0.9 | 2.9 | 45.6 | 61.3 | 0.1 |
| | Distilled | 180 | 72.1 | 27.0 | 0.9 | 2.9 | 44.8 | 60.3 | 0.1 |
| | | 360 | 66.5 | 32.5 | 1.0 | 2.7 | 38.8 | 53.3 | 0.2 |
| 51 | $C_{11}$ Gas Oil | 60 | 77.1 | 22.7 | 0.2 | 2.9 | 42.8 | 57.5 | 0.1 |
| | Redistilled | 120 | 70.6 | 28.9 | 0.5 | 2.9 | 39.4 | 53.2 | 0.2 |
| | in Vacuo | 180 | 66.8 | 32.5 | 0.7 | 2.9 | 37.7 | 48.2 | 0.3 |

[a]The composition of the total reaction mixture by packed column gas chromatography.
[b]n-Dodecanol and 2-methylundecanol determined by capillary gas chromatography.
[c]Expressed as a percentage of total $C_{12}$ oxygenated products.
[d]n-Dodecanol and 2-methylundecanol determined by capillary gas chromatography.
[e]Mostly $C_{12}$ aldehydes: minor amounts of higher aldehydes and traces of alcohols are included.
[f]Mostly dimers are recorded; the minor amounts of trimers formed usually did not register.

The analyses of the total reaction mixture by packed column GC show that, concurrent with the decrease of the percentage of the $C_{11}$ feeds, most $C_{12}$ aldehydes formed. There is very little aldehyde dimer and trimer formation; only about 3% of the main aldehyde products.

Analyses by capillary GC show that the two main products are n-dodecanal and 2-methylundecanal derived from the 1-n-undecene component of the feeds. As it is shown by the table, the ratio of these two products in the final reaction mixtures is in the 2.7 to 3.1 range. There are of course, other branched aldehydes present. These are derived from internal and branched olefins. Thus, the amount of the completely linear aldehyde, 1-n-dodecanal, is ranging from 37.7 to 39.4% of the total $C_{12}$ oxygenated products. 1-n-Dodecanal and 2-methylundecanal together represent 48.2 to 51.9%. The rest of the product contains major amounts of other, monobranched 2-alkyl substituted $C_{12}$ aldehydes such as 2-ethyldecanal, 2-propylnonanal, 2-butyloctanal and 2-pentylheptanal. These monobranched aldehydes were apparently derived from isomeric linear internal undecenes. Only minimal amounts of the aldehyde hydroformylation products were reduced by hydrogen to give the corresponding alcohols. The only identifiable alcohol by-products were n-dodecanol and 2-methylundecanol. Their combined concentration was only 1 to 3% of that of the total aldehydes.

The three reaction mixtures obtained in the above described three examples of $C_{11}$ coker distillate hydroformylation were worked up in a manner similar to that described in Examples 41 to 45.

It was noted that the reaction mixtures derived from the vacuum distilled $C_{11}$ feeds were of definitely lighter brown color than that from the atmospheric distillate feed. The removal of cobalt by the usual aqueous acetic acid, air treatment reduced the color of all the mixtures. However, the difference between the now generally tion and trimerization occurred during distillation. The residual dimers were only about 2.5% of the total oxygenated products formed. The trimers were less than 1% although it is noted that their accurate determination by GC was not possible.

Examples 52-55

Hydroformylation of $C_{12}$ Gas Oil with Cobalt in the 110 to 150° C. Temperature Range A series of four hydroformylation experiments was carried out with a previously described, vacuum distilled combined $C_{12}$ fraction of gas oil in a manner described in Examples 44 and 45 to determine the effect of temperature on reaction rate and selectivity. Each run was carried out using 1/1 $H_2$/CO at 3000 psi. The reaction temperatures employed were 110, 120, 130 and 150° C. The reaction mixtures were sampled at intervals and analyzed by packed and capillary GC as usual. The results are summarized in Table XXXII.

The results of the table show that the $C_{12}$ fraction was more reactive than the lower boiling fractions produced by the same Fluid-coker unit. About 0.1% cobalt was found effective in the firs three examples of the present series, while 0.2 to 0.4% cobalt was required in the previous experiments.

As the temperature was increased from 100 to 130° C. in Examples 52, 53 and 54, the reaction rate significantly increased. At 150° C. in Example 4, only 0.05% cobalt was used. Hydroformylation occurred, nevertheless, indicating increased activity. The composition of the final reaction mixtures indicated that in the hydroformylations 130 and 150° C., at about ⅔ of the feed was converted to aldehydes.

It was found that selectivity of hydroformylation to produce a high n/i ratio of the two major aldehyde products decreased with increasing temperature. Also, more aldehyde dimer by-product and alcohol hydrogenation products were formed at 150° C. than at lower temperatures.

For the selective production of aldehydes with good olefin conversions, temperatures in the order of 130° C. are preferable. The data indicate that, in general, the 1-n-dodecene is selectively hydroformylated at first, producing a high ratio of n-tridecanal and 2-methyldodecanal. Thereafter, the linear internal olefin components are converted to various 2-alkyl substituted aldehydes. Concurrently, hydroformylation of the minor branched olefins also occurs to give some further branched aldehydes. Thus, with increasing conversion, product linearity decreases.

2-methyldodecanal and 17.6% of 2-alkyl substituted aldehydes plus minor amounts of alcohols in the order of 2%.

The detailed structure of the isomeric aldehydes is illustrated by FIG. 18 which shows the aldehyde region of the capillary gas chromatogram of a reaction mixture. Based on GC/MS studies, the figure indicates that besides the major n-tridecanal, the 2-methyl and higher 2-alkyl branched isomeric aldehydes are present n decreasing amounts. Mass spectrometric studies also showed that 2-methyldodecanal 3-methyldodecanal are present in comparable amounts.

TABLE XXXII

Hydroformylation of the $C_{12}$ Olefinic Fractions of Light Gas Oil from a Fluid Coker in the Presence of Cobalt Catalyst with 1/1 $H_2$/CO at 3000 psi

| Example No. | Reaction Conditions | | | | Total Mixture, %[a] | | | Two Main Products[b] | | | 2 Alcohols[d] |
|---|---|---|---|---|---|---|---|---|---|---|---|
| | Temp. °C. | °F. | Catalyst Added Complex | Co % | Time Min. | Unreacted | Aldehydes[e] | Dimers[f] | n/i Ratio | n-[c] % | n + i[c] % | n + i[c] % |
| 52 | 110 | 230 | $Co_2(CO)_8$ | 0.1 | 60 | 91.2 | 8.7 | 0.1 | | | | |
| | | | | | 180 | 73.2 | 26.6 | 0.1 | 3.7 | 58.1 | 73.7 | 0.1 |
| | | | | | 360 | 70.1 | 29.4 | 0.5 | 3.3 | 48.0 | 62.8 | 0.3 |
| 53 | 120 | 248 | $(RCO_2)_3Co$[g] | 0.1 | 60 | 93.4 | 6.5 | 0.1 | | | | |
| | | | | | 180 | 77.1 | 22.8 | 0.1 | 3.6 | 57.4 | 73.2 | |
| | | | | | 360 | 69.6 | 30.0 | 0.5 | 3.1 | 47.5 | 62.8 | 0.2 |
| 54 | 130 | 266 | $Co_2(CO)_8$ | 0.1 | 60 | 73.0 | 26.0 | 0.05 | 3.4 | 55.6 | 72.0 | 0.1 |
| | | | | | 180 | 66.1 | 33.0 | 0.5 | 2.9 | 44.1 | 59.1 | 0.3 |
| 55 | 150 | 302 | $Co_2(CO)_8$ | 0.05 | 60 | 95.3 | | | | | | |
| | | | | | 180 | 75.6 | 23.8 | 0.5 | 2.9 | 52.3 | 70.1 | 0.1 |
| | | | | | 360 | 65.9 | 32.9 | 1.0 | 2.3 | 35.7 | 50.9 | 0.9 |

[a]The composition of the total reaction mixtures by packed column gas chromatography.
[b]n-Tridecanol and 2-methyldodecanol determined by capillary gas chromatography.
[c]Expressed as a percentage of total $C_{13}$ oxygenated products
[d]n-Tridecanol and 2-methyldodecanol determined by capillary gas chromatography
[e]Mostly $C_{13}$ aldehydes; minor amounts of higher aldehydes and traces of alcohols are included.
[f]Mostly dimers are recorded; the minor amounts of trimers formed usually did not register.
[g]Cobalt naphthenate was used as a catalyst precursor.

For example, at 130° C. in Example 54, the percentage of n-tridecanal decreases from 55.6 to 44.1% as the percentage of unconverted feed drops from 73 to 66%.

Example 53 additionally shows a low temperature generation of the active catalyst species from a cobalt carboxylate rather than dicobalt octacarbonyl. In this Example, the use of cobalt naphthenate at 120° C. resulted in approximately the same conversion as that of $Co_2(CO)_8$ at 110° C. in Example 52.

The four reaction mixtures of these four examples were worked up to isolate the products in a manner similar to that of Examples 44 and 45. All the hydroformylation product mixtures were clear dark brown liquids, free from precipitates. They were readily decobalted with aqueous acetic acid plus air treatment in the usual manner. The cobalt free mixtures were lighter brown. They were worked up separately.

Fractional distillation of the cobalt free mixtures yielded almost colorless distillate fractions of unconverted components and colorless to light yellow $C_{13}$ aldehyde products. The aldehyde products were distilled using a 1½ ft column between about 70 and 80° C. under about 0.1 mm pressure with an oil bath of 130–160° C. During the slow distillation of about 8 hours, significant additional unsaturated aldehyde dimer formation occurred. This was the major factor in determining the isolated product yields. If alcohols are the desired products, hydrogenation of the decobalted reaction mixture prior to fractional distillation is preferred.

The distillate aldehyde products of the four examples were combined to provide sufficient amounts for subsequent hydrogenation. According to capillary GC, the combined product contained 40% n-tri-decanal, 14.4%

Example 56

Hydroformylation-Acetalization of $C_{12}$ Light Gas Oil with Methanol in the Presence 0.1% Cobalt in the 120–150° C. Range A $C_{12}$ Fluid-coker naphtha fraction of bp. 207 to 217° C. was hydroformylated in a one to three molar mixture with methanol at 3000 psi (207 atm), in the presence of 0.1% cobalt added as a toluene solution of $Co_2CO_8$ at 130° C. The reaction took off immediately, and proceeded at a faster rate than without the added methanol. Nevertheless, to complete the reaction of branched olefin components, the temperature was raised to 140° C. after 2 hours and to 150° C. after a total of 4 hours. The reaction was discontinued after a total of 6 hours. GC analysis of the reaction mixture after standing at room temperature showed a highly selective formation of the dimethyl acetal derivatives of the $C_{13}$ aldehyde products and negligible dimer formation.

The reaction mixture was diluted with aqueous methanol to separate the cobalt and then was distilled in vacuo. The dimethyl acetal of the tridecanal hydroformylation product was distilled using a 2 ft. packed column and obtained as a clear colorless liquid between 80 and 85° C. at 0.05 mm. Capillary GC/MS indicated that the isomer distribution was similar to that observed in the absence of methanol.

Examples 57–60

Hydroformylation of $C_{13}$ Gas Oil with Cobalt in the 130 to 170° C. Temperature Range A series of four hydroformylation experiments were carried out with a previously described, vacuum distilled combined $C_{13}$ fraction of gas oil in a manner described in Examples 41 to 45. The reaction conditions were the same as those in the previous example. The experiments were to determine the effect of increased reaction temperature up to 170° C. The results are summarized in Table XXXIII.

The data of the table show that the rate of the reaction increased right up to 170° C. This is in contrast to the hydroformylation behavior found in studies of the $C_8$ naphtha fraction.

As it is indicated by these data, reaction temperatures below 150° C. were advantageous for the selective production of aldehydes (Examples 57 and 58). The percentage of dimer and trimer by-products increased with the temperature. At 170° C., major amounts of alcohols were formed (Example 60).

It was also observed that the percentage of the n-aldehyde component of the total aldehyde product decreased with the temperature. Thus, the data show that reduced reaction temperatures results in increased product linearity and decreased by-product formation. It should be noted, though, that the sharply decreased n-aldehyde content of the 170° C. reaction mixture is largely due to hydrogenation to n-alcohol. At 170° C., aldehyde formation is essentially complete in 60 minutes. Thereafter, the prevalent reaction is aldehyde hydrogenation to alcohols.

All the hydroformylation product mixtures were clear brown liquids, free from precipitates. They were readily decobalted with aqueous acetic acid plus air treatment in the usual manner. Some additional dimerization of the aldehyde product occurred during distillation at 0.1 mm using a 2 ft packed column and a heating bath of about 135° C. The aldehydes distilled between 75 and 85° C. at 0.1 mm.

It was interesting to observe during the distillation of the reaction mixtures, that the color of both the unconverted components and the aldehyde products were dependent on the reaction temperature. The mixture from the 130° C. reaction yielded yellow distillates of both unconverted gas oil components and aldehyde products. The mixtures of the 140 and 150° C. reactions gave colorless hydrocarbon distillate but yellow aldehyde products. The 170° C. reaction mixture yielded colorless distillates of both hydrocarbon and aldehyde fractions.

The above observations indicate that during hydroformylation, double bond hydrogenation and, probably, desulfurization via hydrogenation become increasingly significant side reactions with increasing reaction temperatures. It is felt, though, that these hydrogenations are better carried out during the subsequent hydrogenation of the reaction mixture which provides the usually desired higher alcohol product.

The distilled aldehyde products all contained tetradecanal and 2-methyltridecanal as the major components. As it was also found in the previous examples, other 2-alkyl substituted $C_{14}$ aldehydes, when combined, constituted the third group of product components. It was shown by GC/MS studies that the 2-alkyl substituents of these aldehydes ranged from $C_2$ to $C_6$ n-alkyl.

Examples 61–63

Hydroformylation of $C_{14}$ Gas Oil with Cobalt in the 110 to 130° C. Temperature Range A series of three hydroformylation experiments were carried out with a previously described, vacuum distilled combined $C_{14}$ fraction of gas oil in a manner described in Examples 44 and 45. The reaction conditions were the same as in Examples 52 to 54, however, the amount of cobalt catalyst used was increased from 0.1 to 0.3%. The results are shown in Table XXXIV.

The data indicate that the reaction rate was the smallest, but product linearity was the greatest, at 110° C., the low temperature of Example 61. Conversely, at 130° C., i.e., the high temperature of Example 49, the reaction rate was the greatest but product linearity was the smallest. Since the reaction temperatures were relatively low in all three examples, there was no significant aldehyde dimer and trimer formation. The amount of alcohol hydrogenation by-products also remained low, around 3% of the aldehydes.

The product linearity is best indicated by the percentage of the n-aldehyde (and n-alcohol) in the total oxygenated products At the end of the hydroformylation, this value was 45.2% at 110° C., 42.2% at 120° C. and 40.8% at 130° C. The percentage of the 1-n-olefin derived n-aldehyde was inversely dependent on the hydroformylation of the less reactive internal and branched olefins which provide branched aldehydes. Thus, the n-aldehyde percentage was inversely proportional to the total olefin conversion.

The n/i ratio of the two main aldehyde products, n-petadecanal to 2-methyl-tetradecanal, was more inde-

TABLE XXXIII

Hydroformylation of $C_{13}$ Olefinic Fractions of Light Gas Oil From a Fluid Coker in the Presence of 0.1% Cobalt Catalyst Derived From $Co_2(CO)_8$ with 1/1 $H_2$/CO at 3000 psi

| Example No. | Reaction Conditions °C. | °F. | Min. | Total Mixture, % by Packed Column GC | | | n %[a] in Total Products | Capillary GC Four Key Products[b] | | |
|---|---|---|---|---|---|---|---|---|---|---|
| | | | | Unreacted | Aldehydes (Alcohols) | Dimers (Trimers) | | n/i Ratio | 100 n % / (n + i) | Alcohols |
| 57 | 130 | 266 | 60 | 78.5 | 21.0 | 0.5 | | 1.91 | 65.6 | 1.0 |
| | | | 180 | 68.5 | 31.2 | 0.5 | 40.2 | 1.56 | 61.0 | 20 |
| 58 | 140 | 284 | 60 | 73.1 | 26.4 | 0.5 | | 1.70 | 61.8 | 1.3 |
| | | | 180 | 65.4 | 33.7 | 0.9 | 35.7 | 1.48 | 59.6 | 3.4 |
| 59 | 150 | 302 | 60 | 70.6 | 28.6 | 0.8 | | 1.45 | 59.3 | 1.9 |
| | | | 180 | 65.3 | 33.3 | 1.4 | 34.1 | 1.27 | 56.0 | 7.7 |
| 60 | 160 | 338 | 60 | 66.6 | 32.2 | 1.2 | | 1.14 | 53.3 | 10.3 |
| | | | 180 | 63.3 | 33.7 | 3.0 | 26.5 | 1.14 | 53.3 | 31.6 |

[a] n-Tetradecanal in total $C_{14}$ oxygenated products.
[b] n-Tetradecanal, 2-methyl-tridecanal and the two corresponding alcohols.

pendent of olefin conversion since both of these products can be derived from the reactive 1-n-olefin component, 1-n-tetradecene. (2-Methyl-tetradecanal can be also derived from 2-tetradecene). This n/i ratio was largely dependent on the temperature. It was inversely proportional to it as it is indicated by the data of the table.

The data of these and the previous examples suggest that a preferred method of hydroformylation is carried out at variable temperatures wherein the 1-n-olefin component is substantially converted at 130° C. or below, and the other olefins are mainly reacted at temperatures exceeding 130° C. up to 170° C.

tion. Minor amounts (0.5%) of n-pentadecanol were also present.

Example 64

Hydroformylation of a $C_{14}$ Fraction of Light Gas Oil by $H_2/CO$ with Cobalt under 3000 psi Pressure at Variable Temperatures and the Hydrogenation of the $C_{15}$ Aldehyde Product The $C_{14}$ olefinic feed for the present hydroformylation was separated from a light Fluid-coker gas oil by a double 15/10 type distillation. It was hydroformylated either in the presence of 0.2 or 0.1%. As a catalyst precursor, $Co_2(CO)_8$ was used. It was introduced at

TABLE XXXIV

Hydroformylation of $C_{14}$ Olefinic Fractions of Light Gas Oil From a Fluid Coker in the Presence of 0.3% Cobalt Catalyst Derived From $Co_2(CO)_8$ with 1/1 $H_2/CO$ at 3000 psi

| Example No. | Reaction Conditions Temp. °C. | Time min | Total Mixture, % by Packed Column GC Unreacted | Aldehydes (Alcohols) | Dimers (Trimers) | Capillary GC All Products n %[a] | n + i[b] %[b] | Four Key Products[c] n/i Ratio[d] | 100 n % n + i | Alcohol %[e] |
|---|---|---|---|---|---|---|---|---|---|---|
| 61 | 10 | 10 | 91.5 | 8.5 | 0 | | | 3.35 | | |
| | | 60 | 75.0 | 24.5 | 0.5 | 51.4 | 67.5 | 3.18 | 76.1 | ~2 |
| | | 180 | 68.5 | 29.0 | 2.5 | 45.2 | 61.1 | 2.84 | 74.0 | ~3 |
| 62 | 120 | 10 | 86.5 | 13.3 | 0.2 | | | 3.33 | | |
| | | 60 | 71.5 | 28.0 | 0.5 | 47.7 | 63.5 | 3.02 | 75.1 | ~2 |
| | | 180 | 67.2 | 29.8 | 3.0 | 42.2 | 57.7 | 2.72 | 73.1 | ~3 |
| 63 | 130 | 10 | 76.3 | 23.0 | 0.7 | | | 3.02 | | |
| | | 60 | 67.1 | 32.0 | 0.9 | 42.3 | 58.1 | 2.67 | 72.8 | ~3 |
| | | 90 | 66.9 | 32.1 | 1.0 | 40.8 | 56.5 | 2.59 | 72.2 | ~3 |

[a]The percentage of n-pentadecanal in the total $C_{15}$ aldehydes and alcohols.
[b]The percentage of n-pentadecanal and 2-methyltetradecanal in the total products.
[c]n-Pentadecanal, 2-methyltetradecanal and their alcohol hydrogenation products.
[d]The ratio of n-pentadecanal to 2-methyltetradecanal.
[e]The two main alcohols as a percentage of the four key products.

Such a variable temperature operation can be carried out in reactor system comprising reactors operating at different temperatures.

All the hydroformylation product mixtures were decobalted with aqueous acetic acid plus air treatment in the usual manner, and then fractionally distilled in vacuo. The $C_{15}$ aldehyde product was obtained as a clear yellow liquid distillate boiling between 95 and 111° C. at 0.1 mm. Using a relatively low temperature bath of 120–140° C., relatively little, about 5%, of the aldehyde was converted into dimers and trimers during distillation.

Analyses of the distilled $C_{15}$ aldehyde product showed that it was essentially free from hydrocarbon impurities. Combined GC/MS studies indicated the presence of about 47% n-pentadecanal, 15.5% 2-methyltetradecanal and 16% 2-($C_2$ to $C_6$ alkyl) substituted aldehydes. A distinct dibranched $C_{16}$ aldehyde was also found in the mixture in about 7.9% concentra- 120° C. as an approximately 6% solution in isomeric xylenes. The temperature was increased from 120 to 150° C. during the course of the reaction to convert the various types of olefins at their minimum reaction temperature.

The results of both hydroformylation experiments, using 0.2 and 0.1% cobalt, respectively, are shown by Table XXXV. Good olefin conversion was achieved at both catalyst concentrations. The maximum aldehyde content of the reaction mixtures was about 30%. However, the n-aldehyde selectivities appeared to be slightly higher at 0.1% Co.

The decrease in pressure drop with the reaction time indicated and the composition of the reaction mixture by packed GC showed that the reaction was essentially complete in 4 hours. As expected, the reaction was faster at the higher catalyst concentration. The final reaction mixtures still contained only minimum amounts of by-products, in the range of 2 to 3% of dimers.

TABLE XXXV

Hydroformylation of $C_{14}$ Olefinic Fraction of Billings Fluid Coker Naphtha In the Presence of Cobalt Catalyst Derived From $Co_2(CO)_8$ at Temperatures Increasing From 120 to 150° C. at 3000 psi

| Cat. Conc. Co % | Reaction Conditions Temp. °C. | Time Min. | Components of Total Mixture by Packed GC, % Un-reacted | Alde-hydes | Alco-hols[a] | Dimers[b] | Distribution of Isomeric $C_{15}$ Aldehydes Derived From n-Tetradecenes % Normal | Carbon No. of 2-n-Alkyl Group 1[c] | 2 | 3 | 4 | 5 | 6 | Linearity of Aldehydes n i[d] | n Me[c] | Alcohols & Formates in Oxo Products % | Ratio of n-Alcohol to n-Formate |
|---|---|---|---|---|---|---|---|---|---|---|---|---|---|---|---|---|---|
| 0.2 | 120 | 10 | 96.1 | 96.1 | | | | | | | | | | | | | |
| | | 30 | 85.7 | 13.8 | | 0.5 | 48.9 | 15.0 | 5.5 | 2.2 | 1.3 | | | 0.96 | 3.25 | | |
| | | 60 | 77.1 | 21.5 | | 1.4 | 48.8 | 15.4 | 5.5 | 2.6 | 1.6 | 1.5 | | 0.95 | 3.16 | 8.7 | |
| | 130 | 120 | 69.9 | 28.3 | 0.1 | 1.7 | 40.0 | 13.7 | 5.7 | 3.4 | 2.2 | 1.8 | 1.7 | 0.67 | 2.92 | 14.8 | 3.0 |
| | 140 | 180 | 66.0 | 29.7 | 2.0 | 2.3 | 35.6 | 12.5 | | | | | | 0.55 | 2.86 | 13.2 | 2.8 |
| | 150 | 240 | 64.4 | 29.3 | 3.8 | 2.5 | 33.1 | 12.0 | | 3.7 | 2.5 | 2.2 | 2.0 | 0.49 | 2.75 | 14.5 | 2.4 |

TABLE XXXV-continued

Hydroformylation of $C_{14}$ Olefinic Fraction of Billings Fluid Coker Naphtha In the Presence of
Cobalt Catalyst Derived From $Co_2(CO)_8$ at Temperatures Increasing From 120 to 150° C. at 3000 psi

| Cat. Conc. Co % | Reaction Conditions Temp. °C. | Reaction Conditions Time Min. | Components of Total Mixture by Packed GC, % Un-reacted | Components of Total Mixture by Packed GC, % Alde-hydes | Components of Total Mixture by Packed GC, % Alco-hols[a] | Components of Total Mixture by Packed GC, % Dimers[b] | Distribution of Isomeric $C_{15}$ Aldehydes Derived From n-Tetradecenes % Normal | Carbon No. of 2-n-Alkyl Group 1[c] | 2 | 3 | 4 | 5 | 6 | Linearity of Aldehydes n/i[d] | Linearity of Aldehydes n/Me[c] | Alcohols & Formates in Oxo Products % | Ratio of n-Alcohol to n-Formate |
|---|---|---|---|---|---|---|---|---|---|---|---|---|---|---|---|---|---|
| 0.1 | 120 | 10 | 98.0 | 2.0 | | | | | | | | | | | | | |
| | | 30 | 96.0 | 4.0 | | | 56.0 | 16.6 | 5.7 | | | | | 1.27 | 3.37 | | |
| | | 60 | 90.0 | 10.0 | | | 55.5 | 16.4 | 6.1 | 2.1 | 1.6 | 1.5 | | 1.24 | 3.38 | 6.1 | |
| | 130 | 120 | 75.6 | 23.0 | 0.1 | 1.3 | 42.3 | 14.2 | 5.5 | 3.2 | 2.0 | 1.6 | 1.5 | 0.73 | 2.99 | 14.6 | 2.2 |
| | 140 | 180 | 69.2 | 28.8 | 0.2 | 1.8 | 38.3 | 13.7 | 5.5 | 3.6 | 2.2 | 1.8 | 1.8 | 0.62 | 2.80 | 16.0 | 2.4 |
| | 150 | 240 | 66.0 | 29.5 | 2.2 | 2.3 | 36.5 | 13.5 | 5.8 | 3.8 | 2.4 | 2.1 | 2.0 | 0.57 | 2.71 | 16.9 | 3.5 |

[a]Includes only those alcohols and formate esters which could be separated.
[b]Includes all the high boiling by-products analyzable by GC.
[c]2-Methyltetradecanal.
[d]The isomeric $C_{15}$ aldehydes include all branched compounds.
[e]The experiment was carried out at variable temperatures up to 150° C., in the same manner as above.

Capillary GC showed that the n-pentadecanal was the most prevalent $C_{15}$ aldehyde isomer formed. It was, of course mostly derived from the main and most reactive olefin component of the feed 1-n-tetradecene. Thus, its percentages, 56.0 to 48.9%, were particularly high during the early stages of the reaction. At the completion of the reaction, the n-pentadecanal concentration was 33.1 to 36.1% of the isomeric pentadecanals.

The monobranched pentadecanals derived from and were the largest group of branched isomers. The percentage of the largest branched $C_{15}$ aldehyde isomer 2-methyl-tetradecanal ranged from 12.0 to 13.5. The second largest isomer, 2-ethyl-tridecanal was present in concentrations ranging from 5.7 to 5.8%. The other monobranched $C_{15}$ aldehydes derived from n-pentadecenes were also present in concentrations ranging from 1.8 to 3.8%. As expected, these minor aldehyde isomers had n-propyl, n-butyl, n-pentyl and n-hexyl branches in the 2-position. The largest of these minors, 2-propyl-tridecanal was present in the 2.1 to 3.9% concentration range. It is noted that at low feed conversion the recorded relative concentrations of these minor isomers in the table are low because of the limitation of the GC method of determination.

The selectivity of the hydroformylation of the 1-pentadecene component is characterized by the ratio of n-pentadecanal to 2-methyltetradecanal (n/Me). This ratio is decreasing from a top value of about 3.4 dow to 2.7 with increasing linearity is described by the ratio of the normal isomer to the sum of all the iso-, i.e. branched, aldehydes. This ratio also drops from 1.27 to 0.49.

Capillary GC also showed the presence of significant amounts isomeric $C_{15}$ alcohols and $C_{15}$ formates in the reaction mixture. Their GC peaks partially overlapped, but n-pentadecanol and n-pentadecyl formate could be distinguished. The combined amounts of alcohols and formates in the final reaction mixture ranged from 14.5 to 17.0% of the total oxygenated products. The ratios of the n-alcohol to the n-alkyl formate were from 2.4 to 3.5.

Sulfur GC of the reaction mixture indicated that most of the sulfur compound components are in the retention time region of the $C_{14}$ hydrocarbon feed. Relatively very small amounts of sulfur were found in the aldehyde region.

The hydroformylation reaction mixtures were decobalted with aerated aqueous acetic acid as usual. Then they were hydrogenated in the presence of 10% of a CoS/MoS based catalyst and 5% water at 3000 psi (306 atm) in the 150 to 170° C. temperature range. The reduction of the aldehydes was complete in 20 hours. Sulfur GC indicated that most of the sulfur compounds in the feed region remained unchanged during hydrogenation.

The hydrogenation of the aldehyde components of the reaction mixture was studied in some detail. Hydrogenations were carried out under comparative conditions at 150, 155 and 160° C. under 3000 psi pressure in a 1 liter stirred autoclave with reaction mixtures described above. Samples taken after 2, 5 and 20 hours were analyzed for aldehyde and alcohol content by capillary GC. The results are shown by Table XXXVI.

The data of the table show that hydrogenation occurs at a moderate rate at all three temperatures. The conversion of the n-pentadecanal to n-pentadecanol is 96% or more. The conversion of all the isomeric aldehydes is about 85 90% as a minimum. (The total conversion could not be exactly determined because of GC peak overlap between aldehydes and alcohols. This overlap of minor alcohol components was disregarded and all the components having shorter retention times than n-pentadecanal were counted as aldehydes.)

It is noted that the data of Table XXXVI show a slightly decreased aldehyde to alcohol conversion with increased temperature. This is apparently due to a slight decrease in catalyst activity in the three experiments of increasing temperature. It is interesting to note that the amount of n-pentadecane secondary product derived from n-pentadecanol increased with the temperature from a level below detection to an amount equal to 1.3% of that of n-pentadecanol. It appears that the n-alcohol to n-paraffin conversion is more temperature dependent than the n-aldehyde to n-alcohol conversion.

The hydrogenated reaction mixtures from the hydroformylation of $C_{14}$ Fluid-coker light gas oil fraction were combined and worked up to isolate the isomeric $C_{15}$ alcohol products. The combined mixture was then washed with fifty volume percent of a 10% aqueous sodium hydroxide solution to remove the $H_2S$ and any carboxylic acid by-products. This wash resulted in emulsion formation. The emulsion phase was largely broken by the addition of xylene. The emulsion phase was largely broken by the addition of xylene. The organic phase was then washed with water and dried over anhydrous MgSO$_4$.

TABLE XXXVI

Hydrogenation of the C$_{15}$ Aldehyde Components of the Hydroformylation Reaction Mixture Derived from C$_{14}$ Fluid-Coker Naphtha from Billings[a]

| | Conversion to C$_{15}$ Alcohol Products Based on Alcohol Product to Aldehyde Precursor Ratio | | | | | |
|---|---|---|---|---|---|---|
| Re- | At 150° C. (E-7630) Alcohol % | | At 155° C. (E-7633) Alcohol % | | At 160° C. (E-7636) Alcohol % | |
| Action Time[b] Hrs. | Nor- mal[c] | To- tal[d] | Nor- mal[c] | To- tal[d] | Nor- mal[c] | To- tal[d] |
| 2 | 45 | 31 | 38 | 33 | 32 | 24 |
| 5 | 68 | 54 | 62 | 50 | 58 | 44 |
| 20 | 98 | 90 | 98 | 88 | 96 | 85 |

[a]Hydrogenation with 6 wt % CoS/MoS catalyst on alumina support in the presence of 5% water under 3000 psi pressure
[b]From the time the mixture reached reaction temperature
[c]The percentage of n-pentadecanal converted to n-pentadecanol
[d]The percentage of C$_{15}$ aldehydes converted to C$_{15}$ alcohols based on oxygenated compounds up to and including n-pentadecanal.

The xylene solvent was then mostly removed by film evaporation in vacuo and the residual liquid was fractionally distilled in vacuo.

Fractional distillation recovered the unreacted C$_{14}$ hydrocarbons as a clear colorless liquid between 61 and 72° C. at about 0.1 mm. The oxo-product residua was about 1 kg. On further distillation the C$_{15}$ alcohol product was distilled between 112 and 129° C. at 0.1 mm. About 70% of the oxo-products were obtained as the C$_{15}$ alcohol distillate, a colorless clear liquid. Another 17% was received as a yellow liquid distillate mixture between 129 and 245° C. This mixture contained C$_{15}$ alcohols and dimers in a 1 to 2 ratio. The residue was about 12%.

During the distillation of the C$_{15}$ alcohol, it was noted that the n-pentadecanol crystallized on cooling from the higher boiling more linear fractions. Linear detergent alcohols can be apparently isolated from the present alcohol mixtures by crystallization.

Example 65

Hydroformylation of C$_{15}$ Gas Oil with 0.1% Cobalt at 140° C.

The previously described, vacuum distilled combined C$_{15}$ fraction of gas oil was hydroformylated in a manner described in Examples 41 to 45 at 140° C. under the conditions of Examples 49 to 52. The results are summarized in Table XXXVII.

TABLE XXXVII

Hydroformylation of C$_{15}$ Olefinic Fraction of Gas Oil from a Fluid Coker in the Presence of 0.1% Cobalt Catalyst Derived from Co$_2$(CO)$_8$ with 1/1 H$_2$/CO at 3000 psi

| | Reaction Mixture Components, % | | Two Major Products |
|---|---|---|---|
| Time Min | Un- reacted | Aldehydes[b] (Alcohols) | n/i Ratio[c] |
| 60 | 97 | 3 | 3.14 |
| 180 | 89 | 11 | 2.87 |
| 360 | 71 | 29 | 2.76 |

[a]Determined on packed column GC.
[b]Mostly aldehydes.
[c]n-Hexadecanal to 2-methylpentadecanal The data of the table show that at the low concentration of catalyst used, there was a long induction period. After 1 hour reaction time, less than 3% of aldehydes were formed. In three hours, product formation was still minimal. The maximum rate of hydroformylation was reached after 4 hours as indicated by the rate of synthesis gas consumption. A complete conversion of the 1-n-pentadecene feed component was obtained in 5 hours. After 6 hours, the amount of products in the reaction mixture was 29% and gas consumption was low. Thus, the reaction was discontinued.

Analyses of the reaction products showed high selectivity to aldehydes. The amount of alcohols and dimers each was about 1% in the final reaction mixture. The main reaction products were n-hexadecanal and 2-methylpentadecanal in an n/i ratio of 2.76. These two products amounted to 73.5% of all the C$_{16}$ aldehyde products. Most of the rest were 2-alkyl substituted C$_{16}$ aldehydes.

The final reaction mixture was decobalted as usual and fractionally distilled at 0.1 mm to separate the C$_{16}$ aldehyde product. The aldehyde was obtained as a clear yellow liquid distillate, boiling between 115 and 125° C. at 0.1 mm using a heating bath of 150 to 160° C. During fractional distillation, significant aldehyde dimer and trimer formation occurred. Only 70% of the C$_{16}$ aldehyde present in the reaction mixture was recovered by distillation.

Examples 66–70

Hydrogenation of the C$_{11}$–C$_{15}$ Aldehydes Derived from Coker Distillates to Produce the Corresponding Alcohols The combined distilled C$_{11}$ to C$_{15}$ aldehyde products were hydrogenated in the presence of a sulfur insensitive cobalt/molybdenum based hydrogenation catalyst in the manner previously described in the Experimental procedures. After about 24 hours hydrogenation at 232° C. under 300 psi pressure, the reaction mixtures were analyzed by GC/MS for aldehyde conversion. (In the case of the C$_{15}$ aldehyde, the reaction time was 48 hours.) It was found that the aldehydes were completely converted. The products were mostly the corresponding alcohols. However, some conversion to paraffins also occurred, possibly via the main alcohol products.

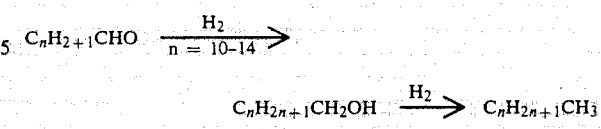

The product distributions obtained in the Examples are listed in the following:

| Example Number | Carbon No. of Product | Product Distribution % | |
|---|---|---|---|
| | | Alcohol | Paraffin |
| 66 | 11 | 87 | 13 |
| 67 | 12 | 87 | 13 |
| 68 | 13 | 88 | 12 |
| 69 | 14 | 89 | 11 |
| 70 | 15 | 68 | 32 |

An examination of the isomer distribution of the paraffin by-products by GC/MS showed a higher ratio of normal to iso paraffins than the n/i of the parent aldehydes. This indicated that the n-aldehydes and n-alcohols were preferably hydrogenated to paraffins. Consequently, the percentages of the n-alcohols, and the n/i ratios of n-alcohols to 2-methyl substituted alcohols, somewhat were lower than the n-aldehyde percentages and the aldehyde n/i ratios of the feeds. Since the hydrogenation to paraffins was a minor side reaction, the order of decreasing concentrations of alcohol types (normal, 2-methyl substituted, 2-ethyl and higher alkyl substituted alcohols) remained the same as that of the aldehyde feeds.

The reaction mixtures of the hydrogenations were fractionally distilled to separate the alcohol products from the paraffin by-products. Both were obtained as colorless liquid distillates of the following approximate boiling ranges:

| Carbon Number | Boiling Range, °C./mm | |
|---|---|---|
| | Alcohol Product | Paraffin By-Product |
| 11 | 135–146/20 | 97–132/20 |
| 12 | 148–158/20 | 94–135/20 |
| 13 | 145–149/10 | 96–144/10 |
| 14 | 147–163/10 | 114–145/10 |
| 15 | 163–172/10 | 117–157/10 |

GC/MS studies indicated that the alcohols had qualitatively the same isomer distribution as the parent aldehydes. The n-alcohols and the 2-methyl branched alcohols were the main components. GC/MS showed that the paraffins were derived from the aldehyde feed without structural isomerization. The paraffin forming side reaction occurred at the highest rate in case of the linear aldehyde component of the feed as indicated by the predominant formation of the n-paraffin.

Semilinear Dialkyl Phthalate Plasticizers

The $C_5$ to $C_{15}$ semilinear alcohols of the present invention can be converted to the corresponding dialkyl phthalate esters, via known methods. The alcohols are reacted with phthalic anhydride, preferably in the presence of a non-oxidizing acid catalyst such as p-toluene sulfonic acid or an alkyl titanate. The resulting phthalate esters have a unique combination of plasticizer properties as illustrated by the following examples.

Example 71

Semilinear Diundecyl Phthalate Plasticizer

The semilinear undecyl phthalate, DUP-F, and a linear undecyl phthalate, Jaflex DUP, were compounded with a Geon 30 polyvinylchloride and additives in the following proportions: parts per 100 wt. parts of PVC Geon 30, 100; phthalate plasticizer 50, Calcined Clay, 10; Dythal XL, 7; Stearic acid, 0.2. The physical properties of the resulting plasticized compositions were then tested. The data obtained are the following:

| | DUP-F | Jayflex DUP |
|---|---|---|
| Hardness Shore D | 36 | 39 |
| 100% Modulus, psi | 1890 | 2190 |
| Tensile Strength, psi | 3040 | 3110 |
| Elongation, % | 325 | 302 |

The higher hardness and modulus of the DUP-F composition indicates decreased plasticizer effectiveness. To obtain similar physical properties, a higher amount of DUP-F is to be used. Since the plasticizer has a lower cost by volume than PVC, reduced plasticizer effectiveness decreases the cost of plasticized PVC.

DUP-F and Jayflex DUP were also compared in a plastisol test in the following formulation: Geon 121, 100; Plasticizer, 70; Mark 7101, 2. After aging the plastisols at 100° F. (38° C.) the comparative Brookfield viscosity data were:

| | DUP-F | J-DUP |
|---|---|---|
| cps after 2 hours at 3 rpm | 4870 | 1970 |
| 30 rpm | 36850 | 15750 |
| cps after 24 hours at 3 rpm | 6120 | 2060 |
| 30 rpm | 41800 | 17250 |

To determined processability, a hot bench gelation test and dynamic mechanical analyses (at 10° C./min and rad./min and 1% strain) were carried out. The comparative results were:

| | DUP-F | J-DUP |
|---|---|---|
| Gel point, °C. | 247 | 264 |
| Gel onset, °C. | 73 | 81 |
| Gel complete, °C. | 144 | 144 |
| Fusion complete, °C. | 196 | 196 |

These data indicate a more facile processing for the Flexicoker alcohol based, DUP-F plasticizer.

The color stability on heating at 350° F. (177° C.) was the same for the DUP-F and J-DUP composition. Only the low temperature properties of the semilinear DUP-F were inferior to those of the linear J-DUP. In this respect, the properties of the semilinear DUP-F are in between those of the corresponding branched and linear ester compositions.

Example 72

Semilinear Didodecyl Phthalate Plasticizer

The semilinear dodecyl phthalate, DDP-F, was compared as a plasticizer with branched ditridecyl phthalate, J-DTDP, and branched undecyl decyl phthalate, J-UDP. Plasticized PVC compositions were formulated as follows: Geon 30, 100; Plasticizer, 62; Tribase EXL (lead silicate sulfate stabilizer); CaCO$_3$, 15; Stearic acid, 0.25; BPA antioxidant, 1. After milling at 350° F. (177° C.) and molding at 360° F. (182° C.) the following properties were found:

| | DDP-F | DTDP | UDP |
|---|---|---|---|
| Shore A Hardness, 7 day | 84.7 | 84 | 84 |
| Shore D Hardness, 7 day | 35.5 | 38 | 37 |
| Original Physicals, 0.040" | | | |
| Tensile Strength, psi | 2483 | 2555 | 2584 |
| 100% Modulus, psi | 1749 | 1856 | 1868 |
| Elongation, % | 307 | 293 | 280 |
| Aged Physicals, 0.040" 7 days 136° C. | | | |
| Retained Tensile Strength, % | 103 | 107 | 130 |
| Retained 100% Modulus, % | 139 | 146 | Too brittle |
| Retained Elongation, % | 64 | 56 | Too brittle |
| Weight Loss, % | 4.8 | 9.7 | 14.6 |
| Clash Berg, $T_f$, 0.070", °C. | −31 | −23.3 | −27 |
| Bell Brittleness $T_b$, 0.070", °C. | −28 | −21.9 | −22 |
| Pad Volume Resistivity 0.040", 90° C., ohm-cm × 10" | 0.30 | 1.68 | 1.94 |

These results indicate that the semilinear didodecyl phthalate is a fine plasticizer. Its reduced weight loss and lower Clash Berg and Bell Brittleness Temperatures indicate volatility and low temperature characteristics superior to related branched phthalate esters.

Example 73

Semilinear Ditridecyl Phthalate Plasticizer

The semilinear ditridecyl phthalate plasticizer, DTP-F, and a commercial branched ditridecyl phthalate plasticizer, DTDP, were compared in a PVC formulation described in the previous example with the following results:

|  | DTP-F | DTDP |
|---|---|---|
| Original Physicals |  |  |
| Shore A Hardness | 92 | 91 |
| 100% Modulus, psi | 1740 | 1770 |
| Tensile Strength, psi | 2420 | 2500 |
| Elongation, % | 285 | 304 |
| Aged Physical, 7 days/136° C. |  |  |
| Retained Tensile, % | 102 | 105 |
| Retained Elongation, % | 77 | 56 |
| Weight Loss, % | 2.8 | 9.6 |
| Low Temperature Properties |  |  |
| Clash Berg, $T_f$, °C. | −30 | −23 |
| Bell Brittleness, $T_b$, °C. | −25 | −22 |
| Pad Volume Resistivity |  |  |
| 40 mil, 90° C., ohm-cm × $10^n$ | 2.2 | 9.5 |

The data indicate that DTP-F is a fine plasticizer with superior elongation retention and permanence at high temperature and better low temperature properties than DTDP.

Semilinear Surfactants

The semilinear alcohols of the present invention are converted to novel surfactants via known methods. These methods are described in the appropriate volumes and references therein of the Surfactant Science Series, edited by M. J. Schick and F. M. Fowkes and published by Marcel Dekker, Inc., New York. Volume 7, Part 1 in 1976 by W. M. Linfield covers "Anionic Surfactants". "Cationic Surfactants" are discussed in Volume 4 of 1970 by E. Jungermann. "Nonionic Surfactants" by M. J. Schick are in Volume 1 of 1966. The relevant material of these volumes is incorporated by reference.

Example 74

Heptaethoxylated Semilinear Alcohol Surfactants

Semilinear $C_{13}$ and $C_{14}$ alcohols of the present invention were ethoxylated in the presence of sodium hydroxyde as a base catalyst to provide nonionic surfactants with an average of 9 ethoxy groups per molecule.

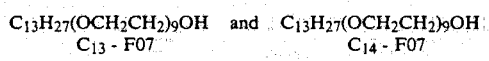

$C_{13}H_{27}(OCH_2CH_2)_9OH$ and $C_{13}H_{27}(OCH_2CH_2)_9OH$
$C_{13}$ - F07               $C_{14}$ - F07

In contrast to the sluggish and incomplete ethoxylation of branched aldol alcohols, these ethoxylations proceeded readily to completion.

These surfactants were then compared with a similarly ethoxylated linear $C_{12}$ to $C_{15}$ alcohol, Neodol 25-7.

The surface tension, in dynes per cm at 78° F. (25° C.), of aqueous solutions of these surfactants at various concentrations according to the ASTM D-1331 test method were the following:

|  | 0.0001% | 0.001% | 0.01% |
|---|---|---|---|
| $C_{13}$-F07 | 57 | 36 | 30 |
| $C_{14}$-F07 | 61 | 38 | 35 |
| Neodol 25-7 | 5 | 34 | 30 |

These data indicated similar surface tension reductions at the practical concentrations.

The cloud points of the 1% aqueous solutions of these semilinear and linear surfactants by ASTM-D2024 also similar.

|  | Cloud Point | |
|---|---|---|
|  | °C. | °F. |
| $C_{13}$-F07 | 40 | 104 |
| $C_{14}$-F07 | 44 | 111 |
| Neodol 2507 | 46 | 116 |

The ambient temperature wetting times of 0.1% aqueous solutions of the semilinear surfactants were superior to those of the linear surfactants, according to the Draves test (ASTM-D2281):

|  | Wetting Time, Seconds | | |
|---|---|---|---|
|  | 24° C. | 4° C. Below Cloud | 10° C. Above Cloud |
| $C_{13}$-F07 | 8.5 | 7.4 | 10.0 |
| $C_{14}$-F07 | 6.7 | 11.8 | 12.3 |
| Neodol 25-7 | 14.0 | 11.0 | 13.5 |

Aqueous solutions of the semilinear surfactants had a definitely reduced foam stability according to the Ross-Miles test:

|  | Foam Height, cm at 122° F. (50° C.) | | | |
|---|---|---|---|---|
|  | 0.1% | | 1.0% | |
|  | Initial | 5 Min. | Initial | 5 Min. |
| $C_{13}$-F07 | 9 | 1 | 7 | 2 |
| $C_{14}$-F07 | 9 | 2 | 5 | 1 |
| Neodol 250-7 | 12 | 6 | 15 | 12 |

This is advantageous in many nonfoaming applications.

Example 75

Nonaethoxylated Semilinear Alcohol Surfactants

Semilinear $C_{13}$ and $C_{14}$ alcohols were ethoxylated to provide surfactants of increased hydrophilic character with an average of 9 ethoxy groups. These surfactants $C_{13}$-F09 and $C_{14}$-F09 were compared with a similarly ethoxylated linear alcohol, Neodol 25-9, in the tests of the previous example. The results are shown by the following tabulations:

|  | Surface Tension Dynes/cm | | | Cloud Point at 1% | |
|---|---|---|---|---|---|
|  | 0.0001% | 0.001% | 0.01% | °C. | °F. |
| $C_{13}$-F09 | 52 | 40 | 33 | 78 | 173 |
| $C_{14}$-F09 | 57 | 36 | 33 | 74 | 165 |
| Neodol 25-9 | 56 | 34 | 32 | 74 | 165 |

|  | Wetting Time, Seconds | | |
|---|---|---|---|
|  | 24° C. | 4° C. Below Cloud | 10° C. Above Cloud |

-continued

|  | | | | |
|---|---|---|---|---|
| $C_{13}$-F07 | 14 | 8 | 23 | |
| $C_{14}$-F07 | 16 | 9 | 9 | |
| Neodol 25-7 | 19 | — | — | |

| | Foam Height, cm at 122° F. (50° C.) | | | |
|---|---|---|---|---|
| | 0.1% | | 1.0% | |
| | Initial | 5 Min. | Initial | 5 Min. |
| $C_{13}$-F07 | 15 | 3 | 21 | 6 |
| $C_{14}$-F07 | 14 | 4 | 17 | 5 |
| Neodol 250-7 | 15 | 12 | 17 | 13 |

It is apparent from the test results that the surfactant properties of the novel semilinear alcohols can be advantageously changed dependent on their carbon number and degree of ethoxylation. Since the present semilinear alcohols can be readily produced with even and uneven carbon numbers of choice, they can often provide surfactants of optimum properties without added cost.

Both the semilinear alcohols and their ethoxylated derivatives were readily sulfated and sulfonated to provide anionic surfactants of similarly attractive surfactant properties.

This invention has been described and illustrated by means of specific embodiments and examples; however, it must be understood that numerous changes and modifications may be made within the invention without departing from its spirit and scope as defined in the claims which follow.

We claim as our invention:

1. A hydroformylation-hydrogenation process comprising reacting an olefinic cracked petroleum distillate feed, produced from petroleum residua by high temperature thermal cracking, and containing $C_5$ to $C_{35}$-1-n-alkyl olefins as the major type of olefin components, and organic sulfur compounds in concentrations exceeding 0.1% sulfur
   (1) at first with carbon monoxide and hydrogen at temperatures between about 50 and 250° C. and pressures in the range of 50 and 6000 psi
   in the presence of a Group VIII transition metal carbonyl complex catalyst in effective amounts
   to produce aldehydes of a semilinear character having an average of less than one alkyl branch per molecule and 20% by weight or more linear isomers,
   (2) then with molecular hydrogen
   at temperatures between 100 and 250° C. and pressures between 200 psi and 5000 psi (13.6 and 340 atm)
   in the presence of a hydrogenation catalyst in effective amounts the catalyst being sulfur resistant cobalt, molybdenum, nickel, or tungsten or a sulfide thereof
   to produce the corresponding alcohols of a semilinear character having an average of less than one alkyl branch per molecule.

2. The process of claim 1 wherein the olefins have 5 to 12 carbon atoms.

3. The process of claim 1 wherein the hydrogenation catalyst is cobalt sulfide or molybdenum sulfide.

4. The process of claim 1 or 2 wherein the olefins have 8 to 12 carbon atoms.

* * * * *